United States Patent
Kan et al.

(10) Patent No.: US 10,889,570 B2
(45) Date of Patent: Jan. 12, 2021

(54) BENZAZEPINE DERIVATIVES

(71) Applicant: OTSUKA PHARMACEUTICAL CO., LTD., Tokyo (JP)

(72) Inventors: Keizo Kan, Osaka (JP); Masatoshi Takuwa, Osaka (JP); Hirotaka Tanaka, Osaka (JP); Hideto Fujiwara, Osaka (JP); Hokuto Yamabe, Osaka (JP); Satoshi Matsuda, Osaka (JP); Kazuhiro Ohdachi, Osaka (JP); Taiki Hanari, Osaka (JP); Yasuhiro Menjo, Osaka (JP); Tatsuya Urushima, Osaka (JP); Shigekazu Fujita, Osaka (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/480,842

(22) PCT Filed: Jun. 29, 2018

(86) PCT No.: PCT/JP2018/024786
§ 371 (c)(1),
(2) Date: Jul. 25, 2019

(87) PCT Pub. No.: WO2019/004421
PCT Pub. Date: Jan. 3, 2019

(65) Prior Publication Data
US 2019/0389838 A1 Dec. 26, 2019

(30) Foreign Application Priority Data
Jun. 30, 2017 (JP) .................... PCT/JP2017/024211

(51) Int. Cl.
| | | |
|---|---|---|
| A61K 31/55 | (2006.01) | |
| A61P 13/12 | (2006.01) | |
| C07D 223/16 | (2006.01) | |
| C07D 401/06 | (2006.01) | |
| C07D 401/10 | (2006.01) | |
| C07D 401/14 | (2006.01) | |
| C07D 403/06 | (2006.01) | |
| C07D 405/12 | (2006.01) | |
| C07D 409/12 | (2006.01) | |

(52) U.S. Cl.
CPC ......... *C07D 401/14* (2013.01); *C07D 401/10* (2013.01); *C07D 403/06* (2013.01); *C07D 223/16* (2013.01)

(58) Field of Classification Search
CPC ....... A61K 31/55; A61P 13/12; C07D 223/16; C07D 401/06; C07D 401/10; C07D 401/14; C07D 403/06; C07D 405/12; C07D 409/12
See application file for complete search history.

(56) References Cited

U.S. PATENT DOCUMENTS

| | | |
|---|---|---|
| 5,258,510 A | 11/1993 | Ogawa et al. |
| 5,498,609 A | 3/1996 | Ogawa et al. |
| 5,622,947 A | 4/1997 | Ogawa et al. |
| 5,710,150 A | 1/1998 | Taniguchi et al. |
| 6,096,735 A | 8/2000 | Ogawa et al. |
| 6,495,542 B1 | 12/2002 | Setoi et al. |
| 2008/0234250 A1 | 9/2008 | Pitt |
| 2013/0131045 A1 | 5/2013 | Kan et al. |
| 2015/0376198 A1 | 12/2015 | Roberts et al. |

FOREIGN PATENT DOCUMENTS

| | | |
|---|---|---|
| EP | 0 716 083 A1 | 6/1996 |
| EP | 2 495 236 A1 | 9/2012 |
| JP | 4-321669 A | 11/1992 |
| JP | 9-221476 A | 8/1997 |

(Continued)

OTHER PUBLICATIONS

Shoaf S.E. et al., "Effects of CYP3A4 inhibition and induction on the pharmacokinetics and pharmacodynamics of tolvaptan, a non-peptide AVP antagonist in healthy subjects", British Journal of Clinical Pharmacology, 2011, vol. 73, No. 4, pp. 579-587 (total 9 pages).

Sorbera L.A. et al., "Tolvaptan; Treatment of Heart Failure Vasopressin $V_2$ Antagonist", Drugs of the Future, 2002, vol. 27, No. 4, pp. 350-357 (total 8 pages).

Furukawa M. et al., "Liquid chromatography-tandem mass spectrometry method for determining tolvaptan and its nine metabolites in rat serum: application to a pharmacokinetic study", Archives of Pharmacal Research, Mar. 24, 2014, vol. 37, pp. 1578-1587 (total 10 pages).

Kazumi Kondo et al., "7-Chloro-5-hydroxy-1[2-methyl-4(2-methylbenzoyl-amino)benzoyl]-2,3,4,5-tetrahydro-1H-1-benzazepine (OPC-41061): A Potent, Orally Active Nonpeptide Arginine Vasopressin $V_2$ Receptor Antagonist", Bioorganic & Medical Chemistry, 1999, vol. 7, pp. 1743-1754, *table 3; compounds 30-34* (total 12 pages).

(Continued)

*Primary Examiner* — Brenda L Coleman
(74) *Attorney, Agent, or Firm* — Sughrue Mion, PLLC

(57) ABSTRACT

The present invention provides novel benzazepine compounds of Formula (1), or salts thereof, having vasopressin $V_{1a}$ and $V_2$ antagonisms, and medical uses thereof.
In the formula, $R^1$ is optionally substituted $C_{1-6}$ alkyl, etc.; L is —C(=O)—NH—, etc.; Ring $A^1$ is a hydrocarbon ring, etc.; Ring $A^2$ is a hydrocarbon ring, etc.; and each of Rings $A^1$ and $A^2$ may have at least one substituent.

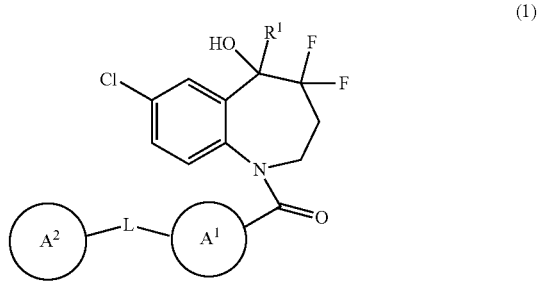

(1)

58 Claims, No Drawings

(56) References Cited

FOREIGN PATENT DOCUMENTS

| | | |
|---|---|---|
| JP | 10-120592 A | 5/1998 |
| JP | 2000-212165 A | 8/2000 |
| JP | 2000-351768 A | 12/2000 |
| JP | 2008-509972 A | 4/2008 |
| JP | 2016-513112 A | 5/2016 |
| WO | 1991/05549 A1 | 5/1991 |
| WO | 1994/01113 A1 | 1/1994 |
| WO | 1994/04525 A1 | 3/1994 |
| WO | 1994/08582 A1 | 4/1994 |
| WO | 95/06035 A1 | 3/1995 |
| WO | 1995/34540 A1 | 12/1995 |
| WO | 99/37637 A1 | 7/1999 |
| WO | 2011/052519 A1 | 5/2011 |

OTHER PUBLICATIONS

International Search Report for PCT/JP2018/024786 dated Sep. 12, 2018 [PCT/ISA/210].

International Preliminary Report on Patentability dated Dec. 31, 2019 from the International Bureau in International Application No. PCT/JP2018/024786.

International Preliminary Report on Patentability dated Dec. 31, 2019 from the International Bureau in International Application No. PCT/JP2017/024211 (priority application).

Yea et al., "New Benzylureas as a Novel Series of Potent, Nonpeptidic Vasopressin V2 Receptor Agonists", Journal of Medicinal Chemistry, 2008, vol. 51, No. 24, pp. 8124-8134.

BENZAZEPINE DERIVATIVES

CROSS REFERENCE TO RELATED APPLICATIONS

This application is a National Stage of International Application No. PCT/JP2018/024786 filed on Jun. 29, 2018, which claims priority from International Application No. PCT/JP2017/024211 filed on Jun. 30, 2017.

TECHNICAL FIELD

The present invention relates to benzazepine derivatives and salts thereof. The present invention also relates to medicines, comprising a benzazepine derivative and a salt thereof as an active ingredient, useful for diagnosing, preventing, and/or treating diseases associated with vasopressin receptors.

BACKGROUND ART

Vasopressin is an antidiuretic hormone and is known to function to increase blood pressure. Vasopressin $V_{1a}$ receptor and vasopressin $V_2$ receptor are known as a subgroup of vasopressin receptors, each of which is associated with vascular constriction and reabsorption of water in the collecting duct.

Tolvaptan has a benzo-heterocyclic structure and is used for treating various diseases, especially as a vasopressin $V_2$ receptor antagonist. It has been known to be metabolized primarily by a hepatic metabolizing enzyme, CYP3A4 (NPL 1 to 3). Various compounds have been known to have a benzo-heterocyclic structure (PTL 1 to 9), but no compounds having difluorine and hydroxy on positions 4 and 5, respectively, of a benzazepine ring among benzo-heterocycles have been known to have vasopressin antagonisms as both vasopressin $V_{1a}$ and $V_2$ antagonists.

CITATION LIST

Patent Literature

[PTL 1] WO 2011/052519
[PTL 2] JP 10-120592 A
[PTL 3] JP 9-221476 A
[PTL 4] WO 1994/04525
[PTL 5] WO 1994/01113
[PTL 6] JP 4-321669 A
[PTL 7] WO 1991/05549
[PTL 8] WO 1995/34540
[PTL 9] WO 1994/08582

Non Patent Literature

[NPL 1] Shoaf S.E. et al. Br J Clin Pharmacol. 2011, 73:579-87
[NPL 2] Sorbera L.A. et al. Drugs of the Future. 2002, 27(4):350-357
[NPL 3] Furukawa M. et al. Arch. Pharm. Res. 2014 37:1578-87

SUMMARY OF INVENTION

Technical Problem

One object of the present invention is to provide novel benzazepine compounds, or salts thereof, having vasopressin $V_1a$ and $V_2$ antagonisms and the favorable metabolic stability and absorption property and medical uses of the compounds.

Solution to Problem

After extensive studies, the present inventors have achieved to develop novel benzazepine compounds and salts thereof having vasopressin antagonisms and the favorable metabolic stability and absorption property. The present invention has been accomplished on the basis of the findings.

In one embodiment, the present invention provides a benzazepine compound of Formula (1):

[Chem. 1]

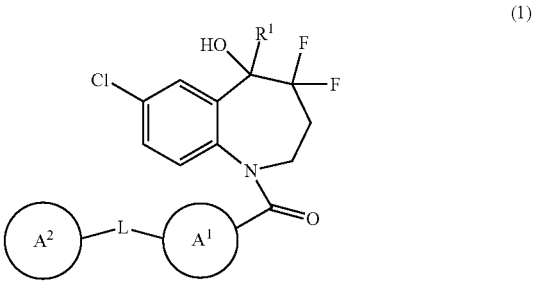

(1)

wherein $R^1$ is deuterium, OH, COOH, optionally substituted $C_{1-6}$ alkyl, optionally substituted $C_{1-6}$ alkyl-O—CO—, or optionally substituted $C_{2-6}$ alkenyl;

L is a direct bond or —C(=O)—NH—;
Ring $A^1$ is a hydrocarbon ring or heterocycle;
Ring $A^2$ is a hydrocarbon ring or heterocycle; and
each of Rings $A^1$ and $A^2$ may have at least one substituent, or a salt thereof (referred to as the "present compound" hereinafter).

Advantageous Effects of Invention

The present compound with vasopressin antagonisms as both vasopressin $V_1a$ and $V_2$ antagonists may be useful for treating, preventing, and/or diagnosing various diseases associated with vasopressin receptors. The present compound may also have the favorable metabolic stability so as to extend the duration of pharmacological effects and have the favorable absorption property.

DESCRIPTION OF EMBODIMENTS

Examples of "halo" or "halogen" herein include fluorine, chlorine, bromine, and iodine. A preferable example is fluorine or chlorine.

Examples of "$C_{1-6}$ alkyl" herein include straight- or branched-chain alkyl groups having 1 to 6 carbon atoms and specifically include methyl, ethyl, propyl, isopropyl, butyl, isobutyl, sec-butyl, tert-butyl, pentyl, isopentyl, neopentyl, hexyl, isohexyl, and 3-methylpentyl.

Examples of "$C_{2-6}$ alkenyl" herein include straight- or branched-chain alkenyl groups having 2 to 6 carbon atoms and 1 to 3 double bonds and specifically include vinyl (ethenyl), 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl, and 5-hexenyl.

The term "halo-$C_{1-6}$ alkyl" herein is $C_{1-6}$ alkyl substituted with the same or different 1 to 7, preferably 1 to 3, halogen, and includes, for example, monofluoromethyl, difluoromethyl, trifluoromethyl, 2-chloroethyl, 2-bromoethyl, 2,2-difluoroethyl, 2,2,2-trifluoroethyl, 2,2,2-trifluoro-1-methylethyl, pentafluoroethyl, 2-trifluoromethylpropyl, and 4-fluorobutyl.

Examples of "$C_{3-6}$ cycloalkyl" herein include saturated cyclic alkyl groups having 3 to 6 carbon ring atoms and specifically include cyclopropyl, cyclobutyl, cyclopentyl, and cyclohexyl.

Examples of the "hydrocarbon ring" herein include saturated or unsaturated 3- to 15-membered monocyclic, bicyclic, or tricyclic hydrocarbon rings. The "unsaturated" ring refers to an aromatic ring or a saturated ring comprising a partially unsaturated bond. Examples of the "hydrocarbon ring" include:

(a) saturated or unsaturated 3- to 8-membered, preferably 5- or 6-membered, monocyclic hydrocarbon rings; specifically, cyclopropane, cyclobutane, cyclopentane, cyclohexane, cycloheptane, cyclooctane, cyclobutene, cyclopentene, cyclohexene, cycloheptene, cyclooctene, and benzene; and (b) saturated or unsaturated 7- to 15-membered bicyclic or tricyclic hydrocarbon rings, preferably saturated or unsaturated 7- to 12-membered bicyclic hydrocarbon rings; specifically, indene, dihydroindene, naphthalene, dihydronaphthalene, tetrahydronaphthalene, anthracene, and phenanthrene.

Examples of "heterocycle" herein include saturated or unsaturated monocyclic or polycyclic heterocycles comprising at least one, for example, 1 to 5, ring heteroatom independently selected from the group consisting of nitrogen, oxygen, and sulfur and include, for example, saturated or unsaturated 3- to 15-membered monocyclic, bicyclic, or tricyclic heterocycles. Any of the rings in the bicyclic or tricyclic heterocycle may comprise a heteroatom or all of the rings may comprise a heteroatom. The "unsaturated" ring refers to an aromatic ring or a saturated ring comprising a partially unsaturated bond. A preferable heterocycle is saturated or unsaturated 5- to 10-membered heteromonocycles or heterobicycles comprising at least one ring nitrogen atom. A ring atom in the heterocycle may be substituted with oxo to form an oxide. The term "heterocycle" includes, for example:

(a) saturated or unsaturated 3- to 8-membered, preferably 3- to 6-membered, more preferably 5- or 6-membered, heteromonocycles comprising at least one, for example, 1 to 4, preferably 1 or 2, nitrogen atom as the ring heteroatom; specifically, pyrrole, imidazole, pyrazole, pyridine, tetrahydropyridine, pyrimidine, pyrazine, pyridazine, triazole, tetrazole, dihydrotriazine, azetidine, pyrrolidine, imidazolidine, piperidine, pyrazolidine, piperazine, azepane, and 1,4-diazepane;

(b) saturated or unsaturated 7- to 15-membered bicyclic or tricyclic heterocycles comprising at least one, for example, 1 to 5, nitrogen atom as the ring heteroatom, preferably saturated or unsaturated 7- to 12-membered bicyclic or tricyclic heterocycles comprising 1 to 3 nitrogen atoms as the ring heteroatom; specifically, indole, indoline (dihydroindole), isoindole, isoindoline (dihydroisoindole), benzimidazole, dihydrobenzimidazole, indazole, indazoline (dihydroindazole), quinoline, dihydroquinoline, tetrahydroquinoline, decahydroquinoline, isoquinoline, dihydroisoquinoline, tetrahydroisoquinoline, benzotriazole, tetrazolopyridine, tetrazolopyridazine, dihydrotriazolopyridazine, imidazopyridine, naphthyridine, tetrahydronaphthyridine, hexahydronaphthyridine, cinnoline, quinoxaline, dihydroquinoxaline, tetrahydroquinoxaline, quinazoline, dihydroquinazoline, tetrahydroquinazoline, pyrazolopyridine, tetrahydropyridoindole, benzazepine, tetrahydrobenzazepine, carbazole, phenanthridine, and dihydrophenanthridine;

(c) saturated or unsaturated 3- to 8-membered, preferably 5- or 6-membered, heteromonocycles comprising 1 or 2 oxygen atoms as the ring heteroatom; specifically, furan, tetrahydropyran, tetrahydrofuran, and dioxane;

(d) saturated or unsaturated 7- to 12-membered heterobicycles comprising at least one, for example, 1 to 3, oxygen atom as the ring heteroatom; specifically, benzofuran, dihydrobenzofuran, chromane, benzodioxole, and benzodioxane;

(e) saturated or unsaturated 3- to 8-membered, preferably 5- or 6-membered, heteromonocycles comprising 1 or 2 sulfur atoms as the ring heteroatom; specifically, thiophene, tetrahydrothiophene, thiopyran, and tetrahydrothiopyran;

(f) saturated or unsaturated 7- to 12-membered heterobicycles comprising at least one, for example, 1 to 3, sulfur atom as the ring atom; specifically, benzothiophene;

(g) saturated or unsaturated 3- to 8-membered, preferably 5- or 6-membered, heteromonocycles comprising 1 or 2 oxygen atoms and at least one, for example, 1 to 3, nitrogen atom as the ring heteroatom; specifically, oxazole, isoxazole, oxadiazole, and morpholine;

(h) saturated or unsaturated 7- to 12-membered heterobicycles comprising 1 or 2 oxygen atoms and at least one, for example, 1 to 3, nitrogen atom as the ring heteroatom; specifically, benzoxazole, dihydrobenzoxazole, benzoxadiazole, benzoisoxazole, benzoxazine, dihydrobenzoxazine, furopyridine, furopyrrole, benzoxazepine, and tetrahydrobenzoxazepine;

(i) saturated or unsaturated 3- to 8-membered, preferably 5- or 6-membered, heteromonocycles comprising 1 or 2 sulfur atoms and at least one, for example, 1 to 3, nitrogen atom as the ring heteroatom; specifically, thiazole, thiazoline (dihydrothiazole), thiadiazole, isothiazole, and thiazolidine;

(j) saturated or unsaturated 7- to 12-membered heterobicycles comprising 1 or 2 sulfur atoms and at least one, for example, 1 to 3, nitrogen atom as the ring heteroatom; specifically, benzothiazole, dihydrobenzothiazole, benzothiadiazole, thienopyridine, imidazothiazole, dihydroimidazothiazole, thienopyrazine, benzothiazine, dihydrobenzothiazine, benzothiazepine, and tetrahydrobenzothiazepine; and (k) saturated or unsaturated 7- to 12-membered heterobicycles comprising 1 or 2 oxygen atoms and at least one, for example, 1 to 3, sulfur atom as the ring heteroatom; specifically, benzoxathiin.

Each group defined herein may constitute a part of another group and may optionally bind to another group via a linker such as —O—, —CO—, —COO—, —S—, —SO—, —SO$_2$—, —SO$_2$—O—, —O—CO—, and —SO$_2$—NH—. For example, a group wherein $C_{1-6}$ alkyl binds to another group via —O— is represented as $C_{1-6}$ alkyl-O—. The $C_{1-6}$ alkyl group in the $C_{1-6}$ alkyl-O— group has the same definition as $C_{1-6}$ alkyl.

In some embodiments, $R^1$ is preferably deuterium; OH; COOH; $C_{1-6}$ alkyl optionally substituted with 1 to 3 groups independently selected from the group consisting of optionally substituted amino, optionally substituted $C_{1-6}$ alkyl-O—, optionally substituted $C_{1-6}$ alkyl-SO$_2$—O—, optionally substituted silyl-O—, OH, optionally substituted $C_{1-6}$ alkyl-COO—, tetrahydropyranyl-O—, and heterocycle; optionally substituted $C_{1-6}$ alkyl-O—CO—; or optionally substituted $C_{2-6}$ alkenyl, the optionally substituted amino being, for example, amino optionally substituted with 1 or 2 groups independently selected from the group consisting of $C_{1-6}$ alkyl optionally substituted with OH, optionally substituted $C_{1-6}$ alkyl-$SO_2$—, optionally substituted $C_{1-6}$ alkyl-O—CO—, and benzyl-O—CO—, the optionally substituted $C_{1-6}$ alkyl in the optionally substituted $C_{1-6}$ alkyl-O—, optionally substituted $C_{1-6}$ alkyl-$SO_2$—, optionally substituted $C_{1-6}$ alkyl-$SO_2$—O—, optionally substituted $C_{1-6}$ alkyl-COO—, and optionally substituted $C_{1-6}$ alkyl-O—CO— being, for example, $C_{1-6}$ alkyl optionally substituted with 1 to 3 groups independently selected from the group consisting of halogen, $C_{1-6}$ alkyl-O—, optionally substituted phenyl, optionally substituted phenyl-$SO_2$—NH—, and naphthalenyl-$SO_2$—NH—, the optionally substituted phenyl being phenyl optionally substituted with 1 to 3 groups independently selected from the group consisting of halogen, $C_{1-6}$ alkyl, and $NO_2$, the optionally substituted silyl-O— being, for example, silyl-O— optionally substituted with the same or different 1 to 3 $C_{1-6}$ alkyl, the heterocycle being, for example, thiazole or pyridine, and the optionally substituted $C_{2-6}$ alkenyl being, for example, $C_{2-6}$ alkenyl optionally substituted with the same or different 1 to 3 halogen.

More preferably, $R^1$ is deuterium; OH; or $C_{1-6}$ alkyl optionally substituted with 1 to 3 groups independently selected from the group consisting of optionally substituted amino, optionally substituted $C_{1-6}$ alkyl-O—, and OH.

Particularly preferably, $R^1$ is $C_{1-6}$ alkyl substituted with OH.

In Formula (1), Ring $A^1$ is preferably a saturated or unsaturated 3- to 8-membered monocyclic hydrocarbon ring, or a saturated or unsaturated 3- to 15-membered monocyclic, bicyclic, or tricyclic heterocycle comprising at least one, for example, 1 to 5, heteroatom independently selected from the group consisting of nitrogen, oxygen, and sulfur as the ring atom.

More preferably, Ring $A^1$ is:

(a) a saturated or unsaturated 3- to 8-membered monocyclic hydrocarbon ring, preferably, cyclopropane, cyclobutane, cyclopentane, cyclohexane, cycloheptane, cyclooctane, cyclobutene, cyclopentene, cyclohexene, cycloheptene, cyclooctene, or benzene, more preferably, benzene, (b) a saturated or unsaturated 5- or 6-membered heteromonocycle comprising at least one, for example, 1 to 4, nitrogen atom as the ring heteroatom, preferably, pyrrole, imidazole, pyrazole, pyridine, tetrahydropyridine, pyrimidine, pyrazine, pyridazine, triazole, tetrazole, dihydrotriazine, azetidine, pyrrolidine, imidazolidine, piperidine, pyrazolidine, piperazine, azepane, or 1,4-diazepane, more preferably, pyridine or pyrazine, particularly preferably, pyridine, (c) a saturated or unsaturated 7- to 15-membered heterobicycle comprising at least one, for example, 1 to 5, nitrogen atom as the ring heteroatom, preferably, indole, indoline (dihydroindole), isoindole, isoindoline (dihydroisoindole), benzimidazole, dihydrobenzimidazole, indazole, indazoline (dihydroindazole), quinoline, dihydroquinoline, tetrahydroquinoline, decahydroquinoline, isoquinoline, dihydroisoquinoline, tetrahydroisoquinoline, benzotriazole, tetrazolopyridine, tetrazolopyridazine, dihydrotriazolopyridazine, imidazopyridine, naphthyridine, tetrahydronaphthyridine, hexahydronaphthyridine, cinnoline, quinoxaline, dihydroquinoxaline, tetrahydroquinoxaline, quinazoline, dihydroquinazoline, tetrahydroquinazoline, pyrazolopyridine, tetrahydropyridoindole, benzazepine, tetrahydrobenzazepine, carbazole, phenanthridine, or dihydrophenanthridine, more preferably, tetrahydroisoquinoline, (d) a saturated or unsaturated 5- or 6-membered heteromonocycle comprising 1 or 2 oxygen atoms and at least one, for example, 1 to 3, nitrogen atom as the ring heteroatom, preferably, oxazole, or (e) a saturated or unsaturated 5- or 6-membered heteromonocycle comprising 1 or 2 sulfur atoms and at least one, for example, 1 to 3, nitrogen atom as the ring heteroatom, preferably, thiazole.

Particularly Preferably, Ring $A^1$ is Benzene or Pyridine.

Ring $A^1$ may have at least one or more, preferably, 1 to 4, more preferably, 1, substituent. Such a substituent is preferably and independently selected from the group consisting of optionally substituted $C_{1-6}$ alkyl, optionally substituted $C_{1-6}$ alkyl-O—, halogen, and oxo. Such a substituent includes more preferably $C_{1-6}$ alkyl optionally substituted with the same or different 1 to 3 halogen; $C_{1-6}$ alkyl-O— optionally substituted with 1 to 3 groups independently selected from the group consisting of halogen, $C_{1-6}$ alkyl-O—, and halo-$C_6$ alkyl-O—; halogen; and oxo. Such a substituent includes still more preferably halogen, $C_{1-6}$ alkyl, $C_{1-6}$ alkyl-O—, and $C_{1-6}$ alkyl-O—$C_{1-6}$ alkyl-O—. Such a substituent includes still more preferably halogen, $C_{1-6}$ alkyl, and $C_{1-6}$ alkyl-O—. Such a substituent is particularly preferably halogen.

In some embodiments, Ring $A^1$ is benzene, pyridine, pyrazine, or tetrahydroisoquinoline, preferably, benzene or pyridine, which may have any of the above substituents.

In Formula (1), Ring $A^2$ is preferably a saturated or unsaturated 3- to 8-membered monocyclic hydrocarbon ring, or a saturated or unsaturated 3- to 15-membered monocyclic, bicyclic, or tricyclic heterocycle comprising at least one, for example, 1 to 5, heteroatom independently selected from the group consisting of nitrogen, oxygen, and sulfur as the ring atom.

More preferably, Ring $A^2$ is:

(a) a saturated or unsaturated 3- to 8-membered monocyclic hydrocarbon ring, preferably, cyclopropane, cyclobutane, cyclopentane, cyclohexane, cycloheptane, cyclooctane, cyclobutene, cyclopentene, cyclohexene, cycloheptene, cyclooctene, or benzene, more preferably, benzene, (b) a saturated or unsaturated 5- or 6-membered heteromonocycle comprising at least one, for example, 1 to 4, nitrogen atom as the ring heteroatom, preferably, pyrrole, imidazole, pyrazole, pyridine, tetrahydropyridine, pyrimidine, pyrazine, pyridazine, triazole, tetrazole, dihydrotriazine, azetidine, pyrrolidine, imidazolidine, piperidine, pyrazolidine, piperazine, azepane, or 1,4-diazepane, more preferably, pyridine, (c) a saturated or unsaturated 5- or 6-membered heteromonocycle comprising 1 or 2 oxygen atoms as the ring heteroatom, preferably, furan, tetrahydropyran, tetrahydrofuran, or dioxane, more preferably, furan, (d) a saturated or unsaturated 7- to 12-membered heterobicycle comprising at least one, for example, 1 to 3, oxygen atom as the ring heteroatom, preferably, benzofuran, (e) a saturated or unsaturated 5- or 6-membered heteromonocycle comprising 1 or 2 sulfur atoms as the ring heteroatom, preferably, thiophene, tetrahydrothiophene, tetrahydrothiopyran, more preferably, thiophene, (f) a saturated or unsaturated 7- to 15-membered heterobicycle comprising at least one, for example, 1 to 5, nitrogen atom as the ring heteroatom, preferably, indole, indoline (dihydroindole), isoindole, isoindoline (dihydroisoindole), benzimidazole, dihydrobenzimidazole, indazole, indazoline (dihydroindazole), quinoline, dihydroquinoline, tetrahydroquinoline, decahydroquinoline, isoquinoline, dihydroisoquinoline, tetrahydroisoquinoline, benzotriazole, tetrazolopyridine, tetrazolopyridazine, dihydrotriazolopyridazine, imidazopyridine, naphthyridine, tetrahydronaphthyridine, hexahydronaphthyridine, cinnoline, quinoxaline, dihydroquinoxaline, tetrahydroquinoxaline, quinazoline, dihydroquinazoline, tetrahydroquinazoline, pyrazolopyridine, tetrahydropyridoindole, benzazepine, tetrahydrobenzazepine, carbazole, phenanthridine, or dihydrophenanthridine, more preferably, tetrahydroisoquinoline, (g) a saturated or unsaturated 5- or 6-membered heteromonocycle comprising 1 or 2 oxygen atoms and at least one, for example, 1 to 3, nitrogen atom as the ring heteroatom, preferably, oxazole, or (h) a saturated or unsaturated 5- or 6-membered heteromonocycle comprising 1 or 2 sulfur atoms and at least one, for example, 1 to 3, nitrogen atom as the ring heteroatom, preferably, thiazole.

Particularly Preferably, Ring $A^2$ is Benzene.

Ring $A^2$ may have at least one or more, preferably, 1 to 4, more preferably, 1 to 3, particularly preferably, 2, substituent. Such a substituent is preferably and independently selected from the group consisting of optionally substituted $C_{1-6}$ alkyl, optionally substituted $C_{1-6}$ alkyl-O—, optionally substituted $C_{3-6}$ cycloalkyl, halogen, oxo, optionally substituted phenyl, and optionally substituted pyridyl. Such a substituent includes more preferably $C_{1-6}$ alkyl optionally substituted with the same or different 1 to 3 halogen; $C_{1-6}$ alkyl-O— optionally substituted with the same or different 1 to 3 halogen; $C_{3-6}$ cycloalkyl optionally substituted with the same or different 1 to 3 halogen; halogen; oxo; phenyl optionally substituted with 1 to 3 groups independently selected from the group consisting of halogen, $C_{1-6}$ alkyl, and $C_{1-6}$ alkyl-O—; and pyridyl optionally substituted with the same or different 1 to 3 halogen. Such a substituent is still more preferably and independently selected from the group consisting of halogen; $C_{1-6}$ alkyl optionally substituted with halogen; $C_{1-6}$ alkyl-O— optionally substituted with halogen; $C_{3-6}$ cycloalkyl, particularly preferably, cyclopropyl or cyclobutyl; phenyl optionally substituted with halogen, $C_{1-6}$ alkyl, halo-$C_{1-6}$ alkyl, $C_{1-6}$ alkyl-O—, or halo-$C_{1-6}$ alkyl-O—; and pyridyl. Such a substituent is still more preferably and independently selected from the group consisting of halogen, $C_{1-6}$ alkyl, halo-$C_{1-6}$ alkyl, and phenyl optionally substituted with halogen. Such a substituent is particularly preferably and independently selected from halogen or phenyl.

When Ring $A^2$ has multiple substituents on its ring carbon atoms, the substituents may combine together with the carbon atoms to form $C_{3-6}$ cycloalkyl, preferably, cyclopropyl or cyclobutyl, so that Ring $A^2$ may form a spiro ring.

In some embodiments, Ring $A^2$ is benzene, pyridine, furan, thiophene, or tetrahydroisoquinoline, preferably, benzene, which may have any of the above substituents.

When L is —C(=O)—NH—, Formula (1) includes both of the following embodiments:

[Chem. 2]

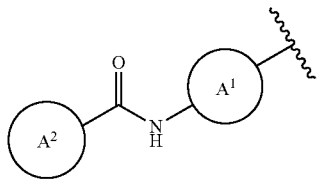

-continued

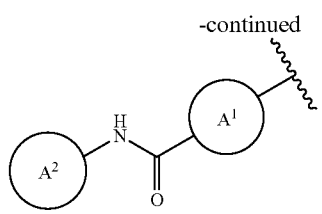

wherein the wavy line is a binding point and $A^1$ and $A^2$ are the same as defined above.

The present invention includes the embodiments illustrated as follows.

Item 1. A benzazepine compound of Formula (1):

[Chem. 3]

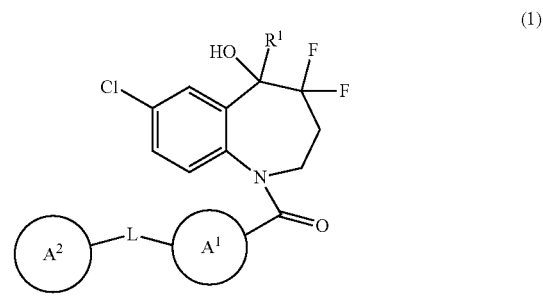

(1)

wherein $R^1$ is deuterium, OH, COOH, optionally substituted $C_{1-6}$ alkyl, optionally substituted $C_{1-6}$ alkyl-O—CO—, or optionally substituted $C_{2-6}$ alkenyl;
L is a direct bond or —C(=O)—NH—;
Ring $A^1$ is a hydrocarbon ring or heterocycle;
Ring $A^2$ is a hydrocarbon ring or heterocycle; and
each of Rings $A^1$ and $A^2$ may have at least one substituent, or a salt thereof.

Item 2. The compound according to Item 1, wherein Ring $A^1$ is a saturated or unsaturated 3- to 8-membered monocyclic hydrocarbon ring, or a saturated or unsaturated 3- to 15-membered monocyclic, bicyclic, or tricyclic heterocycle comprising as the ring member 1 to 5 heteroatoms independently selected from the group consisting of nitrogen, oxygen, and sulfur, Ring $A^2$ is a saturated or unsaturated 3- to 8-membered monocyclic hydrocarbon ring, or a saturated or unsaturated 3- to 15-membered monocyclic, bicyclic, or tricyclic heterocycle comprising as the ring member 1 to 5 heteroatoms independently selected from the group consisting of nitrogen, oxygen, and sulfur, and each of Rings $A^1$ and $A^2$ may have at least one substituent, or a salt thereof.

Item 3. The compound according to either Item 1 or 2, or a salt thereof, wherein Ring A' is a saturated or unsaturated 3- to 8-membered monocyclic hydrocarbon ring, a saturated or unsaturated 5- or 6-membered heteromonocycle comprising as the ring heteroatom 1 to 4 nitrogen atoms, a saturated or unsaturated 7- to 15-membered heterobicycle comprising as the ring heteroatom 1 to 5 nitrogen atoms, a saturated or unsaturated 5- or 6-membered heteromonocycle comprising as the ring heteroatom 1 or 2 oxygen atoms and at least one nitrogen atom, or a saturated or unsaturated 5- or 6-membered heteromonocycle comprising as the ring heteroatom 1 or 2 sulfur atoms and at least one nitrogen atom, Ring A² is a saturated or unsaturated 3- to 8-membered monocyclic hydrocarbon ring, a saturated or unsaturated 5- or 6-membered heteromonocycle comprising as the ring heteroatom 1 to 4 nitrogen atoms, a saturated or unsaturated 5- or 6-membered heteromonocycle comprising as the ring heteroatom 1 or 2 oxygen atoms, a saturated or unsaturated 7- to 12-membered heterobicycle comprising as the ring heteroatom 1 to 3 oxygen atoms, a saturated or unsaturated 5- or 6-membered heteromonocycle comprising as the ring heteroatom 1 or 2 sulfur atoms, a saturated or unsaturated 7- to 15-membered heterobicycle comprising as the ring heteroatom 1 to 5 nitrogen atoms, a saturated or unsaturated 5- or 6-membered heteromonocycle comprising as the ring heteroatom 1 or 2 oxygen atoms and at least one nitrogen atom, or a saturated or unsaturated 5- or 6-membered heteromonocycle comprising as the ring heteroatom 1 or 2 sulfur atoms and at least one nitrogen atom, and each of Rings A¹ and A² may have at least one substituent.

Item 4. The compound according to any one of Items 1 to 3, wherein Ring A¹ is benzene, pyridine, pyrazine, or tetrahydroisoquinoline and Ring A¹ may have 1 to 4 substituents independently selected from the group consisting of optionally substituted $C_{1-6}$ alkyl, optionally substituted $C_{1-6}$ alkyl-O—, halogen, and oxo;

Ring A² is benzene, pyridine, furan, thiophene, or tetrahydroisoquinoline and Ring A² may have 1 to 4 substituents independently selected from the group consisting of optionally substituted $C_{1-6}$ alkyl, optionally substituted $C_{1-6}$ alkyl-O—, optionally substituted $C_{3-6}$ cycloalkyl, halogen, oxo, optionally substituted phenyl, and optionally substituted pyridyl, provided that when Ring A² has multiple substituents on its ring carbon atoms, then the substituents may combine together with the carbon atoms to form $C_{3-6}$ cycloalkyl; or a salt thereof.

Item 5. The compound according to Item 4, wherein, in Ring A¹, a substituent of the optionally substituted $C_{1-6}$ alkyl or optionally substituted $C_{1-6}$ alkyl-O— is each independently the same or different 1 to 3 groups selected from the group consisting of halogen and $C_{1-6}$ alkyl-O—, in Ring A², a substituent of the optionally substituted $C_{1-6}$ alkyl or optionally substituted $C_{1-6}$ alkyl-O— is each independently the same or different 1 to 3 halogen, a substituent of the optionally substituted $C_{3-6}$ cycloalkyl is the same or different 1 to 3 halogen, a substituent of the optionally substituted phenyl is 1 to 3 groups independently selected from the group consisting of halogen, $C_{1-6}$ alkyl, and $C_{1-6}$ alkyl-O—, and a substituent of the optionally substituted pyridyl is the same or different 1 to 3 halogen, or a salt thereof.

Item 6. The compound according to any one of Items 1 to 5, wherein R¹ is deuterium; OH; COOH; $C_{1-6}$ alkyl optionally substituted with 1 to 3 groups independently selected from the group consisting of optionally substituted amino, optionally substituted $C_{1-6}$ alkyl-O—, optionally substituted $C_{1-6}$ alkyl-SO₂—O—, optionally substituted silyl-O—, OH, optionally substituted $C_{1-6}$ alkyl-COO—, tetrahydropyranyl-O—, thiazolyl, and pyridyl; optionally substituted $C_{1-6}$ alkyl-O—CO—; or optionally substituted $C_{2-6}$ alkenyl, the optionally substituted amino is amino optionally substituted with 1 or 2 groups independently selected from the group consisting of $C_{1-6}$ alkyl optionally substituted with OH, optionally substituted $C_{1-6}$ alkyl-SO₂—, optionally substituted $C_{1-6}$ alkyl-O—CO—, and benzyl-O—CO—, the optionally substituted $C_{1-6}$ alkyl in the optionally substituted $C_{1-6}$ alkyl-O—, optionally substituted $C_{1-6}$ alkyl-SO₂—, optionally substituted $C_{1-6}$ alkyl-SO₂—O—, optionally substituted $C_{1-6}$ alkyl-COO—, and optionally substituted $C_{1-6}$ alkyl-O—CO— is $C_{1-6}$ alkyl optionally substituted with 1 to 3 groups independently selected from the group consisting of halogen, $C_{1-6}$ alkyl-O—, optionally substituted phenyl, optionally substituted phenyl-SO₂—NH—, and naphthalenyl-SO₂—NH—, the optionally substituted phenyl being phenyl optionally substituted with 1 to 3 groups independently selected from the group consisting of halogen, $C_{1-6}$ alkyl, and NO₂, the optionally substituted silyl-O— is silyl-O— optionally substituted with the same or different 1 to 3 $C_{1-6}$ alkyl, and the optionally substituted $C_{2-6}$ alkenyl is $C_{2-6}$ alkenyl optionally substituted with the same or different 1 to 3 halogen, or a salt thereof.

Item 7. The compound according to any one of Items 1 to 6, wherein R¹ is deuterium; OH; or $C_{1-6}$ alkyl optionally substituted with optionally substituted amino, optionally substituted $C_{1-6}$ alkyl-O—, or OH, the optionally substituted amino is amino optionally substituted with $C_{1-6}$ alkyl optionally substituted with OH, and the optionally substituted $C_{1-6}$ alkyl-O— is $C_{1-6}$ alkyl-O— optionally substituted with the same or different 1 to 3 halogen, or a salt thereof.

Item 8. The compound according to any one of Items 1 to 7, wherein R¹ is $C_{1-6}$ alkyl substituted with OH, or a salt thereof.

Item 9. The compound according to any one of Items 1 to 8, wherein Ring A¹ is benzene optionally substituted with halogen, $C_{1-6}$ alkyl, halo-$C_6$ alkyl, $C_{1-6}$ alkyl-O—, halo-$C_{1-6}$ alkyl-O—, $C_{1-6}$ alkyl-O—$C_{1-6}$ alkyl-O—, halo-$C_{1-6}$ alkyl-O—$C_{1-6}$ alkyl-O—, $C_{1-6}$ alkyl-O-halo-$C_{1-6}$ alkyl-O—, or halo-$C_6$ alkyl-O-halo-$C_{1-6}$ alkyl-O—; pyridine optionally substituted with halogen; pyrazine; or tetrahydroisoquinoline optionally substituted with oxo; and Ring A² is benzene optionally substituted with 1 to 3 groups independently selected from the group consisting of halogen, $C_{1-6}$ alkyl, halo-$C_{1-6}$ alkyl, $C_{1-6}$ alkyl-O—, halo-$C_{1-6}$ alkyl-O—, $C_{3-6}$ cycloalkyl, optionally substituted phenyl, and pyridyl, the optionally substituted phenyl being phenyl optionally substituted with halogen, $C_{1-6}$ alkyl, halo-$C_{1-6}$ alkyl, $C_{1-6}$ alkyl-O—, or halo-$C_{1-6}$ alkyl-O—; pyridine optionally substituted with $C_{1-6}$ alkyl, halo-$C_{1-6}$ alkyl, or phenyl; furan optionally substituted with $C_{1-6}$ alkyl; thiophene optionally substituted with $C_{1-6}$ alkyl; or tetrahydroisoquinoline optionally substituted with 1 to 3 groups independently selected from the group consisting of halogen, $C_{1-6}$ alkyl, and oxo, provided that when tetrahydroisoquinoline has multiple $C_{1-6}$ alkyl groups on its ring carbon atoms, then the $C_{1-6}$ alkyl groups may combine together with the carbon atoms to form $C_{3-6}$ cycloalkyl, or a salt thereof.

Item 10. The compound according to any one of Items 1 to 9, wherein R¹ is $C_{1-6}$ alkyl substituted with OH, Ring A¹ is benzene optionally substituted with halogen, $C_{1-6}$ alkyl, $C_{1-6}$ alkyl-O—, or $C_6$ alkyl-O—$C_{1-6}$ alkyl-O—; or pyridine optionally substituted with halogen, and Ring A² is benzene optionally substituted with 1 to 3 groups independently selected from the group consisting of halogen, $C_{1-6}$ alkyl, halo-$C_{1-6}$ alkyl, $C_{1-6}$ alkyl-O—, halo-$C_{1-6}$ alkyl-O—, $C_{3-6}$ cycloalkyl, optionally substituted phenyl, and pyridyl, the optionally substituted phenyl being phenyl optionally substituted with halogen, $C_{1-6}$ alkyl, halo-$C_{1-6}$ alkyl, $C_{1-6}$ alkyl-O—, or halo-$C_{1-6}$ alkyl-O—, or a salt thereof.

Item 11. The compound according to any one of Items 1 to 10, wherein R¹ is $C_{1-6}$ alkyl substituted with OH, Ring A[1] is benzene optionally substituted with halogen, $C_{1-6}$ alkyl, or $C_{1-6}$ alkyl-O—, and Ring A[2] is benzene optionally substituted with 1 to 3 groups independently selected from the group consisting of halogen, $C_{1-6}$ alkyl, halo-$C_{1-6}$ alkyl, and phenyl optionally substituted with halogen, or a salt thereof.

Item 12. The compound according to any one of Items 1 to 11, wherein R[1] is $C_{1-6}$ alkyl substituted with OH, Ring A[1] is benzene, or benzene substituted with halogen, and Ring A[2] is benzene substituted with 1 to 3 groups independently selected from the group consisting of halogen and phenyl, or a salt thereof.

Item 13. The compound according to any one of Items 1 to 10, wherein R[1] is $C_{1-6}$ alkyl substituted with OH, Ring A[1] is pyridine, Ring A[2] is benzene optionally substituted with 1 to 3 groups independently selected from the group consisting of halogen, $C_{1-6}$ alkyl, halo-$C_{1-6}$ alkyl, and phenyl optionally substituted with halogen, or a salt thereof.

Item 14. The compound according to any one of Items 1 to 9, wherein R[1] is $C_{1-6}$ alkyl substituted with OH, Ring A[1] is benzene optionally substituted with halogen, $C_{1-6}$ alkyl-O—, or halo-$C_{1-6}$ alkyl-O—; or pyridine, and Ring A[2] is benzene optionally substituted with 1 to 3 groups independently selected from the group consisting of halogen, $C_{1-6}$ alkyl, halo-$C_{1-6}$ alkyl, and phenyl optionally substituted with halogen; pyridine optionally substituted with phenyl or halo-$C_{1-6}$ alkyl; or tetrahydroisoquinoline optionally substituted with 1 to 3 groups independently selected from the group consisting of halogen and oxo, or a salt thereof.

Item 15. The compound according to any one of Items 1 to 14, wherein L is —C(=O)—NH—, or a salt thereof.

Item 16. A compound, or a salt thereof, selected from the following compound group.

[Chem. 4-1]

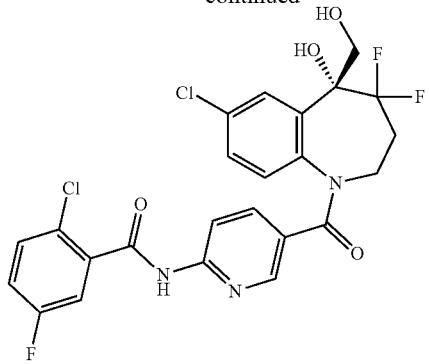

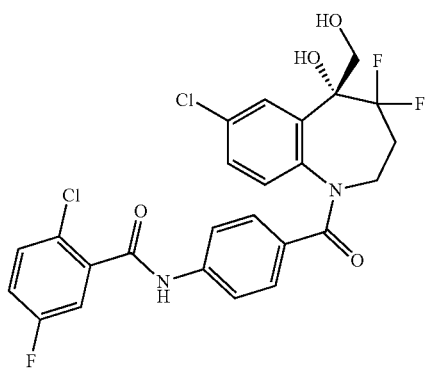

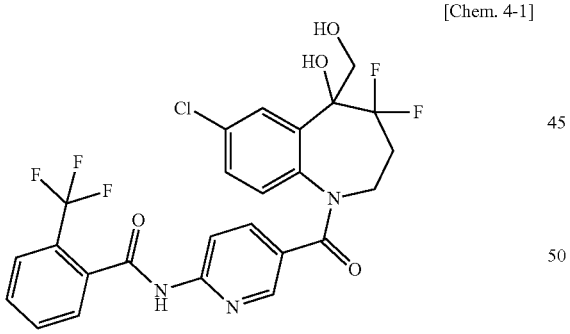

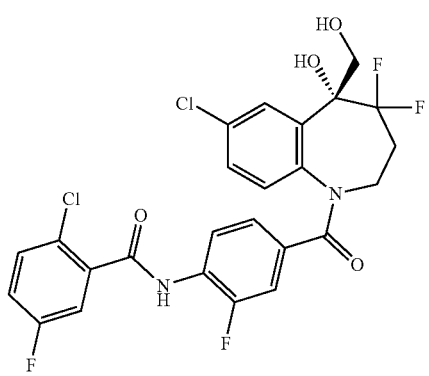

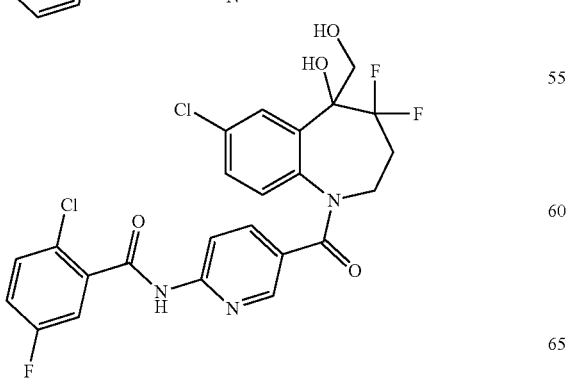

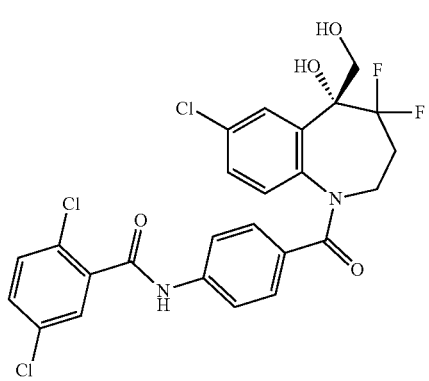

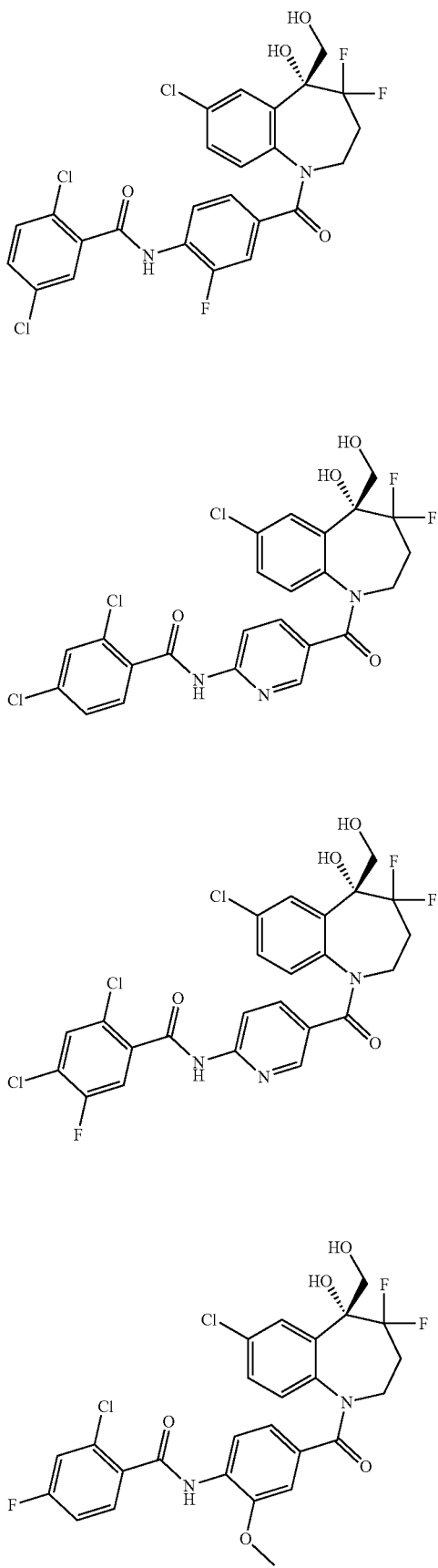
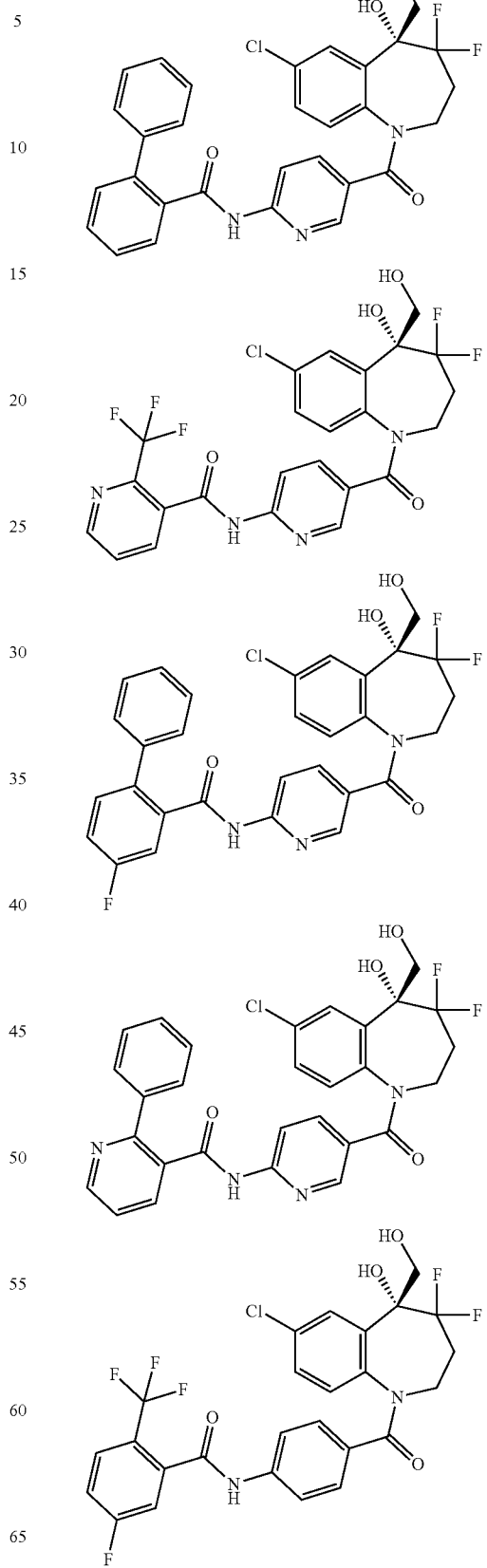
[Chem. 4-2]

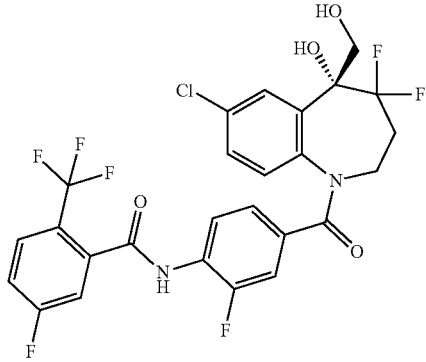
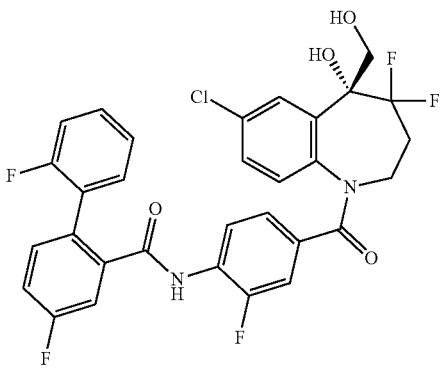
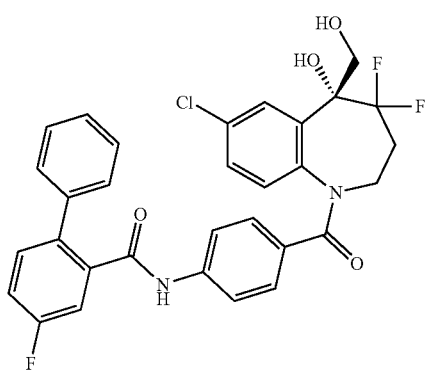
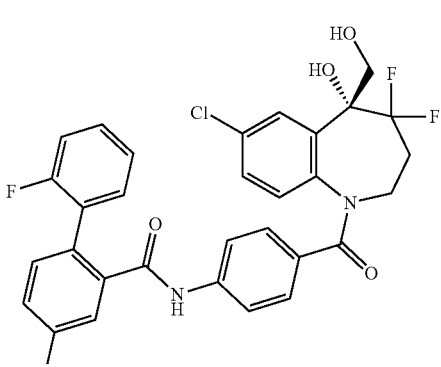
[Chem. 4-3]
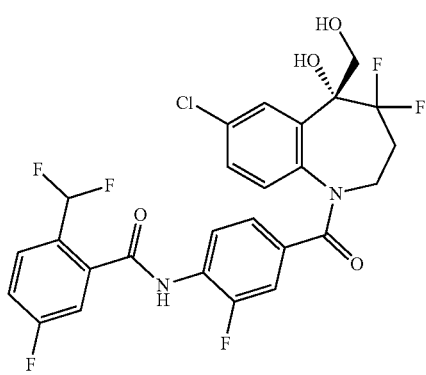
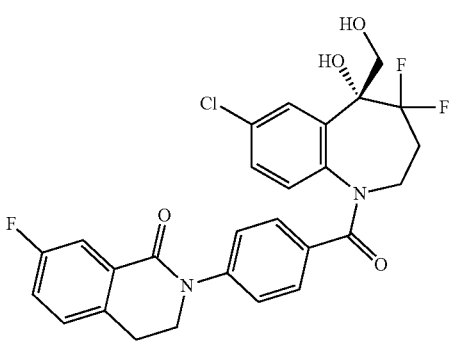
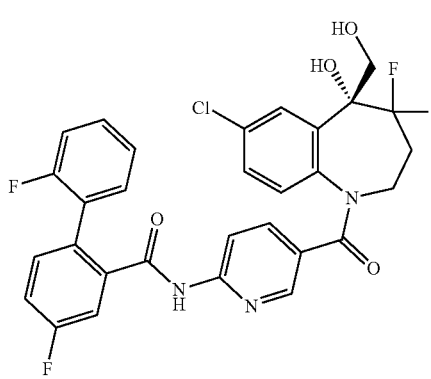
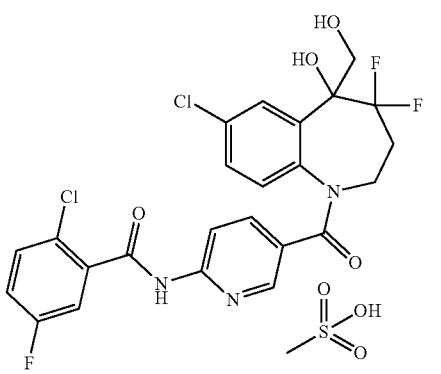

-continued

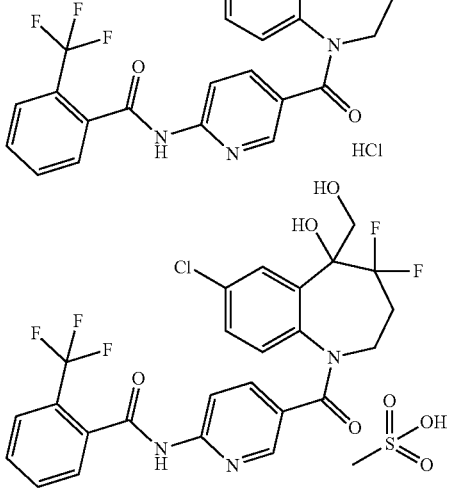

Item 17. A vasopressin receptor antagonist comprising a compound according to any one of Items 1 to 16 or a salt thereof.

Item 18. A pharmaceutical composition, comprising as the active ingredient a compound according to any one of Items 1 to 16 or a salt thereof, for treating, preventing, and/or diagnosing a disease selected from the group consisting of Meniere's disease, hypertension, edema, ascites, heart failure, renal dysfunction, renal failure, polycystic kidney disease, syndrome of inappropriate vasopressin secretion, hepatic cirrhosis, hyponatremia, hypokalemia, diabetes, circulation insufficiency, kinesia, water metabolism disorder, and ichemic disorder.

Item 19. A method of treating, preventing, and/or diagnosing a disease selected from the group consisting of Meniere's disease, hypertension, edema, ascites, heart failure, renal dysfunction, renal failure, polycystic kidney disease, syndrome of inappropriate vasopressin secretion, hepatic cirrhosis, hyponatremia, hypokalemia, diabetes, circulation insufficiency, kinesia, water metabolism disorder, and ichemic disorder, comprising administering a compound according to any one of Items 1 to 16 or a salt thereof to a subject.

Item 20. A compound according to any one of Items 1 to 16 or a salt thereof for use in the treatment, prevention, and/or diagnosis of a disease selected from the group consisting of Meniere's disease, hypertension, edema, ascites, heart failure, renal dysfunction, renal failure, polycystic kidney disease, syndrome of inappropriate vasopressin secretion, hepatic cirrhosis, hyponatremia, hypokalemia, diabetes, circulation insufficiency, kinesia, water metabolism disorder, and ichemic disorder.

Item 21. Use of a compound according to any one of Items 1 to 16 or a salt thereof in the manufacture of a medicament for treating, preventing, and/or diagnosing a disease selected from the group consisting of Meniere's disease, hypertension, edema, ascites, heart failure, renal dysfunction, renal failure, polycystic kidney disease, syndrome of inappropriate vasopressin secretion, hepatic cirrhosis, hyponatremia, hypokalemia, diabetes, circulation insufficiency, kinesia, water metabolism disorder, and ichemic disorder.

The present invention also encompasses any combinations of preferable embodiments or options for different elements or features herein as well as the embodiments illustrated above as long as such combinations are not incompatible.

(General Method of Preparation)

The present compound may be prepared, for example, according to the general method of preparation as shown below but the method of preparing the present compound is not limited thereto.

Starting materials used herein may be commercially available or may be prepared according to known methods or any methods in accordance therewith.

Any non-limiting solvents, acids, bases, protective groups, and leaving groups that are commonly used in the field of organic synthetic chemistry may be used in the preparation of the present compound.

Products during the preparation of the present compound may be used in a subsequent reaction as they are dissolved in reaction solutions or in the form of crude products. Products may be also isolated from reaction mixtures according to conventional methods and easily purified according to conventional purification processes. Such purification processes include, for example, filtration, extraction, concentration, evaporation, crystallization, recrystallization, distillation, chromatography, and optical resolution.

Alkylation, hydrolysis, amination, esterification, amidation, etherification, oxidation, and reduction in the preparation of the present compound may be conducted according to known methods.

Reagents and methods typically used herein are described in, for example, ORGANIC FUNCTIONAL GROUP PREPARATIONS 2nd edition, ACADEMIC PRESS, INC. 1989; Comprehensive Organic Transformations, VCH Publishers Inc., 1989, P. G. M. Wuts; T. W. Greene "Greene's Protective Groups in Organic Synthesis" 4th edition, 2006; and John Wiley & Sons, New York, 1991, P. 309.

Reaction Scheme-1

[Chem.5]

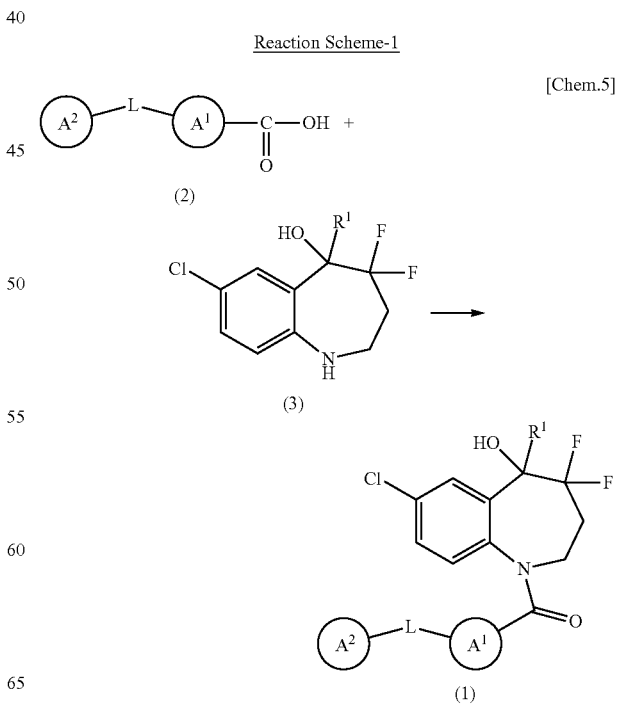

In the scheme, $R^1$, $A^1$, $A^2$, and L are the same as defined above.

The present compound may be prepared by amidation using Compound (2) and Compound (3). Specifically, Compound (1) may be prepared by reaction of Compound (2) or a reactive derivative in its carboxy group and Compound (3) or a reactive derivative in its imino group.

Preferable reactive derivatives of Compound (2) in the carboxy group include, for example, acid halides, acid azides, acid anhydrides, activated amides, and activated esters. More preferable reactive derivatives include acid chlorides; acid azides; mixed acid anhydrides with acids such as substituted phosphates (e.g., dialkyl phosphates, phenyl phosphates, diphenyl phosphates, dibenzyl phosphates, and halogenated phosphates), dialkyl phosphite, sulfurous acid, thiosulfuric acid, sulfuric acid, sulfonic acid (e.g., methanesulfonic acid), aliphatic carboxylic acid (e.g., acetic acid, propionic acid, butyric acid, isobutyric acid, pivalic acid, pentanoic acid, isopentanoic acid, 2-ethylbutyric acid, and trichloroacetic acid), and aromatic carboxylic acid (e.g., benzoic acid); symmetric acid anhydrides; activated amides with imidazole, 4-substituted imidazole, dimethylpyrazole, triazole, or tetrazole; activated esters (e.g., cyanomethyl ester, methoxymethyl ester, dimethyliminomethyl ester, vinyl ester, propargyl ester, p-nitrophenyl ester, 2,4-dinitrophenyl ester, trichlorophenyl ester, pentachlorophenyl ester, and mesylphenyl ester); and esters with N-hydroxy compounds (e.g., N,N-dimethylhydroxylamine, 1-hydroxy-2-(1H)-pyridone, N-hydroxysuccinimide, N-hydroxyphthalimide, and HOBt). Such reactive derivatives may be selected from these derivatives in view of the type of Compound (2) to be used.

In the case where Compound (2) is used in the form of a free acid or a salt thereof in Reaction Scheme-1, the reaction may be conducted in the presence of a condensing agent. Such a condensing agent may be any known agents commonly used in the field and includes, for example, DCC; N-cyclohexyl-N'-morpholinoethylcarbodiimide; N-cyclohexyl-N'-(4-diethylaminocyclohexyl)carbodiimide; N,N'-diethylcarbodiimide; N,N'-diisopropylcarbodiimide; WSC or its HCl salt; N,N'-carbonylbis(2-methylimidazole); pentamethyleneketene-N-cyclohexylimine; diphenylketene-N-cyclohexylimine; ethoxyacetylene, 1-alkoxy-1-chloroethylene; trialkyl phosphite; ethyl polyphosphate; isopropyl polyphosphate; phosphorus oxychloride (phosphoryl chloride); phosphorus trichloride; diphenylphosphoryl azide; thionyl chloride; oxalyl chloride; alkyl haloformate such as ethyl chloroformate and isopropyl chloroformate; triphenylphosphine; 2-ethyl-7-hydroxybenzisoxazolium salt; 2-ethyl-5-(m-sulfophenyl)isoxazolium hydroxide intramolecular salt; benzotriazol-1-yloxy-tris(dimethylamino)phosphonium hexafluorophosphate; 1-(p-chlorobenzenesulfonyloxy)-6-chloro-1H-benzotriazole; and so-called Vilsmeier reagents prepared in reactions of DMF with an agent such as thionyl chloride, phosgene, trichloromethyl chloroformate, and phosphorus oxychloride. The reaction may be also implemented in the presence of the above condensing agent and an active esterifying agent such as N-hydroxysuccinimide, N-hydroxyphthalimide, and HOBt.

Preferable reactive derivatives of Compound (3) in the imino group include, for example, Schiff base-type imino or enamine-type tautomers thereof generated in reactions of Compound (3) with carbonyl compounds such as aldehydes and ketones; silyl derivatives generated in reactions of Compound (3) with silyl compounds such as bis(trimethylsilyl)acetamide, mono(trimethylsilyl)acetamide, and bis(trimethylsilyl)urea; and derivatives generated in reactions of Compound (3) with phosphorus trichloride or phosgene.

Reaction Scheme-1 is typically carried out in a conventional solvent that does not negatively affect the reaction. Such a solvent includes, for example, water; alcohol solvents such as MeOH, EtOH, isopropanol, n-butanol, trifluoroethanol, and ethylene glycol; ketone solvents such as acetone and methyl ethyl ketone; ether solvents such as THF, dioxane, $Et_2O$, diisopropyl ether, and diglyme; ester solvents such as AcOMe and AcOEt; aprotic polar solvents such as MeCN, DMF, and DMSO; hydrocarbon solvents such as n-pentane, n-hexane, n-heptane, and cyclohexane; halogenated hydrocarbon solvents such as DCM, and ethylene chloride; and other organic solvents; and mixed solvents thereof.

Reaction Scheme-1 may be carried out in the presence of a base. Such a base may be any known inorganic and organic bases commonly used in the field. Such inorganic bases include, for example, alkali metals (e.g., sodium and potassium), alkali metal hydrogen carbonates (e.g., lithium hydrogen carbonate, sodium hydrogen carbonate, and potassium hydrogen carbonate), alkali metal hydroxides (e.g., LiOH, NaOH, and KOH), alkali metal carbonates (e.g., $Li_2CO_3$, $Na_2CO_3$, $K_2CO_3$, and $Cs_2CO_3$), alkali metal lower alkoxides (e.g., sodium methoxide and sodium ethoxide), and alkali metal hydrides (e.g., NaH and KH). Such organic bases include, for example, trialkylamine (e.g., trimethylamine, triethylamine, and N-ethyldiisopropylamine), pyridine, quinoline, piperidine, imidazole, picoline, dimethylaminopyridine, dimethylaniline, N-methylmorpholine, DBN, DABCO, and DBU. Bases in the form of a liquid may double as a solvent. The base herein is used alone or in a mixture of two or more. The amount of the base used herein is typically 0.1 to 10 moles, preferably 0.1 to 3 moles, relative to 1 mole of Compound (2).

The ratio of Compound (2) to Compound (3) used in Reaction Scheme-1 is typically at least 1 mole, preferably about 1 to 5 moles, of the former relative to 1 mole of the latter.

The reaction temperature is not limited and the reaction typically proceeds under any conditions such as cooling, room temperature, and heating. The reaction may be carried out preferably under a temperature from room temperature to 100° C. for 30 minutes to 30 hours, preferably 30 minutes to 5 hours.

Reaction Scheme-2

[Chem.6]

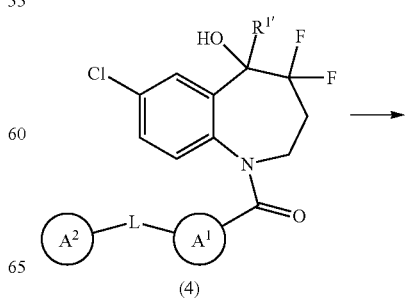

(4)

-continued

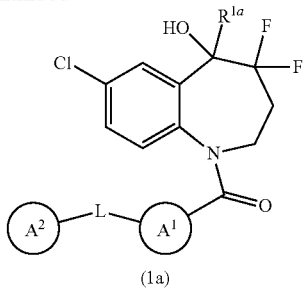

(1a)

In the scheme, $A^1$, $A^2$, and L are the same as defined above, $R^{1'}$ is hydroxyalkyl wherein OH is protected with a protective group, and $R^{1a}$ is $C_{1-6}$ alkyl substituted with OH.

Reaction Scheme-2 is a process of preparing the present compound wherein $R^1$ of Compound (3) is hydroxyalkyl wherein OH is protected with a protective group. Deprotection of the OH-protective group on $R^{1'}$ of Compound (4) in the absence of a solvent or in the presence of an inert solvent may provide Compound (1a).

Any non-limiting protective groups for hydroxy that are commonly used in the field of organic synthetic chemistry may be used for the OH-protective group. Such an OH-protective group includes, for example, alkyl groups (e.g., methyl, ethyl, isopropyl, tert-butyl, trifluoromethyl, hydroxymethyl, 2-hydroxyethyl, and acetylmethyl); alkyl (alkenyl)carbonyl groups (e.g., acetyl, propionyl, butyryl, isobutyryl, pentanoyl, pivaloyl, valeryl, isovaleryl, chloroacetyl, dichloroacetyl, trichloroacetyl, trifluoroacetyl, methoxyacetyl, acryloyl, propioloyl, methacryloyl, crotonoyl, isocrotonoyl, and (E)-2-methyl-2-butenoyl); arylcarbonyl groups (e.g., benzoyl, α-naphthoyl, β-naphthoyl, 2-bromobenzoyl, 4-bromobenzoyl, 4-chlorobenzoyl, 2,4,6-trimethylbenzoyl, 4-toluoyl, 4-anisoyl, 4-nitrobenzoyl, 2-nitrobenzoyl, 2-(methoxycarbonyl)benzoyl, and 4-phenylbenzoyl); tetrahydro(thio)pyranyl(furanyl) groups (e.g., tetrahydropyran-2-yl, 3-bromotetrahydropyran-2-yl); silyl groups (e.g., trimethylsilyl, triethylsilyl, isopropyldimethylsilyl, tert-butyldimethylsilyl, methyldiisopropylsilyl, methyl di-tert-butylsilyl, triisopropylsilyl, diphenylmethylsilyl, diphenylbutylsilyl, diphenylisopropylsilyl, and phenyldiisopropylsilyl); alkoxymethyl groups (e.g., methoxymethyl, 1,1-dimethyl-1-methoxymethyl, ethoxymethyl, propoxymethyl, isopropoxymethyl, butoxymethyl, tert-butoxymethyl, 2-methoxyethoxymethyl, 2,2,2-trichloroethoxymethyl, and bis(2-chloroethoxy)methyl); and aralkyl groups (e.g., benzyl, α-naphthylmethyl, β-naphthylmethyl, diphenylmethyl, triphenylmethyl, α-naphthyldiphenylmethyl, 9-anthrylmethyl, 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, and 4-cyanobenzyl). Any deprotection processes that are commonly used in the field may be applied.

The inert solvent used herein includes, for example, water; ether solvents such as dioxane, tetrahydrofuran, diethyl ether, 1,2-dimethoxyethane, diethylene glycol dimethyl ether, and ethylene glycol dimethyl ether; halogenated hydrocarbon solvents such as methylene chloride, chloroform, 1,2-dichloroethane, and carbon tetrachloride; aromatic hydrocarbon solvents such as benzene, toluene, and xylene; lower alcohol solvents such as methanol, ethanol, and isopropanol; and polar solvents such as DMF, DMSO, hexamethylphosphoric triamide, and acetonitrile. The inert solvent is used alone or in a mixture of two or more.

Reaction Scheme-2 is carried out according to a conventional method such as hydrolysis and reduction.

Such a hydrolysis process is preferably carried out in the presence of a base or an acid including Lewis acids. Such a base includes, for example, inorganic bases such as alkali metal hydroxides (e.g., sodium hydroxide and potassium hydroxide), alkaline earth metal hydroxides (e.g., magnesium hydroxide and calcium hydroxide), alkali metal carbonates (e.g., sodium carbonate and potassium carbonate), alkaline earth metal carbonates (e.g., magnesium carbonate and calcium carbonate), and alkali metal hydrogen carbonates (e.g., sodium hydrogen carbonate and potassium hydrogen carbonate); and organic bases such as trialkylamines (e.g., trimethylamine and triethylamine), picoline, DBN, DABCO, and DBU. Such an acid includes organic acids (e.g., formic acid, acetic acid, propionic acid, trichloroacetic acid, and trifluoroacetic acid) and inorganic acids (e.g., hydrochloric acid, hydrobromic acid, and sulfuric acid). Deprotection using trihaloacetic acids (e.g., trichloroacetic acid and trifluoroacetic acid) may be carried out in the presence of cation scavengers (e.g., anisole and phenol). Bases or acids in the form of a liquid may double as a solvent.

The reaction temperature in the hydrolysis process is not limited and the reaction typically proceeds under any conditions such as cooling, room temperature, and heating.

The reduction process includes, for example, chemical reduction and catalytic reduction.

A reducing agent used in the chemical reduction includes, for example, metals (e.g., tin, zinc, and iron) and a combination of metal compounds (e.g., chromium chloride and chromium acetate) and organic or inorganic acids (e.g., formic acid, acetic acid, propionic acid, trifluoroacetic acid, p-toluenesulfonic acid, hydrochloric acid, and hydrobromic acid).

A catalyst used in the catalytic reduction includes, for example, conventional catalysts such as platinum catalysts (e.g., platinum plates, platinum sponges, platinum black, colloidal platinum, platinum oxide, and platinum wires), palladium catalysts (e.g., palladium sponges, palladium black, palladium oxide, palladium-carbon, colloidal palladium, palladium-barium sulfate, and palladium-barium carbonate), nickel catalysts (e.g., reduced nickel, oxidized nickel, and Raney nickel), cobalt catalysts (e.g., reduced cobalt and Raney cobalt), iron catalysts (e.g., reduced iron and Raney iron), and copper catalysts (e.g., reduced copper, Raney copper, and Ullmann copper).

The reduction reaction is carried out in a conventional solvent that does not negatively affect the reaction, such as water; alcohols such as methanol, ethanol, trifluoroethanol, and ethylene glycol; ethers such as acetone, diethyl ether, dioxane, and tetrahydrofuran; halogenated hydrocarbons such as chloroform, methylene chloride, and ethylene chloride; esters such as methyl acetate and ethyl acetate; aprotic polar solvents such as acetonitrile and N,N-dimethylformamide; basic solvents such as pyridine; and other organic solvents; and mixed solvents thereof. The reduction reaction is carried out typically under a temperature from room temperature to 200° C., preferably from room temperature to 150° C., for about 1 to 30 hours.

Reaction Scheme-3

[Chem. 7]

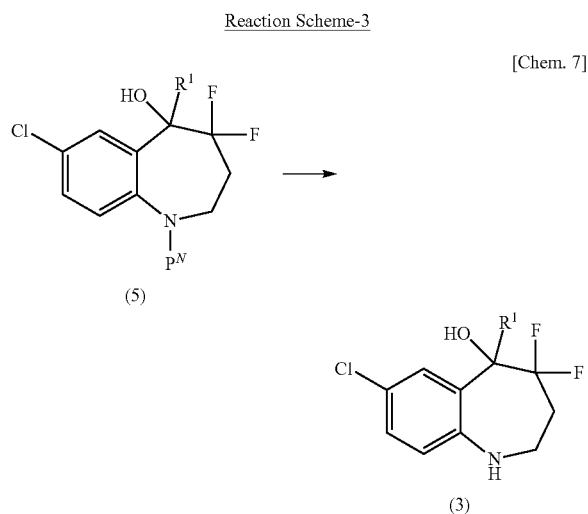

In the scheme, $R^1$ is the same as defined above and $P^N$ is a protective group for amino. Compound (3) may be prepared by elimination of a protective group for amino in Compound (5). The elimination process of a protective group for amino may be carried out according to a conventional method such as the hydrolysis in Reaction Scheme-2 and hydrogenolysis. The protective group for amino includes, for example, alkoxycarbonyl, alkanoyl, and aryl-substituted alkyl.

The alkoxycarbonyl group includes, for example, methoxycarbonyl, ethoxycarbonyl, propoxycarbonyl, butoxycarbonyl, tert-butoxycarbonyl, pentyloxycarbonyl, and hexyloxycarbonyl.

The alkanoyl group includes, for example, formyl, acetyl, propionyl, butyryl, isobutyryl, pentanoyl, tert-butylcarbonyl, and hexanoyl.

The aryl-substituted alkyl group includes, for example, benzyl, 2-phenylethyl, 1-phenylethyl, 3-phenylpropyl, 4-phenylbutyl, 5-phenylpentyl, 6-phenylhexyl, diphenylmethyl, trityl, and $C_{1-6}$ alkyl substituted with phenyl optionally substituted with the same or different 1 to 3 substituents. The substituents on the phenyl group includes, for example, halogen, $C_{1-6}$ alkyl, halo-$C_{1-6}$ alkyl, $C_{1-6}$ alkyl-O—, halo-$C_{1-6}$ alkyl-O—, hydroxy-$C_{1-6}$ alkyl, hydroxy-halo-$C_{1-6}$ alkyl, hydroxy-$C_{1-6}$ alkyl-O—, hydroxy-halo-$C_6$ alkyl-O—, and $C_{3-6}$ cycloalkyl. When the phenyl group is substituted with two or more groups, these groups may be independent and the same or different with each other.

The present compound, starting materials, and intermediate compounds herein include chemically acceptable geometric isomers, stereoisomers, optical isomers, and tautomers. Each isomer may be separated by conventional optical resolution or prepared from corresponding optically active starting materials.

The present compound, starting materials, and intermediate compounds herein may be in the form of a salt and each targeted compound obtained in each reaction step may also form a salt. In the case where a compound obtained in a reaction step is in its free form, such a compound may be converted into a desired salt thereof by known methods. In the case where the compound is in its salt form, such a compound may be converted into its free form or another desired salt thereof. These salts include those illustrated as follows.

The salts herein include pharmaceutically acceptable acid addition salts and base addition salts. Acids in the acid addition salts include, for example, inorganic acids such as hydrochloric acid, hydrobromic acid, hydroiodic acid, nitric acid, sulfuric acid, and phosphoric acid; organic acids such as formic acid, propionic acid, oxalic acid, carbonic acid, picric acid, methanesulfonic acid, ethanesulfonic acid, p-toluenesulfonic acid, acetic acid, citric acid, tartaric acid, malonic acid, succinic acid, maleic acid, fumaric acid, malic acid, and lactic acid; and amino acids such as lysine, arginine, aspartic acid, and glutamic acid. Bases in the base addition salts include, for example, metals such as alkali metal (e.g., sodium and potassium) and alkaline earth metal (e.g., calcium and magnesium); inorganic bases such as alkali metal carbonate (e.g., lithium carbonate, potassium carbonate, sodium carbonate, and cesium carbonate), alkali metal hydrogen carbonate (e.g., lithium hydrogen carbonate, sodium hydrogen carbonate, and potassium hydrogen carbonate), and alkali metal hydroxide (e.g., lithium hydroxide, sodium hydroxide, potassium hydroxide, calcium hydroxide, and cesium hydroxide); organic bases such as methylamine, diethylamine, trimethylamine, triethylamine, N-ethyldiisopropylamine, ethanolamine, diethanolamine, triethanolamine, ethylenediamine, tris(hydroxymethyl)methylamine, dicyclohexylamine, N,N'-dibenzylethylenediamine, guanidine, pyridine, quinoline, piperidine, imidazole, dimethylaminopyridine, dimethylaniline, picoline, choline, N-methylmorpholine, DBN, DBU, and DABCO; and ammonium salts.

The present compound also includes various hydrates, solvates, and crystalline polymorphs of compounds of Formula (1) and salts thereof.

The present compound includes compounds of Formula (1) wherein any one or more of the atoms are replaced with one or more isotopes as well as compounds of Formula (1) wherein $R^1$ is deuterium. Such isotopes include deuterium ($^2H$), tritium ($^3H$), $^{13}C$, $^{14}N$, and $^{18}O$.

The present compound also includes pharmaceutically acceptable cocrystals or cocrystalline salts. Such cocrystals or cocrystalline salts refer to a crystalline substance formed at room temperature from two or more molecules, each of which has different physical properties (e.g., structures, melting points, and heats of fusion). Such cocrystals and cocrystalline salts may be prepared according to known cocrystallization methods.

The present compound also includes pharmaceutically acceptable prodrugs. Such prodrugs include compounds of Formula (1) wherein any of the substituents are modified with reactive functional groups such as OH, COOH, and amino.

Basically, vasopressin $V_{1a}$ receptor is considered to exist in blood vessels and myocardium and may cause vasoconstriction, while vasopressin $V_2$ receptor is considered to exist in renal tubule and endothelium and may cause water retention. In view of these actions of vasopressin receptors, the present compound with vasopressin antagonisms of both a vasopressin $V_{1a}$ antagonist and vasopressin $V_2$ antagonist may provide, for example, vasodilatory, antihypertensive, hepatic glucose release-inhibitory, mesangial cell-proliferation inhibitory, aquaretic, platelet aggregation inhibitory, antinausea, urea-excretion-stimulatory, Factor VIII suppression, heart hyper-function, mesangial cell contraction inhibitory, hepatic gluconeogenesis inhibitory, aldosterone secretion inhibitory, endothelin production inhibitory, renin secretory regulation, memory regulation, thermoregulatory, or prostaglandin production regulation effects.

The present compound may also be useful for an active ingredient of drugs such as vasodilators, antihypertensives, aquaretics, platelet-aggregation inhibitory agents, urea-excretion stimulatory agents, heart-failure drugs, or renal-failure drugs, and may be useful for diagnosis, prevention, and/or treatment of various diseases associated with vasopressin receptors such as Meniere's disease, hypertension, edema, ascites, heart failure, renal dysfunction, renal failure, polycystic kidney disease (PKD), syndrome of inappropriate vasopressin secretion (SIADH), hepatic cirrhosis, hyponatremia, hypokalemia, diabetes, circulation insufficiency, kinesia, water metabolism disorder, and various ichemic disorders, preferably heart failure, renal failure, and PKD, more preferably PKD.

The present compound may also have better metabolic stability than drugs such as tolvaptan that is known to be metabolized primarily by a hepatic metabolizing enzyme, CYP3A4, and may have extended duration of pharmacological effects. The present compound may also have reduced side effects and high tolerability and safety.

Medical formulations (hereinafter, also referred to as "pharmaceutical compositions") comprising the present compound as an active ingredient are illustrated.

Such medical formulations are prepared by formulating the present compound with pharmaceutically acceptable carriers into conventional forms of a medical formulation. Such carriers include conventional diluents and vehicles such as fillers, bulking agents, binders, moisturizers, disintegrants, surface active agents, and lubricants.

Such medical formulations may be in any forms selected from various forms depending on therapeutic purposes such as tablets, pills, powders, liquids, suspensions, emulsions, granules, capsules, suppositories, and injections (such as solutions and suspensions).

Carriers used in formulating into a tablet form may be any known carriers commonly used in the field and include, for example, vehicles such as lactose; binders such as polyvinylpyrrolidone; disintegrants such as starch; absorption promoters such as sodium lauryl sulfate; humectants such as glycerin and starch; absorbents such as colloidal silicic acid; and lubricants such as polyethylene glycol.

Any tablets with conventional coatings may be formulated, as needed, such as dragees, gelatin-coated tablets, enteric-coated tablets, film-coated tablets, bilayer tablets, and multilayered tablets.

Carriers used in formulating into a pill form may be any known carriers commonly used in the field and include, for example, vehicles such as glucose; binders such as powdered acacia; and disintegrants such as laminaran.

Carriers used in formulating into a suppository form may be any known carriers commonly used in the field and include, for example, cacao butter.

Liquids, emulsions, and suspensions prepared for injections are preferably sterilized and isotonic with blood. Diluents used in formulating into the liquid, emulsion, or suspension form may be any known diluents commonly used in the field and include, for example, water. In preparing isotonic solutions, medical formulations may comprise sufficient amounts of salts for preparation. The medical formulations may also comprise conventional solubilizing agents, buffering agents, soothing agents, and as needed, colorants, preservatives, perfuming agents, flavoring agents, sweetening agents, and other drugs.

The amount of the present compound comprised in a medical formulation is not limited and may be optionally selected from a wide range of amounts. The present compound is preferably comprised in the range of 0.1 to 70 weight % in a medical formulation.

Any non-limiting administration routes for such a medical formulation may be used and such administration routes may be determined depending on various formulation forms, ages, genders, disease conditions of patients, and other conditions. For example, tablets, pills, liquids, suspensions, emulsions, granules, and capsules may be orally administered. Injections may be intravenously administered alone or in combination with conventional replacement fluid such as glucose and amino acid, and as needed, may also be administered alone intramuscularly, intradermally, subcutaneously, or intraperitoneally. Suppositories may be intrarectally administered.

Dosage amounts of such a medical formulation may be optionally selected depending on dose regimens, ages, genders, disease levels of patients, and other conditions, and the present compound may be typically administered in the range of 0.01 to 100 mg, preferably the range of 0.1 to 50 mg, per day to 1 kg of body weights at a time or in several divided amounts. Dosage amounts vary depending on various conditions, and those less than the above ranges may be sufficient or those beyond the above ranges may be required.

EXAMPLES

The present invention is described in detail in Reference Examples, Examples, and Test Examples as below but is not limited thereto. These examples may be modified without departing from the scope of the present invention.

The following abbreviations may be used herein.

REX: Reference example number
EX: Example number
STR: Structural formula (In formulae, structures with "Chiral" refer to absolute configurations.)
RProp: Method of preparation (A product was prepared using a corresponding starting material according to the method described in the Reference Example with the number.)
Prop: Method of preparation (A product was prepared using a corresponding starting material according to the method described in the Example with the number.)
Data: Physical data (NMR1: δ(ppm) in $^1$H-NMR (dimethyl sulfoxide-$d_6$); NMR2: δ(ppm) in $^1$H-NMR ($CDCl_3$); NMR3: δ(ppm) in $^1$H-NMR ($CD_3OD$); NMR4: δ(ppm) in $^1$H-NMR (in a mixed solvent of $CDCl_3$ and dimethyl sulfoxide-$d_6$))
AcOEt: Ethyl acetate
AcOH: Acetic acid
AcOMe: Methyl acetate
AcONa: Sodium acetate
9-BBN: 9-Borabicyclo[3.3.1]nonane
$BBr_3$: Boron tribromide
$Boc_2O$: Di-t-butyl dicarbonate
n-BuLi: n-Butyllithium
CDI: 1,1'-Carbonyldiimidazole
$Cs_2CO_3$: Cesium carbonate
DCE: 1,2-dichloroethane
DCM: Dichloromethane
DEAD: Diethyl azodicarboxylate
DHP: 3,4-Dihydro-2H-pyran
DIBAL: Diisobutylaluminum hydride
DIPEA: Diisopropylethylamine
DMA: N,N-Dimethylacetamide
DMAP: 4-(Dimethylamino)pyridine
DME: Dimethoxyethane
DMEDA: N,N'-dimethyl-1,2-ethylenediamine
DMF: N,N-dimethylformamide
DMSO: Dimethyl sulfoxide
DPPA: Diphenylphosphoryl azide
DPPP: 1,3-Diphenylphosphinopropane Et₂O: Diethyl ether
EtOH: Ethanol
HATU: O-(7-Azabenzotriazol-1-yl)-N,N,N',N'-tetramethyluronium hexafluorophosphate
HCl: Hydrochloric acid
HCO₂Na: Sodium formate
Hexane: n-Hexane
HOBt: 1-Hydroxybenzotriazole
IBX: 2-Iodoxybenzoic acid
Im: Imidazole
IPA: 2-Propanol
IPE: Diisopropyl ether
K₂CO₃: Potassium carbonate
KHCO₃: Potassium hydrogen carbonate
KOtBu: Potassium t-butoxide
KOH: Potassium hydroxide
K₃PO₄: Tripotassium phosphate
LAH: Lithium aluminum hydride
LDA: Lithium diisopropylamide
LHMDS: Lithium hexamethyldisilazide
LiOH: Lithium hydroxide
MCPBA: m-Chloroperbenzoic acid
MeCN: Acetonitrile
MEK: 2-Butanone
MeOH: Methanol
NaBH₄: Sodium borohydride
NaH: Sodium hydride
NaHCO₃: Sodium hydrogen carbonate
NaOH: Sodium hydroxide
NaOtBu: Sodium t-butoxide
Na₂SO₄: Sodium sulfate
NCS: N-Chlorosuccinimide
NH₄Cl: Ammonium chloride
NMO: N-Methylmorpholine
NMP: N-Methylpyrrolidone
Pd/C: Palladium supported on carbon
Pd₂(dba)₃: Tris(dibenzylideneacetone)dipalladium (0)
Ph: Phenyl
PPTS: Pyridinium p-toluenesulfonate
Pyr: Pyridine
TBAF: tetra-n-Butylammonium fluoride
TBDMSCl: t-Butyldimethylsilyl chloride
TEA: Triethylamine
TFA: Trifluoroacetic acid
THF: Tetrahydrofuran
TMPDA: N,N,N',N'-Tetramethyl-1,3-propanediamine
TMSCl: Chlorotrimethylsilane
TsCl: p-Toluenesulfonyl chloride
WSC: 3-Ethyl-1-(3-dimethylaminopropyl)carbodiimide
xantphos: 4,5-Bis(diphenylphosphino)-9,9-dimethyxanthene ZCl: Benzyl chloroformate The "room temperature" herein refers to a temperature typically from about 10° C. to about 35° C. Ratios in mixed solvents refer to a volume ratio (v/v) unless otherwise specified. % refers to % by weight (% (w/w)) unless otherwise specified.

¹H-NMR (proton nuclear magnetic resonance) spectra was measured with a Fourier transform NMR device (any of Bruker AVANCE 300 (300 MHz), Bruker AVANCE 500 (500 MHz), Bruker AVANCE III 400 (400 MHz), and Bruker AVANCE III 500 (500 MHz)) at room temperature. For basic silica gel column chromatography, aminopropylsilane-bonded silica gel was used.

Absolute configuration of compounds was determined by known X-ray crystallography (e.g., Shigeru Ooba and Shigenobu Yano, "Kagakusha no tame no Kisokoza 12 X-ray crystallography" (1 ed., 1999)) or estimated from empirical rules of Shi asymmetric epoxidation (Waldemar Adam, Rainer T. Fell, Chantu R. Saha-Moller and Cong-Gui Zhao: Tetrahedron: Asymmetry 1998, 9, 397-401. Yuanming Zhu, Yong Tu, Hongwu Yu, Yian Shi: Tetrahedron Lett. 1988, 29, 2437-2440).

REFERENCE EXAMPLE

Reference Example 1

To a suspension of Pd/C (NX type; 500 mg) in THF (80 mL) were added methyl 6-(benzylamino)-2-chloro-5-fluoropyridine-3-carboxylate (5 g) and 10% HCl-MeOH (80 mL), and the mixture was stirred for 3 hours. The reaction mixture was filtered through Celite and washed with MeOH. The filtrate was concentrated to give methyl 6-amino-2-chloro-5-fluoropyridine-3-carboxylate (3.83 g).

Reference Example 2

To a suspension of TEA (3.87 mL) and Pd(OH)₂ (280 mg) in THF (50 mL) was added methyl 6-amino-2-chloro-5-fluoropyridine-3-carboxylate (2.837 g), and the mixture was stirred at room temperature under hydrogen atmosphere at 1 atm for 5 hours. The reaction mixture was filtered through Celite and washed with MeOH. The filtrate was concentrated, and saturated aqueous NaHCO₃ solution and AcOEt were added to the resulted residue. The AcOEt layer was separated and dried over anhydrous Na₂SO₄. The mixture was filtered and then the filtrate was concentrated to give methyl 6-amino-5-fluoropyridine-3-carboxylate (2.03 g).

Reference Example 3

To a solution of 2-chloro-5-fluorobenzoic acid (1.026 g) in DCM were added (COCl)₂ (1.543 mL) and DMF (14 μL) at 0° C., and the mixture was stirred for 1 hour and concentrated. The resulted residue was dissolved in DCM (2.0 mL) and the dissolved residue was added to a solution of methyl 6-amino-5-fluoropyridine-3-carboxylate (1 g) and Pyr (15 mL) in DCM (10 mL). The mixture was stirred at room temperature overnight, and then water was added thereto. The precipitated crystal was filtered and washed with water to give methyl 6-(2-chloro-5-fluorobenzamido)-5-fluoropyridine-3-carboxylate (1.25 g).

Reference Example 4

To a solution of methyl 6-(2-chloro-5-fluorobenzamido)-5-fluoropyridine-3-carboxylate (1.25 g) in MeOH (10 mL) was added 5N aqueous NaOH solution (1.148 mL), and the mixture was stirred at room temperature overnight. The reaction solution was acidified with HCl, and the precipitated solid was filtered and washed with water and Et₂O to give 6-(2-chloro-5-fluorobenzamido)-5-fluoropyridine-3-carboxylic acid (678.3 mg).

Reference Example 5

A suspension of 5-bromo-1-indane oxime (108 g) in DCM (600 mL) was cooled with ice, and thereto were added TEA (80 mL) and p-TsCl (109 g). The mixture was stirred at room temperature overnight. About half of the solvent was removed under reduced pressure, and then water was added to the reaction mixture. The mixture was stirred, and the precipitate was filtered and washed with Hexane/AcOEt=1/1 to give a white solid. The aqueous layer was re-extracted with DCM. The combined organic layer was washed with water and saturated brine and dried over anhydrous $Na_2SO_4$. The mixture was filtered and then the filtrate was concentrated, and the precipitate was filtered and washed with Hexane:AcOEt=1:1. The resulted solids were combined to give [(1E)-5-bromo-2,3-dihydro-1H-inden-1-ylidene]amino 4-methylbenzene-1-sulfonate (166.37 g).

Reference Example 6

A suspension of [(1E)-5-bromo-2,3-dihydro-1H-inden-1-ylidene]amino 4-methylbenzene-1-sulfonate (4.77 g) in TFA (24 mL) was stirred at 60° C. for 2 hours. TFA was removed under reduced pressure, and then the resultant was neutralized with saturated aqueous $NaHCO_3$ solution and extracted with DCM. The DCM layer was washed with water and saturated brine and dried over anhydrous $MgSO_4$. The mixture was filtered and then the filtrate was concentrated under reduced pressure. The resulted black oil was purified by medium-pressure column chromatography (Hexane/AcOEt). Fractions were concentrated and solids were filtered and washed with a mixed solvent of Hexane/AcOEt=1:1 to give 6-bromo-1,2,3,4-tetrahydroisoquinolin-1-one (1.14 g).

Reference Example 7

To 2-(difluoromethyl)benzoic acid (2.238 g) were added toluene (20 mL), $(COCl)_2$ (2.268 mL), and a drop of DMF, and the mixture was stirred at room temperature for 1 hour. The reaction solution was concentrated to give an acid chloride. Methyl 6-aminonicotinate (2.374 g) was suspended in Pyr (20 mL), and a solution of the acid chloride in MeCN (10 mL) was added thereto under ice cooling. The mixture was stirred at room temperature for 1 hour, and then water was added thereto and the precipitated crystal was filtered. The crystal was washed with water and dried in air to give methyl 6-[2-(difluoromethyl)benzamido]pyridine-3-carboxylate (3.60 g).

Reference Example 8

To methyl 6-[2-(difluoromethyl)benzamido]pyridine-3-carboxylate (3.60 g) were added THF (18 mL) and 2N aqueous LiOH solution (17.63 mL). The mixture was stirred at room temperature for 2 hours, and then THF was removed under reduced pressure. Water (30 mL) and concentrated HCl (5 mL) were added thereto. A precipitated crystal was filtered and washed with water. The crystal was dried in warm air to give 6-[2-(difluoromethyl)benzamido]pyridine-3-carboxylic acid (3.19 g).

Reference Example 9

A suspension of methyl 5-chloropyrazine-2-carboxylate (0.703 g), 2-chlorobenzamide (0.962 g), $Cs_2CO_3$ (1.67 g), xantphos (0.225 g), and $Pd_2(dba)_3$ (0.12 g) in dioxane (20 mL) was stirred under argon atmosphere at 80° C. for 9 hours. The suspension was cooled, and then AcOEt and water were added to the suspension and the mixture was stirred. Insoluble substances were removed through Celite. The filtrate was separated, and the organic layer was washed with water and saturated brine, dried over anhydrous $MgSO_4$, and filtered. The solvent was removed and the resulted residue was purified by column chromatography (Hexane/AcOEt) to give methyl 5-(2-chlorobenzamido)pyrazine-2-carboxylate (1.05 g).

Reference Example 10

To methyl 5-(2-chlorobenzamido)pyrazine-2-carboxylate (469 mg) was added MeOH (4.7 mL), and then thereto was added 5N aqueous NaOH solution (1.3 mL) under ice cooling. The mixture was stirred at room temperature for 2 hours, and then was adjusted to pH=7 by addition of 1N HCl (6.5 mL) under ice cooling. The precipitate was filtered and dried at 60° C. to give 5-(2-chlorobenzamido)pyrazine-2-carboxylic acid (89 mg). The filtrate was further concentrated and the aqueous layer was adjusted to pH=4 by addition of 1N HCl. A precipitated crystal was filtered and dried at 60° C. to give 5-(2-chlorobenzamido)pyrazine-2-carboxylic acid (330 mg).

Reference Example 11

To a solution of 2-chloro-6-methylbenzoic acid (1.08 g) in DCM (25 mL) were added DMF (50 μL) and $(COCl)_2$ (1.7 mL) under ice cooling. The mixture was stirred at room temperature for 1.5 hours, and then the solvent was removed and the resultant was dissolved in DCM (10 mL). The dissolved resultant was added to a solution of methyl 6-aminonicotinate (0.965 g) and DIPEA (5.5 mL) in DCM (10 mL). The mixture was stirred at room temperature for 37 hours. The solvent was removed, and then AcOEt and water were added to the resultant. The mixture was separated, and the organic layer was washed with water and saturated brine, dried over anhydrous $MgSO_4$, and filtered. The solvent was removed, and the resulted residue was purified by column chromatography (Hexane/AcOEt) to give an ethyl ester. To the ester was added EtOH (12 mL), and then thereto was added 5N aqueous NaOH solution (3.8 mL) under ice cooling. The mixture was stirred under reflux for 7 hours, and then thereto was added 5N HCl (3.8 mL) under ice cooling. The resulted precipitate was filtered and dried at 60° C. to give 6-(2-chloro-6-methylbenzamido)pyridine-3-carboxylic acid (0.686 g).

Reference Example 12

Methyl 5-chloropyrazine-2-carboxylate (879 mg), 2-trifluoromethylbenzamide (1.05 g), $Cs_2CO_3$ (2.31 g), xantphos (0.268 g), and $Pd_2(dba)_3$ (0.141 g) were stirred in dioxane (25.5 mL) under argon atmosphere at 80° C. for 6 hours. The mixture was cooled, and then AcOEt and water were added thereto and the mixture was stirred. Then, insoluble substances were filtered through Celite. The filtrate was separated, and the organic layer was washed with water and saturated brine, dried over anhydrous $Na_2SO_4$, and filtered. The solvent was removed, and then the resulted residue was purified by column chromatography (Hexane/AcOEt). The resultant was confirmed as methyl 5-[(2-(trifluoromethyl)benzamido]pyrazine-2-carboxylate (1.69 g) by $^1$H-NMR ($CDCl_3$). MeOH (16.5 mL) was added thereto, and then thereto was added 5N aqueous NaOH solution (4.1 mL) under ice cooling. The mixture was stirred at room temperature for 4 hours. The mixture was adjusted to pH=4 by addition of 5N HCl (4.1 mL) and the resulted precipitate was filtered and dried at 60° C. to give 5-[2-(trifluoromethyl)benzamido]pyrazine-2-carboxylic acid (1.56 g).

Reference Example 13

2-Methylfuran-3-carboxylic acid (2.87 g) was dissolved in DMA (30 mL) and the mixture was cooled under ice, and then SOCl$_2$ (1.963 mL) was added thereto. The mixture was stirred for 30 minutes and methyl 4-amino-3-methoxybenzoate (3.75 g) was added thereto. Then, the mixture was stirred at room temperature for 1 hour and then water was added thereto. A precipitated crystal was filtered. The resulted solid was dissolved in THF (30 mL), and then 2N aqueous LiOH solution (31.0 mL) was added thereto. The mixture was stirred at 60° C. for 1 hour. 1N HCl (90 mL) was added thereto, and the mixture was stirred for 30 minutes under ice cooling. A precipitated crystal was filtered, washed with water, and then dried in warm air to give 3-methoxy-4-(2-methylfuran-3-amido)benzoic acid (4.81 g).

Reference Example 14

To a solution of methyl 4-amino-3-methoxybenzoate (2.0 g) in Pyr (27 mL) was added 2-(trifluoromethyl)benzoyl chloride (1.7 mL) under nitrogen atmosphere, and the mixture was stirred at room temperature for 2 hours. Water was added to the reaction solution, and the precipitate was filtered and washed with water. To the resulted solid were added MeOH (30 mL) and 5N aqueous NaOH solution (4.4 mL), and the mixture was stirred at room temperature for 1 hour. The reaction solution was neutralized by addition of 5N hydrochloric acid and water. The precipitate was filtered, washed with water, and dried to give 3-methoxy-4-(2-(trifluoromethyl)benzamido)benzoic acid (3.2 g).

Reference Example 15

To a solution of methyl 3-fluoro-4-[2-(trifluoromethyl)benzamido]benzoate (5.03 g) in MeOH (50 mL) was added 1N aqueous NaOH solution (22.11 mL) at room temperature, and the mixture was stirred overnight. 1N HCl was added until the mixture was acidified, and then the mixture was stirred for 2 hours. A precipitated crystal was filtered, washed with water, and dried in air at 60° C. to give 3-fluoro-4-[2-(trifluoromethyl)benzamido]benzoic acid (4.70 g).

Reference Example 16

To a solution of methyl 4-amino-3-(methoxymethoxy)benzoate (10.6 g) in Pyr (100 mL) was added 2-chlorobenzoyl chloride (6.99 mL), and the mixture was stirred at room temperature overnight. After the starting materials were confirmed to be disappeared, the mixture was poured into water and the resulted powder was filtered, washed with water, and dried to give methyl 4-(2-chlorobenzamido)-3-(methoxymethoxy)benzoate (quantitative).

Reference Example 17

To a suspension of methyl 4-(2-chlorobenzamido)-3-(methoxymethoxy)benzoate (17.5 g) in MeOH (200 mL) was added 5N aqueous NaOH (20 mL), and the mixture was stirred at 60° C. for 4.5 hours. After concentration of the mixture, 5N HCl (20 mL) was added to the mixture. The resulted powder was filtered, washed with water, and then dried to give 4-(2-chlorobenzamido)-3-(methoxymethoxy)benzoic acid (15.2 g).

Reference Example 18

To a solution of methyl 4-amino-3-(methoxymethoxy)benzoate (10 g) in Pyr (50 mL) was added 2-(trifluoromethyl)benzoyl chloride (7.67 mL), and the mixture was stirred at room temperature overnight. After confirmation of generation of an ester by LCMS, water was added to the reaction solution and the mixture was extracted with AcOEt. The organic layer was concentrated. MeOH was added to the residue, which gave a solution of the residue. 5N aqueous NaOH solution (20 mL) was added to the solution and the mixture was stirred at 60° C. After stirring for 8 hours, the mixture was cooled, and then concentrated. 5N HCl (20 mL) was added to the concentrate to give a powder, and the powder was filtered, washed with water, and dried to give 3-(methoxymethoxy)-4-[2-(trifluoromethyl)benzamido]benzoic acid (16.5 g).

Reference Example 19

To a solution of 2-chloro-4-fluorobenzoyl chloride (1.0 mL) in DMA (10 mL) was added 4-amino-3-methoxybenzoic acid (1.253 g), and the mixture was stirred at room temperature for 1 hour. Then, water was added thereto, and the mixture was stirred. The precipitated powder was filtered, washed with water, and then dried to give 4-(2-chloro-4-fluorobenzamido)-3-methoxybenzoic acid (2.4 g).

Reference Example 21

2-Chloro-5-fluorobenzoic acid (5.63 g) was dissolved in DMA (50 mL), and SOCl$_2$ (2.82 mL) was added thereto. The mixture was stirred at room temperature for 1.5 hours, and then 4-amino-3-fluorobenzoic acid (5 g) was added thereto. The mixture was stirred at room temperature for 1 hour, and then water was added thereto. The precipitated solid was filtered, washed with water, and then dried at 60° C. to give 4-(2-chloro-5-fluorobenzamido)-3-fluorobenzoic acid (9.59 g).

Reference Example 22

To a solution of 4'-fluoro-[1,1'-biphenyl]-2-carboxylic acid (2.5 g) in anhydrous DCM (40 mL) were added SOCl$_2$ (0.844 mL) and DMF (45 µL) at room temperature, and the mixture was stirred at 40° C. for 3 hours. The reaction solution was concentrated, and a solution of the resulted acid chloride in anhydrous DCM (20 mL) was added dropwise to a solution of methyl 6-aminonicotinate (1.759 g) and Pyr (1.870 mL) in anhydrous DCM (50 mL) at 0° C. The mixture was stirred overnight, and then 1N HCl was added thereto, and the mixture was extracted twice with AcOEt/Hexane (10/1). The combined organic layer was washed with aqueous NaHCO$_3$ solution, dried over anhydrous MgSO$_4$, and then filtered. The filtrate was concentrated under reduced pressure. The residue was purified by silica gel column chromatography (Hexane/AcOEt), and then crystallized with acetone-Et$_2$O. The filtrate was further concentrated, and then purified by silica gel column chromatography (Hexane/AcOEt). The resultant was crystallized with Et$_2$O-n-hexane and filtered. The products were combined to give methyl 6-{4'-fluoro-[1,1'-biphenyl]-2-amido}pyridine-3-carboxylate (3.36 g).

Reference Example 23

To a solution of methyl 6-{4'-fluoro-[1,1'-biphenyl]-2-amido}pyridine-3-carboxylate (3.85 g) in MeOH-THF (50 mL-40 mL) was added 1N aqueous NaOH solution (16.48 mL) at room temperature, and the mixture was stirred overnight. The mixture was acidified with 1N HCl and extracted with AcOEt. The aqueous layer was further extracted with AcOEt, and then the combined organic layer was washed with saturated brine. The organic layer was dried over anhydrous MgSO$_4$, and then filtered, and the filtrate was concentrated under reduced pressure. The resulted white powder was filtered, washed with hexane, and dried in air to give 6-{4'-fluoro-[1,1'-biphenyl]-2-amido}pyridine-3-carboxylic acid (3.26 g).

Reference Example 25

To 2-bromo-1-(difluoromethyl)-4-fluorobenzene (4.95 g) were added DMF (50 mL), MeOH (10 mL), and TEA (10 mL). Pd(OAc)$_2$ (0.494 g) and DPPP (0.907 g) were added thereto, and the mixture was stirred under carbon monoxide atmosphere at 1 atm at 70° C. for 24 hours. Then, water and AcOEt were added thereto, and insoluble substances were filtered. Water was added to the filtrate and the mixture was extracted with AcOEt. The organic layer was washed with brine, dried over anhydrous Na$_2$SO$_4$, and then filtered, and the filtrate was concentrated under reduced pressure to give methyl 2-(difluoromethyl)-5-fluorobenzoate (2.08 g).

Reference Example 26

To methyl 2-(difluoromethyl)-5-fluorobenzoate (2.07 g) were added MeOH (15 mL) and 5N aqueous NaOH solution (4.06 mL), and the mixture was stirred at room temperature for 3 hours. Water and 1N HCl were added thereto, and the mixture was extracted with AcOEt. The organic layer was washed with brine, dried over anhydrous Na$_2$SO$_4$, and then filtered, and the filtrate was concentrated under reduced pressure to give 2-(difluoromethyl)-5-fluorobenzoic acid (1.83 g).

Reference Example 27

To a solution of 4-amino-3-methoxybenzoic acid (1.0 g) in DMA (8.0 mL) was added dropwise o-toluoyl chloride (0.74 mL) under ice cooling under nitrogen atmosphere, and the mixture was stirred at room temperature for 1 day. Water was added thereto, and the precipitate was filtered and washed with water to give 3-methoxy-4-(2-methylbenzamido)benzoic acid (1.6 g).

Reference Example 30

To a solution of 2-chloro-5-methylbenzoic acid (0.83 g) in DMA (6.0 mL) was added dropwise SOCl$_2$ (0.36 mL) at room temperature under nitrogen atmosphere, and the mixture was stirred for 2 hours. To the reaction solution was added 4-amino-3-methoxybenzoic acid (1.0 g), and the mixture was stirred at room temperature for 1 day. Water was added thereto, and the precipitate was filtered and washed with water to give 3-methoxy-4-(2-chloro-5-methylbenzamido)benzoic acid (1.4 g).

Reference Example 31

To a solution of 2-chloro-5-methylbenzoic acid (0.83 g) in DCM (3 mL) were added (COCl)$_2$ (0.51 mL) and DMF (19 μL) under nitrogen atmosphere, and the mixture was stirred at room temperature for 1 hour. The mixture was concentrated and the resulted residue was added dropwise to a solution of methyl 6-aminonicotinate (0.74 g) in Pyr (4.0 mL) under ice cooling, and the mixture was stirred at room temperature for 1 day. Water was added to the reaction solution, and the precipitate was filtered and washed with water. To the resulted solid were added MeOH (12 mL) and 5N aqueous NaOH solution (4.9 mL), and the mixture was stirred at room temperature for 30 minutes. The reaction solution was neutralized by addition of 5N HCl (4.9 mL) and water under ice cooling, and the precipitate was filtered and washed with water to give 6-(2-chloro-5-methylbenzamido)pyridine-3-carboxylic acid (1.03 g).

Reference Example 32

Methyl 5-chloropyrazine-2-carboxylate (4.44 g), 2-chloro-5-fluorobenzamide (6.70 g), Cs$_2$CO$_3$ (10.9 g), Pd$_2$dba$_3$ (0.754 g), and xantphos (1.4 g) were suspended in dioxane (150 mL), and the mixture was stirred under argon atmosphere at 80° C. for 5 hours. The mixture was diluted with AcOEt, and then water was added thereto. Insoluble substances were filtered. The filtrate was extracted with AcOEt, washed with saturated brine, and then dried over anhydrous Na$_2$SO$_4$ and filtered. The filtrate was concentrated under reduced pressure. The residue was purified by column chromatography (AcOEt/Hexane). The resultant was concentrated, and then dried in vacuo to give methyl 5-(2-chloro-5-fluorobenzamido)pyrazine-2-carboxylate (9.6 g).

Reference Example 33

Methyl 5-(2-chloro-5-fluorobenzamido)pyrazine-2-carboxylate (9.6 g) was dissolved in MeOH (100 mL). 5N aqueous NaOH solution (18.60 mL) was added thereto, and the mixture was stirred at room temperature for 4 hours. The mixture was adjusted to pH<4 by addition of 5N HCl and diluted with water. Then, the resulted solid was filtered, washed with water and AcOEt, and dried at 60° C. to give 5-(2-chloro-5-fluorobenzamido)pyrazine-2-carboxylic acid (6.2 g).

Reference Example 35

A mixture of 1,2,3,4-tetrahydroisoquinolin-1-one (1.0 g), 1,4-dioxane (10.0 mL), methyl 6-chloronicotinate (1.39 g), Pd$_2$(dba)$_3$ (0.124 g), xantphos (0.197 g), and Cs$_2$CO$_3$ (2.88 g) was stirred for 1 day under heating to reflux under nitrogen atmosphere. After cooled to room temperature, water was added to the reaction solution and the mixture was extracted with AcOEt. The organic layer was dried over anhydrous Na$_2$SO$_4$, and then filtered, and the filtrate was concentrated under reduced pressure. The residue was purified by silica gel column chromatography (Hexane/AcOEt) to give methyl 6-(1-oxo-1,2,3,4-tetrahydroisoquinolin-2-yl)pyridine-3-carboxylate (1.76 g).

Reference Example 37

To methyl 6-(1-oxo-1,2,3,4-tetrahydroisoquinolin-2-yl)pyridine-3-carboxylate (1.76 g) were added MeOH (10.0 mL) and 5N aqueous NaOH solution (6.23 mL), and the mixture was stirred at room temperature for 3 hours. The reaction solution was acidified by addition of 5N HCl under ice cooling, and the precipitate was filtered and washed with water to give 6-(1-oxo-1,2,3,4-tetrahydroisoquinolin-2-yl)pyridine-3-carboxylic acid (1.63 g).

Reference Example 39

A mixture of 1,2,3,4-tetrahydroisoquinolin-1-one (0.509 g), methyl 4-iodo-3-methoxybenzoate (1.01 g), CuI (66.0 mg), DMEDA (74.0 µL), K$_3$PO$_4$ (1.47 g), and toluene (5.0 mL) was stirred at 90° C. for 1 day under nitrogen atmosphere. The reaction solution was filtered through Celite and the filtrate was concentrated under reduced pressure. The residue was purified by silica gel column chromatography (Haxane/AcOEt) to give methyl 3-methoxy-4-(1-oxo-1,2,3,4-tetrahydroisoquinoline-2-yl)benzoate (1.08 g).

Reference Example 41

To a solution of 4-fluoro-2-methylbenzoic acid (2.77 g) in DMA (50 mL) was added SOCl$_2$ (1.379 mL) under nitrogen atmosphere, and the mixture was stirred at room temperature for 1 hour. Then, 4-amino-3-methoxybenzoic acid (3 g) was added thereto. The mixture was stirred at room temperature for 3 hours, and then water was added thereto. A precipitated crystal was filtered and washed with water to give 4-(4-fluoro-2-methylbenzamido)-3-methoxybenzoic acid (5.20 g).

Reference Example 44

To a solution of 2-(difluoromethyl)pyridine-3-carboxylic acid (1.0 g) in DCM (3 mL) were added (COCl)$_2$ (0.556 mL) and DMF (1 drop) under nitrogen atmosphere, and the mixture was stirred at room temperature for 2 hours and then at 50° C. for 30 minutes. The residue was added dropwise to a solution of methyl 6-aminonicotinate (1.06 g) in Pyr (8.0 mL) under ice cooling, and the mixture was stirred at room temperature for 3 days. Water was added to the reaction solution and the mixture was extracted with AcOEt. The organic layer was washed with saturated brine, dried over anhydrous Na$_2$ SO$_4$, and then filtered. The filtrate was concentrated under reduced pressure. The residue was purified by silica gel column chromatography (Hexane/AcOEt) and recrystallization (Hexane/AcOEt) to give methyl 6-[2-(difluoromethyl)pyridin-3-amido]pyridine-3-carboxylate (732 mg).

Reference Example 45

A mixture of methyl 6-[2-(difluoromethyl)pyridin-3-amido]pyridine-3-carboxylate (732 mg), THF (4.0 mL), and 2N aqueous LiOH solution (3.57 mL) was stirred at room temperature for 2 hours. The reaction solution was neutralized by addition of 5N HCl under ice cooling, and the precipitate was filtered and washed with water to give 6-[2-(difluoromethyl)pyridin-3-amido]pyridine-3-carboxylic acid (603 mg).

Reference Example 48

Methyl 5-chloropyrazine-2-carboxylate (1.0 g), [1,1'-biphenyl]-2-carboxamide (1.257 g), Cs$_2$CO$_3$ (2.454 g), Pd$_2$dba$_3$ (0.170 g), and xantphos (0.315 g) were suspended in dioxane (30 mL), and the mixture was stirred under argon atmosphere at 80° C. overnight. The mixture was diluted with AcOEt, and then water was added thereto. Insoluble substances were filtered. The filtrate was extracted with AcOEt, washed with saturated brine, and then dried over anhydrous Na$_2$SO$_4$. The filtrate was filtered and concentrated under reduced pressure, and then the residue was purified by column chromatography (Hexane/AcOEt). The resultant was concentrated and then dried in vacuo to give methyl 5-{[1,1'-biphenyl]-2-amido}pyrazine-2-carboxylate (1.49 g).

Reference Example 49

Methyl 5-{[1,1'-biphenyl]-2-amido}pyrazine-2-carboxylate (1.49 g) was dissolved in MeOH (30 mL), and thereto was added 5N aqueous NaOH solution (1.788 mL), and the mixture was stirred at room temperature for 24 hours. The mixture was adjusted to pH=5-6 by addition of 5N HCl, and water added thereto. A precipitated crystal was filtered, washed with water and AcOEt, and dried at 60° C. to give 5-{[1,1'-biphenyl]-2-amido}pyrazine-2-carboxylic acid (1.3 g).

Reference Example 53

Methyl 5-chloropyrazine-2-carboxylate (692 mg), 4-fluoro-[1,1'-biphenyl]-2-carboxamide (948.7 mg), Cs$_2$CO$_3$ (1697 mg), Pd$_2$dba$_3$ (183 mg), and xantphos (348 mg) were suspended in dioxane (25 mL), and the mixture was stirred at 80° C. for 2 days under argon atmosphere. The mixture was diluted with AcOEt, and then water was added thereto. The mixture was extracted with AcOEt. The organic layer was washed with saturated brine, and then dried over anhydrous Na$_2$SO$_4$, filtered, and concentrated under reduced pressure. The residue was purified by column chromatography (Hexane/AcOEt). The resultant was concentrated, and then the resulted solid was dispersed and washed with AcOEt/Hexane, filtered, and dried at 60° C. to give methyl 5-{4-fluoro-[1,1'-biphenyl]-2-amido}pyrazine-2-carboxylate (1.1 g).

Reference Example 54

Methyl 5-{4-fluoro-[1,1'-biphenyl]-2-amido}pyrazine-2-carboxylate (1.1 g) was suspended in MeOH (18 mL), and 5N aqueous NaOH solution (1.879 mL) was added thereto. The mixture was stirred at room temperature for 4 days. The mixture was adjusted to pH=5-6 by addition of 5N HCl. Water was added thereto, and the mixture was stirred under ice cooling. A precipitated crystal was filtered and dried at 60° C. to give 5-{4-fluoro-[1,1'-biphenyl]-2-amido}pyrazine-2-carboxylic acid (620.8 mg).

Reference Example 55

4-Fluoro-[1,1'-biphenyl]-2-carboxylic acid (1.0 g) was suspended in toluene (10 mL), and then thereto were added (COCl)$_2$ (0.442 mL) and DMF (16 µL) under ice cooling. Then, the mixture was warmed to room temperature and stirred for 2 hours. The mixture was concentrated under reduced pressure, and a solution of the resulted acid chloride in MeCN (10 mL) was added dropwise to a suspension of methyl 6-aminonicotinate (0.640 g) in Pyr (20 mL) under ice cooling. The mixture was stirred for 1 hour. Water was added to the mixture, and the precipitated solid was filtered. The solid was suspended in MeOH (20 mL), and 5N NaOH (2.102 mL) was added thereto. The mixture was stirred at room temperature overnight. The mixture was adjusted to pH=5 by addition of 5N HCl. Water was added to the mixture, and the precipitated solid was filtered and dried at 60° C. to give 6-{4-fluoro-[1,1'-biphenyl]-2-amido} pyridine-3-carboxylic acid (1.00 g).

Reference Example 58

2-Phenyl-3-pyridinecarboxylic acid (1.00 g) was suspended in toluene (10 mL), and thereto were added (COCl)$_2$ (0.479 mL) and DMF (35 µL) under ice cooling, and the mixture was warmed to room temperature and stirred for 2 hours. The mixture was concentrated under reduced pressure, and the resulted acid chloride was suspended in MeCN (5 mL). Then, thereto were added methyl 6-aminonicotinate (0.694 g) and Pyr (20 mL) under ice cooling, and the mixture was stirred for 1 hour. Then, water was added to the mixture and the resulted solid was filtered. The solid was suspended in MeOH (20 mL), and 5N aqueous NaOH solution (1.825 mL) was added thereto. The mixture was stirred at room temperature overnight. The mixture was adjusted to pH=5 by addition of 5N HCl. Water was added to thereto, and the resulted solid was filtered and dried at 60° C. to give 6-(2-phenylpyridin-3-amido)pyridine-3-carboxylic acid (849.3 mg).

Reference Example 59

Methyl 5-chloropyrazine-2-carboxylate (459 mg), 2-phenylpyridine-3-carboxamide (580.3 mg), $Cs_2CO_3$ (1127 mg), $Pd_2dba_3$ (122 mg), and xantphos (231 mg) were suspended in dioxane (15 mL), and the mixture was stirred at 80° C. for 60 hours under argon atmosphere. The mixture was diluted with AcOEt, and then water was added thereto, and the mixture was extracted with AcOEt. The organic layer was washed with saturated brine, and then dried over anhydrous $Na_2SO_4$ and filtered. The filtrate was concentrated under reduced pressure, and then the resulted residue was purified by column chromatography (Hexane/AcOEt). The resultant was concentrated and dried in vacuo to give methyl 5-(2-phenylpyridin-3-amido)pyrazine-2-carboxylate (417.2 mg).

Reference Example 61

To a suspension of 5-fluoro-2-methylbenzoic acid (3.99 g) in DCM (50 mL) were added $(COCl)_2$ (5.14 mL) and DMF (91 µL) at 0° C., and the mixture was stirred at room temperature for 1 hour. The reaction solution was concentrated, and then azeotroped twice with DCM. A solution of the residue in DCM was added to a solution of methyl 6-amino-5-fluoropyridine-3-carboxylate (2 g) in DCM (30 mL)-Pyr (9.51 mL), and the mixture was stirred overnight. A saturated aqueous $NaHCO_3$ solution was added thereto, and the mixture was extracted with AcOEt. The organic layer was washed with 1N HCl and saturated brine, and then dried over anhydrous $Na_2SO_4$ and filtered. The filtrate was concentrated, and MeOH (50 mL) and 5N aqueous NaOH solution (5.17 mL) were added to the resulted residue. The mixture was stirred at room temperature overnight. The mixture was neutralized by addition of HCl, and the precipitated solid was filtered and dried to give 5-fluoro-6-(5-fluoro-2-methylbenzamido)pyridine-3-carboxylic acid (2.54 g).

Reference Example 62

To a suspension of 6-bromo-1,2,3,4-tetrahydroisoquinolin-1-one (1.0 g), 1-chloro-4-fluoro-2-iodobenzene (1.134 g), DMEDA (0.094 mL), and $K_3PO_4$ (1.878 g) in toluene (10 mL) was added CuI (0.084 g) under nitrogen flow, and the mixture was stirred at 90° C. under nitrogen atmosphere overnight. Then, 1-chloro-4-fluoro-2-iodobenzene (0.3 g) was added thereto at room temperature, and the mixture was stirred at 90° C. under nitrogen atmosphere overnight. The mixture was cooled, and then concentrated. The resulted crude product was purified by medium-pressure column chromatography (Hexane/AcOEt) to give 6-bromo-2-(2-chloro-5-fluorophenyl)-1,2,3,4-tetrahydroisoquinolin-1-one (0.75 g).

Reference Example 69

To a solution of 6-bromo-2-(2-chloro-5-fluorophenyl)-1,2,3,4-tetrahydroisoquinolin-1-one (0.75 g) in DMA (7.5 mL) were added tert-butyl acrylate (0.929 mL), LiCl (0.090 g), and TEA (1.474 mL), and then $PdCl_2(PPh_3)_2$ (0.074 g) was added to the mixture under nitrogen flow. The mixture was stirred at 150° C. under nitrogen atmosphere for 5 hours. Then, water was added thereto at room temperature, and the mixture was extracted with AcOEt. The organic layer was concentrated, and then the resulted crude product was purified by medium-pressure column chromatography (Hexane/AcOEt) to give tert-butyl (2E)-3-[2-(2-chloro-5-fluorophenyl)-1-oxo-1,2,3,4-tetrahydroisoquinolin-6-yl]prop-2-enoate (0.85 g).

Reference Example 70

To a solution of tert-butyl (2E)-3-[2-(2-chloro-5-fluorophenyl)-1-oxo-1,2,3,4-tetrahydroisoquinolin-6-yl]prop-2-enoate (0.85 g) in $THF:H_2O$ (3:2, 10 mL) were added $NaIO_4$ (2.262 g) and $OsO_4$ (immobilized cat; 0.230 g), and the mixture was stirred at 50° C. for 2.5 hours. The mixture was cooled, and then filtered through Celite. Water was added to the filtrate, and the mixture was extracted with AcOEt. The organic layer was dried over anhydrous $MgSO_4$, filtered, and concentrated to give 2-(2-chloro-5-fluorophenyl)-1-oxo-1,2,3,4-tetrahydroisoquinoline-6-carbaldehyde (0.7 g crude). To a solution of 2-(2-chloro-5-fluorophenyl)-1-oxo-1,2,3,4-tetrahydroisoquinoline-6-carbaldehyde (0.7 g) in DCM/t-$BuOH/H_2O$ (1/1/1; 6 mL) were added 2-methyl-2-butene (1.221 mL), $NaClO_2$ (1.042 g), and $NaH_2PO_4$ (1.383 g), and the mixture was stirred at room temperature overnight. Water was added thereto, and the mixture was extracted with AcOEt and washed with saturated brine. The organic layer was dried over anhydrous $MgSO_4$, filtered, and concentrated to give 2-(2-chloro-5-fluorophenyl)-1-oxo-1,2,3,4-tetrahydroisoquinoline-6-carboxylic acid (0.67 g).

Reference Example 79

To a solution of 5-fluoro-2-(trifluoromethyl)benzoic acid (2.54 g) in DMA (20 mL) was added $SOCl_2$ (0.933 mL), and the mixture was stirred at room temperature for 2.5 hours. LC-MS showed that the starting materials remained, and additional $SOCl_2$ (0.170 mL) was added to the mixture. Then, the mixture was stirred for 1 hour. 4-Amino-m-toluic acid (1.757 g) was added thereto, and the mixture was stirred at room temperature overnight. Then, the mixture was homogenized by addition of 5N aqueous NaOH solution (20 mL) and water, and then the aqueous layer was washed with AcOEt. The aqueous layer was acidified by addition of 5N HCl, and then $iPr_2O$ was added thereto. The mixture was stirred for a while, and the precipitated solid was filtered and dried at 60° C. to give 4-[5-fluoro-2-(trifluoromethyl)benzamido]-3-methylbenzoic acid (2.874 g).

Reference Example 81

4,4'-Difluoro-[1,1'-biphenyl]-2-carboxylic acid (1.75 g) was dissolved in DMA (10 mL), and $SOCl_2$ (0.709 mL) was added thereto, and the mixture was stirred at room temperature for 2 hours. 4-Aminobenzoic acid (1.025 g) was added to the reaction solution, and the mixture was stirred at room temperature for 15 hours. LCMS showed that the starting materials disappeared. Water was added to the reaction solution, and the precipitated solid was filtered, washed with water, dried in air at 60° C., and then dried under reduced pressure at 60° C. to give 4-{4,4'-difluoro-[1,1'-biphenyl]-2-amido}benzoic acid (2.58 g).

Reference Example 95

To a solution of 4,2'-difluoro-1,1'-biphenyl-2-carboxylic acid (2.00 g) in DCM (50 mL) were added (COCl)$_2$ (1.495 mL) and DMF (50 μL) under nitrogen atmosphere, and the mixture was stirred at room temperature for 2 hours. The mixture was concentrated, and then the residue was dissolved in DCM (50 mL). Then, thereto were added dropwise methyl 6-aminonicotinate (1.364 g) and Pyr (2.072 mL), and the mixture was stirred at room temperature for 2 hours. The reaction solution was concentrated, and then the concentrate was dissolved in THF (15 mL) and MeOH (15 mL). 5N aqueous NaOH solution (5.12 mL) was added thereto under ice cooling, and the mixture was stirred at room temperature for 2 hours. The reaction solution was neutralized by addition of 5N hydrochloric acid and water under ice cooling, and the resulted precipitate was filtered and washed with water to give 6-{2',4-difluoro-[1,1'-biphenyl]-2-amido}pyridine-3-carboxylic acid (2.60 g).

Reference Example 97

4-Fluoro-2'-methoxy-[1,1'-biphenyl]-2-carboxylic acid (2.5 g) was dissolved in DMA (100 mL), and thereto were added DMF (10 μL) and SOCl$_2$ (0.963 mL), and the mixture was stirred at room temperature for 2 hours. 4-Aminobenzoic acid (1.420 g) was added thereto, and the mixture was stirred at room temperature for 15 hours. Water was added to the reaction solution, and the precipitated solid was filtered and dried in air at 60° C. to give 4-{4-fluoro-2'-methoxy-[1,1'-biphenyl]-2-amido}benzoic acid (3.8 g).

Reference Example 98

4-Fluoro-2'-methoxy-[1,1'-biphenyl]-2-carboxylic acid (2.5 g) was dissolved in DMA (20 mL), and SOCl$_2$ (0.963 mL) was added thereto, and the mixture was stirred at room temperature for 2 hours. 4-Amino-3-fluorobenzoic acid (1.606 g) was added to the reaction solution, and the mixture was stirred at room temperature for 15 hours. Water was added to the reaction solution, and the mixture was extracted with AcOEt. The organic layer was washed with brine, dried over anhydrous Na$_2$SO$_4$, and concentrated. The resulted residue was crystallized from DCM. The resulted solid was dispersed and washed with AcOEt/Hexane=⅓, filtered, and dried in air to give 3-fluoro-4-{4-fluoro-2'-methoxy-[1,1'-biphenyl]-2-amido}benzoic acid (3.32 g).

Reference Example 99

4-Fluoro-2'-methoxy-[1,1'-biphenyl]-2-carboxylic acid (2.5 g) was dissolved in DCM/DMA=2/1 (120 mL), and (COCl)$_2$ (10.15 mL) and Pyr (1.642 mL) were added thereto, and the mixture was stirred at room temperature for 1.5 hours. The reaction solution was concentrated, and thereto were added DCM (50 mL) and DMA (30 mL). Then, methyl 6-aminonicotinate (1.576 g) and Pyr (1.642 mL) were sequentially added thereto, and the mixture was stirred at room temperature for 15 hours. LC-MS showed that the starting materials disappeared but a diacyl was produced in about 10%. The reaction solution was concentrated. The residue was dissolved in MeOH/THF=1/1 (60 mL), and 1N NaOH (30 mL) was added thereto, and the mixture was stirred at room temperature for 15 hours. The reaction solution was concentrated and washed with a small amount of AcOEt, and the aqueous layer was separated. 5N HCl (7 mL) was added to the resulted aqueous layer, and the mixture was adjusted to pH 3-4 by addition of additional 1N HCl. The precipitated solid was filtered and dried in air at 60° C. to give 6-{4-fluoro-2'-methoxy-[1,1'-biphenyl]-2-amido}pyridine-3-carboxylic acid (2.26 g).

Reference Example 109

To a solution of 4,3'-difluoro-1,1'-biphenyl-2-carboxylic acid (2.0 g) in DCM (30 mL) were added (COCl)$_2$ (1.495 mL) and DMF (51 μL) under nitrogen atmosphere, and the mixture was stirred at room temperature for 1.5 hours. A residue was added dropwise to a solution of methyl 6-aminonicotinate (1.364 g) in Pyr (15 mL) under ice cooling, and the mixture was stirred at room temperature for 2 hours. Water was added to the reaction solution, and the precipitate was filtered and washed with water. MeOH (20 mL), THF (20 mL), and 5N aqueous NaOH solution (5.12 mL) were added to the resulted solid, and the mixture was stirred at room temperature for 2 hours. The reaction solution was neutralized by addition of 5N hydrochloric acid and water under ice cooling, and the precipitate was filtered and washed with IPE to give 6-{3',4-difluoro-[1,1'-biphenyl]-2-amido}pyridine-3-carboxylic acid (2.38 g).

Reference Example 116

7-Methyl-1,2,3,4-tetrahydroisoquinolin-1-one (3 g), methyl 4-iodobenzoate (4.88 g), CuI (0.354 g), DMEDA (0.396 mL), and K$_3$PO$_4$ (7.90 g) were mixed in 1,4-dioxane (50 mL), and the mixture was stirred at 90° C. overnight. The mixture was filtered through Celite, and then the filtrate was washed with water and saturated brine. The organic layer was dried over anhydrous Na$_2$SO$_4$ and the solvent was removed. The resulted crude crystal was washed with Et$_2$O and dried in air at 60° C. to give methyl 4-(7-methyl-1-oxo-1,2,3,4-tetrahydroisoquinolin-2-yl)benzoate (4.42 g).

Reference Example 121

A solution of methyl 4-(7-methyl-1-oxo-1,2,3,4-tetrahydroisoquinolin-2-yl)benzoate (4.42 g) in EtOH (90 mL) was cooled under ice, and then thereto were added 5N aqueous NaOH solution (14.97 mL) and water. The mixture was stirred at room temperature for 3 hours. The solvent was removed, and then the residue was adjusted to pH=1 by addition of 5N HCl. The resulted crystal was filtered and dried in air at 60° C. to give 4-(7-methyl-1-oxo-1,2,3,4-tetrahydroisoquinolin-2-yl)benzoic acid (2.45 g).

Reference Example 137

To a solution of 2-chlorobenzoyl chloride (0.227 mL) in DMA (8 mL) was added 4-amino-3-methoxybenzoic acid (300 mg), and the mixture was stirred at room temperature overnight. Water was added to the mixture, and the mixture was stirred for 30 minutes. Then, the precipitate was filtered, washed with water and Et$_2$O, and dried in air at 60° C. to give 4-(2-chlorobenzamido)-3-methoxybenzoic acid (470 mg).

Reference Example 138

To a suspension of 2-(trifluoromethyl)pyridine-3-carboxylic acid (9.76 g) in DCM (200 mL) were added (COCl)$_2$ (13.41 mL) and DMF (0.119 mL) at 0° C., and the mixture was stirred at 0° C. for 1 hour, followed by stirring at 30-40° C. for 2 hours. The reaction solution was concentrated, and then the concentrate was diluted with DCM. The resulted solution was added to a suspension of methyl 6-aminonicotinate (7.77 g) in Pyr (20.65 mL) and DCM (200 mL). The mixture was stirred at room temperature for 2 hours, and then DCM was removed under reduced pressure. Water was added to the residue, and the mixture was extracted with AcOEt. The organic layer was dried over anhydrous Na$_2$SO$_4$, and then filtered and concentrated. The resulted residue was dissolved in MeOH-THF (4:1; 200 mL), and then thereto was added 5N aqueous NaOH solution (20.43 mL), and the mixture was stirred at 60° C. for 2 hours. The reaction solution was concentrated and MeOH was removed. Then, the residue was diluted with water and adjusted to pH (4-5) by addition of HCl aq. The precipitated solid was filtered and washed with water to give 6-[2-(trifluoromethyl)pyridin-3-amido]pyridine-3-carboxylic acid (11.21 g).

Reference Example 139

To a solution of 1-chloromethyl-4-fluoro-1,4-diazoniabicyclo[2.2.2]octane bis(tetrafluoroborate) (Selectfluor; 379 g) in MeCN (950 mL) was added N-[(5Z)-7-chloro-1-(4-methylbenzenesulfonyl)-2,3,4,5-tetrahydro-1H-1-benzazepin-5-ylidene]butan-1-amine (197 g) every 40 minutes five times, and the mixture was stirred at room temperature for 3 days. Concentrated HCl (203 mL) and ice water were added thereto, and the mixture was stirred. The precipitate was filtered and washed with water to give 7-chloro-4,4-difluoro-1-(4-methylbenzenesulfonyl)-2,3,4,5-tetrahydro-1H-1-benzazepin-5-one (187 g).

Reference Example 140

7-Chloro-4,4-difluoro-1-(4-methylbenzenesulfonyl)-2,3,4,5-tetrahydro-1H-1-benzazepin-5-one (240 g) was added to concentrated sulfuric acid (265 mL) under ice cooling, and the mixture was stirred at room temperature for 4 hours. The reaction solution was added to a solution of 50% aqueous NaOH solution (796 g) and ice (3 L), and the precipitate was filtered and washed with warmed water to give 7-chloro-4,4-difluoro-2,3,4,5-tetrahydro-1H-1-benzazepin-5-one (138 g).

Reference Example 141

To a solution of 7-chloro-4,4-difluoro-5-(hydroxymethyl)-1-(4-methylbenzenesulfonyl)-2,3,4,5-tetrahydro-1H-1-benzazepin-5-ol (286 mg) in MeOH (10 mL) were added Mg (250 mg) and I$_2$ (34.7 mg) at room temperature, and the mixture was stirred under nitrogen atmosphere. The mixture was refluxed for 4 hours, and then thereto was added aqueous saturated NaHCO$_3$ solution. The mixture was filtered through Celite and washed with AcOEt. The organic layer was separated, dried over anhydrous Na$_2$SO$_4$, and filtered. The filtrate was concentrated, and the resulted residue was purified by column chromatography (Hexane/AcOEt) to give 7-chloro-4,4-difluoro-5-(hydroxymethyl)-2,3,4,5-tetrahydro-1H-1-benzazepin-5-ol (90 mg).

Reference Example 142

To a solution of 7-chloro-4,4-difluoro-5-(hydroxymethyl)-1-(4-methylbenzenesulfonyl)-2,3,4,5-tetrahydro-1H-1-benzazepin-5-ol (250 mg) in THF (2 mL) was added Im (122 mg) under nitrogen atmosphere at room temperature, and then thereto was added TBDMSCl (135 mg) at 0° C. The mixture was stirred at the same temperature for 1 hour, and then diluted with water and extracted with AcOEt. The organic layer was dried over anhydrous Na$_2$SO$_4$, filtered, and concentrated, and the resulted residue was purified by column chromatography (Hexane/AcOEt) to give 5-{[(tert-butyldimethylsilyl)oxy]methyl}-7-chloro-4,4-difluoro-1-(4-methylbenzenesulfonyl)-2,3,4,5-tetrahydro-1H-1-benzazepin-5-ol (278 mg).

Reference Example 143

5-{[(tert-Butyldimethylsilyl)oxy]methyl}-7-chloro-4,4-difluoro-1-(4-methylbenzenesulfonyl)-2,3,4,5-tetrahydro-1H-1-benzazepin-5-ol (278 mg), MeOH (5 mL), and Mg (63.5 mg) were stirred under nitrogen atmosphere at room temperature. The mixture was refluxed for 5 hours, and then thereto was added aqueous saturated NaHCO$_3$ solution. The mixture was filtered through Celite and washed with AcOEt. The organic layer was separated, dried over anhydrous Na$_2$SO$_4$, and filtered, and concentrated. The resulted residue was purified by column chromatography (Hexane/AcOEt) to give 5-{[(tert-butyldimethylsilyl)oxy]methyl}-7-chloro-4,4-difluoro-2,3,4,5-tetrahydro-1H-1-benzazepin-5-ol (102 mg).

Reference Example 144

A mixture of 7-chloro-4,4-difluoro-2,3,4,5-tetrahydro-1H-1-benzazepin-5-one (113 g), THF (400 mL), Boc$_2$O (114 mL), and DMAP (1.79 g) was stirred at room temperature for 18 hours. The reaction solution was concentrated under reduced pressure, and the residue was recrystallized from a mixed solvent of IPA/Hexane. The filtrate was further concentrated under reduced pressure, recrystallized from a mixed solvent of IPA/Hexane, and washed with Hexane to give tert-butyl 7-chloro-4,4-difluoro-5-oxo-2,3,4,5-tetrahydro-1H-1-benzazepine-1-carboxylate (117 g).

Reference Example 145

To a solution of 7-chloro-4,4-difluoro-5-methyl-1-(4-methylbenzenesulfonyl)-2,3,4,5-tetrahydro-1H-1-benzazepin-5-ol (0.769 g) in MeOH (20 mL) was added Mg (0.465 g) under nitrogen atmosphere at room temperature, and the mixture was refluxed for 5 hours. Then, aqueous saturated NaHCO$_3$ solution was added thereto, and the mixture was filtered through Celite and washed with AcOEt. The organic layer was separated, dried over anhydrous Na$_2$SO$_4$, filtered, and concentrated. Then, the resulted residue was purified by column chromatography (Hexane/AcOEt) to give 7-chloro-4,4-difluoro-5-methyl-2,3,4,5-tetrahydro-1H-1-benzazepin-5-ol (0.414 g).

Reference Example 146

To a solution of trimethylsulfoxonium iodide (0.982 g) in DMSO (12 mL) was added KOtBu (0.375 g), and the mixture was stirred under nitrogen atmosphere at room temperature for 30 minutes. Then, tert-butyl 7-chloro-4,4-difluoro-5-oxo-2,3,4,5-tetrahydro-1H-1-benzazepine-1-carboxylate (0.74 g) was added thereto at room temperature.

The mixture was stirred at room temperature for 2 hours, and then water was added thereto. The mixture was extracted with AcOEt. The combined organic layer was washed with water and brine, dried over anhydrous $Na_2SO_4$, filtered, and concentrated. Then, to the resulted residue were added DMF/$H_2O$=4:1 (12 mL) and AcONa (1.464 g) at room temperature, and the mixture was stirred at 80° C. for 24 hours. The reaction mixture was extracted with AcOEt, washed with water and brine, dried over anhydrous $Na_2SO_4$, filtered, and concentrated. Then, the resulted residue was recrystallized from DCM-Hexane to give tert-butyl 7-chloro-4,4-difluoro-5-hydroxy-5-(hydroxymethyl)-2,3,4,5-tetrahydro-1H-1-benzazepine-1-carboxylate (0.491 g).

Reference Example 147

A mixture of 7-chloro-1-(4-methylbenzenesulfonyl)-2,3,4,5-tetrahydro-1H-1-benzazepin-5-one (20.0 g), n-butylamine (8.48 mL), cyclohexane (150 mL), and TFA (0.661 mL) was stirred under heating to reflux for 12 hours with removing water with Dean-Stark trap. The reaction solution was concentrated under reduced pressure, and the residue was washed with a mixed solvent of AcOEt/Hexane to give N-[(5Z)-7-chloro-1-(4-methylbenzenesulfonyl)-2,3,4,5-tetrahydro-1H-1-benzazepin-5-ylidene]butan-1-amine (21.4 g).

Reference Example 150

A mixture of tert-butyl (5R)-7-chloro-4,4-difluoro-5-hydroxy-5-({[(2R)-2-(4-methylbenzenesulfonamide)-3-phenylpropanoyl]oxy}methyl)-2,3,4,5-tetrahydro-1H-1-benzazepine-1-carboxylate (0.20 g), EtOH (1.0 mL), and 5N aqueous NaOH solution (0.18 mL) was stirred at room temperature for 3 hours. Water was added to the reaction solution, and the mixture was extracted with AcOEt. The organic layer was dried over $Na_2SO_4$, and then filtered, and the filtrate was concentrated under reduced pressure. The residue was purified by silica gel column chromatography (Hexane/AcOEt) to give tert-butyl (5R)-7-chloro-4,4-difluoro-5-hydroxy-5-(hydroxymethyl)-2,3,4,5-tetrahydro-1H-1-benzazepine-1-carboxylate (99 mg).

Reference Example 151

A mixture of [(5R)-7-chloro-4,4-difluoro-5-hydroxy-2,3,4,5-tetrahydro-1H-1-benzazepin-5-yl]methyl (2S)-2-(naphthalene-1-sulfonamido)-3-phenylpropanoate (1.10 g), potassium trimethylsilanolate (1.05 g), and THF (9.0 mL) was stirred at room temperature for 1 hour, and then concentrated under reduced pressure. The residue was purified by silica gel column chromatography (Hexane/AcOEt), and dispersed and washed with a mixed solvent of DCM/Hexane to give (5R)-7-chloro-4,4-difluoro-5-(hydroxymethyl)-2,3,4,5-tetrahydro-1H-1-benzazepin-5-ol (350 mg).

Reference Example 152 tert-Butyl (5R)-7-chloro-4,4-difluoro-5-hydroxy-5-(hydroxymethyl)-2,3,4,5-tetrahydro-1H-1-benzazepine-1-carboxylate (500 mg) was dissolved in EtOH (10 mL), and thereto was added 12N HCl (0.115 mL), and the mixture was refluxed. After 1 hour, the reaction was uncompleted, and 12N HCl (0.5 eq) was additionally added to the mixture, and the mixture was refluxed for 1 hour. The mixture was concentrated, dissolved in AcOEt, and re-concentrated to give a crystal. The crystal was dried in vacuo to give (5R)-7-chloro-4,4-difluoro-5-(hydroxymethyl)-2,3,4,5-tetrahydro-1H-1-benzazepin-5-ol hydrochloride (412.51 mg).

Reference Example 153 tert-Butyl 7-chloro-4,4-difluoro-5-hydroxy-5-(hydroxymethyl)-2,3,4,5-tetrahydro-1H-1-benzazepine-1-carboxylate (200 mg), TEA (0.230 mL), THF (2 mL), 4-bromobenzoyl chloride (145 mg), and DMAP (6.72 mg) were added at room temperature, and the mixture was stirred for 30 minutes. The reaction solution was concentrated, and the resulted residue was purified by column chromatography (Hexane/AcOEt) to give tert-butyl 5-[(4-bromobenzoyloxy)methyl]-7-chloro-4,4-difluoro-5-hydroxy-2,3,4,5-tetrahydro-1H-1-benzazepine-1-carboxylate (317 mg).

Reference Example 154 tert-Butyl (5R)-7-chloro-4,4-difluoro-5-hydroxy-5-(hydroxymethyl)-2,3,4,5-tetrahydro-1H-1-benzazepine-1-carboxylate (21.86 g) was dissolved in THF (200 mL), and then thereto were added TEA (25.1 mL) and 4-bromobenzoyl chloride (13.19 g), and the mixture was stirred at room temperature for 3 hours. Water was added thereto, and the mixture was diluted with AcOEt. The mixture was washed with 1N HCl, 1N NaOH, and saturated brine, dried over anhydrous $Na_2SO_4$, filtered, and concentrated under reduced pressure. To the resulted residue were added AcOEt (20 mL) and DCM (30 mL), which resulted a crystal. The crystal was dispersed and washed with a mixed solvent of AcOEt:DCM:Hexane=2:3:2, and then filtered and dried at 60° C. to give tert-butyl (5R)-5-[(4-bromobenzoyloxy)methyl]-7-chloro-4,4-difluoro-5-hydroxy-2,3,4,5-tetrahydro-1H-1-benzazepine-1-carboxylate (24.7 g; Lot 1). The filtrate was concentrated under reduced pressure, purified by column chromatography (AcOEt/Hexane), and concentrated. Then, the concentrate was crystallized from DCM/AcOEt/Hexane, filtered, and dried at 60° C. to give tert-butyl (5R)-5-[(4-bromobenzoyloxy)methyl]-7-chloro-4,4-difluoro-5-hydroxy-2,3,4,5-tetrahydro-1H-1-benzazepine-1-carboxylate (6.1 g; Lot 2). The filtrate was further concentrated, and then crystallized from DCM/Hexane. The resultant was filtered and dried at 60° C. to give tert-butyl (5R)-5-[(4-bromobenzoyloxy)methyl]-7-chloro-4,4-difluoro-5-hydroxy-2,3,4,5-tetrahydro-1H-1-benzazepine-1-carboxylate (2.2 g; Lot 3). Structures of Lot 1, Lot 2, and Lot 3 were determined by $^1$H-NMR. The optical purity of each lot was 100% ee, 99.9% ee, and 100% ee, respectively. These were combined to give tert-butyl (5R)-5-[(4-bromobenzoyloxy)methyl]-7-chloro-4,4-difluoro-5-hydroxy-2,3,4,5-tetrahydro-1H-1-benzazepine-1-carboxylate (33.0 g) (It is considered to present in the form of 1:1 cocrystal with DCM or a solvate with DCM).

Reference Example 155 tert-Butyl (5R)-5-[(4-bromobenzoyloxy)methyl]-7-chloro-4,4-difluoro-5-hydroxy-2,3,4,5-tetrahydro-1H-1-benzazepine-1-carboxylate (33.0 g) was dissolved in DCM (100 mL), and then thereto was added TFA (46.5 mL), and the mixture was stirred at room temperature. The mixture was stirred for 3 hours and neutralized with saturated sodium bicarbonate water under ice cooling. The mixture was extracted with AcOEt, washed with saturated brine, dried over anhydrous $Na_2SO_4$, filtered, and concentrated under reduced pressure. The resulted solid was filtered and dried at 60° C. to give [(5R)-7-chloro-4,4-difluoro-5-hydroxy-2,3,4,5-tetrahydro-1H-1-benzazepin-5-yl]methyl 4-bromobenzoate (23.35 g).

Reference Example 156 tert-Butyl 7-chloro-4,4-difluoro-5-hydroxy-5-(hydroxymethyl)-2,3,4,5-tetrahydro-1H-1-benzazepine-1-carboxylate (50 mg) was dissolved in THF (2 mL), and then thereto were added TEA (0.057 mL) and 4-bromobenzoyl chloride (30.2 mg), and the mixture was stirred at room temperature. The reaction was quenched with water, and the mixture was diluted with AcOEt. The mixture was washed with 1N HCl, 1N NaOH, and saturated brine, dried over anhydrous $Na_2SO_4$, filtered, and concentrated under reduced pressure. The resulted residue was purified by column chromatography (AcOEt/Hexane) and dried in vacuo. The resulted tert-butyl 5-[(4-bromobenzoyloxy)methyl]-7-chloro-4,4-difluoro-5-hydroxy-2,3,4,5-tetrahydro-1H-1-benzazepine-1-carboxylate was dissolved in DCM (2 mL), and thereto was added TFA (0.318 mL), and the mixture was stirred at room temperature for 2 hours. The mixture was cooled under ice, neutralized with saturated sodium bicarbonate water, and extracted with AcOEt. The extract was dried over anhydrous $Na_2SO_4$, filtered, and concentrated under reduced pressure. The resulted residue was purified by column chromatography (Hexane/AcOEt), concentrated, and then dried in vacuo to give (7-chloro-4,4-difluoro-5-hydroxy-2,3,4,5-tetrahydro-1H-1-benzazepin-5-yl)methyl 4-bromobenzoate (38.3 mg).

Reference Examples 157 and 158 tert-Butyl 7-chloro-4,4-difluoro-5-hydroxy-5-(hydroxymethyl)-2,3,4,5-tetrahydro-1H-1-benzazepine-1-carboxylate (1 g), TEA (1.149 ml), THF (10 mL), (S)-2-(4-methylphenylsulfonamido)-3-phenylpropanoyl chloride (0.929 g), and DMAP (0.034 g) were added at room temperature, and the mixture was stirred for 20 hours. The reaction solution was concentrated under reduced pressure, and the resulted residue was purified by column chromatography (Hexane/AcOEt), and then recrystallized from DCM/n-Hexane to give tert-butyl (5S)-7-chloro-4,4-difluoro-5-hydroxy-5-({[(2S)-2-(4-methylbenzenesulfonamido)-3-phenylpropanoyl]oxy}methyl)-2,3,4,5-tetrahydro-1H-1-benzazepine-1-carboxylate (430 mg; Reference Example 157) and tert-butyl (5R)-7-chloro-4,4-difluoro-5-hydroxy-5-({[(2S)-2-(4-methylbenzenesulfonamido)-3-phenylpropanoyl]oxy}methyl)-2,3,4,5-tetrahydro-1H-1-benzazepine-1-carboxylate (740 mg; Reference Example 158).

Reference Example 159

To a solution of 7-chloro-4,4-difluoro-1-(4-methylbenzenesulfonyl)-2,3,4,5-tetrahydro-1H-1-benzazepin-5-one (1.50 g) in anhydrous THF (20 mL) was added lithium aluminum deuteride (0.163 g) at 0° C., and the mixture was stirred overnight. To the reaction solution were added water (0.16 mL), 15% aqueous NaOH solution (0.16 mL), and water (0.48 mL), and the mixture was stirred, and then filtered through Celite and washed with AcOEt. Water was added to the filtrate, and the filtrate was extracted with AcOEt. The combined organic layer was washed with water and saturated brine, dried over anhydrous $Na_2SO_4$, and concentrated under reduced pressure. The residue was purified by silica gel column chromatography (Hexane/AcOEt) to give 7-chloro-4,4-difluoro-1-(4-methylbenzenesulfonyl)-2,3,4,5-tetrahydro(5-$^2$H)-1H-1-benzazepin-5-ol (1.04 g).

Reference Example 160

To a solution of 7-chloro-4,4-difluoro-1-(4-methylbenzenesulfonyl)-2,3,4,5-tetrahydro(5-$^2$H)-1H-1-benzazepin-5-ol (1.04 g) in anhydrous MeOH (20 mL) was added magnesium (0.390 g), and the mixture was stirred at room temperature for 3 hours. The mixture was diluted with AcOEt (20 mL), and then thereto was added 5N HCl (10.16 mL) at 0° C. Then, water was added thereto, and the mixture was stirred. The mixture was stirred at room temperature and extracted with AcOEt. The organic layer was washed with saturated sodium bicarbonate water and saturated brine, dried over anhydrous $Na_2SO_4$, and concentrated under reduced pressure to give 7-chloro-4,4-difluoro-2,3,4,5-tetrahydro(5-$^2$H)-1H-1-benzazepin-5-ol (473 mg).

Reference Example 161 tert-Butyl 7-chloro-4,4-difluoro-5-hydroxy-5-(hydroxymethyl)-2,3,4,5-tetrahydro-1H-1-benzazepine-1-carboxylate (133 g), THF (1200 mL), TEA (153 mL), DMAP (4.47 g), and (R)-2-(4-methylphenylsulfonamido)-3-phenylpropanoyl chloride (148 g) were mixed under ice cooling, and the mixture was stirred at room temperature for 3 hours. The precipitate was filtered and the filtrate was concentrated under reduced pressure. The residue was recrystallized (Ether/Hexane). The filtrate was purified by silica gel column chromatography (Hexane/AcOEt) and recrystallization (Ether/Hexane), a combination of which gave tert-butyl (5R)-7-chloro-4,4-difluoro-5-hydroxy-5-({[(2R)-2-(4-methylbenzenesulfonamido)-3-phenylpropanoyl]oxy}methyl)-2,3,4,5-tetrahydro-1H-1-benzazepine-1-carboxylate (92.4 g).

Reference Example 162

As a filtrate of tert-butyl (5R)-7-chloro-4,4-difluoro-5-hydroxy-5-({[(2R)-2-(4-methylbenzenesulfonamide)-3-phenylpropanoyl]oxy}methyl)-2,3,4,5-tetrahydro-1H-1-benzazepine-1-carboxylate, tert-butyl (5S)-7-chloro-4,4-difluoro-5-hydroxy-5-({[(2R)-2-(4-methylbenzenesulfonamido)-3-phenylpropanoyl]oxy}methyl)-2,3,4,5-tetrahydro-1H-1-benzazepine-1-carboxylate (128 g) was obtained.

Reference Example 163

5-Fluoro-2-(pyridin-2-yl)benzoic acid (688 mg) was dissolved in DMA (20 mL), and thereto was added $SOCl_2$ (0.301 mL), and the mixture was stirred at room temperature for 2 hours. Methyl 4-amino-3-fluorobenzoate hydrochloride (651 mg) was added to the reaction solution, and the mixture was stirred at room temperature for 15 hours. Aqueous $NaHCO_3$ solution was added to the reaction solution, and the mixture was extracted with AcOEt. The organic layer was washed with aqueous $NaHCO_3$ solution and brine, dried over anhydrous $Na_2SO_4$, and concentrated. The precipitated solid was dispersed and washed with AcOEt/Hexane=½, and the resulted solid was filtered and dried in air to give methyl 3-fluoro-4-[5-fluoro-2-(pyridin-2-yl)benzamido]benzoate (970 mg).

Reference Example 164

Methyl 3-fluoro-4-[5-fluoro-2-(pyridin-2-yl)benzamido]benzoate (970 mg) was dissolved in MeOH/THF=3/1, and thereto was added 5N aqueous NaOH solution (2.63 mL), and the mixture was stirred at 60° C. for 6 hours. The reaction solution was concentrated, acidified by addition of 5N HCl (3.68 mL), concentrated, and dried under reduced pressure. The residue was dissolved in ethanol and an inorganic substance was filtered. The filtrate was concentrated. THF was added to the residue, and the mixture was concentrated again and dried at 50° C. under reduced pressure to give 3-fluoro-4-[5-fluoro-2-(pyridin-2-yl)benzamido]benzoic acid hydrochloride (1.02 g).

Reference Example 165

To a solution of tert-butyl (5R)-7-chloro-4,4-difluoro-5-hydroxy-5-({[(2R)-2-(4-methylbenzenesulfonamido)-3-phenylpropanoyl]oxy}methyl)-2,3,4,5-tetrahydro-1H-1-benzazepine-1-carboxylate (2 g) in DCM (4 mL) was added TFA (2.317 mL) at room temperature, and the mixture was stirred for 1 hour. The mixture was neutralized with aqueous saturated NaHCO$_3$ solution, and then diluted with AcOEt. The precipitated solid was filtered and washed with water and AcOEt to give [(5R)-7-chloro-4,4-difluoro-5-hydroxy-2,3,4,5-tetrahydro-1H-1-benzazepin-5-yl]methyl (2R)-2-(4-methylbenzenesulfonamido)-3-phenylpropanoate (1.35 g).

Reference Example 166

Trimethylsulfoxonium iodide (228 mg), DMSO (4 mL), and KOtBu (87 mg) were stirred under nitrogen atmosphere at room temperature for 30 minutes. 7-Chloro-4,4-difluoro-1-(4-methylbenzenesulfonyl)-2,3,4,5-tetrahydro-1H-1-benzazepin-5-one (200 mg) was added thereto at room temperature, and the mixture was stirred for 2 hours. The mixture was diluted with water and extracted with AcOEt. The organic layer was washed with water and saturated brine, and then dried over anhydrous Na$_2$SO$_4$ and filtered. The filtrate was concentrated and the resulted residue was purified by column chromatography (Hexane/AcOEt) to give 7-chloro-4,4-difluoro-1-(4-methylbenzenesulfonyl)-1,2,3,4-tetrahydrospiro[1-benzazepin-5,2'-oxirane] (200 mg; including ca. 0.2 eq. of AcOEt).

Reference Example 167

To a solution of methyltriphenylphosphonium bromide (956 mg) and 7-chloro-4,4-difluoro-1-(4-methylbenzenesulfonyl)-2,3,4,5-tetrahydro-1H-1-benzazepin-5-one (860 mg) in anhydrous THF (10 mL) was added KOtBu (300 mg) under nitrogen atmosphere at 0° C. The mixture was stirred at room temperature for 2 hours, and then water was added thereto, and the mixture was extracted with AcOEt. The organic layer was dried over anhydrous Na$_2$SO$_4$, and then filtered and concentrated. The resulted residue was purified by column chromatography (Hexane/AcOEt) to give 7-chloro-4,4-difluoro-1-(4-methylbenzenesulfonyl)-5-methylidene-2,3,4,5-tetrahydro-1H-1-benzazepine (270 mg).

Reference Example 168

To a solution of 7-chloro-4,4-difluoro-1-(4-methylbenzenesulfonyl)-5-methylidene-2,3,4,5-tetrahydro-1H-1-benzazepine (270 mg) in THF/H$_2$O/acetone (1/1/2; 8 mL) were added NMO (165 mg) and 4% OsO$_4$ aq. (447 mg) under nitrogen atmosphere. The mixture was stirred at room temperature for one week, and then saturated aqueous Na$_2$SO$_3$ solution was added thereto, and the mixture was extracted with AcOEt. The organic layer was washed with water, dried over anhydrous Na$_2$SO$_4$, filtered, and concentrated. The resulted residue was purified by column chromatography (Hexane/AcOEt) to give 7-chloro-4,4-difluoro-5-(hydroxymethyl)-1-(4-methylbenzenesulfonyl)-2,3,4,5-tetrahydro-1H-1-benzazepin-5-ol (210 mg).

Reference Example 169

To a solution of 7-chloro-4,4-difluoro-1-(4-methylbenzenesulfonyl)-2,3,4,5-tetrahydro-1H-1-benzazepin-5-one (1 g) in THF (10 mL) was added dropwise 1.0M methylmagnesium bromide (3.37 mL) under nitrogen atmosphere at 0° C. The mixture was stirred at 0° C. for 2 hours, and then saturated aqueous NH$_4$Cl solution was added thereto, and the mixture was extracted with AcOEt. The organic layer was dried over anhydrous Na$_2$SO$_4$, filtered, and concentrated. The resulted residue was recrystallized from DCM/AcOEt/Hexane to give 7-chloro-4,4-difluoro-5-methyl-1-(4-methylbenzenesulfonyl)-2,3,4,5-tetrahydro-1H-1-benzazepin-5-ol (769 mg).

Reference Example 170

To a solution of trimethylsulfoxonium iodide (80 g) in DMSO (500 mL) was added KOtBu (30.4 g) under nitrogen atmosphere, and the mixture was stirred at room temperature for 1 hour. Then, thereto was added tert-butyl 7-chloro-4,4-difluoro-5-oxo-2,3,4,5-tetrahydro-1H-1-benzazepine-1-carboxylate (60 g) at room temperature, and the mixture was stirred for 2.5 hours, and then ice water (2 L) was poured into the mixture. The mixture was filtered and washed with water. AcOEt and water were added to the resulted residue, and the mixture was extracted with AcOEt. The organic layer was washed with saturated brine, dried over anhydrous Na$_2$SO$_4$, filtered, and concentrated. DMF/H$_2$O=2:1 (600 mL) and AcONa (119 g) were added to the resulted residue at room temperature, and the mixture was stirred at 80° C. for 24 hours. The reaction solution was poured into ice water (2 L), and the mixture was filtered and washed with water. AcOEt and water were added to the resulted residue, and the mixture was extracted with AcOEt. The organic layer was washed with saturated brine, dried over anhydrous Na$_2$SO$_4$, filtered, and concentrated. The resulted residue was pulverized by addition of DCM (2 mL/g) and Hexane (2 mL/g). An insoluble substance was filtered to give tert-butyl 7-chloro-4,4-difluoro-5-hydroxy-5-(hydroxymethyl)-2,3,4,5-tetrahydro-$^1$H-1-benzazepine-1-carboxylate (29.4 g). The filtrate was concentrated, and the residue was purified by column chromatography (Hexane/AcOEt) to give tert-butyl 7-chloro-4,4-difluoro-5-hydroxy-5-(hydroxymethyl)-2,3,4,5-tetrahydro-$^1$H-1-benzazepine-1-carboxylate (4.82 g) and t-butyl 7-chloro-4,4-difluoro-1,2,3,4-tetrahydrospiro[1-benzazepin-5,2'-oxetane]-1-carboxylat e (18.38 g).

Reference Examples 171 and 172

A mixture of tert-butyl 7-chloro-4,4-difluoro-5-hydroxy-5-(hydroxymethyl)-2,3,4,5-tetrahydro-$^1$H-1-benzazepine-1-carboxylate (2.0 g), THF (20 mL), TEA (2.3 mL), DMAP (0.067 g), and N-(1-naphthalenesulfonyl)-L-phenylalanyl chloride (2.47 g) was stirred at room temperature for 2 hours. The reaction solution was concentrated under reduced pressure, and the resulted residue was purified by silica gel column chromatography (Hexane/AcOEt) to give tert-butyl (5S)-7-chloro-4,4-difluoro-5-hydroxy-5-({[(2S)-2-(naphthalene-1-sulfonamido)-3-phenylpropanoyl]oxy}methyl)-2, 3,4,5-tetrahydro-1H-1-benzazepine-1-carboxylate (1.56 g; Reference Example 171) for a high polarity product and tert-butyl (5R)-7-chloro-4,4-difluoro-5-hydroxy-5-({[(2S)-2-(naphthalene-1-sulfonamido)-3-phenylpropanoyl]oxy}methyl)-2,3,4,5-tetrahydro-1H-1-benzazepine-1-carboxylate (1.51 g; Reference Example 172) for a low polarity product.

Reference Example 174

To a solution of tert-butyl (5R)-7-chloro-4,4-difluoro-5-hydroxy-5-({[(2S)-2-(naphthalene-1-sulfonamido)-3-phenylpropanoyl]oxy}methyl)-2,3,4,5-tetrahydro-1H-1-benzazepine-1-carboxylate (1.3 g) in DCM (8.0 mL) was added TFA (2.143 mL) under nitrogen atmosphere. The resulting solution was stirred at room temperature for 1.5 hours. A saturated aqueous $NaHCO_3$ solution was added thereto, and the mixture was extracted with AcOEt. The combined organic layers were dried over $Na_2SO_4$, filtered, and concentrated under reduced pressure to give [(5R)-7-chloro-4,4-difluoro-5-hydroxy-2,3,4,5-tetrahydro-1H-1-benzazepin-5-yl]methyl (2S)-2-(naphthalene-1-sulfonamido)-3-phenylpropanoate (1.18 g, contained AcOEt ca. 0.9 eq.).

Reference Example 175

A mixture of [(5S)-7-chloro-4,4-difluoro-5-hydroxy-2,3,4,5-tetrahydro-1H-1-benzazepin-5-yl]methy l (2S)-2-(naphthalene-1-sulfonamido)-3-phenylpropanoate (827 mg), potassium trimethylsilanolate (784 mg), and THF (7.0 mL) was stirred at room temperature for 1 hour, and then concentrated under reduced pressure. The residue was purified by silica gel column chromatography (Hexane/AcOEt), and then dispersed and washed with a mixed solvent of DCM/Hexane to give (5S)-7-chloro-4,4-difluoro-5-(hydroxymethyl)-2,3,4,5-tetrahydro-1H-1-benzazepin-5-ol (257 mg).

Reference Example 176

A mixture of tert-butyl (5S)-7-chloro-4,4-difluoro-5-hydroxy-5-(hydroxymethyl)-2,3,4,5-tetrahydro-1H-1-benzazepine-1-carboxylate (0.97 g), EtOH (10 mL), and concentrated HCl (0.667 mL) was stirred at 70° C. for 1 hour. The reaction solution was concentrated under reduced pressure. AcOEt was added to the residue, and the mixture was further concentrated under reduced pressure to give (5S)-7-chloro-4,4-difluoro-5-(hydroxymethyl)-2,3,4,5-tetrahydro-1H-1-benzazepin-5-ol hydrochloride (820 mg).

Reference Example 177 tert-Butyl 7-chloro-4,4-difluoro-1,2,3,4-tetrahydrospiro[1-benzazepin-5,2'-oxetane]-1-carboxylat e (200 mg) and tetrabutylammonium sulfate (377 mg) were added to toluene/$H_2O$=1:1 (1 mL) at room temperature, and then the mixture was stirred at 100° C. for 1.5 days. The reaction mixture was purified by basic silica gel column chromatography (Hexane/AcOEt) to give 7-chloro-4,4-difluoro-5-(2-hydroxyethyl)-2,3,4,5-tetrahydro-1H-1-benzazepin-5-ol (122 mg).

Reference Example 178

To a solution of 7-chloro-4,4-difluoro-5-(2-hydroxyethyl)-2,3,4,5-tetrahydro-1H-1-benzazepin-5-ol (1.728 g) and Im (1.271 g) in DCM (30 mL) was added TBDMSCl (1.125 g) at 0° C. The mixture was stirred at room temperature for 10 minutes, and then diluted with water and extracted with AcOEt. The combined organic layer was dried over anhydrous $Na_2SO_4$, filtered, and concentrated. The resulted residue was purified by column chromatography (Hexane/AcOEt) to give 5-{2-[(tert-butyldimethylsilyl)oxy]ethyl}-7-chloro-4,4-difluoro-2,3,4,5-tetrahydro-1H-1-benzazepin-5-ol (2.016 g).

Reference Example 179

To a solution of 7-chloro-4,4-difluoro-1-(4-methylbenzenesulfonyl)-1,2,3,4-tetrahydrospiro[1-benzazepin-5,2'-oxirane] (8 g) in DMF:$H_2O$=4:1 (50 mL) was added $NaN_3$ (6.50 g) under nitrogen atmosphere at room temperature. The mixture was stirred at 70° C. for 4 hours, and then water was added thereto. The precipitated crystal was filtered and washed with water. The resultant was washed with IPA to give 5-(azidomethyl)-7-chloro-4,4-difluoro-1-(4-methylbenzenesulfonyl)-2,3,4,5-tetrahydro-1H-1-benzazepin-5-ol (quantitative yield).

Reference Example 180

To a solution of 5-(azidomethyl)-7-chloro-4,4-difluoro-1-(4-methylbenzenesulfonyl)-2,3,4,5-tetrahydro-1H-1-benzazepin-5-ol (9.8 g) in EtOH (80 mL) was added Zn powder (5.79 g) at room temperature under nitrogen atmosphere, and the mixture was stirred at the same temperature for 30 minutes. The reaction mixture was filtered and the filtrate was concentrated. The resulted crude product was dried in vacuo. $Boc_2O$ (6.10 mL) was added to a solution of the resultant in THF (80 mL), and the mixture was stirred under nitrogen atmosphere at room temperature for 30 minutes. The reaction solution was concentrated and the resulted residue was purified by column chromatography (Hexane/AcOEt) to give tert-butyl N-{[7-chloro-4,4-difluoro-5-hydroxy-1-(4-methylbenzenesulfonyl)-2,3,4,5-tetrahydro-1H-1-benzazepin-5-yl]methyl}carbamate (6.92 g).

Reference Example 181

To a solution of tert-butyl N-{[7-chloro-4,4-difluoro-5-hydroxy-1-(4-methylbenzenesulfonyl)-2,3,4,5-tetrahydro-1H-1-benzazepin-5-yl]methyl}carbamate (6.92 g) in MeOH (80 mL) were added iodine (3.40 mg) and magnesium (3.7 g) under nitrogen atmosphere, and the mixture was refluxed for 3 hours. 1N HCl (294 mL) was added to the reaction solution, and the reaction solution was extracted with AcOEt. The combined organic layer was dried over anhydrous $Na_2SO_4$, filtered, and concentrated. The resulted residue was purified by column chromatography (Hexane/AcOEt) to give tert-butyl N-[(7-chloro-4,4-difluoro-5-hydroxy-2,3,4,5-tetrahydro-1H-1-benzazepin-5-yl)methyl]carbamate (4.05 g).

Reference Example 182

To a solution of 4-(2-chloro-5-fluorobenzamido)-3-methoxybenzoic acid (1.338 g) in DMA (15 mL) was added $SOCl_2$ (0.316 mL) under nitrogen atmosphere at room temperature, and the mixture was stirred for 2 hours. tert-Butyl N-[(7-chloro-4,4-difluoro-5-hydroxy-2,3,4,5-tetrahydro-1H-1-benzazepin-5-yl)methyl]carbamate (1 g) was added thereto at room temperature, and the mixture was stirred for 1 day. Saturated aqueous $NaHCO_3$ solution was added thereto, and the precipitated solid was filtered and washed with water. The resulted crude crystal was purified by column chromatography (Hexane/AcOEt) to give tert-butyl N-({7-chloro-1-[4-(2-chloro-5-fluorobenzamido)-3-methoxybenzoyl]-4,4-difluoro-5-hydroxy-2,3,4,5-tetrahydro-1H-1-benzazepin-5-yl}methyl)carbamate (1.73 g; including ca. 0.7 eq. of AcOEt).

Reference Example 183

To a solution of tert-butyl (5S)-7-chloro-4,4-difluoro-5-hydroxy-5-(hydroxymethyl)-2,3,4,5-tetrahydro-1H-1-benzazepine-1-carboxylate (515 mg) in anhydrous THF (5.0 mL) was added 55% NaH (154 mg) under nitrogen atmosphere under ice cooling. TsCl (283 mg) was added to the reaction solution at the same temperature, and the mixture was stirred at room temperature for 2 hours. 1N aqueous NaOH solution was added to the reaction solution, and the mixture was extracted with AcOEt. The organic layer was dried over anhydrous $Na_2SO_4$, and then filtered. The filtrate was concentrated under reduced pressure, and the residue was purified by silica gel column chromatography (Hexane/AcOEt) to give tert-butyl (5S)-7-chloro-4,4-difluoro-1,2,3,4-tetrahydrospiro[1-benzazepin-5,2'-oxirane]-1-carboxylate (371 mg).

Reference Example 185

A mixture of tert-butyl (5S)-7-chloro-4,4-difluoro-1,2,3,4-tetrahydrospiro[1-benzazepin-5,2'-oxirane]-1-carboxylate (371 mg), EtOH (5.5 mL), and $NaBH_4$ (81 mg) was stirred at 50° C. for 6 hours. Water was added to the reaction solution, and the mixture was extracted with AcOEt. The organic layer was dried over anhydrous $Na_2SO_4$, and then filtered. The filtrate was concentrated under reduced pressure, and the residue was purified by silica gel column chromatography (Hexane/AcOEt) to give tert-butyl (5R)-7-chloro-4,4-difluoro-5-hydroxy-5-methyl-2,3,4,5-tetrahydro-1H-1-benzazepine-1-carboxylate (334 mg).

Reference Example 187

A mixture of tert-butyl (5R)-7-chloro-4,4-difluoro-5-hydroxy-5-methyl-2,3,4,5-tetrahydro-1H-1-benzazepine-1-carboxylate (334 mg), DCM (4.0 mL), and TFA (0.740 mL) was stirred for 1 hour. The reaction solution was neutralized with saturated sodium bicarbonate water and extracted with AcOEt. The organic layer was dried over anhydrous $Na_2SO_4$, and then filtered. The filtrate was concentrated under reduced pressure, and the residue was purified by silica gel column chromatography (Hexane/AcOEt) to give (5R)-7-chloro-4,4-difluoro-5-methyl-2,3,4,5-tetrahydro-1H-1-benzazepin-5-ol (183 mg).

Reference Example 189

To a solution of 2-chloro-N-{5-[7-chloro-4,4-difluoro-5-hydroxy-5-(hydroxymethyl)-2,3,4,5-tetrahydro-1H-1-benzazepine-1-carbonyl]pyridin-2-yl}-5-fluorobenzamide (820 mg) in DCM (5 mL) were added TMPDA (0.736 mL) and TsCl (337 mg) at 0° C. The mixture was stirred at 0° C. for 6 hours, and then sodium bicarbonate water was added thereto, and the mixture was extracted with AcOEt, dried over anhydrous $Na_2SO_4$, filtered, and concentrated to give N-[5-({7-chloro-4,4-difluoro-1,2,3,4-tetrahydrospiro[1-benzazepin-5,2'-oxiran]-1-yl}carbonyl)pyridin-2-yl]-2-(trifluoromethyl)benzamide (882 mg).

Reference Example 190

A suspension of pentamethylcyclopentadienyliridium (III) chloride dimer (0.829 g) and N-((1R,2R)-2-amino-1,2-diphenylethyl)-2,3,4,5,6-pentafluorobenzenesulfonamide (1.48 g) in water (800 mL) was stirred under nitrogen atmosphere at 50° C. for 4 hours. The suspension was cooled, and then $HCO_2Na$ (198 g) was added thereto, and the mixture was stirred at room temperature for 1 hour. The mixture was cooled to 0° C., and DCM (500 mL) and 7-chloro-4,4-difluoro-2,3,4,5-tetrahydro-1H-1-benzazepin-5-one (225 g) were sequentially added thereto, and the mixture was stirred at 0° C. overnight. The DCM layer was separated and concentrated to give (5R)-7-chloro-4,4-difluoro-1-(4-methylbenzenesulfonyl)-2,3,4,5-tetrahydro-1H-1-benzazepin-5-ol (228 g).

Reference Example 191

To a solution of (5R)-7-chloro-4,4-difluoro-1-(4-methylbenzenesulfonyl)-2,3,4,5-tetrahydro-1H-1-benzazepin-5-ol (284 g) in MeOH (1 L) was added magnesium (17.80 g) at room temperature, and the mixture was stirred with heating at 70° C. AcOEt (1 L) was added to the reaction solution, and the mixture was stirred. The reaction solution was slowly poured into a mixed solution of 5N HCl (1.465 L), water (500 mL), and AcOEt (1 L), and the mixture was stirred. The mixture was extracted with AcOEt after solids were dissolved. The organic layer was washed with saturated sodium bicarbonate water, dried over anhydrous $MgSO_4$, and filtered. The filtrate was concentrated. Hexane (1 L) and $Et_2O$ (300 mL) were added to the concentrate, and the mixture was heated to reflux and dispersed and washed. The resultant was directly filtered under hot filtration to give a powder, and the powder was dried to give (5R)-7-chloro-4,4-difluoro-2,3,4,5-tetrahydro-1H-1-benzazepin-5-ol (119 g).

Reference Example 192

To a solution of 6-[2-(trifluoromethyl)benzamido]pyridine-3-carboxylic acid (2.280 g) in DMA (40 mL) was added $SOCl_2$ (1.0 mL), and the mixture was stirred at room temperature overnight. Then, thereto was added a solution of (5R)-7-chloro-4,4-difluoro-2,3,4,5-tetrahydro-1H-1-benzazepin-5-ol (1.145 g) in DMA (20 mL), and the mixture was stirred at room temperature overnight. AcOEt and water were added thereto, and the mixture was extracted with AcOEt, washed with saturated sodium bicarbonate water and saturated brine, filtered, and concentrated. Then, the residue was purified by medium-pressure column chromatography (Hexane/AcOEt). The resulted crude crystal was recrystallized from AcOEt/Hexane to give (5R)—N-{5-[(5R)-7-chloro-4,4-difluoro-5-hydroxy-2,3,4,5-tetrahydro-1H-1-benzazepine-1-carbonyl]pyridin-2-yl}-2-(trifluoromethyl)benzamide (1.2 g).

Reference Example 195

To a solution of 6-{[1,1'-biphenyl]-2-amido}pyridine-3-carboxylic acid (440 mg) in DMA (20 mL) was added dropwise $SOCl_2$ (0.104 mL) in a water bath. The mixture was stirred at the same temperature for 40 minutes, and then thereto was added a solution of (5R)-7-chloro-4,4-difluoro-2,3,4,5-tetrahydro-1H-1-benzazepin-5-ol (323 mg) in DMA (3 mL). The mixture was stirred for 2 hours, and then aqueous $NaHCO_3$ solution was added thereto, and the mixture was extracted with AcOEt/Hexane (10/1). The combined organic layer was washed with water and dried over anhydrous MgSO$_4$, filtered, and concentrated. The resulted residue was purified by column chromatography (Hexane/AcOEt), crystallized from acetone-hexane, and the crystal was filtered and washed with Et$_2$O/hexane (1/20) to give N-{5-[(5R)-7-chloro-4,4-difluoro-5-hydroxy-2,3,4,5-tetrahydro-1H-1-benzazepine-1-carbonyl]pyridin-2-yl}-[1,1'-biphenyl]-2-carboxamide (390 mg).

Reference Example 196

To a solution of 4-(2-chloro-5-fluorobenzamido)benzoic acid (264 mg) in DMA (3.0 mL) was added SOCl$_2$ (75 μL), and the mixture was stirred at room temperature for 30 minutes. Then, thereto was added (5R)-7-chloro-4,4-difluoro-2,3,4,5-tetrahydro-1H-1-benzazepin-5-ol (200 mg) at 0° C., and the mixture was stirred for 4 hours. Then, saturated aqueous NaHCO$_3$ solution was added thereto, and the mixture was extracted with AcOEt. The organic layer was dried over anhydrous Na$_2$SO$_4$, filtered, and concentrated. The resulted residue was purified by column chromatography (Hexane/AcOEt) and crystallized from AcOEt/Hexane to give 2-chloro-N-{4-[(5R)-7-chloro-4,4-difluoro-5-hydroxy-2,3,4,5-tetrahydro-1H-1-benzazepine-1-carbonyl]phenyl}-5-fluorobenzamide (374.4 mg).

Reference Example 199

To a solution of 6-{4-fluoro-[1,1'-biphenyl]-2-amido}pyridine-3-carboxylic acid (360 mg) in DMA (4.0 mL) was added SOCl$_2$ (86.0 μL) under nitrogen atmosphere under ice cooling, and the mixture was stirred at the same temperature for 2 hours. Then, (5R)-7-chloro-4,4-difluoro-2,3,4,5-tetrahydro-1H-1-benzazepin-5-ol (250 mg) was added thereto at the same temperature, and the mixture was stirred at room temperature for 3 days. Saturated sodium bicarbonate water was added to the reaction solution, and the mixture was extracted with AcOEt. The organic layer was washed with 1N aqueous NaOH solution and saturated brine, and then dried over Na$_2$SO$_4$. Na$_2$SO$_4$ was filtered, and the filtrate was concentrated under reduced pressure and the resulted residue was purified by silica gel column chromatography (Hexane/AcOEt) to give N-{5-[(5R)-7-chloro-4,4-difluoro-5-hydroxy-2,3,4,5-tetrahydro-1H-1-benzazepine-1-carbonyl]pyridin-2-yl}-4-fluoro-[1,1'-biphenyl]-2-carboxamide (429 mg).

Reference Example 201

4-{4-Fluoro-[1,1'-biphenyl]-2-amido}benzoic acid (746 mg) was dissolved in DMA (10 mL), and thereto was added SOCl$_2$ (0.187 mL), and the mixture was stirred at room temperature for 2 hours. (5R)-7-Chloro-4,4-difluoro-2,3,4,5-tetrahydro-1H-1-benzazepin-5-ol (400 mg) was added to the reaction solution, and the mixture was stirred at room temperature for 15 hours. 1N Aqueous NaOH solution was added to the reaction solution, and the mixture was extracted with AcOEt. The organic layer was washed with 1N aqueous NaOH solution and brine, dried over anhydrous Na$_2$SO$_4$, and concentrated. The residue was purified by column chromatography (Hexane/AcOEt) to give N-{4-[(5R)-7-chloro-4,4-difluoro-5-hydroxy-2,3,4,5-tetrahydro-1H-1-benzazepine-1-carbonyl]phenyl}-4-fluoro-[1,1'-biphenyl]-2-carboxamide (940 mg).

EXAMPLE

Example 1

To a solution of 6-(2-chlorobenzamido)pyridine-3-carboxylic acid (113 mg) in DMA (1.0 mL) was added SOCl$_2$ (30.0 μL) under nitrogen atmosphere under ice cooling, and the mixture was stirred at the same temperature for 2 hours. 7-Chloro-4,4-difluoro-5-(hydroxymethyl)-2,3,4,5-tetrahydro-1H-1-benzazepin-5-ol (90.0 mg) was added thereto at the same temperature, and the mixture was stirred at room temperature for 3 days. Saturated aqueous NaHCO$_3$ solution and water were added to the reaction solution, and the precipitate was filtered and purified by basic silica gel column chromatography (Hexane/AcOEt) to give 2-chloro-N-{5-[7-chloro-4,4-difluoro-5-hydroxy-5-(hydroxymethyl)-2,3,4,5-tetrahydro-1H-1-benzazepine-1-carbonyl]pyridin-2-yl}benzamide (50.0 mg).

Example 2

To a solution of 6-[2-(trifluoromethyl)benzamido]pyridine-3-carboxylic acid (164 mg) in DMA (2 mL) was added SOCl$_2$ (38 μL), and the mixture was stirred at 0° C. for 2 hours under nitrogen atmosphere, and then 5-{[(tert-butyldimethylsilyl)oxy]methyl}-7-chloro-4,4-difluoro-2,3,4,5-tetrahydro-1H-1-benzazepin-5-ol (100 mg) was added thereto at 0° C. The mixture was stirred at room temperature for 3 days, and then saturated aqueous NaHCO$_3$ solution was added thereto. The precipitated solid was filtered and washed with water. Solids were dissolved in THF (2 mL), and a 1M solution of TBAF in THF (0.529 mL) was added thereto, and the mixture was stirred for 2 hours under nitrogen atmosphere. Water was added thereto, and the mixture was extracted with AcOEt. The organic layer was dried over anhydrous Na$_2$SO$_4$, filtered, and concentrated. The resulted residue was purified by column chromatography (Hexane/AcOEt) and recrystallized from EtOH to give N-{5-[7-chloro-4,4-difluoro-5-hydroxy-5-(hydroxymethyl)-2,3,4,5-tetrahydro-1H-1-benzazepine-1-carbonyl]pyridin-2-yl}-2-(trifluoromethyl)benzamide (86 mg).

Example 3

To a solution of 6-(2-chloro-5-fluorobenzamido)pyridine-3-carboxylic acid (654 mg) in DMA (7 mL) was added SOCl$_2$ (0.161 mL), and the mixture was stirred at 0° C. for 2 hours under nitrogen atmosphere. 7-Chloro-4,4-difluoro-5-(hydroxymethyl)-2,3,4,5-tetrahydro-1H-1-benzazepin-5-ol (450 mg) was added thereto at 0° C., and the mixture was stirred at room temperature for 18 hours. Saturated aqueous NaHCO$_3$ solution was added thereto, and the precipitated solid was washed with water and purified by column chromatography (Hexane/AcOEt) to give 2-chloro-N-{5-[7-chloro-4,4-difluoro-5-hydroxy-5-(hydroxymethyl)-2,3,4,5-tetrahydro-1H-1-benzazepine-1-carbonyl]pyridin-2-yl}-5-fluorobenzamide (740 mg).

Example 8

To a solution of 6-[2-(trifluoromethyl)benzamido]pyridine-3-carboxylic acid (651 mg) in DMA (7.0 mL) was added SOCl$_2$ (152 μL) under nitrogen atmosphere under ice cooling, and the mixture was stirred at the same temperature for 2 hours. 7-Chloro-4,4-difluoro-5-methyl-2,3,4,5-tetrahydro-1H-1-benzazepin-5-ol (400 mg) was added thereto at the same temperature, and the mixture was stirred at room temperature for 2.5 days. Saturated aqueous NaHCO₃ solution and water were added to the reaction solution. The precipitate was filtered and washed with water, and then purified by basic silica gel column chromatography (Hexane/AcOEt) and recrystallization (Hexane/AcOEt) to give N-[5-(7-chloro-4,4-difluoro-5-hydroxy-5-methyl-2,3,4,5-tetrahydro-1H-1-benzazepine-1-carbonyl)pyridin-2-yl]-2-(trifluoromethyl)benzamide (836 mg).

Example 13

To a solution of 6-(2-trifluorobenzamide)nicotinic acid (549 mg) in DMA (6 mL) was added SOCl₂ (0.128 mL) under nitrogen atmosphere under ice cooling, and the mixture was stirred at room temperature for 2 hours. Then, (5R)-7-chloro-4,4-difluoro-5-(hydroxymethyl)-2,3,4,5-tetrahydro-1H-1-benzazepin-5-ol (500 mg) was added thereto at room temperature, and the mixture was stirred for 3 days. Saturated aqueous NaHCO₃ solution and water were added to the reaction solution, and the precipitate was filtered. The resulted solid was mixed with ethanol (10 mL) and 5N aqueous NaOH solution (0.885 mL), and the mixture was stirred at room temperature for 30 minutes. The reaction solution was neutralized by addition of ice water and 5N HCl, and the precipitate was filtered and washed with water. The resulted solid was purified by basic silica gel column chromatography (Hexane/AcOEt) to give N-{5-[(5R)-7-chloro-4,4-difluoro-5-hydroxy-5-(hydroxymethyl)-2,3,4,5-tetrahydro-1H-1-benzazepine-1-carbonyl]pyridin-2-yl}-2-(trifluoromethyl)benzamide (400 mg).

Example 14

To a solution of 6-(2-chloro-5-fluorobenzamido)pyridine-3-carboxylic acid (160 mg) in DMA (2.0 mL) was added SOCl₂ (39 μL) under nitrogen atmosphere under ice cooling, and the mixture was stirred at the same temperature for 2 hours. Then, (5S)-7-chloro-4,4-difluoro-5-(hydroxymethyl)-2,3,4,5-tetrahydro-1H-benzo[b]azepin-5-ol (110 mg) was added thereto at the same temperature, and the mixture was stirred at room temperature for 3 hours. Saturated aqueous NaHCO₃ solution and water were added to the reaction solution, and the precipitate was filtered and purified by basic silica gel column chromatography (Hexane/AcOEt/MeOH) to give 2-chloro-N-{5-[(5 S)-7-chloro-4,4-difluoro-5-hydroxy-5-(hydroxymethyl)-2,3,4,5-tetrahydro-1H-1-benzazepine-1-carbonyl]pyridin-2-yl}-5-fluorobenzamide (156 mg).

Example 15

To a solution of 6-(2-chloro-5-fluorobenzamido)pyridine-3-carboxylic acid (203 mg) in DMA (2.5 mL) was added SOCl₂ (50 μL) under nitrogen atmosphere at 0° C., and the mixture was stirred for 2 hours. Then, (5R)-7-chloro-4,4-difluoro-5-(hydroxymethyl)-2,3,4,5-tetrahydro-1H-1-benzazepin-5-ol (140 mg) was added thereto at 0° C., and the mixture was stirred at room temperature for 3 hours. Saturated aqueous NaHCO₃ solution was added thereto. The precipitated crystal was filtered, washed with water, and purified by basic silica gel column chromatography (Hexane/AcOEt/MeOH) and recrystallization (Hexane/AcOEt) to give 2-chloro-N-{5-[(5R)-7-chloro-4,4-difluoro-5-hydroxy-5-(hydroxymethyl)-2,3,4,5-tetrahydro-1H-1-benzazepine-1-carbonyl]pyridin-2-yl}-5-fluorobenzamide (202 mg).

Example 16

To a solution of 6-[2-(trifluoromethyl)benzamido]pyridine-3-carboxylic acid (581 mg) in DMA (5.0 mL) was added SOCl₂ (136 μL) under nitrogen atmosphere under ice cooling, and the mixture was stirred at the same temperature for 2 hours. Then, 7-chloro-4,4-difluoro-5-(hydroxyethyl)-2,3,4,5-tetrahydro-1H-1-benzazepin-5-ol (400 mg) was added thereto at the same temperature, and the mixture was stirred at room temperature for 3 hours. Saturated aqueous NaHCO₃ solution and water were added to the reaction solution, and the precipitate was filtered and then purified by basic silica gel column chromatography (Hexane/AcOEt) to give N-{5-[7-chloro-4,4-difluoro-5-hydroxy-5-(2-hydroxyethyl)-2,3,4,5-tetrahydro-1H-1-benzazepine-1-carbonyl]pyridin-2-yl}-2-(trifluoromethyl)benzamide (53 mg).

Example 17

To a solution of 6-(2-chlorobenzamido)pyridine-3-carboxylic acid (248 mg) in DMA (1.5 mL) was added SOCl₂ (65.0 μL) under nitrogen atmosphere under ice cooling, and the mixture was stirred at the same temperature for 2 hours. Then, [(5R)-7-chloro-4,4-difluoro-5-hydroxy-2,3,4,5-tetrahydro-1H-1-benzazepin-5-yl]methyl 4-bromobenzoate (400 mg) was added thereto at the same temperature, and the mixture was stirred at room temperature for 1 day. Saturated aqueous NaHCO₃ solution and water were added to the reaction solution, and the precipitate was filtered. Ethanol (2.0 mL) and 5N aqueous NaOH solution (0.448 mL) were added to the resulted solid, and the mixture was stirred at room temperature for 20 minutes. The reaction solution was neutralized by addition of ice water and 5N HCl, and the precipitate was filtered and washed with water. The resulted solid was purified by silica gel column chromatography (Hexane/AcOEt) and recrystallization (Hexane/AcOEt) to give 2-chloro-N-{5-[(5R)-7-chloro-4,4-difluoro-5-hydroxy-5-(hydroxymethyl)-2,3,4,5-tetrahydro-1H-1-benzazepine-1-carbonyl]pyridin-2-yl}benzamide (200 mg).

Example 19

6-(2,3-Dichlorobenzamido)pyridine-3-carboxylic acid (153 mg) was dissolved in DMA (1 mL), and then, SOCl₂ (42 μL) was added thereto under ice cooling. The mixture was stirred for 30 minutes. Then, (5R)-7-chloro-4,4-difluoro-5-(hydroxymethyl)-2,3,4,5-tetrahydro-1H-1-benzazepin-5-ol (100 mg) was added thereto, and the mixture was stirred at room temperature overnight. Saturated aqueous NaHCO₃ solution was added thereto, and the mixture was extracted with AcOEt. The organic layer was washed with brine, dried over anhydrous Na₂SO₄, filtered and then concentrated. The residue was purified by column chromatography (Hexane/AcOEt), crystallized from Hexane/AcOEt, and filtered to give 2,3-dichloro-N-{5-[(5R)-7-chloro-4,4-difluoro-5-hydroxy-5-(hydroxymethyl)-2,3,4,5-tetrahydro-1H-1-benzazepine-1-carbonyl]pyridin-2-yl}benzamide (135 mg).

Example 21

4-[2-(Trifluoromethyl)benzamido]benzoic acid (152 mg) was dissolved in DMA (2 mL), and then, SOCl₂ (42 μL) was added thereto. The mixture was stirred at room temperature for 2.5 hours. Then, (5R)-7-chloro-4,4-difluoro-5-(hydroxymethyl)-2,3,4,5-tetrahydro-1H-1-benzazepin-5-ol (100 mg) was added thereto, and the mixture was stirred at room temperature for 3 hours. The mixture was diluted with AcOEt, and water was added thereto. The mixture was extracted with AcOEt/Hexane. The organic layer was washed with 1N HCl, 1N NaOH, and saturated brine, and dried over anhydrous $Na_2SO_4$. $Na_2SO_4$ was filtered, and the filtrate was concentrated under reduced pressure. Then, the resulted residue was purified by column chromatography (AcOEt/Hexane, followed by AcOEt/MeOH) and concentrated to give a crystal. The crystal was dispersed and washed with AcOEt/Hexane and filtered. The resultant was dried in vacuo at 60° C. to give N-{4-[(5R)-7-chloro-4,4-difluoro-5-hydroxy-5-(hydroxymethyl)-2,3,4,5-tetrahydro-1H-1-benzazepine-1-carbonyl]phenyl}-2-(trifluoromethyl)benzamide (135.8 mg).

Example 23

4-(2-Chloro-5-fluorobenzamido)benzoic acid (145 mg) was dissolved in DMA (2 mL), and then $SOCl_2$ (42 µL) was added thereto. The mixture was stirred at room temperature for 2.5 hours. Then, (5R)-7-chloro-4,4-difluoro-5-(hydroxymethyl)-2,3,4,5-tetrahydro-1H-1-benzazepin-5-ol (100 mg) was added thereto, and the mixture was stirred at room temperature for 3 hours. The mixture was diluted with AcOEt, and water was added thereto. The mixture was extracted with AcOEt/Hexane. The organic layer was washed with 1N HCl, 1N NaOH, and saturated brine, dried over anhydrous $Na_2SO_4$, and then filtered. The filtrate was concentrated under reduced pressure. The residue was purified by column chromatography (AcOEt/Hexane, followed by AcOEt/MeOH) and concentrated to give a crystal. The crystal was dispersed and washed with AcOEt/Hexane and filtered. The resultant was dried in vacuo at 60° C. to give 2-chloro-N-{4-[(5R)-7-chloro-4,4-difluoro-5-hydroxy-5-(hydroxymethyl)-2,3,4,5-tetrahydro-1H-1-benzazepine-1-carbonyl]phenyl}-5-fluorobenzamide (124.7 mg).

Example 24

4-(2-Chloro-5-fluorobenzamido)-3-fluorobenzoic acid (154 mg) was dissolved in DMA (2 mL), and then $SOCl_2$ (42 µL) was added thereto. The mixture was stirred at room temperature for 2.5 hours. Then, (5R)-7-chloro-4,4-difluoro-5-(hydroxymethyl)-2,3,4,5-tetrahydro-1H-1-benzazepin-5-ol (100 mg) was added thereto, and the mixture was stirred at room temperature for 3 hours. The mixture was diluted with AcOEt, and water was added thereto. The mixture was extracted with AcOEt/Hexane and washed with 1N HCl, 1N NaOH, and saturated brine. The organic layer was dried over anhydrous $Na_2SO_4$, and then filtered. The filtrate was concentrated under reduced pressure. The residue was purified by column chromatography (AcOEt/Hexane, followed by AcOEt/MeOH) and concentrated to give a crystal. The crystal was dispersed and washed with AcOEt/Hexane and filtered. The resultant was dried in vacuo at 60° C. to give 2-chloro-N-{4-[(5R)-7-chloro-4,4-difluoro-5-hydroxy-5-(hydroxymethyl)-2,3,4,5-tetrahydro-1H-1-benzazepine-1-carbonyl]-2-fluorophenyl}-5-fluorobenzamide (114.9 mg).

Example 25

4-(2,5-Dichlorobenzamido)benzoic acid (153 mg) was dissolved in DMA (2 mL), and then $SOCl_2$ (42 µL) was added thereto. The mixture was stirred at room temperature for 2.5 hours. Then, (5R)-7-chloro-4,4-difluoro-5-(hydroxymethyl)-2,3,4,5-tetrahydro-1H-1-benzazepin-5-ol (100 mg) was added thereto, and the mixture was stirred at room temperature for 3 hours. The mixture was extracted with AcOEt and water was added thereto. The mixture was extracted with AcOEt/Hexane. The organic layer was washed with 1N HCl, 1N NaOH, and saturated brine, dried over anhydrous $Na_2SO_4$, and then filtered. The filtrate was concentrated under reduced pressure. The residue was purified by column chromatography (AcOEt/Hexane, followed by AcOEt/MeOH). After concentration, the concentrate was dried in vacuo, and the resulted amorphous substance was dried in vacuo at 60° C. to give 2,5-dichloro-N-{4-[(5R)-7-chloro-4,4-difluoro-5-hydroxy-5-(hydroxymethyl)-2,3,4,5-tetrahydro-1H-1-benzazepine-1-carbonyl]phenyl} benzamide (95.8 mg).

Example 26

4-(2,5-Dichlorobenzamido)-3-fluorobenzoic acid (162 mg) was dissolved in DMA (2 mL), and $SOCl_2$ (42 µL) was added thereto. The mixture was stirred at room temperature for 2.5 hours. Then, (5R)-7-chloro-4,4-difluoro-5-(hydroxymethyl)-2,3,4,5-tetrahydro-1H-1-benzazepin-5-ol (100 mg) was added thereto, and the mixture was stirred at room temperature for 3 hours. The mixture was diluted with AcOEt and water was added thereto. The mixture was extracted with AcOEt/Hexane. The organic layer was washed with 1N HCl, 1N NaOH, and saturated brine, dried over anhydrous $Na_2SO_4$, and then filtered. The filtrate was concentrated under reduced pressure. The residue was purified by column chromatography (AcOEt/Hexane, followed by AcOEt/MeOH). After concentration, the concentrate was dried in vacuo, and the resulted amorphous substance was dried in vacuo at 60° C. to give 2,5-dichloro-N-{4-[(5R)-7-chloro-4,4-difluoro-5-hydroxy-5-(hydroxymethyl)-2,3,4,5-tetrahydro-1H-1-benzazepine-1-carbonyl]-2-fluorophenyl}benzamide (154 mg).

Example 33

6-(2,3-Dichlorobenzamido)pyridine-3-carboxylic acid (124 mg) was dissolved in DMA (1 mL), and the solution was cooled under ice. Then, $SOCl_2$ (34 µL) was added thereto, and the mixture was stirred for 30 minutes. Then, (5S)-7-chloro-4,4-difluoro-5-(hydroxymethyl)-2,3,4,5-tetrahydro-1H-1-benzazepin-5-ol hydrochloride (100 mg) was added thereto, and the mixture was stirred at room temperature for 2 hours. Saturated aqueous $NaHCO_3$ solution was added thereto, and the mixture was extracted with AcOEt. The organic layer was washed with brine, dried over anhydrous $Na_2SO_4$, filtered, and then concentrated. The residue was purified by column chromatography (Hexane/AcOEt), crystallized from Hexane/AcOEt, and filtered to give 2,3-dichloro-N-{5-[(5S)-7-chloro-4,4-difluoro-5-hydroxy-5-(hydroxymethyl)-2,3,4,5-tetrahydro-1H-1-benzazepine-1-carbonyl]pyridin-2-yl}benzamide (120 mg).

Example 34

To a solution of 4-(2-chloro-5-fluorobenzamido)-3-methoxybenzoic acid (459 mg) in DMA (6.0 mL) was added $SOCl_2$ (120 µL) under nitrogen atmosphere under ice cooling, and the mixture was stirred at the same temperature for 2 hours. Then, 5-(2-(tert-butyldimethylsilyloxy)ethyl)-7-chloro-4,4-difluoro-2,3,4,5-tetrahydro-1H-benzo[b]azepin-5-ol (500 mg) was added thereto at the same temperature, and the mixture was stirred at room temperature for 1 day. In another reaction vessel, $SOCl_2$ (120 µL) was added to a solution of 4-(2-chloro-5-fluorobenzamido)-3-methoxybenzoic acid (459 mg) in DMA (6.0 mL) under nitrogen atmosphere under ice cooling, and the mixture was stirred at the same temperature for 2 hours. The mixture was added to the reaction solution at room temperature, and the mixture was stirred for 1 day. Saturated aqueous NaHCO$_3$ solution and water were added to the reaction solution, and the precipitate was filtered. 1M TBAF/THF solution (2.55 mL) was added to a solution of the resulted solid in THF (4.0 mL), and the mixture was stirred at room temperature for 1 hour. Water was added to the reaction solution, and the mixture was extracted with AcOEt. The organic layer was washed with saturated brine, dried over anhydrous Na$_2$SO$_4$, and then filtered. The filtrate was concentrated under reduced pressure. The residue was purified by column chromatography (Hexane/AcOEt/MeOH) and recrystallization (Hexane/AcOEt) to give 2-chloro-N-{4-[7-chloro-4,4-difluoro-5-hydroxy-5-(2-hydroxyethyl)-2,3,4,5-tetrahydro-1H-1-benzazepine-1-carbonyl]-2-methoxyphenyl}-5-fluorobenzamide (205 mg).

Example 37

To a solution of 4-(5-fluoro-2-methylbenzamido)benzoic acid (162 mg) in DMA (2.5 mL) was added SOCl$_2$ (43.0 µL) under nitrogen atmosphere under ice cooling, and the mixture was stirred at the same temperature for 2 hours. Then, (5R)-7-chloro-4,4-difluoro-5-(hydroxymethyl)-2,3,4,5-tetrahydro-1H-1-benzazepin-5-ol (120 mg) was added thereto at the same temperature, and the mixture was stirred at room temperature for 1 day. Saturated aqueous NaHCO$_3$ solution and water were added to the reaction solution, and the precipitate was filtered and purified by basic silica gel column chromatography (Hexane/AcOEt/MeOH) to give N-{4-[(5R)-7-chloro-4,4-difluoro-5-hydroxy-5-(hydroxymethyl)-2,3,4,5-tetrahydro-1H-1-benzazepine-1-carbonyl]phenyl}-5-fluoro-2-methylbenzamide (159 mg).

Example 51

6-(2,4-Dichlorobenzamido)pyridine-3-carboxylic acid (165 mg) was dissolved in DMA (2 mL), and then SOCl$_2$ (44 µL) was added thereto. The mixture was stirred at room temperature. After the mixture was stirred for 2 hours, (5R)-7-chloro-4,4-difluoro-5-(hydroxymethyl)-2,3,4,5-tetrahydro-1H-1-benzazepin-5-ol (100 mg) was added thereto, and the mixture was stirred overnight. The mixture was diluted with AcOEt, and then water was added thereto. The mixture was extracted with AcOEt/Hexane, washed with 1N HCl, 1N NaOH, and saturated brine, dried over anhydrous Na$_2$SO$_4$, and then filtered. The filtrate was concentrated under reduced pressure. The residue was purified by column chromatography (AcOEt/Hexane, followed by AcOEt/MeOH). After concentration, the concentrate was dried in vacuo, and the resulted amorphous substance was dried in vacuo at 60° C. to give 2,4-dichloro-N-{5-[(5R)-7-chloro-4,4-difluoro-5-hydroxy-5-(hydroxymethyl)-2,3,4,5-tetrahydro-1H-1-benzazepine-1-carbonyl]pyridin-2-yl}benzamide (80.5 mg).

Example 52

6-(2,4-Dichloro-5-fluorobenzamido)pyridine-3-carboxylic acid (175 mg) was dissolved in DMA (2 mL), and then SOCl$_2$ (44 µL) was added thereto. The mixture was stirred at room temperature. After 2 hours, (5R)-7-chloro-4,4-difluoro-5-(hydroxymethyl)-2,3,4,5-tetrahydro-1H-1-benzazepin-5-ol (100 mg) was added thereto, and the mixture was stirred overnight. The mixture was diluted with AcOEt, and then water was added thereto. The mixture was extracted with AcOEt/Hexane. The organic layer was washed with 1N HCl, 1N NaOH, and saturated brine, dried over anhydrous Na$_2$SO$_4$, and then filtered. The filtrate was concentrated under reduced pressure. The residue was purified by column chromatography (AcOEt/Hexane, followed by AcOEt/MeOH). After concentration, the concentrate was dried in vacuo, and the resulted amorphous substance was dried in vacuo at 60° C. to give 2,4-dichloro-N-{5-[(5R)-7-chloro-4,4-difluoro-5-hydroxy-5-(hydroxymethyl)-2,3,4,5-tetrahydro-1H-1-benzazepine-1-carbonyl]pyridin-2-yl}-5-fluorobenzamide (61.8 mg).

Example 57

3-Methoxy-4-(2-methylfuran-3-amido)benzoic acid (161 mg) was dissolved in DMA (2 mL), and then SOCl$_2$ (48 µL) was added thereto. The mixture was stirred at room temperature for 2 hours. Then, (5R)-7-chloro-4,4-difluoro-5-(hydroxymethyl)-2,3,4,5-tetrahydro-1H-1-benzazepin-5-ol (110 mg) was added thereto, and the mixture was stirred for 3 days. The mixture was diluted with AcOEt, and water was added thereto. The mixture was extracted with AcOEt/Hexane. The organic layer was washed with 1N HCl, 1N NaOH, and saturated brine, dried over anhydrous Na$_2$SO$_4$, and then filtered. The filtrate was concentrated under reduced pressure. The residue was purified by column chromatography (AcOEt/Hexane, followed by AcOEt/MeOH), concentrated, and then dried in vacuo. The resulted solid was filtered and dried in vacuo at 60° C. to give N-{4-[(5R)-7-chloro-4,4-difluoro-5-hydroxy-5-(hydroxymethyl)-2,3,4,5-tetrahydro-1H-1-benzazepine-1-carbonyl]-2-methoxyphenyl}-2-methylfuran-3-carboxamide (132.7 mg).

Example 58

4-(2-Chloro-4-fluorobenzamido)-3-methoxybenzoic acid (189 mg) was dissolved in DMA (2 mL), and then SOCl$_2$ (48 µL) was added thereto. The mixture was stirred at room temperature for 2 hours. Then, (5R)-7-chloro-4,4-difluoro-5-(hydroxymethyl)-2,3,4,5-tetrahydro-1H-1-benzazepin-5-ol (110 mg) was added thereto, and the mixture was stirred for 3 days. The mixture was diluted with AcOEt, and water was added thereto. The mixture was extracted with AcOEt/Hexane. The organic layer was washed with 1N HCl, 1N NaOH, and saturated brine, dried over anhydrous Na$_2$SO$_4$, and then filtered. The filtrate was concentrated under reduced pressure. The residue was purified by column chromatography (AcOEt/Hexane, followed by AcOEt/MeOH). After concentration, the concentrate was dried in vacuo, and the resulted amorphous substance was dried in vacuo at 60° C. to give 2-chloro-N-{4-[(5R)-7-chloro-4,4-difluoro-5-hydroxy-5-(hydroxymethyl)-2,3,4,5-tetrahydro-1H-1-benzazepine-1-carbonyl]-2-methoxyphenyl}-4-fluorobenzamide (141.3 mg).

Example 63

To a solution of 6-{[1,1'-biphenyl]-2-amido}pyridine-3-carboxylic acid (126 mg) and DMA (1.5 mL) was added SOCl$_2$ (30.0 µL) at room temperature under nitrogen atmosphere, and the mixture was stirred for 2 hours. Then, (5R)-7-chloro-4,4-difluoro-5-(hydroxymethyl)-2,3,4,5-tetrahydro-1H-1-benzazepin-5-ol (80 mg) was added thereto at room temperature, and the mixture was stirred for 7 hours. Saturated aqueous NaHCO$_3$ solution and water were added to the reaction solution, and the precipitate was filtered and purified by basic silica gel column chromatography (Hexane/AcOEt/MeOH) to give N-{5-[(5R)-7-chloro-4,4-difluoro-5-hydroxy-5-(hydroxymethyl)-2,3,4,5-tetrahydro-1H-1-benzazepine-1-carbonyl]pyridin-2-yl}-[1,1'-biphenyl]-2-carboxamide (104 mg).

Example 65 tert-Butyl N-({7-chloro-1-[4-(2-chloro-5-fluorobenzamido)-3-methoxybenzoyl]-4,4-difluoro-5-hydroxy-2,3,4,5-tetrahydro-1H-1-benzazepin-5-yl}methyl)carbamate (1.2 g), EtOH (10 mL), and concentrated HCl (0.449 mL) were mixed at room temperature under nitrogen atmosphere, and the mixture was refluxed for 3 hours. The reaction solution was concentrated under reduced pressure, and the residue was purified by basic silica gel column chromatography (Hexane/AcOEt/MeOH) and acidic silica gel column chromatography (Hexane/AcOEt/MeOH) to give N-{4-[5-(aminomethyl)-7-chloro-4,4-difluoro-5-hydroxy-2,3,4,5-tetrahydro-1H-1-benzazepine-1-carbonyl]-2-methoxyphenyl}-2-chloro-5-fluorobenzamide (715 mg).

Example 66

To a solution of under nitrogen atmosphere, 6-[2-(trifluoromethyl)pyridin-3-amido]pyridine-3-carboxylic acid (123 mg) and DMA (1.5 mL) was added $SOCl_2$ (30 µL) at room temperature, and the mixture was stirred for 2 hours. Then, (5R)-7-chloro-4,4-difluoro-5-(hydroxymethyl)-2,3,4,5-tetrahydro-1H-1-benzazepin-5-ol (80 mg) was added thereto at room temperature, and the mixture was stirred for 1 day. Saturated aqueous $NaHCO_3$ solution and water were added to the reaction solution. The precipitate was filtered, washed with water, and purified by basic silica gel column chromatography (Hexane/AcOEt/MeOH) to give N-{5-[(5R)-7-chloro-4,4-difluoro-5-hydroxy-5-(hydroxymethyl)-2,3,4,5-tetrahydro-1H-1-benzazepine-1-carbonyl]pyridin-2-yl}-2-(trifluoromethyl)pyridine-3-carboxamide (83 mg).

Example 71

To a solution of 4-(2-chloro-4-fluorobenzamido)-3-methylbenzoic acid (194 mg) in DMA (2.5 mL) was added $SOCl_2$ (43.0 µL) at room temperature under nitrogen atmosphere, and the mixture was stirred for 2 hours. Then, (5R)-7-chloro-4,4-difluoro-5-(hydroxymethyl)-2,3,4,5-tetrahydro-1H-1-benzazepin-5-ol hydrochloride (120 mg) was added thereto at room temperature, and the mixture was stirred for 1 day. Saturated aqueous $NaHCO_3$ solution and water were added to the reaction solution, and the precipitate was filtered and purified by basic silica gel column chromatography (Hexane/AcOEt/MeOH) to give 2-chloro-N-{4-[(5R)-7-chloro-4,4-difluoro-5-hydroxy-5-(hydroxymethyl)-2,3,4,5-tetrahydro-1H-1-benzazepine-1-carbonyl]-2-methylphenyl}-4-fluorobenzamide (174 mg).

Example 91

To a solution of 6-{4'-fluoro-[1,1'-biphenyl]-2-amido}pyridine-3-carboxylic acid (753 mg) in DMA (6.0 mL) was added $SOCl_2$ (162 µL) under ice cooling under nitrogen atmosphere, and the mixture was stirred at the same temperature for 2 hours. Then, [(5R)-7-chloro-4,4-difluoro-5-hydroxy-2,3,4,5-tetrahydro-1H-1-benzazepin-5-yl]methyl 4-bromobenzoate (500 mg) was added thereto at the same temperature, and the mixture was stirred at room temperature for 1 day. Saturated aqueous $NaHCO_3$ solution and water were added to the reaction solution, and the precipitate was filtered. The resulted solid was mixed with EtOH (10 mL) and 5N aqueous NaOH solution (1.11 mL), and the mixture was stirred at room temperature for 10 minutes. The reaction solution was neutralized by addition of ice water and 5N HCl, and the precipitate was filtered and washed with water. The resulted solid was purified by basic silica gel column chromatography (Hexane/AcOEt/MeOH) to give N-{5-[(5R)-7-chloro-4,4-difluoro-5-hydroxy-5-(hydroxymethyl)-2,3,4,5-tetrahydro-1H-1-benzazepine-1-carbonyl]pyridin-2-yl}-4'-fluoro-[1,1'-biphenyl]-2-carboxamide (620 mg).

Example 96

6-{4-Fluoro-[1,1'-biphenyl]-2-amido}pyridine-3-carboxylic acid (542 mg) was dissolved in DMA (5 mL) and then $SOCl_2$ (0.133 mL) was added thereto. The mixture was stirred at room temperature for 2 hours. Then, [(5R)-7-chloro-4,4-difluoro-5-hydroxy-2,3,4,5-tetrahydro-1H-1-benzazepin-5-yl]methyl 4-bromobenzoate (480 mg) was added thereto, and the mixture was stirred at room temperature for 4 days. Water was added thereto, and the resulted solid was filtered. The solid was suspended in EtOH (20 mL), and 5N aqueous NaOH solution (1.075 mL) was added thereto. The mixture was stirred for 1 hour, and then adjusted to pH=8 by addition of 1N HCl. The mixture was extracted with AcOEt. The organic layer was washed with 1N HCl, 1N NaOH, and saturated brine. The organic layer was dried over anhydrous $Na_2SO_4$, and then filtered. The filtrate was concentrated under reduced pressure. The residue was purified by column chromatography (basic silica gel column (NH-Si) manufactured by Biotage: AcOEt/Hexane, followed by AcOEt/MeOH) and (acidic silica gel column (Kp-Si) manufactured by Biotage: AcOEt/Hexane). After concentration, the concentrate was dried in vacuo, and the resulted amorphous substance was dried in vacuo at 60° C. to give N-{5-[(5R)-7-chloro-4,4-difluoro-5-hydroxy-5-(hydroxymethyl)-2,3,4,5-tetrahydro-1H-1-benzazepine-1-carbonyl]pyridin-2-yl}-4-fluoro-[1,1'-biphenyl]-2-carboxamide (511.5 mg).

Example 97

6-(2-Phenylpyridine-3-amido)pyridine-3-carboxylic acid (160 mg) was dissolved in DMA (2 mL), and then $SOCl_2$ (45 µL) was added thereto. The mixture was stirred at room temperature for 2 hours. Then, (5R)-7-chloro-4,4-difluoro-5-(hydroxymethyl)-2,3,4,5-tetrahydro-1H-1-benzazepin-5-ol (110 mg) was added thereto, and the mixture was stirred for 2 days. The mixture was diluted with AcOEt, and water was added thereto. The mixture was extracted with AcOEt/Hexane. The organic layer was washed with 1N HCl, 1N NaOH, and saturated brine, dried over anhydrous $Na_2SO_4$, and then filtered. The filtrate was concentrated under reduced pressure. The residue was purified by column chromatography (AcOEt/Hexane, followed by AcOEt/MeOH). After concentration, the concentrate was dried in vacuo, and the resulted amorphous substance was dried in vacuo at 60° C. to give N-{5-[(5R)-7-chloro-4,4-difluoro-5-hydroxy-5-(hydroxymethyl)-2,3,4,5-tetrahydro-1H-1-benzazepine-1-carbonyl]pyridin-2-yl}-2-phenylpyridine-3-carboxamide (115.9 mg).

Example 99

To a solution of 4-(2-chlorobenzamido)-3-methoxybenzoic acid (684 mg) in DMA (6.0 mL) was added $SOCl_2$ (162

μL) under ice cooling under nitrogen atmosphere, and the mixture was stirred at the same temperature for 2 hours. Then, [(5R)-7-chloro-4,4-difluoro-5-hydroxy-2,3,4,5-tetrahydro-1H-1-benzazepin-5-yl]methyl 4-bromobenzoate (500 mg) was added thereto at the same temperature, and the mixture was stirred at room temperature for 1 day. Saturated aqueous NaHCO$_3$ solution and water were added to the reaction solution, and the precipitate was filtered. EtOH (10 mL) and 5N aqueous NaOH solution (1.11 mL) were added to the resulted solid, and the mixture was stirred at room temperature for 30 minutes. The reaction solution was neutralized by addition of ice water and 5N HCl, and the precipitate was filtered and washed with water. The resulted solid was dissolved in AcOEt and washed with 1N aqueous NaOH solution and saturated brine. The organic layer was dried over anhydrous Na$_2$SO$_4$, and then filtered. The filtrate was concentrated under reduced pressure. The residue was purified by silica gel column chromatography (Hexane/AcOEt) to give 2-chloro-N-{4-[(5R)-7-chloro-4,4-difluoro-5-hydroxy-5-(hydroxymethyl)-2,3,4,5-tetrahydro-1H-1-benzazepine-1-carbonyl]-2-methoxyphenyl}benzamide (620 mg).

Example 100

To a solution of 4-(2-chloro-5-fluorobenzamido)-3-methoxybenzoic acid (189 mg) in DMA (4 mL) was added SOCl$_2$ (43 μL) at 0° C., and the mixture was stirred for 2 hours. Then, a solution of 7-chloro-4,4-difluoro-2,3,4,5-tetrahydro(5-$^2$H)-1H-1-benzazepin-5-ol (114 mg) in DMA (2 mL) was added thereto, and the mixture was stirred at room temperature overnight. Water was added to the reaction solution, and the mixture was extracted with AcOEt. The organic layer was washed with water and saturated brine, dried over anhydrous Na$_2$SO$_4$, and concentrated under reduced pressure. The residue was purified by medium-pressure column chromatography (Hexane/AcOEt) and recrystallized from Hexane to give 2-chloro-N-{4-[7-chloro-4,4-difluoro-5-hydroxy-2,3,4,5-tetrahydro(5-$^2$H)-1H-1-benzazepine-1-carbonyl]-2-methoxyphenyl}-5-fluorobenzamide (155 mg).

Example 101

To a solution of 4-(2-chloro-5-fluorobenzamido)-3-methoxybenzoic acid (224 mg) in DMA (4 mL) was added SOCl$_2$ (48 μL) at 0° C., and the mixture was stirred for 2 hours. Then, a solution of 7-chloro-4,4-difluoro-2,3,4,5-tetrahydro(5-$^2$H)-1H-1-benzazepin-5-ol (129 mg) in DMA (2 mL) was added thereto, and the mixture was stirred at room temperature overnight. Water was added to the reaction solution, and the mixture was extracted with AcOEt, washed with water and saturated brine, dried over anhydrous Na$_2$SO$_4$, and concentrated under reduced pressure. The concentrate was purified by medium-pressure column chromatography (Hexane/AcOEt) and recrystallized from MeCN to give N-{4-[7-chloro-4,4-difluoro-5-hydroxy-2,3,4,5-tetrahydro(5-$^2$H)-1H-1-benzazepine-1-carbonyl]-2-methoxyphenyl}-2-(trifluoromethyl)benzamide (183 mg).

Example 102

To a solution of 4-(5-fluoro-2-methylbenzamido)-3-fluorobenzoic acid (92 mg) in DMA (1.0 mL) was added SOCl$_2$ (23 μL) under ice cooling under nitrogen atmosphere, and the mixture was stirred at the same temperature for 2 hours. Then, (5R)-7-chloro-4,4-difluoro-5-methyl-2,3,4,5-tetrahydro-1H-1-benzazepin-5-ol (60 mg) was added thereto at the same temperature, and the mixture was stirred at room temperature for 1 day. Saturated aqueous NaHCO$_3$ solution and water were added to the reaction solution, and the precipitate was filtered. The resulted solid was dissolved in AcOEt and washed with 1N aqueous NaOH solution and saturated brine. The organic layer was dried over anhydrous Na$_2$SO$_4$, and then filtered. The filtrate was concentrated under reduced pressure. The residue was purified by silica gel column chromatography (Hexane/AcOEt) to give N-{4-[(5R)-7-chloro-4,4-difluoro-5-hydroxy-5-methyl-2,3,4,5-tetrahydro-1H-1-benzazepine-1-carbonyl]-2-fluorophenyl}-5-fluoro-2-methylbenzamide (100 mg).

Example 125

To a solution of N-[5-({7-chloro-4,4-difluoro-1,2,3,4-tetrahydrospiro[1-benzazepin-5,2'-oxirane]-1-yl}carbonyl)pyridin-2-yl]-2-(trifluoromethyl)benzamide (100 mg) in MeOH (1 mL) was added ethanolamine (0.112 mL), and the mixture was stirred at 70° C. for 4 hours. Saturated aqueous NaHCO$_3$ solution was added thereto, and the mixture was extracted with AcOEt and dried over anhydrous Na$_2$SO$_4$. Na$_2$SO$_4$ was filtered, and the filtrate was concentrated under reduced pressure and dried in vacuo to give N-[5-(7-chloro-4,4-difluoro-5-hydroxy-5-{[(2-hydroxyethyl)amino]methyl}-2,3,4,5-tetrahydro-1H-1-benzazepine-1-carbonyl)pyridin-2-yl]-2-(trifluoromethyl)benzamide (107.2 mg).

Example 127

To a solution of 4-[5-fluoro-2-(trifluoromethyl)benzamido]benzoic acid (769 mg) in DMA (7 mL) was added dropwise SOCl$_2$ (0.172 mL). The mixture was stirred for 1 hour, and then [(5R)-7-chloro-4,4-difluoro-5-hydroxy-2,3,4,5-tetrahydro-1H-1-benzazepin-5-yl]methyl 4-bromobenzoate (700 mg) was added thereto. The mixture was stirred for 5 days. Saturated aqueous NaHCO$_3$ solution was added thereto, and the resulted solid was filtered. The resultant was suspended in EtOH (15 mL), and 5N aqueous NaOH solution (1.567 mL) was added dropwise thereto. The mixture was stirred at room temperature for 30 minutes. Then, 5N HCl was added thereto. The resulted solid was filtered, washed with water, and then dissolved in THF. The solution was dried over anhydrous Na$_2$SO$_4$, filtered, and concentrated, and then the crude product was purified by medium-pressure column chromatography (Hexane/AcOEt/MeOH) and dried at 60° C. under reduced pressure to give N-{4-[(5R)-7-chloro-4,4-difluoro-5-hydroxy-5-(hydroxymethyl)-2,3,4,5-tetrahydro-1H-1-benzazepine-1-carbonyl]phenyl}-5-fluoro-2-(trifluoromethyl)benzamide (772 mg).

Example 132

To a solution of 3-fluoro-4-[5-fluoro-2-(trifluoromethyl)benzamido]benzoic acid (812 mg, 2.351 mmol) in DMA (7 mL) was added dropwise SOCl$_2$ (0.172 mL). The mixture was stirred for 1 hour, and then [(5R)-7-chloro-4,4-difluoro-5-hydroxy-2,3,4,5-tetrahydro-1H-1-benzazepin-5-yl]methyl 4-bromobenzoate (700 mg) was added thereto, and the mixture was stirred for 2 days. Saturated aqueous NaHCO$_3$ solution was added thereto, and the resulted solid was filtered. The resultant was suspended in EtOH (15 mL), and 5N aqueous NaOH solution (1.567 mL) was added dropwise thereto. The mixture was stirred for 30 minutes. 5 N HCl was added to the mixture, and the resulted solid was filtered, washed with water, and then dissolved in THF. The solution was dried over anhydrous Na$_2$SO$_4$, filtered, concentrated, and then the crude product was purified by column chromatography (Hexane/AcOEt/MeOH) and dried under reduced pressure at 60° C. to give N-{4-[(5R)-7-chloro-4,4-difluoro-5-hydroxy-5-(hydroxymethyl)-2,3,4,5-tetrahydro-1H-1-benzazepine-1-carbonyl]-2-fluorophenyl}-5-fluoro-2-(trifluoromethyl)benzamide (840 mg).

Example 153

To a solution of 4-{4-fluoro-[1,1'-biphenyl]-2-amido}benzoic acid (901 mg) in DMA (7 mL) was added dropwise SOCl$_2$ (0.196 mL). The mixture was stirred for 1 hour, and then [(5R)-7-chloro-4,4-difluoro-5-hydroxy-2,3,4,5-tetrahydro-1H-1-benzazepin-5-yl]methyl 4-bromobenzoate (600 mg) was added thereto. The mixture was stirred for 2 days. Saturated aqueous NaHCO$_3$ solution was added thereto, and the resulted solid was filtered. The resultant was suspended in EtOH (15 mL), and 5N aqueous NaOH solution (1.343 mL) was added dropwise thereto. The mixture was stirred at room temperature for 30 minutes. 5N HCl was added thereto, and the resulted solid was filtered, washed with water, and then dissolved in THF. The solution was dried over anhydrous Na$_2$SO$_4$, filtered, concentrated, and then the crude product was purified by column chromatography (Hexane/AcOEt/MeOH) and dried under reduced pressure at 60° C. to give N-{4-[(5R)-7-chloro-4,4-difluoro-5-hydroxy-5-(hydroxymethyl)-2,3,4,5-tetrahydro-1H-1-benzazepine-1-carbonyl]phenyl}-4-fluoro-[1,1'-biphenyl]-2-carboxamide (722 mg).

Example 157

To a solution of 4-[2-(difluoromethyl)-5-fluorobenzamido]-3-fluorobenzoic acid (659 mg) in DMA (7 mL) was added dropwise SOCl$_2$ (0.147 mL). The mixture was stirred for 1 hour, and then [(5R)-7-chloro-4,4-difluoro-5-hydroxy-2,3,4,5-tetrahydro-1H-1-benzazepin-5-yl]methyl 4-bromobenzoate (600 mg) was added thereto. The mixture was stirred for 2 days. Saturated aqueous NaHCO$_3$ solution was added thereto, and the resulted solid was filtered. The resultant was suspended in EtOH (15 mL), and 5N NaOH (1.343 mL) was added dropwise thereto. The mixture was stirred for 30 minutes. 5N HCl was added thereto, and the resulted solid was filtered, washed with water, and then dissolved in THF. The solution was dried over anhydrous Na$_2$SO$_4$, filtered, concentrated, and then the crude product was purified by column chromatography (Hexane/AcOEt/MeOH) and dried under reduced pressure at 60° C. to give N-{4-[(5R)-7-chloro-4,4-difluoro-5-hydroxy-5-(hydroxymethyl)-2,3,4,5-tetrahydro-1H-1-benzazepine-1-carbonyl]-2-fluorophenyl}-2-(difluoromethyl)-5-fluorobenzamide (603 mg).

Example 160

To a solution of 4-{[1,1'-biphenyl]-2-amido}benzoic acid (167 mg) in DMA (2 mL) was added SOCl$_2$ (0.049 mL) at room temperature under nitrogen atmosphere, and the mixture was stirred for 2 hours. Then, (5S)-7-chloro-4,4-difluoro-5-methyl-2,3,4,5-tetrahydro-1H-1-benzazepin-5-ol (100 mg) was added thereto, and the mixture was stirred at room temperature overnight. Saturated aqueous NaHCO$_3$ solution (4 mL) and water were added thereto, and the mixture was extracted with AcOEt (4 mL) three times. The combined organic layer was washed with 1N aqueous NaOH solution and saturated brine, dried over anhydrous Na$_2$SO$_4$, filtered, and then solvent was removed. The residue was purified by silica gel column chromatography (Hexane/AcOEt) to give N-{4-[(5S)-7-chloro-4,4-difluoro-5-hydroxy-5-methyl-2,3,4,5-tetrahydro-1H-1-benzazepine-1-carbonyl]phenyl}-[1,1'-biphenyl]-2-carboxamide (163 mg).

Example 165

To a solution of 6-{2',4-difluoro-[1,1'-biphenyl]-2-amido}pyridine-3-carboxylic acid (952 mg) in DMA (7 mL) was added dropwise SOCl$_2$ (0.196 mL). The mixture was stirred for 2 hours. Then, [(5R)-7-chloro-4,4-difluoro-5-hydroxy-2,3,4,5-tetrahydro-1H-1-benzazepin-5-yl]methyl 4-bromobenzoate (600 mg) was added thereto, and the mixture was stirred overnight. Saturated aqueous NaHCO$_3$ solution was added thereto, and the resulted solid was filtered. The resultant was suspended in EtOH (15 mL), and 5N NaOH (1.343 mL) was added dropwise thereto. The mixture was stirred for 30 minutes. 5N HCl was added thereto, and the resulted solid was filtered and washed with water. Then, the solid was dissolved in AcOEt. 1N NaOH was added thereto, and the AcOEt layer was washed with water and saturated brine, dried over anhydrous Na$_2$SO$_4$, filtered, and concentrated. The resulted crude product was purified by column chromatography (Hexane/AcOEt) and dried under reduced pressure at 60° C. to give N-{5-[(5R)-7-chloro-4,4-difluoro-5-hydroxy-5-(hydroxymethyl)-2,3,4,5-tetrahydro-1H-1-benzazepine-1-carbonyl]pyridin-2-yl}-2',4-difluoro-[1,1'-biphenyl]-2-carboxamide (642 mg).

Example 168

To a solution of 4-{2',4-difluoro-[1,1'-biphenyl]-2-amido}-3-fluorobenzoic acid (748 mg) in DMA (7 mL) was added dropwise SOCl$_2$ (0.147 mL). The mixture was stirred for 2 hours. Then, [(5R)-7-chloro-4,4-difluoro-5-hydroxy-2,3,4,5-tetrahydro-1H-1-benzazepin-5-yl]methyl 4-bromobenzoate (600 mg) was added thereto, and the mixture was stirred for 2 days. Saturated aqueous NaHCO$_3$ solution was added thereto, and the resulted solid was filtered. The resultant was suspended in EtOH (15 mL). 5N NaOH (1.343 mL) was added dropwise thereto, and the mixture was stirred for 30 minutes. 5N HCl was added thereto, and the resulted solid was filtered, washed with water, and then dissolved in THF. The THF solution was dried over anhydrous Na$_2$SO$_4$, filtered, concentrated, and then the crude product was purified by column chromatography (Hexane/AcOEt/MeOH) and dried under reduced pressure at 60° C. to give N-{4-[(5R)-7-chloro-4,4-difluoro-5-hydroxy-5-(hydroxymethyl)-2,3,4,5-tetrahydro-1H-1-benzazepine-1-carbonyl]-2-fluorophenyl}-2',4-difluoro-[1,1'-biphenyl]-2-carboxamide (706 mg).

Example 169

To a solution of 4-{2',4-difluoro-[1,1'-biphenyl]-2-amido}benzoic acid (712 mg) in DMA (7 mL) was added dropwise SOCl$_2$ (0.147 mL). The mixture was stirred for 2 hours. Then, [(5R)-7-chloro-4,4-difluoro-5-hydroxy-2,3,4,5-tetrahydro-1H-1-benzazepin-5-yl]methyl 4-bromobenzoate (600 mg) was added thereto, and the mixture was stirred for 2 days. Saturated aqueous NaHCO$_3$ solution was added thereto, and the resulted solid was filtered. The resultant was suspended in EtOH (15 mL), and 5N NaOH (1.343 mL) was added dropwise thereto. The mixture was stirred for 30 minutes. 5N HCl was added thereto, and the resulted solid was filtered, washed with water, and then dissolve in THF.

The THF solution was dried over anhydrous Na₂SO₄, filtered, and concentrated, and then the crude product was purified by column chromatography (Hexane/AcOEt/MeOH) and dried under reduced pressure at 60° C. to give N-{4-[(5R)-7-chloro-4,4-difluoro-5-hydroxy-5-(hydroxymethyl)-2,3,4,5-tetrahydro-1H-1-benzazepine-1-carbonyl]phenyl}-2',4-difluoro-[1,1'-biphenyl]-2-carboxamide (664 mg).

Example 187

To a solution of 4-(7-fluoro-1-oxo-1,2,3,4-tetrahydroisoquinolin-2-yl)benzoic acid (192 mg) in DMA (3 mL) was added dropwise SOCl₂ (49 μL). The mixture was stirred for 2 hours. Then, [(5R)-7-chloro-4,4-difluoro-5-hydroxy-2,3,4,5-tetrahydro-1H-1-benzazepin-5-yl]methyl 4-bromobenzoate (150 mg) was added thereto, and the mixture was stirred for 3 days. Saturated aqueous NaHCO₃ solution was added thereto, and the resulted solid was filtered. The resultant was suspended in EtOH (10 mL), and 5N aqueous NaOH solution (0.336 mL) was added dropwise thereto. The mixture was stirred for 30 minutes. 5N HCl was added thereto, and the resulted solid was filtered, washed with water, and then dissolved in AcOEt. 1N NaOH was added thereto, and the organic layer was washed with water and saturated brine, and dried over anhydrous Na₂SO₄. The resultant was filtered and concentrated. The obtained crude product was purified by column chromatography (Hexane/AcOEt) and dried under reduced pressure at 60° C. to give 2-{4-[(5R)-7-chloro-4,4-difluoro-5-hydroxy-5-(hydroxymethyl)-2,3,4,5-tetrahydro-1H-1-benzazepine-1-carbonyl]phenyl}-7-fluoro-1,2,3,4-tetrahydroisoquinolin-1-one (126 mg).

Example 219

To a solution of 2-chloro-N-{4-[(5R)-7-chloro-4,4-difluoro-5-hydroxy-2,3,4,5-tetrahydro-1H-1-benzazepine-1-carbonyl]-2-fluorophenyl}-4,5-difluorobenzamide (0.60 g) in DMSO (5 mL) was added IBX (0.616 g), and the mixture was stirred at room temperature overnight. Water was added thereto, and the mixture was extracted with AcOEt, washed with saturated brine, filtered, and concentrated. The concentrate was purified by medium-pressure column chromatography (Hexane/AcOEt), and the crude product was recrystallized from Et₂O to give 2-chloro-N-[4-(7-chloro-4,4-difluoro-5,5-dihydroxy-2,3,4,5-tetrahydro-1H-1-benzazepine-1-carbonyl)-2-fluorophenyl]-4,5-difluorobenzamide (460 mg).

Example 220

To a solution of 2-chloro-N-{5-[7-chloro-4,4-difluoro-5-hydroxy-5-(hydroxymethyl)-2,3,4,5-tetrahydro-1H-1-benzazepine-1-carbonyl]pyridin-2-yl}-5-fluorobenzamide (100 mg) in AcOEt (1 mL) was added a solution of MsOH in AcOEt (0.046 mL), and the mixture was stirred at room temperature for 2 days. IPE (1.0 mL) was added thereto, and the precipitated solid was filtered and dried under reduced pressure at 80° C. for 2 days to give 2-chloro-N-{5-[7-chloro-4,4-difluoro-5-hydroxy-5-(hydroxymethyl)-2,3,4,5-tetrahydro-1H-1-benzazepine-1-carbonyl]pyridin-2-yl}-5-fluorobenzamide methanesulfonate (112.1 mg).

Example 223

To a solution of 2,4-dichloro-N-{5-[(5R)-7-chloro-4,4-difluoro-5-hydroxy-5-(hydroxymethyl)-2,3,4,5-tetrahydro-1H-1-benzazepine-1-carbonyl]pyridin-2-yl}-5-fluorobenzamide (100 mg) in AcOEt (1 mL) was added a solution of HCl in AcOEt (0.043 mL), and the mixture was stirred at room temperature overnight. IPE (1.0 mL) was added thereto, and the precipitated solid was filtered and dried under reduced pressure at 80° C. for 2 days to give 2,4-dichloro-N-{5-[(5R)-7-chloro-4,4-difluoro-5-hydroxy-5-(hydroxymethyl)-2,3,4,5-tetrahydro-1H-1-benzazepine-1-carbonyl]pyridin-2-yl}-5-fluorobenzamide hydrochloride (48.3 mg).

The following tables show structures, methods for preparation, and physical data of Reference Example compounds and Example compounds.

TABLE 1-1

| REX | STR |
|---|---|
| 1 | |
| 2 | |
| 3 | |
| 4 | |
| 5 | |

TABLE 1-1-continued

| REX | STR |
|---|---|
| 6 | 6-bromo-3,4-dihydroisoquinolin-1(2H)-one |
| 7 | methyl 6-(2-(difluoromethyl)benzamido)nicotinate |
| 8 | 6-(2-(difluoromethyl)benzamido)nicotinic acid |
| 9 | methyl 5-(2-chlorobenzamido)pyrazine-2-carboxylate |
| 10 | 5-(2-chlorobenzamido)pyrazine-2-carboxylic acid |
| 11 | 6-(2-chloro-6-methylbenzamido)nicotinic acid |
| 12 | 5-(2-(trifluoromethyl)benzamido)pyrazine-2-carboxylic acid |
| 13 | 3-methoxy-4-(2-methylfuran-3-carboxamido)benzoic acid |
| 14 | 3-methoxy-4-(2-(trifluoromethyl)benzamido)benzoic acid |
| 15 | 3-fluoro-4-(2-(trifluoromethyl)benzamido)benzoic acid |
| 16 | methyl 4-(2-chlorobenzamido)-3-(methoxymethoxy)benzoate |
| 17 | 4-(2-chlorobenzamido)-3-(methoxymethoxy)benzoic acid |
| 18 | 3-(methoxymethoxy)-4-(2-(trifluoromethyl)benzamido)benzoic acid |
| 19 | 4-(2-chloro-4-fluorobenzamido)-3-methoxybenzoic acid |

TABLE 1-1-continued

| REX | STR |
|---|---|
| 20 | 2-chloro-6-fluoro-N-(4-carboxy-2-methoxyphenyl)benzamide |
| 21 | 2-chloro-5-fluoro-N-(4-carboxy-2-fluorophenyl)benzamide |
| 22 | methyl 6-[(4'-fluorobiphenyl-2-ylcarbonyl)amino]pyridine-3-carboxylate |
| 23 | 6-[(4'-fluorobiphenyl-2-ylcarbonyl)amino]pyridine-3-carboxylic acid |
| 24 | 3-methyl-N-(4-carboxy-2-methoxyphenyl)thiophene-2-carboxamide |
| 25 | methyl 2-(difluoromethyl)-5-fluorobenzoate |
| 26 | 2-(difluoromethyl)-5-fluorobenzoic acid |
| 27 | 2-methyl-N-(4-carboxy-2-methoxyphenyl)benzamide |
| 28 | 2-ethyl-N-(4-carboxy-2-methoxyphenyl)benzamide |
| 29 | 2-methyl-5-fluoro-N-(4-carboxy-2-methoxyphenyl)benzamide |
| 30 | 2-chloro-5-methyl-N-(4-carboxy-2-methoxyphenyl)benzamide |
| 31 | 2-chloro-5-methyl-N-(5-carboxypyridin-2-yl)benzamide |

TABLE 1-1-continued
| REX | STR |
|---|---|
| 32 | 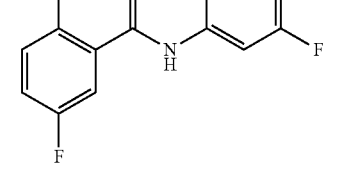 |
| 33 | 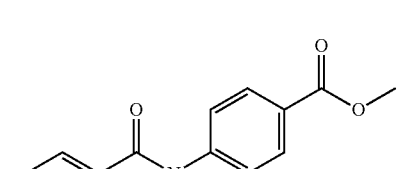 |
| 34 | 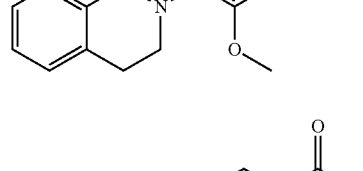 |
| 35 | 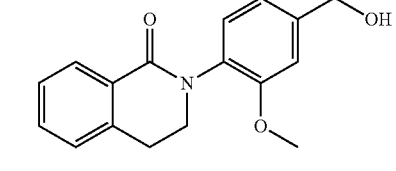 |
| 36 | 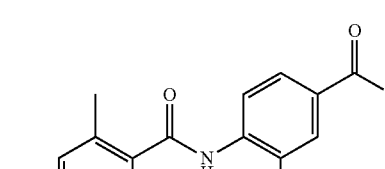 |
| 37 | 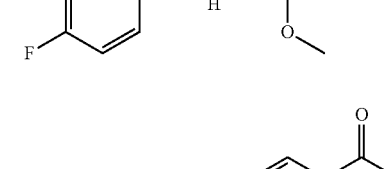 |
| 38 | |
| 39 | |
| 40 | |
| 41 | |
| 42 | |
| 43 | |

TABLE 1-1-continued

| REX | STR |
|---|---|
| 44 | |
| 45 | |
| 46 | |
| 47 | |
| 48 | |
| 49 | |
| 50 | |
| 51 | |
| 52 | |
| 53 | |
| 54 | |

TABLE 1-1-continued

| REX | STR |
|---|---|
| 55 | |
| 56 | |
| 57 | |
| 58 | |
| 59 | |
| 60 | |
| 61 | |
| 62 | |
| 63 | |
| 64 | |
| 65 | |
| 66 | |
| 67 | |

TABLE 1-1-continued
| REX | STR |
|---|---|
| 68 | 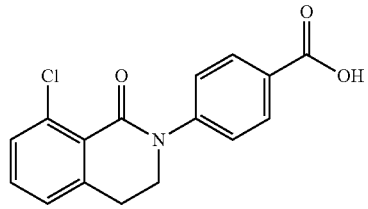 |
| 69 | 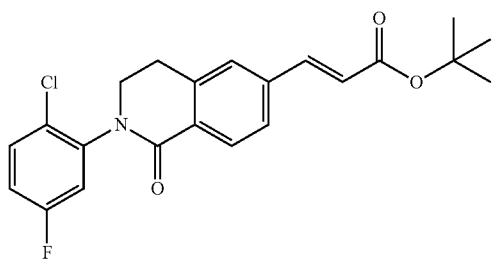 |
| 70 | 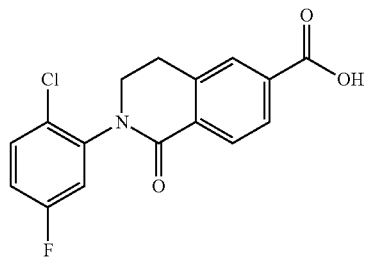 |
| 71 | 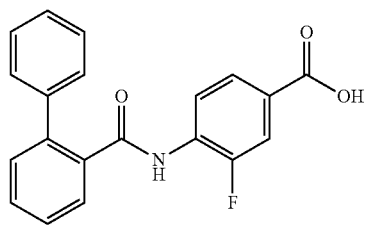 |
| 72 | 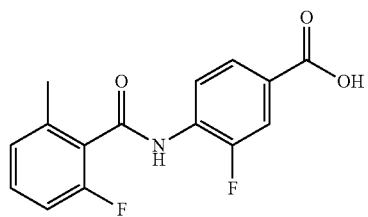 |
| 73 | 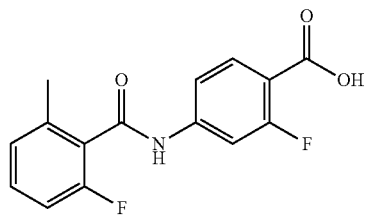 |
| 74 | 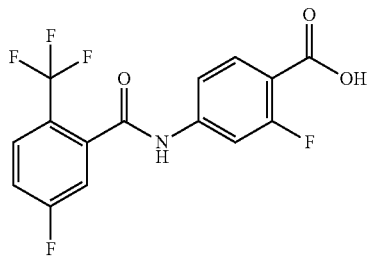 |
| 75 | 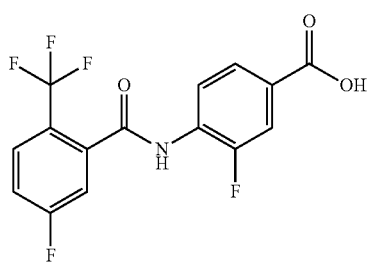 |
| 76 | 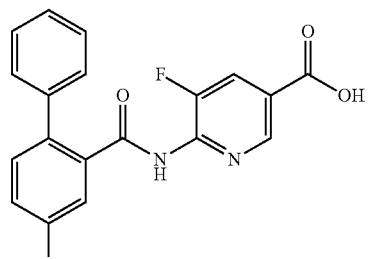 |
| 77 | 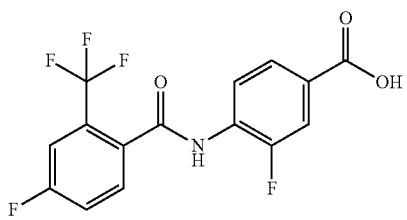 |
| 78 | 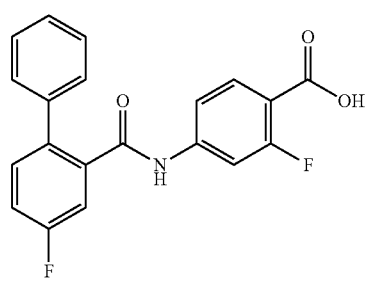 |
| 79 | 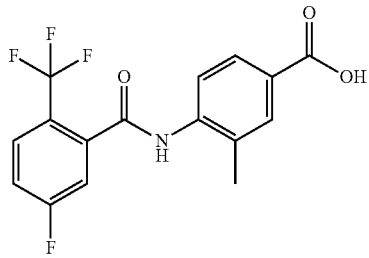 |

TABLE 1-1-continued
| REX | STR |
|---|---|
| 80 | 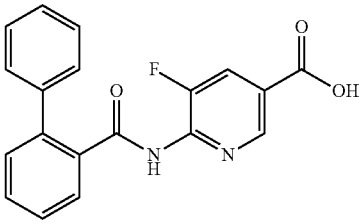 |
| 81 | 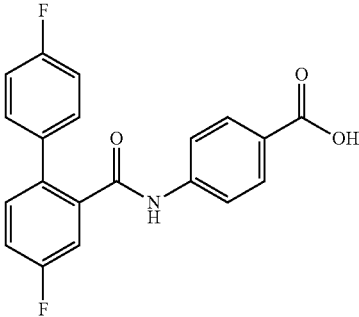 |
| 82 | 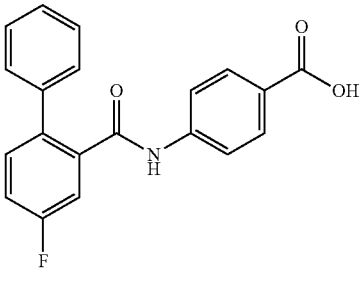 |
| 83 | 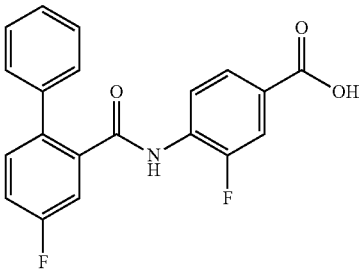 |
| 84 | 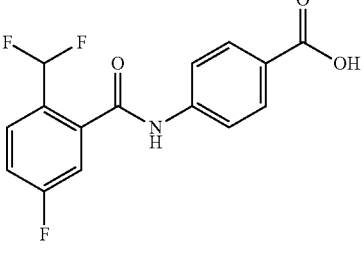 |
| 85 | 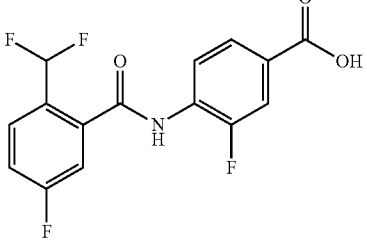 |
| 86 | 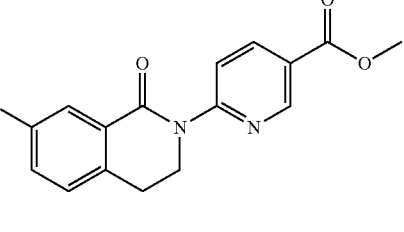 |
| 87 | 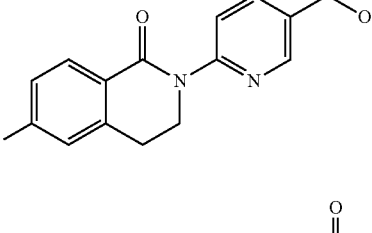 |
| 88 | 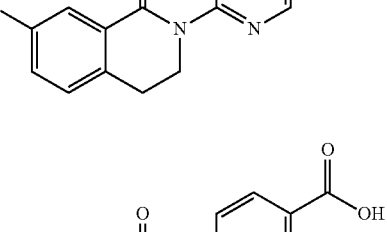 |
| 89 | 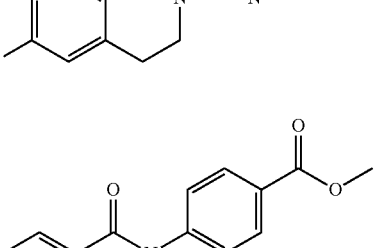 |
| 90 | 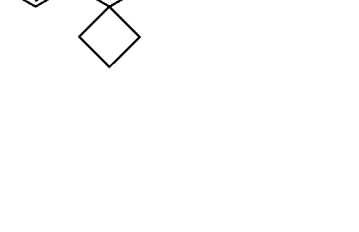 |

TABLE 1-1-continued

| REX | STR |
|---|---|
| 91 | |
| 92 | |
| 93 | |
| 94 | |
| 95 | |
| 96 | |
| 97 | |
| 98 | |
| 99 | |
| 100 | |

TABLE 1-1-continued
| REX | STR |
|---|---|
| 101 | 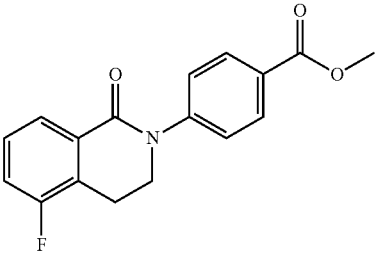 |
| 102 | 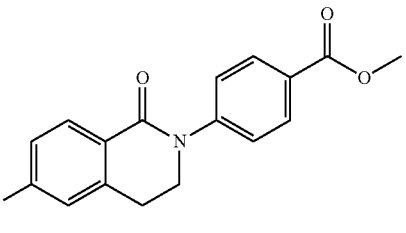 |
| 103 | 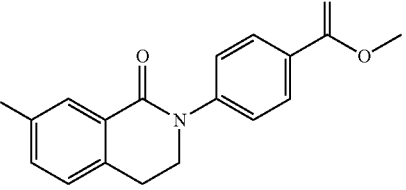 |
| 104 | 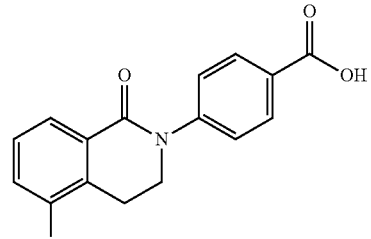 |
| 105 | 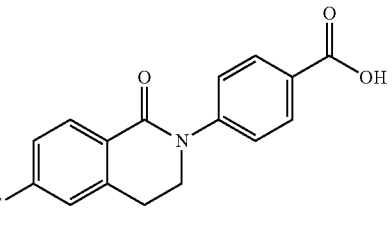 |
| 106 | 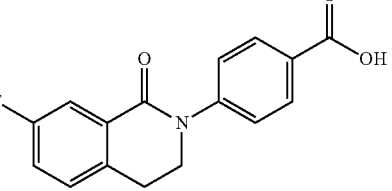 |
| 107 | 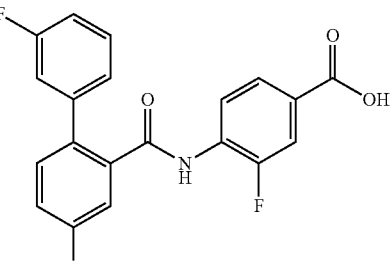 |
| 108 | 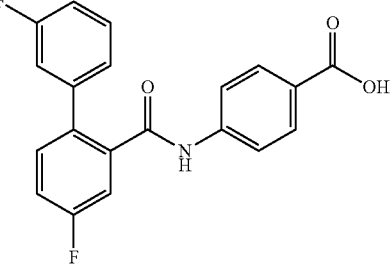 |
| 109 | 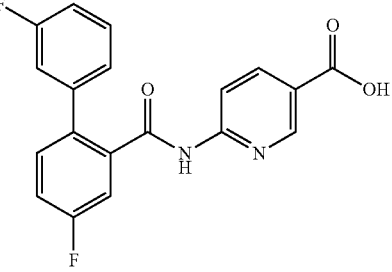 |
| 110 | 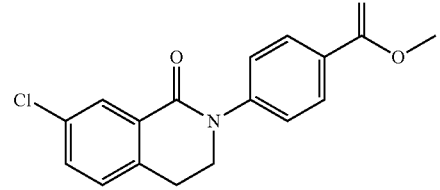 |
| 111 | 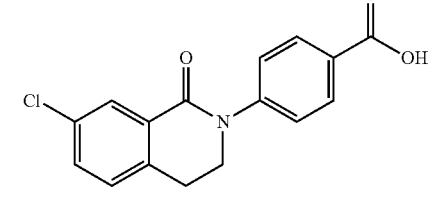 |
| 112 | 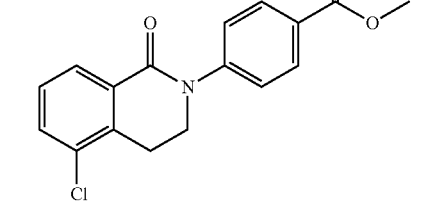 |

TABLE 1-1-continued

| REX | STR |
|---|---|
| 113 | (structure) |
| 114 | (structure) |
| 115 | (structure) |
| 116 | (structure) |
| 117 | (structure) |
| 118 | (structure) |
| 119 | (structure) |
| 120 | (structure) |
| 121 | (structure) |
| 122 | (structure) |
| 123 | (structure) |
| 124 | (structure) |

TABLE 1-1-continued
| REX | STR |
|---|---|
| 125 | 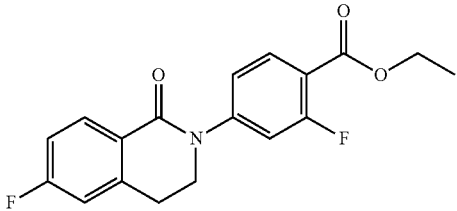 |
| 126 | 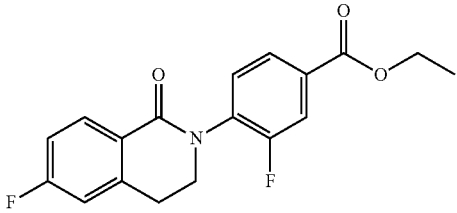 |
| 127 | 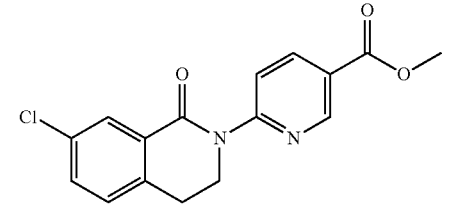 |
| 128 | 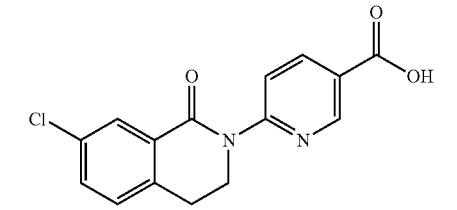 |
| 129 | 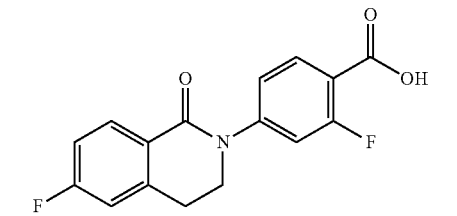 |
| 130 | 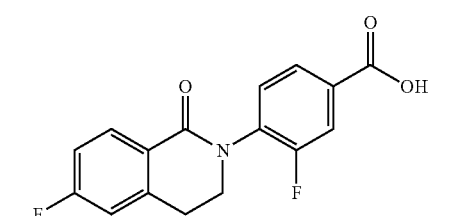 |
| 131 | 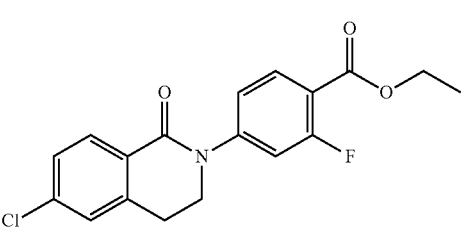 |
| 132 | 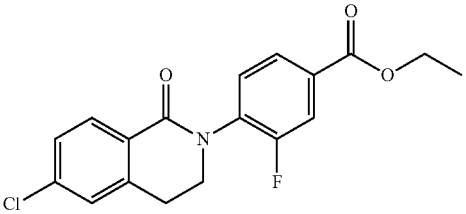 |
| 133 | 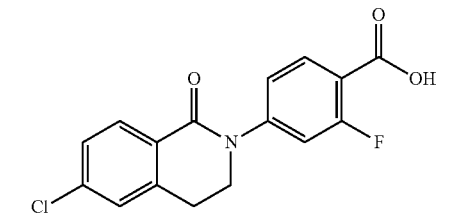 |
| 134 | 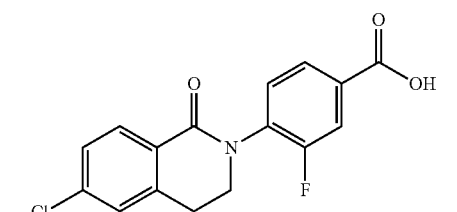 |
| 135 | 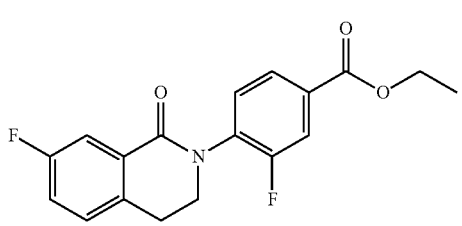 |
| 136 | 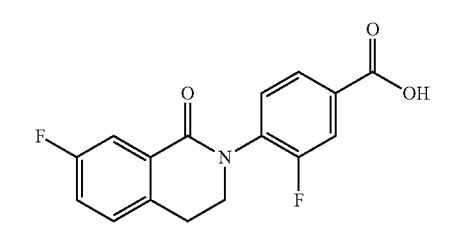 |
| 137 | 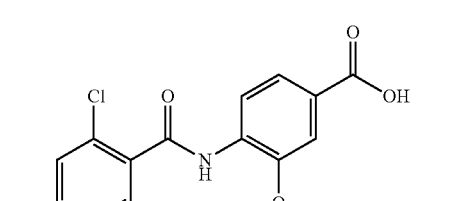 |
| 138 | 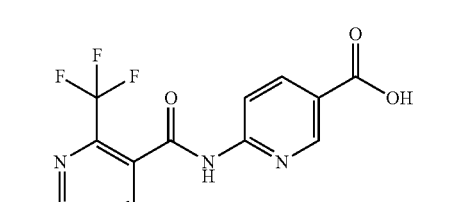 |

TABLE 1-1-continued

| REX | STR |
|-----|-----|
| 139 | |
| 140 | |
| 141 | |
| 142 | |
| 143 | |

TABLE 1-1-continued

| REX | STR |
|-----|-----|
| 144 | |
| 145 | |
| 146 | |
| 147 | |
| 148 | |

TABLE 1-1-continued

| REX | STR |
|---|---|
| 149 | (structure) |
| 150 | (structure) |
| 151 | (structure) |
| 152 | (structure) |
| 153 | (structure) |
| 154 | (structure) |
| 155 | (structure) |

TABLE 1-1-continued

| REX | STR |
|---|---|
| 156 | |
| 157 | |
| 158 | |
| 159 | |
| 160 | |
| 161 | |
| 162 | |

TABLE 1-1-continued
| REX | STR |
|---|---|
| 163 | 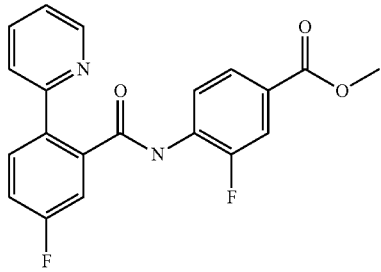 |
| 164 | 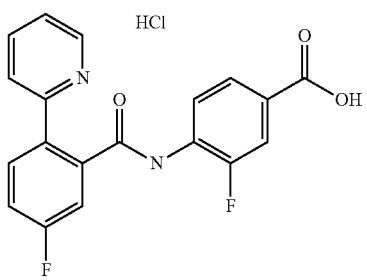 |
| 165 | 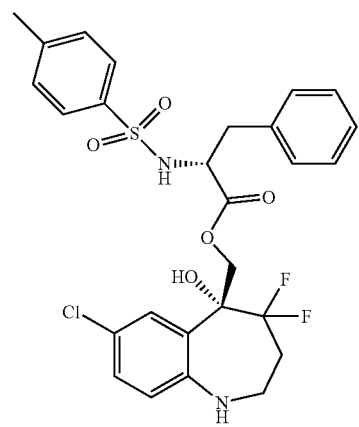 |
| 166 | 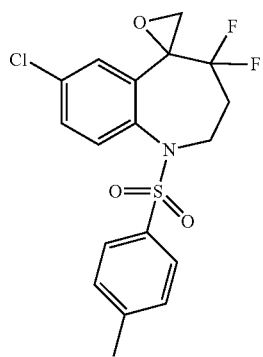 |
| 167 | 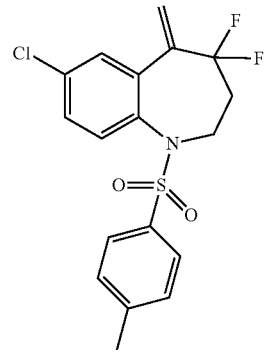 |
| 168 | 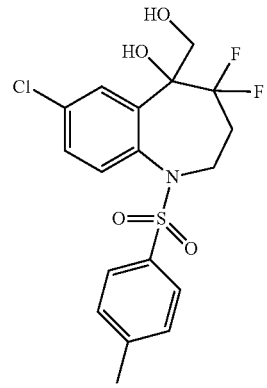 |
| 169 | 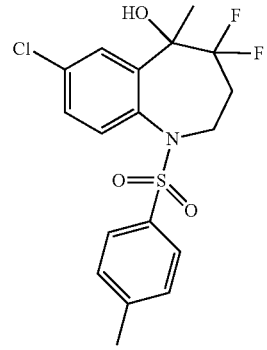 |
| 170 | 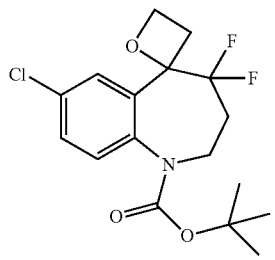 |

TABLE 1-1-continued
| REX | STR |
|---|---|
| 171 | 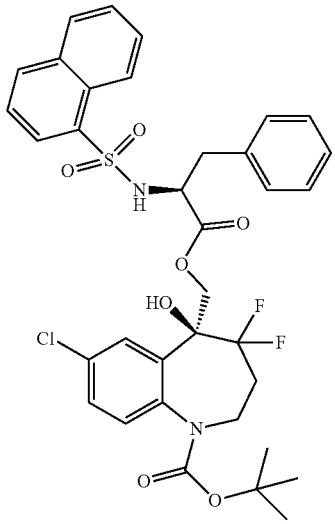 |
| 172 | 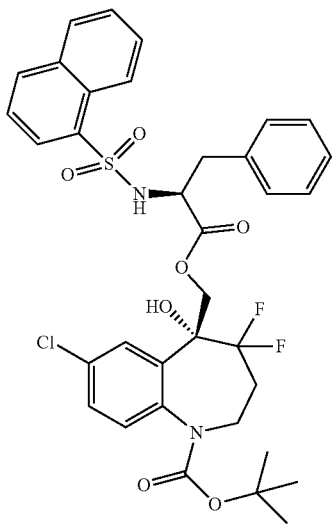 |
| 173 | 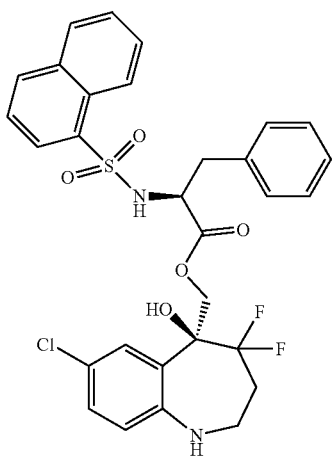 |
| 174 | 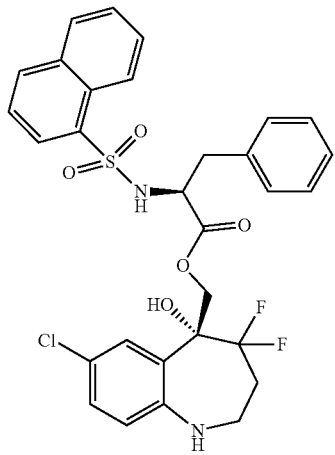 |
| 175 | 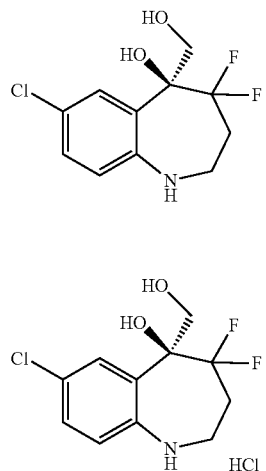 |
| 176 | 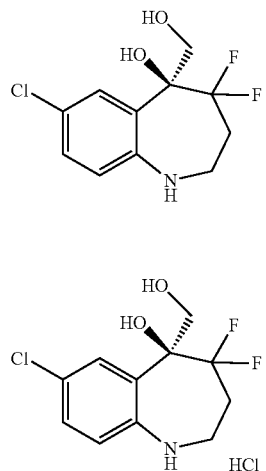 |
| 177 | 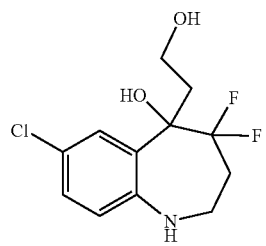 |
| 178 | 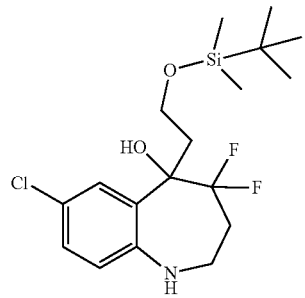 |

TABLE 1-1-continued
| REX | STR |
|---|---|
| 179 | 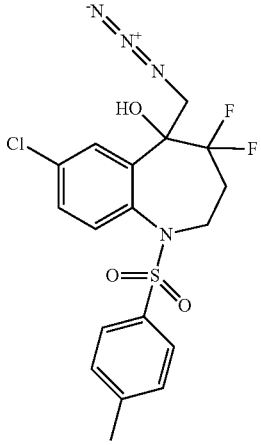 |
| 180 | 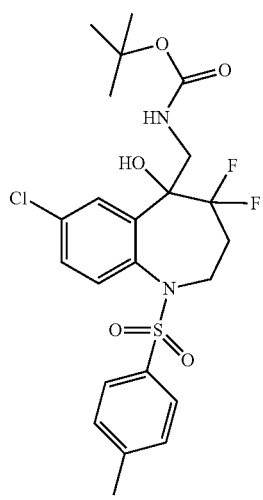 |
| 181 | 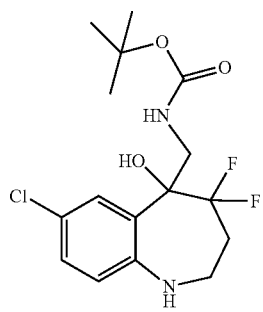 |
TABLE 1-1-continued
| REX | STR |
|---|---|
| 182 | 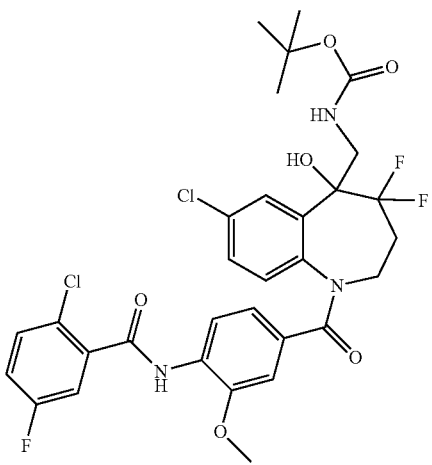 |
| 183 | 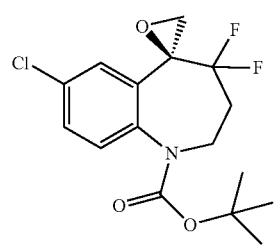 |
| 184 | 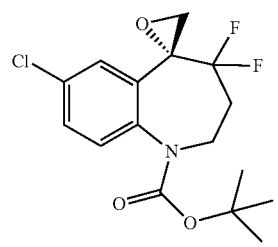 |
| 185 | 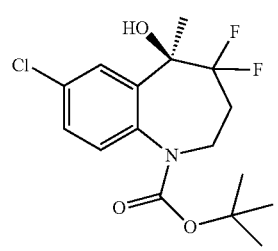 |
| 186 | 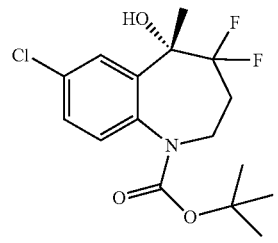 |

TABLE 1-1-continued

| REX | STR |
|---|---|
| 187 | |
| 188 | |
| 189 | |
| 190 | |
| 191 | |
| 192 | |

TABLE 1-1-continued

| REX | STR |
|---|---|
| 193 | |
| 194 | |
| 195 | |
| 196 | |
| 197 | |

TABLE 1-1-continued

| REX | STR |
|---|---|
| 198 | (structure) |
| 199 | (structure) |
| 200 | (structure) |
| 201 | (structure) |
| 202 | (structure) |

In the table, REX154 is considered to present in the form of a 1:1 cocrystal with DCM or a solvate with DCM.

TABLE 2

| REX | RProp | Data |
|---|---|---|
| 1 | | NMR1(400 MHz); 7.81(1H, d, J = 11.0 Hz), 6.50-5.45(2H, br), 3.77(3H, s). |
| 2 | | NMR2(400 MHz); 7.60-7.50(1H, m), 7.77(1H, dd, J = 11.0 Hz, 1.8 Hz), 5.24-4.95(2H, br), 3.89(3H, s). |
| 3 | | NMR2(400 MHz); 8.79(1H, d, J = 1.7 Hz), 8.12(1H, dd, J = 9.1 Hz, 1.8 Hz), 7.37-7.32(2H, m), 7.32-7.27(2H, m), 3.96(3H, s). |
| 4 | | NMR1(400 MHz); 13.65(1H, brs), 11.30(1H, s), 8.78-8.71(1H, m), 8.18(1H, dd, J = 10.2 Hz, 1.8 Hz), 7.63(1H, dd, J = 8.9 Hz, 4.8 Hz), 7.54(1H, d, J = 8.4 Hz, 3.0 Hz), 7.42(1H, dt, J = 8.4 Hz, 3.0 Hz). |
| 5 | | NMR2(400 MHz); 7.96-7.87(2H, m), 7.56-7.46(2H, m), 7.42-7.31(3H, m), 4.87-4.61(2H, br), 3.08-2.96(2H, m), 2.44(3H, s). |
| 6 | | NMR2(400 MHz); 7.92(1H, d, J = 8.3 Hz), 7.49(1H, dd, J = 8.3 Hz, 1.9 Hz), 7.43-7.37(1H, m), 6.65-6.37(1H, br), 3.57(2H, td, J = 6.6 Hz, 2.9 Hz), 2.99(2H, t, J = 6.6 Hz). |
| 7 | | NMR2(400 MHz); 8.87-8.75(2H, m), 8.46-8.33(2H, m), 7.84(1H, d, J = 7.5 Hz), 7.71(1H, d, J = 7.7 Hz), 7.66(1H, t, J = 7.6 Hz), 7.59(1H, t, J = 7.7 Hz), 7.30(1H, t, J = 55.6 Hz), 3.95(3H, s). |
| 8 | | NMR1(400 MHz); 13.22(1H, brs), 11.47(1H, s), 8.90-8.86(1H, m), 8.36-8.26(2H, m), 7.83-7.61(4H, m), 7.32(1H, t, J = 55.3 Hz). |

TABLE 2-continued

| REX | RProp | Data |
|---|---|---|
| 9 | | NMR2(400 MHz); 9.79(1H, brs), 9.01(1H, brs), 8.91(1H, brs), 7.88-7.82(1H, m), 7.55-7.40(3H, m), 4.04(3H, s). |
| 10 | | NMR1(400 MHz); 11.56(1H, brs), 9.42(1H, brs), 8.91(1H, brs), 7.64(1H, dd, J = 8.0 Hz, 1.5 Hz), 7.57(1H, dd, J = 8.0 Hz, 1.5 Hz), 7.53(1H, ddd, J = 8.0 Hz, 7.2 Hz, 1.8 Hz), 7.46(1H, ddd, J = 7.5 Hz, 7.3 Hz, 1.5 Hz). |
| 11 | | NMR1(400 MHz); 13.20(1H, brs), 11.47(1H, brs), 8.88-8.83(1H, m), 8.37-8.30(2H, m), 7.39-7.33(2H, m), 7.32-7.23(1H, m), 2.30(3H, s). |
| 12 | | NMR1(400 MHz); 11.64(1H, brs), 9.39(1H, brs), 8.91(1H, brs), 7.70-7.88(4H, m). |
| 13 | | NMR1(400 MHz); 12.90(1H, brs), 9.00(1H, s), 8.04(1H, d, J = 8.2 Hz), 7.62(1H, d, J = 2.1 Hz), 7.58(1H, dd, J = 8.2 Hz, 1.7 Hz), 7.56(1H, d, J = 1.7 Hz), 7.02(1H, d, J = 2.1 Hz), 3.92(3H, s), 2.56(3H, s). |
| 14 | | NMR1(400 MHz); 12.92(1H, s), 9.96(1H, s), 8.15(1H, d, J = 4.4 Hz), 7.83(1H, d, J = 8.0 Hz), 7.80-7.73(1H, m), 7.73-7.64(2H, m), 7.61(1H, dd, J = 8.4 Hz, 1.2 Hz), 7.55(1H, d, J = 1.6 Hz), 3.87(3H, s). |
| 15 | | NMR1(500 MHz); 13.42-13.91(1H, m), 10.72(1H, s), 8.08(1H, t, J = 8.0 Hz), 7.91-7.68(6H, m). |
| 16 | | NMR2(400 MHz); 8.84(1H, brs), 8.65(1H, d, J = 8.9 Hz), 7.85-7.76(3H, m), 7.50-7.38(3H, m), 5.08(2H, brs), 3.91(3H, s), 3.50(3H, s). |
| 17 | | NMR2(400 MHz); 8.88(1H, s), 8.70(1H, d, J = 8.4 Hz), 7.88-7.81(3H, m), 7.51-7.40(3H, m), 5.32(2H, s), 3.51(3H, s). |
| 18 | | NMR1(400 MHz); 9.96(1H, s), 8.15(1H, d J = 8.3 Hz), 7.84-7.55(6H, m), 5.33(2H, s), 3.51(3H, s). |
| 19 | | NMR1(400 MHz); 12.94(1H, s), 9.90(1H, s), 8.21(1H, d, J = 7.8 Hz), 7.68-7.56(4H, m), 7.33(1H, dt, J = 8.5 Hz, 2.4 Hz), 3.88(3H, s). |
| 20 | 19 | NMR3(400 MHz); 8.36(1H, d, J = 8.4 Hz), 7.73(1H, dd, J = 8.4 Hz, 1.8 Hz), 7.69(1H, d, J = 1.7 Hz), 7.53-7.48(1H, m), 7.37(1H, d, J = 8.1 Hz), 7.24(1H, t, J = 8.6 Hz), 3.96(3H, s). |
| 21 | | NMR1(500 MHz); 13.20(1H, brs), 10.73(1H, s), 8.16(1H, t, J = 8.0 Hz), 7.83(1H, d, J = 8.4 Hz), 7.76(1H, dd, J = 11.1 Hz, 1.6 Hz), 7.62(1H, dd, J = 8.9 Hz, 4.8 Hz), 7.58(1H, dd, J = 8.4 Hz, 3.0 Hz), 7.41(1H, dt, J = 8.6 Hz, 3.0 Hz). |
| 22 | | NMR2(400 MHz); 8.55(1H, dd, J = 2.0 Hz, 1.0 Hz), 8.39(1H, s), 8.36-8.21(2H, m), 7.72(1H, dd, J = 9.5 Hz, 1.4 Hz), 7.56(1H, dt, J = 7.5 Hz, 1.4 Hz), 7.47(1H, dt, J = 7.5 Hz, 1.3 Hz), 7.44-7.35(3H, m), 7.11-7.03(2H, m), 3.91(3H, s). |
| 23 | | NMR1(400 MHz); 13.15(1H, s), 11.11(1H, s), 8.78(1H, d, J = 1.8 Hz), 8.24(1H, d, J = 8.7 Hz, 2.3 Hz), 8.17-8.07(1H, m), 7.64-7.54(2H, m), 7.52-7.37(4H, m), 7.26-7.16(2H, m). |
| 24 | 19 | NMR2(400 MHz); 8.60(1H, d, J = 8.5 Hz), 8.53(1H, s), 7.82(1H, dd, J = 8.5 Hz, 1.7 Hz), 7.63(1H, d, J = 1.7 Hz), 7.39(1H, d, J = 4.9 Hz), 6.96(1H, d, J = 4.9 Hz), 4.01(3H, s), 2.60(3H, s). |
| 25 | | NMR2(500 MHz); 7.83(1H, dd, J = 8.4 Hz, 5.4 Hz), 7.76-7.70(1H, m), 7.50(1H, t, J = 55.4 Hz), 7.38-7.30(1H, m), 3.95(3H, s). |
| 26 | | NMR2(500 MHz); 7.92-7.83(2H, m), 7.54(1H, t, J = 55.3 Hz), 7.44-7.33(1H, m). |
| 27 | | NMR1(500 MHz); 9.43(1H, s), 8.15(1H, d, J = 8.0 Hz), 7.61(1H, dd, J = 13.0 Hz, 1.5 Hz), 7.56(1H, dd, J = 2.0 Hz), 7.50(1H, d, J = 7.5 Hz), 7.43-7.36(1H, m), 7.33-7.26(2H, m), 3.88(3H, s), 2.41(3H, m). |
| 28 | 27 | NMR1(500 MHz); 12.91(1H, brs), 9.44(1H, s), 8.14(1H, d, J = 8.0 Hz), 7.61(1H, dd, J = 8.5 Hz, 1.5 Hz), 7.55(1H, d, J = 1.5 Hz), 7.47(1H, d, J = 7.5 Hz), 7.43(1H, ddd, J = 7.5 Hz, 7.5 Hz, 1.5 Hz), 7.34(1H, d, J = 7.5 Hz), 7.30(1H, ddd, J = 7.5 Hz, 7.5 Hz, 1.0 Hz), 3.88(3H, s). 2.76(2H, q, J = 7.5 Hz), 1.19(3H, t, J = 7.5 Hz). |
| 29 | 27 | NMR1(500 MHz); 12.93(1H, brs), 9.64(1H, s), 8.11(1H, d, J = 8.0 Hz), 7.61(1H, dd, J = 7.5 Hz, 1.5 Hz), 7.56(1H, d, J = 1.5 Hz), 7.37-7.29(2H, m), 7.43(1H, ddd, J = 8.5 Hz, 8.5 Hz, 3.0 Hz), 3.88(3H, s), 2.37(3H, s). |
| 30 | | NMR1(500 MHz); 12.92(1H, brs), 9.77(1H, s), 8.20(1H, d, J = 8.0 Hz), 7.61(1H, d, J = 7.5 Hz), 7.55(1H, d, J = 1.0 Hz), 7.45-7.37(2H, m), 7.32(1H, dd, J = 8.0 Hz, 1.5 Hz), 3.88(3H, s), 2.34(3H, s). |

TABLE 2-continued

| REX | RProp | Data |
|---|---|---|
| 31 | | NMR1(500 MHz); 13.22(1H, brs), 11.34(1H, s), 8.86-8.84(1H, m), 8.36-8.27(2H, m), 7.50-7.38(2H, m), 7.32(1H, dd, J = 8.0 Hz, 2.0 Hz), 2.34(3H, s). |
| 32 | | NMR2(500 MHz); 9.77(1H, d, J = 1.3 Hz), 9.18(1H, s), 8.97(1H, d, J = 1.5 Hz), 7.59(1H, dd, J = 8.3 Hz, 3.1 Hz), 7.48(1H, dd, J = 8.9 Hz, 4.8 Hz), 7.26-7.18(1H, m), 4.04(3H, s). |
| 33 | | NMR1(500 MHz); 13.54(1H, brs), 11.83(1H, s), 9.50(1H, s), 9.00(1H, d, J = 1.2 Hz), 7.68-7.59(2H, m), 7.43(1H, dt, J = 8.6 Hz, 3.1 Hz). |
| 34 | 30 | NMR3(400 MHz); 7.97(1H, s), 7.93(1H, d, J = 8.3 Hz), 7.71(1H, d, J = 8.3 Hz), 7.58(1H, dd, J = 8.9 Hz, 4.7 Hz), 7.46(1H, dd, J = 8.2 Hz, 3.0 Hz), 7.32-7.20(1H, m), 2.43(3H, s). |
| 35 | | NMR2(500 MHz); 9.05(1H, dd, J = 2.5 Hz, 1.0 Hz), 8.29(1H, dd, J = 9.0 Hz, 2.5 Hz), 8.23(1H, dd, J = 9.0 Hz, 1.0 Hz), 8.20(1H, dd, J = 8.0 Hz, 1.0 Hz), 7.51(1H, ddd, J = 7.5 Hz, 7.5 Hz, 1.5 Hz), 7.43-7.37(1H, m), 7.31-7.26(1H, m), 4.39(2H, t, J = 6.5 Hz), 3.95(3H, s), 3.13(2H, t, J = 6.5 Hz). |
| 36 | 30 | NMR1(500 MHz); 13.54-12.35(1H, br), 10.01(1H, s), 8.22(1H, d, J = 8.2 Hz), 7.87-7.79(2H, m), 7.61(1H, d, J = 8.3 Hz), 7.55(1H, s), 3.88(3H, s). |
| 37 | | NMR1(500 MHz); 13.20(1H, brs), 8.96(1H, dd, J = 2.5 Hz, 0.5 Hz), 8.29(1H, dd, J = 9.0 Hz, 4.0 Hz), 8.13(1H, dd, J = 8.5 Hz, 0.5 Hz), 8.04(1H, dd, J = 7.5 Hz, 1.0 Hz), 7.58(1H, ddd, J = 7.5 Hz, 7.5 Hz, 1.5 Hz), 7.47-7.38(2H, m), 4.29(2H, t, J = 6.5 Hz), 3.13(2H, t, J = 6.5 Hz). |
| 38 | 27 | NMR1(500 MHz); 13.07(1H, brs), 11.05(1H, s), 7.90(1H, dd, J = 8.5 Hz, 8.5 Hz), 7.74(1H, dd, J = 13.5 Hz, 2.0 Hz), 7.69-7.60(2H, m), 7.52(1H, dd, J = 8.5 Hz, 2.0 Hz), 7.44(1H, ddd, J = 8.5 Hz, 8.5 Hz, 3.0 Hz). |
| 39 | | NMR2(500 MHz); 8.14(1H, dd, J = 7.5 Hz, 1.0 Hz), 7.71(1H, dd, J = 7.5 Hz, 1.5 Hz), 7.68(1H, J = 1.5 Hz), 7.47(1H, ddd, J = 7.5 Hz, 7.5 Hz, 1.5 Hz), 7.41-7.34(2H, m), 7.26-7.22(1H, m), 3.94(3H, s), 3.90(3H, s), 3.90-3.77(2H, m), 3.15(2H, t, J = 1.5 Hz). |
| 40 | 37 | NMR1(500 MHz); 13.10(1H, brs), 7.91(1H, dd, J = 8.0 Hz, 1.0 Hz), 7.63-7.57(2H, m), 7.54(1H, ddd, J = 7.5 Hz, 1.5 Hz), 7.43(1H, J = 7.5 Hz), 7.41-7.25(2H, m), 3.85(3H, s), 3.78(2H, t, J = 1.5 Hz), 3.12(2H, t, J = 1.5 Hz). |
| 41 | | NMR2(500 MHz); 8.65(1H, d, J = 8.4 Hz), 8.29(1H, s), 7.84 (1H, dd, J = 8.5 Hz, 1.8 Hz), 7.64(1H, d, J = 1.8 Hz), 7.55(1H, dd, J = 8.4 Hz, 5.8 Hz), 7.11-6.90(2H, m), 4.04-3.90(3H, m), 2.55(3H, s). |
| 42 | 30 | NMR1(500 MHz); 13.21(1H, brs), 10.71(1H, s), 8.17(1H, dd, J = 8.0 Hz, 8.0 Hz), 7.95-7.85(2H, m), 7.82(1H, d, J = 8.5 Hz), 7.75(1H, dd, J = 6.0 Hz, 1.5 Hz). |
| 43 | 30 | NMR1(500 MHz); 13.21(1H, brs), 10.75(1H, s), 8.18(1H, dd, J = 8.0 Hz, 8.0 Hz), 7.98(1H, d, J = 6.5 Hz), 7.88-7.79(2H, m), 7.76(1H, dd, J = 6.0 Hz, 1.5 Hz). |
| 44 | | NMR2 (500 MHz); 8.90(1H, dd, J = 2.5 Hz, 1.0 Hz), 8.84(1H, dd, J = 5.0 Hz, 1.5 Hz), 8.67(1H, brs), 8.42(1H, dd, J = 8.5 Hz, 0.5 Hz), 8.39(1H, dd, J = 8.5 Hz, 2.0 Hz), 8.08(1H, dd, J = 2.5 Hz, 1.5 Hz), 7.58(1H, dd, J = 8.0 Hz, 5.0 Hz), 7.00(1H, t, J = 54.5 Hz), 3.96(3H, s). |
| 45 | | NMR1(500 MHz); 13.25(1H, brs), 11.60(1H, s), 8.89-8.86(1H, m), 8.81(1H, dd, J = 5.0 Hz, 1.5 Hz), 8.35(1H, dd, J = 8.5 Hz, 2.5 Hz), 8.30(1H, d, J = 8.5 Hz), 8.19(1H, d, J = 7.5 Hz), 7.70(1H, dd, J = 8.0 Hz, 5.0 Hz), 7.17(1H, t, J = 54.0 Hz). |
| 46 | 30 | NMR1(500 MHz); 12.79(1H, brs), 10.66(1H, s), 7.94(2H, d, J = 9.0 Hz), 7.84(2H, d, J = 9.0 Hz), 7.67(1H, dd, J = 11.0 Hz, 8.5 Hz), 7.45(1H, dd, J = 12.0 Hz, 8.0 Hz), 2.37(3H, s). |
| 47 | 30 | NMR1(500 MHz); 13.06(1H, brs), 10.82(1H, s), 7.88(1H, dd, J = 8.5 Hz, 8.5 Hz), 7.76(1H, dd, J = 13.5 Hz, 2.0 Hz), 7.69(1H, dd, J = 11.0 Hz, 8.5 Hz), 7.54(1H, dd, J = 8.5 Hz, 2.0 Hz), 7.46(1H, dd, J = 11.5 Hz, 8.0 Hz), 2.37(3H, s). |
| 48 | | NMR2(500 MHz); 9.68-9.58(1H, m), 8.74(1H, s), 7.97-7.78(2H, m), 7.67-7.30(8H, m), 3.99(3H, s). |
| 49 | | NMR1(500 MHz); 13.45(1H, brs), 11.46(1H, s), 9.31(1H, s), 8.90(1H, s), 7.81-7.15(9H, m). |
| 50 | 30 | NMR1(500 MHz); 13.19(1H, brs), 10.44(1H, s), 8.03(1H, dd, J = 8.0 Hz, 8.0 Hz), 7.81(1H, dd, J = 8.5 Hz, 1.5 Hz), 7.75(1H, dd, J = 10.0 Hz, 2.0 Hz), 7.65(1H, dd, |

TABLE 2-continued

| REX | RProp | Data |
|---|---|---|
| | | J = 11.0 Hz, 8.0 Hz), 7.44(1H, dd, J = 12.0 Hz, 8.0 Hz), 2.38(3H, s). |
| 51 | 30 | NMR1(500 MHz); 12.86(1H, brs), 9.97(1H, s), 7.84(1H, d, J = 1.5 Hz), 7.80(1H, dd, J = 8.5 Hz, 1.5 Hz), 7.71-7.60(2H, m), 7.44(1H, dd, J = 12.0 Hz, 8.0 Hz), 2.41(3H, s), 2.33(3H, s). |
| 52 | 30 | NMR1(500 MHz); 12.93(1H, brs), 9.68(1H, s), 7.84(1H, d, J = 3.0 Hz), 7.65-7.56(2H, m), 7.56(1H, d, J = 1.5 Hz), 7.41(1H, dd, J = 12.0 Hz, 8.0 Hz), 3.88(3H, s), 2.37(3H, s). |
| 53 | | NMR2(500 MHz); 9.61(1H, s), 8.64(1H, s), 8.09(1H, brs), 7.56(1H, dd, J = 8.8 Hz, 2.7 Hz), 7.50-7.18(7H, m), 3.99(3H, s). |
| 54 | | NMR1(500 MHz); 15.50-12.50(1H, br), 11.54(1H, s), 9.29(1H, brs), 8.91(1H, s), 7.78-7.05(8H, m). |
| 55 | | NMR1(500 MHz); 13.16(1H, brs), 11.21(1H, brs), 8.77(1H, s), 8.23(1H, d, J = 8.9 Hz), 8.10(1H, brs), 7.56-7.24(8H, m). |
| 56 | 30 | NMR1(400 MHz); 12.80(1H, s), 10.90(1H, s), 7.98-7.94(3H, m), 7.81-7.41(3H, m), 7.61-7.56(1H, m). |
| 57 | 30 | NMR1(400 MHz); 12.90(1H, brs), 10.10(1H, s), 8.17(1H, d, J = 8.0 Hz), 7.93-7.89(1H, m), 7.63-7.52(4H, m), 3.88(3H, s). |
| 58 | | NMR1(500 MHz); 13.18(1H, s), 11.37(1H, s), 8.90-8.71(2H, m), 8.28(1H, d, J = 7.9 Hz), 8.19(1H, brs), 8.02(1H, d, J = 7.4 Hz), 7.65(2H, d, J = 7.1 Hz), 7.56-7.22(4H, m). |
| 59 | | NMR1(500 MHz); 11.74(1H, s), 9.39(1H, brs), 8.94(1H, s), 8.90-8.72(1H, m), 8.18-8.00(1H, m), 7.81-7.12(6H, m), 3.90(3H, s). |
| 60 | 54 | NMR1(500 MHz); 13.48(1H, m), 11.69(1H, s), 9.38(1H, brs), 8.92(1H, s), 8.85-8.75(1H, m), 8.07(1H, dd, J = 7.7 Hz, 1.7 Hz), 7.73-7.61(2H, m), 7.52(1H, dd, J = 7.7 Hz, 4.8 Hz), 7.50-7.31(3H, m). |
| 61 | | NMR1(500 MHz); 14.30-12.84(1H, br), 11.08(1H, s), 8.77(1H, d, J = 1.2 Hz), 8.18(1H, dd, J = 10.2 Hz, 1.8 Hz), 7.40-7.34(2H, m), 7.28(1H, td, J = 8.6 Hz, 2.8 Hz), 2.39(3H, s). |
| 62 | | NMR2(400 MHz); 8.10(1H, d, J = 8.3 Hz), 7.52(1H, dd, J = 8.3 Hz, 1.9 Hz), 7.43(1H, d, J = 0.8 Hz), 7.34(1H, dd, J = 8.8 Hz, 5.6 Hz), 7.28-7.25(1H, m), 7.09-7.04(1H, m), 3.90-3.78(2H, m), 3.32-3.25(1H, m), 3.11-3.03(1H, m). |
| 63 | 35 | NMR2(500 MHz); 9.04(1H, d, J = 1.5 Hz), 8.32-8.27(1H, m), 8.21(1H, d, J = 9.0 Hz), 8.13(1H, d, J = 7.5 Hz), 7.38(1H, d, J = 8.5 Hz), 7.89(1H, s), 4.39(2H, t, J = 6.5 Hz), 3.95(3H, s), 3.11(2H, t, J = 6.5 Hz). |
| 64 | 39 | NMR2(500 MHz); 8.13-8.05(3H, m), 7.48(2H, d, J = 8.5 Hz), 7.56(1H, dd, J = 8. Hz 5, 2.0 Hz), 7.28-7.24(1H, m), 4.04(2H, t, J = 6.5 Hz), 3.93(3H, s), 3.15(2H, t, J = 6.5 Hz). |
| 65 | 37 | NMR1(500 MHz); 13.29(1H, brs), 8.95(1H, dd, J = 2.5 Hz, 0.5 Hz), 8.29(1H, dd, J = 9.0 Hz, 2.5 Hz), 8.11(1H, dd, J = 9.0 Hz, 0.5 Hz), 8.02(1H, d, J = 8.5 Hz), 7.57-7.54(1H, m), 7.50(1H, dd, J = 8.5 Hz, 2.0 Hz), 4.29(2H, t, J = 6.5 Hz), 3.14(2H, t, J = 6.5 Hz). |
| 66 | 37 | NMR1(500 MHz); 12.95(1H, s), 7.98(2H, d, J = 8.5 Hz), 7.95(1H, d, J = 8.5 Hz), 7.56(2H, d, J = 8.5 Hz), 7.53(1H, d, J = 2.0 Hz), 7.47(1H, dd, J = 8.5 Hz, 2.0 Hz), 4.03(2H, t, J = 6.5 Hz), 3.16(2H, t, J = 6.5 Hz). |
| 67 | 39 | NMR2(500 MHz); 8.08(2H, dd, J = 8.5 Hz, 1.5 Hz), 7.52(2H, dd, J = 8.5 Hz, 1.5 Hz), 7.42(1H, d, J = 8.0 Hz), 7.35(1H, dt, J = 7.5 Hz, 1.5 Hz), 7.17(1H, d, J = 7.5 Hz), 3.99(2H, t, J = 5.5 Hz), 3.95-3.83(3H, m), 3.14(2H, t, J = 5.5 Hz). |
| 68 | 37 | NMR1(500 MHz); 12.96(1H, s), 7.98(2H, d, J = 8.5 Hz), 7.58(2H, d, J = 8.5 Hz), 7.53-7.42(2H, m), 7.37(1H, d, J = 7.0 Hz), 3.96(2H, t, J = 6.0 Hz), 3.14(2H, t, J = 6.0 Hz). |
| 69 | | NMR2(400 MHz); 8.14(1H, d, J = 8.0 Hz), 7.59(1H, d, J = 16.0 Hz), 7.53-7.50(1H, m), 7.38-7.33(2H, m), 7.28-7.20(1H, m), 7.12-6.98(1H, m), 6.46(1H, d, J = 16.0 Hz), 3.91-3.80(2H, m), 3.36-3.13(1H, m), 3.14-3.07(1H, m), 1.52(9H, s). |
| 70 | | NMR3(400 MHz); 8.12(1H, d, J = 8.0 Hz), 8.06-8.03(2H, m), 7.54(1H, dd, J = 8.8 Hz, 5.6 Hz), 7.45(1H, dd, J = 8.4 Hz, 2.8 Hz), 7.26-7.20(1H, m), 4.00-3.89(2H, m), 3.41-3.24(2H, m). |
| 71 | 30 | NMR1(500 MHz); 13.51-12.65(1H, br), 10.26(1H, brs), 7.90-7.84(1H, m), 7.75-7.70(1H, m), 7.67-7.57(3H, m), 7.52-7.43(4H, m), 7.41-7.36(2H, m), 7.35-7.30(1H, m). |

TABLE 2-continued

| REX | RProp | Data |
|---|---|---|
| 72 | 30 | NMR3(400 MHz); 8.24(1H, t, J = 8.2 Hz), 7.91-7.87(1H, m), 7.79(1H, dd, J = 11.3 Hz, 1.8 Hz), 7.39-7.34(1H, m), 7.13(1H, d, J = 7.7 Hz), 7.04(1H, t, J = 8.9 Hz), 2.43(3H, s). |
| 73 | 30 | NMR1(500 MHz); 13.05(1H, s), 11.08(1H, s), 7.89(1H, t, J = 8.5 Hz), 7.76(1H, dd, J = 8.5 Hz, 2.0 Hz), 7.52(1H, dd, J = 8.5 Hz, 2.0 Hz), 7.47-7.39(1H, m), 7.22-7.13(2H, m), 2.33(3H, s). |
| 74 | 30 | NMR1(500 MHz); 13.45-12.43(1H, br), 11.11(1H, s), 7.97(1H, dd, J = 8.8 Hz, 5.1 Hz), 7.90(1H, t, J = 8.6 Hz), 7.78(1H, dd, J = 8.6 Hz, 2.5 Hz), 7.70(1H, dd, J = 13.3 Hz, 1.9 Hz), 7.61(1H, dt, J = 8.4 Hz, 2.3 Hz), 7.50(1H, dd, J = 8.6 Hz, 1.9 Hz). |
| 75 | 30 | NMR1(500 MHz); 13.20(1H, s), 10.79(1H, s), 8.12(1H, t, J = 8.0 Hz), 7.94(1H, dd, J = 9.0 Hz, 5.0 Hz), 7.83(1H, d, J = 8.5 Hz), 7.76(1H, dd, J = 11.0 Hz, 1.5 Hz), 7.71(1H, dd, J = 8.5 Hz, 2.5 Hz), 7.58(1H, dt, J = 8.5 Hz, 2.0 Hz). |
| 76 | 61 | NMR1(500 MHz); 13.62(1H, brs), 11.06(1H, s), 8.65(1H, s), 8.05(1H, d, J = 10.2 Hz), 7.50-7.42(3H, m), 7.37-7.31(5H, m). |
| 77 | 30 | NMR3(400 MHz); 8.22(1H, t, J = 8.0 Hz), 7.89(1H, dd, J = 8.5 Hz, 0.98 Hz), 7.81(1H, d, J = 1.8 Hz), 7.78-7.73(1H, m), 7.61(1H, dd, J = 9.1 Hz, 2.5 Hz), 7.51(1H, dt, J = 8.3 Hz, 2.5 Hz). |
| 78 | 30 | NMR1(500 MHz); 13.02(1H, brs), 10.80(1H, s), 7.83-7.79(1H, m), 7.57-7.51(3H, m), 7.48-7.44(1H, m), 7.40-7.29(6H, m). |
| 79 | | NMR1(500 MHz); 13.40-12.10(1H, br), 10.23(1H, s), 8.03-7.90(1H, m), 7.89-7.60(4H, m), 7.50-7.59(1H, m), 2.32(3H, s). |
| 80 | 61 | NMR1(500 MHz); 13.57(1H, brs), 10.98(1H, s), 8.67(1H, s), 8.06(1H, dd, J = 1.7 Hz, 10.2 Hz), 7.62-7.57(2H, m), 7.51-7.30(7H, m). |
| 81 | | NMR1(400 MHz); 13.10-12.30(1H, br), 10.66(1H, s), 7.88(2H, d, J = 8.6 Hz), 7.65(2H, d, J = 8.6 Hz), 7.57-7.38(5H, m), 7.21(2H, t, J = 8.8 Hz). |
| 82 | 30 | NMR1(500 MHz); 12.64(1H, brs), 10.64(1H, s), 7.86(2H, d, J = 8.3 Hz), 7.63(2H, d, J = 8.3 Hz), 7.54-7.49(2H, m), 7.46-7.34(5H, m), 7.32-7.28(1H, m). |
| 83 | 30 | NMR1(500 MHz); 13.13(1H, brs), 10.39(1H, s), 7.92-7.88(1H, m), 7.73(1H, d, J = 8.3 Hz), 7.66(1H, d, J = 11.1 Hz), 7.53-7.48(2H, m), 7.46-7.36(5H, m), 7.35-7.31(1H, m). |
| 84 | 30 | NMR1(500 MHz); 12.79(1H, brs), 10.90(1H, s), 7.95(2H, d, J = 8.8 Hz), 7.86-7.81(3H, m), 7.71(1H, dd, J = 8.8 Hz, 2.1 Hz), 7.56(1H, dt, J = 8.5 Hz, 2.6 Hz), 7.28(1H, t, J = 55.3 Hz). |
| 85 | 30 | NMR1(500 MHz); 13.22(1H, brs), 10.73(1H, s), 8.02(1H, t, J = 8.0 Hz), 7.85-7.80(2H, m), 7.76(1H, dd, J = 11.0 Hz, 1.8 Hz), 7.69(1H, d, J = 8.8 Hz), 7.56(1H, dt, J = 8.5 Hz, 2.6 Hz), 7.27(1H, t, J = 55.3 Hz). |
| 86 | 35 | NMR2(500 MHz); 9.05(1H, s), 8.30(1H, dd, J = 8.8 Hz, 2.4 Hz), 8.21(1H, dd, J = 9.2 Hz, 0.6 Hz), 7.87(1H, dd, J = 9.2 Hz, 2.7 Hz), 7.26(1H, t, J = 8.2 Hz), 7.21(1H, dt, J = 8.3 Hz, 2.8 Hz), 4.39(2H, t, J = 6.3 Hz), 3.95(3H, s), 3.10(2H, t, J = 6.4 Hz). |
| 87 | 35 | NMR2(500 MHz); 9.04(1H, s), 8.29(1H, dd, J = 8.8 Hz, 2.3 Hz), 8.21(1H, d, J = 8.7 Hz), 8.20(1H, d, J = 9.3 Hz), 7.08(1H, dt, J = 8.6 Hz, 2.6 Hz), 6.97(1H, dd, J = 8.7 Hz, 2.5 Hz), 4.40(2H, t, J = 6.3 Hz), 3.95(3H, s), 3.12(2H, t, J = 6.4 Hz). |
| 88 | 37 | NMR2(500 MHz); 9.09(1H, s), 8.34(1H, dd, J = 8.8 Hz, 2.4 Hz), 8.23(1H, dd, J = 8.7 Hz, 0.5 Hz), 7.87(1H, dd, J = 9.1 Hz, 2.7 Hz), 7.26(1H, t, J = 8.2 Hz), 7.22(1H, dt, J = 8.3 Hz, 2.8 Hz), 4.40(2H, t, J = 6.4 Hz), 3.11(2H, t, J = 6.4 Hz). |
| 89 | 37 | NMR2(500 MHz); 9.10(1H, s), 8.34(1H, dd, J = 8.8 Hz, 2.3 Hz), 8.31(1H, d, J = 8.8 Hz), 8.22(1H, dd, J = 8.7 Hz, 5.8 Hz), 7.08(1H, dt, J = 8.6 Hz, 2.5 Hz), 6.98(1H, dd, J = 8.6 Hz, 2.4 Hz), 4.42(2H, t, J = 6.3 Hz), 3.13(2H, t, J = 6.4 Hz). |
| 90 | 39 | NMR2(500 MHz); 8.16(1H, d, J = 7.8 Hz), 8.10(2H, d, J = 8.7 Hz), 7.59(1H, t, J = 7.7 Hz), 7.55(1H, d, J = 7.7 Hz), 7.51(2H, d, J = 8.7 Hz), 7.39(1H, t, J = 7.7 Hz), 4.07(2H, s), 3.93(3H, s), 2.44(2H, m), 2.18(2H, m), 2.08(2H, m). |

TABLE 2-continued

| REX | RProp | Data |
|---|---|---|
| 91 | 30 | NMR1(400 MHz); 13.21(1H, brs), 10.66(1H, s), 7.99(1H, t, J = 7.9 Hz), 7.85-7.65(6H, m), 7.32(1H, t, J = 55.4 Hz). |
| 92 | 30 | NMR1(500 MHz); 13.00(1H, brs), 10.84, (1H, s), 7.83(1H, t, J = 8.6 Hz), 7.63(1H, dd, J = 8.9 Hz, 2.1 Hz), 7.58(1H, d, J = 13.4 Hz), 7.55-7.48(2H, m), 7.43-7.35(3H, m), 7.26-7.18(2H, m). |
| 93 | 30 | NMR1(500 MHz); 14.17-11.90(1H, br), 10.39(1H, s), 7.86(1H, t, J = 7.5 Hz), 7.74(1H, d, J = 8.4 Hz), 7.68(1H, d, J = 10.9 Hz), 7.59(1H, dd, J = 9.0 Hz, 2.1 Hz), 7.53-7.46(2H, m), 7.44-7.35(2H, m), 7.25-7.18(2H, m). |
| 94 | 30 | NMR1(500 MHz); 14.02-11.41(1H, br), 10.67(1H, s), 7.88(2H, d, J = 8.7 Hz), 7.67(2H, d, J = 8.7 Hz), 7.60(1H, dd, J = 8.9 Hz, 2.3 Hz), 7.53-7.46(2H, m), 7.42-7.34(2H, m), 7.25-7.17(2H, m). |
| 95 |  | NMR1(500 MHz); 13.11(1H, brs), 11.26(1H, s), 8.81(1H, d, J = 2.1 Hz), 8.24(1H, dd, J = 8.7 Hz, 2.1 Hz), 8.06(1H, d, J = 8.7 Hz), 7.61-7.57(1H, m), 7.50-7.46(2H, m), 7.42-7.33(2H, m), 7.25-7.16(2H, m). |
| 96 | 95 | NMR1(500 MHz); 13.12(1H, brs), 11.08(1H, s), 8.78(1H, d, J = 1.7 Hz), 8.19(1H, dd, J = 8.7 Hz, 2.3 Hz), 7.99(1H, d, J = 8.7 Hz), 7.54(1H, d, J = 9.0 Hz, 2.7 Hz), 7.39(1H, dt, J = 8.6 Hz, 2.7 Hz), 7.31(1H, dd, J = 8.6 Hz, 5.6 Hz), 7.21-7.10(4H, m), 2.11(3H, s). |
| 97 |  | NMR2(400 MHz); 7.97(2H, d, J = 8.7 Hz), 7.66(1H, dd, J = 9.0 Hz, 2.7 Hz), 7.51(1H, brs), 7.45-7.38(1H, m), 7.37-7.19(5H, m), 7.13(1H, dt, J = 7.5 Hz, 0.8 Hz), 6.91(1H, d, J = 8.0 Hz), 3.64(3H, s). |
| 98 |  | NMR2(400 MHz); 8.65-8.50(1H, m), 7.91-7.78(2H, m), 7.71-7.58(2H, m), 7.45-7.20(4H, m), 7.13-7.02(1H, m), 6.92-6.81(1H, m), 3.67(3H, s). |
| 99 |  | NMR2(400 MHz); 8.83-8.69(1H, m), 8.36-8.12(2H, m), 7.58-7.15(6H, m), 7.14-6.96(1H, m), 6.95-6.79(1H, m), 3.68(3H, s). |
| 100 | 37 | NMR1(500 MHz); 12.95(1H, s), 8.00(2H, d, J = 8.7 Hz), 7.97(1H, d, J = 7.7 Hz), 7.71(1H, t, J = 7.0 Hz), 7.66(1H, t, J = 7.3 Hz), 7.57(2H, d, J = 8.7 Hz), 7.43(1H, t, J = 7.7 Hz), 4.03(2H, s), 2.36(2H, m), 2.12(2H, m), 1.98(2H, m). |
| 101 | 39 | NMR2(500 MHz); 8.15(2H, d, J = 8.8 Hz), 7.97(1H, d, J = 7.2 Hz), 7.48(2H, d, J = 8.8 Hz), 7.37(1H, dt, J = 8.1 Hz, 5.4 Hz), 7.30-7.21(1H, m), 4.05(2H, t, J = 6.4 Hz), 3.93(3H, s), 3.19(2H, t, J = 6.5 Hz). |
| 102 | 39 | NMR2(500 MHz); 8.17(1H, dd, J = 8.2 Hz, 5.8 Hz), 8.09(2H, d, J = 8.8 Hz), 7.7(1H, dt, J = 8.6 Hz, 2.6 Hz), 7.48(2H, d, J = 8.8 Hz), 6.95(1H, dd, J = 8.7 Hz, 2.6 Hz), 4.05(2H, t, J = 6.4 Hz), 3.93(3H, s), 3.16(2H, t, J = 6.4 Hz). |
| 103 | 39 | NMR2(500 MHz); 8.09(2H, d, J = 8.8 Hz), 7.84(1H, dd, J = 9.1 Hz, 2.7 Hz), 7.48(2H, d, J = 8.8 Hz), 7.24(1H, dd, J = 8.3 Hz, 5.2 Hz), 7.19(1H, dt, J = 8.3 Hz, 2.8 Hz),, 4.04(2H, t, J = 6.4 Hz), 3.93(3H, s), 3.14(2H, t, J = 6.5 Hz). |
| 104 | 37 | NMR2(500 MHz); 8.09(2H, d, J = 8.7 Hz), 7.98(1H, d, J = 7.7 Hz), 7.53(2H, d, J = 8.7 Hz), 7.38(1H, dt, J = 8.1 Hz, 5.5 Hz), 7.25(1H, t, J = 8.1 Hz), 4.07(2H, t, J = 6.5 Hz), 3.20(2H, t, J = 6.5 Hz). |
| 105 | 37 | NMR2(500 MHz); 8.18(1H, dd, J = 8.7 Hz, 5.8 Hz), 8.14(2H, d, J = 8.8 Hz), 7.52(2H, d, J = 8.8 Hz), 7.07(1H, dt, J = 8.6 Hz, 2.6 Hz), 6.96(1H, dd, J = 8.7 Hz, 2.4 Hz), 4.07(2H, t, J = 6.4 Hz), 3.17(2H, t, J = 6.4 Hz). |
| 106 | 37 | NMR2(500 MHz); 8.16(2H, d, J = 8.7 Hz), 7.85(1H, dd, J = 9.2 Hz, 2.7 Hz), 7.53(2H, d, J = 8.7 Hz), 7.25(1H, dd, J = 8.4 Hz, 5.2 Hz), 7.20(1H, dt, J = 8.3 Hz, 2.7 Hz), 4.06(2H, t, J = 6.3 Hz), 3.15(2H, t, J = 6.4 Hz). |
| 107 | 30 | NMR1(500 MHz); 14.17-11.94(1H, br), 10.45(1H, s), 7.88(1H, t, J = 7.9 Hz), 7.75(1H, d, J = 8.3 Hz), 7.68(1H, d, J = 10.9 Hz), 7.58-7.52(2H, m), 7.48-7.40(2H, m), 7.26-7.22(2H, m), 7.20-7.15(1H, m). |
| 108 | 30 | NMR1(500 MHz); 12.76(1H, brs), 10.69(1H, s), 7.88(2H, d, J = 8.7 Hz), 7.65(2H, d, J = 8.7 Hz), 7.58-7.54(2H, m), 7.46(1H, dt, J = 8.5 Hz, 2.8 Hz), 7.43-7.38(1H, m), 7.22(2H, d, J = 7.5 Hz), 7.17-7.12(1H, m). |
| 109 |  | NMR1(500 MHz); 13.98-12.05(1H, br), 11.26(1H, s), 8.79(1H, d, J = 1.8 Hz), 8.25(1H, dd, J = 8.6 Hz, 2.3 Hz), |

TABLE 2-continued

| REX | RProp | Data |
|---|---|---|
| | | 8.12-8.07(1H, brs), 7.55-7.50(2H, m), 7.44(1H, dt, J = 8.6 Hz, 2.7 Hz), 7.42-7.37(1H, m), 7.22-7.18(2H, m), 7.17-7.11(1H, m). |
| 110 | 39 | NMR2(400 MHz): 8.13(1H, d, J = 2.2 Hz), 8.09(2H, d, J = 8.8 Hz), 7.48(2H, d, J = 8.7 Hz), 7.45(1H, dd, J = 8.1 Hz, 2.4 Hz), 7.21(1H, d, J = 8.2 Hz), 4.03(2H, t, J = 6.2 Hz), 3.93(3H, s), 3.13(2H, t, J = 6.4 Hz). |
| 111 | 37 | NMR1(400 MHz): 13.22-12.71(1H, br), 7.99(2H, d, J = 8.7 Hz), 7.90(1H, d, J = 2.3 Hz), 7.62(1H, dd, J = 8.1 Hz, 2.3 Hz), 7.56(2H, d, J = 8.7 Hz), 7.45(1H, d, J = 8.2 Hz), 4.03(2H, t, J = 6.2 Hz), 3.14(2H, t, J = 6.4 Hz). |
| 112 | 39 | NMR1(400 MHz): 8.01(2H, d, J = 8.8 Hz), 7.97(1H, dd, J = 7.8 Hz, 1.1 Hz), 7.72(1H, dd, J = 8.0 Hz, 1.2 Hz), 7.60(2H, d, J = 8.8 Hz), 7.45(1H, t, J = 7.9 Hz), 4.07(2H, t, J = 6.4 Hz), 3.87(3H, s), 3.20(2H, t, J = 6.4 Hz). |
| 113 | 37 | NMR1(400 MHz): 12.96(1H, brs), 8.03-7.94(3H, m), 7.72(1H, dd, J = 8.0 Hz, 1.2 Hz), 7.56(2H, d, J = 8.7 Hz), 7.45(1H, t, J = 7.9 Hz), 4.06(2H, t, J = 6.4 Hz), 3.20(2H, t, J = 6.4 Hz). |
| 114 | 30 | NMR1(500 MHz); 12.75(1H, brs), 10.68(1H, s), 7.92(2H, br d, J = 8.7 Hz), 7.87(2H, br d, J = 8.7 Hz), 7.42-7.38(2H, m), 7.27(1H, dt, J = 0.9 Hz, 7.5 Hz), 7.03(1H, d, J = 7.8 Hz), 2.19-2.13(1H, m), 0.93-0.90(2H, m), 0.71-0.68(2H, m). |
| 115 | 30 | NMR2(500 MHz); 8.75(1H, t, J = 7.5 Hz), 8.29(1H, d, J = 3.2 Hz), 7.99(1H, d, J = 9.2 Hz), 7.87(1H, dd, J = 1.7 Hz, 11.4 Hz), 7.63(1H, dd, J = 0.8 Hz, 7.6 Hz), 7.43(1H, dt, J = 1.0 Hz, 7.6 Hz), 7.30(1H, t, J = 7.5 Hz), 7.07(1H, d, J = 7.9 Hz), 2.31-2.26(1H, m), 1.10-1.06(2H, m), 0.85-0.82(2H, m). |
| 116 | | NMR2(400 MHz): 8.07-8.10(2H, m), 7.97(1H, d, J = 1.3 Hz), 7.47-7.51(2H, m), 7.30(1H, dd, J = 7.7 Hz, 1.3 Hz), 7.15(1H, d, J = 7.7 Hz), 4.02(1H, t, J = 6.2 Hz), 3.93(3H, s), 3.11(1H, t, J = 6.2 Hz), 2.40(3H, s). |
| 117 | 37 | NMR1(500 MHz); 13.13-12.65(1H, br), 7.97(2H, d, J = 10.7 Hz), 7.83(1H, d, J = 9.2 Hz), 7.55(2H, d, J = 10.8 Hz), 7.42(1H, d, J = 9.5 Hz), 7.30(1H, t, J = 9.6 Hz), 4.02(2H, t, J = 8.0 Hz), 3.06(2H, t, J = 8.1 Hz), 2.33(3H, s). |
| 118 | 39 | NMR2(500 MHz): 8.09(2H, d, J = 11.0 Hz), 8.04(1H, d, J = 8.9 Hz), 7.50(2H, d, J = 11.0 Hz), 7.36(1H, d, J = 8.7 Hz), 7.30(1H, t, J = 9.6 Hz), 4.04(2H, t, J = 7.9 Hz), 3.93(3H, s), 3.09(2H, t, J = 8.1 Hz), 2.36(3H, s). |
| 119 | 95 | NMR1(400 MHz); 13.70-12.20(1H, br), 11.20(1H, s), 8.85(1H, dd, J = 1.0 Hz, 2.1 Hz), 8.36-8.30(2H, m), 7.43(1H, dd, J = 1.3 Hz, 7.6 Hz), 7.38(1H, dt, J = 1.3 Hz, 7.6 Hz), 7.24(1H, dt, J = 1.0 Hz, 7.6 Hz), 7.02(1H, br d, J = 7.8 Hz), 2.22-2.15(1H, m), 0.93-0.88(2H, m), 0.71-0.67(2H, m). |
| 120 | 35 | NMR2(400 MHz): 9.04(1H, brs), 8.33-8.27(1H, m). 8.24-8.13(3H, m), 7.49-7.44(1H, m), 7.23(1H, d, J = 8.1 Hz), 4.38(2H, t, J = 6.6 Hz), 3.95(3H, s), 3.10(2H, t, J = 6.4 Hz). |
| 121 | | NMR1(400 MHz); 12.93(1H, brs), 7.99-7.96(2H, m), 7.77(1H, d, J = 1.4 Hz), 7.57-7.53(2H, m), 7.36(1H, dd, J = 7.7 Hz, 1.4 Hz), 7.27(1H, d, J = 7.7 Hz), 3.99(2H, t, J = 6.2 Hz), 3.09(2H, t, J = 6.2 Hz), 2.36(3H, s). |
| 122 | 30 | NMR1(500 MHz); 13.08(1H, brs), 11.05(1H, s), 7.91(1H, t, J = 8.6 Hz), 7.84(1H, dd, J = 8.7 Hz, 5.3 Hz), 7.79-7.71(2H, m), 7.60-7.53(2H, m), 7.28(1H, t, J = 55.2 Hz). |
| 123 | 35 | NMR2(400 MHz): 9.05(1H, brd, J = 2.2 Hz), 8.30(1H, dd, J = 8.8 Hz, 2.4 Hz), 8.21(1H, brd, J = 8.8 Hz), 8.14(1H, brd, J = 7.8 Hz), 7.58(1H, dd, J = 7.9 Hz, 1.2 Hz), 7.36(1H, t, J = 7.9 Hz), 4.40(2H, t, J = 6.3 Hz), 3.95(3H, s), 3.22(2H, t, J = 6.4 Hz). |
| 124 | 37 | NMR1(400 MHz): 13.29(1H, brs), 8.97(1H, brd, J = 2.3 Hz), 8.30(1H, dd, J = 8.7 Hz, 2.4 Hz), 8.12(1H, brd, J = 8.7 Hz), 8.04(1H, brd, J = 7.8 Hz), 7.75(1H, dd, J = 8.0 Hz, 1.2 Hz), 7.48(1H, t, J = 7.9 Hz), 4.33(2H, t, J = 6.7 Hz), 3.18(2H, t, J = 6.4 Hz). |
| 125 | 39 | NMR2(500 MHz); 8.17(1H, dd, J = 8.7 Hz, 5.8 Hz), 7.99(1H, t, J = 8.3 Hz), 7.27(2H, d, J = 7.9 Hz), 7.07(1H, dt, J = 8.6 Hz, 2.6 Hz), 6.96(1H, dd J = 8.7 Hz, 2.5 Hz), 4.4(2H, q, J = 7.2 Hz), 4.03(2H, t, J = 6.4 Hz), 3.16(2H, t, J = 6.4 Hz), 1.40(3H, t, J = 7.1 Hz). |

TABLE 2-continued

| REX | RProp | Data |
|---|---|---|
| 126 | 39 | NMR2(500 MHz); 8.17(1H, dd, J = 8.7 Hz, 5.8 Hz), 7.89(1H, d, J = 8.3 Hz), 7.85(1H, d, J = 10.8 Hz), 7.47(1H, t, J = 8.0 Hz), 7.07(1H, dt, J = 8.6 Hz, 2.6 Hz), 6.96(1H, dd, J = 8.8 Hz, 2.5 Hz), 4.4(2H, q, J = 7.2 Hz), 3.96(2H, t, J = 6.3 Hz), 3.18(2H, t, J = 6.4 Hz), 1.41(3H, t, J = 7.1 Hz). |
| 127 | 35 | NMR2: 9.04(1H, brs), 8.33-8.27(1H, m), 8.24-8.13(2H, m), 7.49-7.44(1H, m), 7.23(1H, d, J = 8.1 Hz), 4.38(2H, t, J = 6.6 Hz), 3.95(3H, s), 3.10(2H, t, J = 6.4 Hz). |
| 128 | 37 | NMR1(400 MHz): 13.30(1H, brs), 8.96(1H, d, J = 2.3 Hz), 8.30(1H, dd, J = 8.7 Hz, 2.2 Hz), 8.11(1H, d, J = 8.7 Hz), 7.96(1H, brs), 7.65(1H, brd, J = 8.1 Hz), 7.47(1H, d, J = 8.1 Hz), 4.29(2H, t, J = 6.2 Hz), 3.12(2H, t, J = 6.3 Hz). |
| 129 | 37 | NMR1(400 MHz); 13.71-12.56(1H, br), 8.01(1H, dd, J = 8.6 Hz, 6.0 Hz), 7.88(1H, m), 7.39(2H, m), 7.25(2H, m), 4.03(2H, t, J = 6.2 Hz), 3.16(2H, t, J = 6.0 Hz). |
| 130 | 37 | NMR1(400 MHz); 13.82-12.83(1H, br), 7.99(1H, dd, J = 8.6 Hz, 6.0 Hz), 7.84(1H, d, J = 9.0 Hz), 7.76(1H, d, J = 10.4 Hz), 7.62(1H, t, J = 7.8 Hz), 7.29(1H, d, J = 9.7 Hz), 7.24(1H, t, J = 8.8 Hz), 3.95(2H, t, J = 6.2 Hz), 3.18(2H, t, J = 6.4 Hz). |
| 131 | 39 | NMR2(500 MHz); 8.09(1H, d, J = 8.4 Hz), 7.98(1H, t, J = 8.1 Hz), 7.37(1H, dd, J = 8.4 Hz, 2.1 Hz), 7.26(3H, m), 4.40(2H, q, J = 7.2 Hz), 4.03(2H, t, J = 6.4 Hz), 3.15(2H, t, J = 6.4 Hz), 1.40(3H, t, J = 7.2 Hz). |
| 132 | 39 | NMR2(500 MHz); 8.09(1H, d, J = 8.4 Hz), 7.90(1H, dd, J = 8.3 Hz, 1.7 Hz), 7.85(1H, dd, J = 10.8 Hz, 1.8 Hz), 7.46(1H, t, J = 8.0 Hz), 7.36(1H, dd, J = 8.4 Hz, 2.1 Hz), 7.27(1H, d, J = 2.0 Hz), 4.40(2H, q, J = 7.1 Hz), 3.95(2H, t, J = 6.3 Hz), 3.16(2H, t, J = 6.4 Hz), 1.41(3H, t, J = 7.2 Hz). |
| 133 | 37 | NMR1(400 MHz); 13.66-12.67(1H, br), 7.95(1H, d, J = 8.4 Hz), 7.89(1H, t, J = 8.5 Hz), 7.53(1H, d, J = 2.0 Hz), 7.47(1H, dd, J = 8.4 Hz, 2.2 Hz), 7.44(1H, m), 7.38(1H, dd, J = 8.5 Hz, 2.0 Hz), 4.03(2H, t, J = 6.3 Hz), 3.15(2H, t, J = 6.3 Hz). |
| 134 | 37 | NMR1(400 MHz); 13.77-12.80(1H, br), 7.93(1H, d, J = 8.3 Hz), 7.84(1H, dd, J = 8.3 Hz, 1.6 Hz), 7.77(1H, dd, J = 10.8 Hz, 1.6 Hz), 7.63(1H, t, J = 7.9 Hz), 7.54(1H, d, J = 2.0 Hz), 7.48(1H, dd, J = 8.4 Hz, 2.1 Hz), 3.95(2H, t, J = 6.6 Hz), 3.17(2H, t, J = 6.4 Hz). |
| 135 | 39 | NMR2(500 MHz); 7.90(1H, dd, J = 6.9 Hz, 1.3 Hz), 7.86(1H, dd, J = 10.9 Hz, 1.8 Hz), 7.84(1H, dd, J = 10.1 Hz, 2.7 Hz), 7.47(1H, t, J = 8.0 Hz), 7.25(1H, dd, 8.4 Hz, 5.2 Hz), 7.20(1H, dd, J = 8.4 Hz, 2.8 Hz), 4.40(2H, q, J = 7.2 Hz), 3.95(2H, t, J = 6.3 Hz), 3.16(2H, t, J = 6.4 Hz), 1.41(3H, t, J = 7.2 Hz). |
| 136 | 37 | NMR1(400 MHz); 7.84(1H, d, J = 8.8 Hz), 7.77(1H, d, J = 8.2 Hz), 7.64(2H, m), 7.45(2H, m), 3.95(2H, t, J = 6.2 Hz), 3.15(2H, t, J = 6.6 Hz). |
| 137 | | NMR1(500 MHz); 12.92(1H, s), 9.85(1H, s), 8.22(1H, d, J = 8.0 Hz), 7.65-7.57(2H, m), 7.56-7.53(2H, m), 7.52-7.47(1H, m), 7.45(1H, t, J = 7.2 Hz), 3.88(3H, s). |
| 138 | | NMR2(500 MHz); 13.54-12.92(1H, br), 11.64(1H, s), 8.96-8.78(2H, m), 8.36(1H, dd, J = 10.9 Hz, 2.8 Hz), 8.33-8.18(2H, m), 7.84(1H, dd, J = 9.8 Hz, 6.0 Hz). |
| 139 | | NMR2(500 MHz); 7.55-7.43(5H, m), 7.28-7.23(2H, m), 4.12-4.02(2H, m), 2.46-2.31(5H, m). |
| 140 | | NMR2(500 MHz); 7.69(1H, d, J = 2.5 Hz), 7.28-7.23(1H, m), 6.67(1H, d, J = 9.0 Hz), 4.70(1H, brs), 3.44-3.34(2H, m), 2.71-2.55(2H, m). |
| 141 | | NMR2(400 MHz); 7.75(1H, d, J = 2.4 Hz), 7.14(1H, dd, J = 8.3 Hz, 2.4 Hz), 6.71(1H, d, J = 8.3 Hz), 4.19-4.04(2H, m), 4.01-3.85(1H, m), 3.75-3.58(1H, m), 3.29-3.04(2H, m), 2.49-2.28(2H, m), 2.13-2.00(1H, m). |
| 142 | | NMR2(400 MHz); 8.00(1H, s), 7.81(2H, d, J = 8.0 Hz), 7.39(2H, d, J = 8.0 Hz), 7.18(1H, dd, J = 8.4 Hz, 2.4 Hz), 6.86(1H, d, J = 8.4 Hz), 4.68(1H, d, J = 10.0 Hz), 4.34-3.94(2H, m), 3.86-3.68(1H, m), 3.32-3.07(1H, m), 2.94-2.68(1H, m), 2.48(3H, m), 2.37-2.17(1H, m), 0.91(9H, s), 0.14(3H, s), 0.07(3H, s). |
| 143 | | NMR2(400 MHz); 7.79(1H, d, J = 2.4 Hz), 7.09(1H, dd, J = 8.4 Hz, 2.4 Hz), 6.64(1H, d, J = 8.4 Hz), 4.23(1H, d, J = 10.0 Hz), 3.91(1H, dt, J = 10.0 Hz, 2.4 Hz), 3.88-3.83(1H, m), 3.75-3.53(1H, m), 3.29-3.26(1H, m), 3.16-2.98(1H, m), 2.46-2.16(2H, m), 0.83(9H, s), −0.03(1H, s), −0.12(1H, s). |

TABLE 2-continued

| REX | RProp | Data |
|---|---|---|
| 144 | | NMR2(500 MHz); 7.91-7.81(1H, m), 7.62-7.33(2H, m), 3.94-3.67(2H, m), 2.73-2.55(2H, m), 1.60-1.31(9H, m). |
| 145 | | NMR2(400 MHz); 7.58(1H, d, J = 2.4 Hz), 7.13(1H, dd, J = 8.4 Hz, 2.4 Hz), 6.71(1H, d, J = 8.4 Hz), 4.56(1H, brs), 3.69(1H, brs), 3.21(1H, ddd, J = 13.6 Hz, 7.6 Hz, 4.0 Hz), 3.10(1H, ddd, J = 13.2 Hz, 9.2 Hz, 3.2 Hz), 2.56(1H, dddd, J = 30.8 Hz, 14.4 Hz, 9.2 Hz, 4.0 Hz), 2.27(1H, dddd, J = 27.0 Hz, 14.4 Hz, 7.2 Hz, 3.6 Hz), 1.69-1.63(3H, m). |
| 146 | | NMR2(400 MHz); 7.96-7.84(1H, m), 7.39-6.97(2H, m), 4.50-4.10(1H, m), 4.03-3.59(2H, m), 3.56-3.35(1H, m), 3.21-2.84(1H, m), 2.75-1.72(3H, m), 1.66-1.16(9H, m). |
| 147 | | NMR2(400 MHz); 7.56-7.51(2H, m), 7.45(1H, d, J = 2.4 Hz), 7.41-7.37(1H, m), 7.37-7.33(1H m), 7.21(2H, d, J = 8.0 Hz), 3.76(2H, t, J = 6.2 Hz), 2.92(2H, t, J = 7.2 Hz), 2.40(3H, s), 2.14-2.02(2H, m), 1.73(2H, tt, J = 6.0 Hz, 6.0 Hz), 1.67-1.53(2H, m), 1.38(2H, tq, J = 7.2 Hz, 7.2 Hz), 0.96(3H, t, J = 7.2 Hz). |
| 148 | 150 | NMR2(400 MHz); 7.96-7.84(1H, m), 7.39-6.97(2H, m), 4.50-4.10(1H, m), 4.03-3.59(2H, m), 3.56-3.35(1H, m), 3.21-2.84(1H, m), 2.75-1.72(3H, m), 1.66-1.16(9H, m). |
| 149 | 154 | NMR2(400 MHz); 8.03-7.93(1H, m), 7.90-7.70(2H, m), 7.63-7.46(2H, m), 7.43-7.29(1H, m), 7.25-7.01(1H, m), 5.06-4.65(1H, m), 4.60-4.06(2H, m), 3.86-3.44(1H, m), 3.21-2.88(1H, m), 2.90-2.43(1H, m), 2.38-1.93(1H, m), 1.67-1.18(9H, m). |
| 150 | | NMR2(400 MHz); 7.96-7.84(1H, m), 7.39-6.97(2H, m), 4.50-4.10(1H, m), 4.03-3.59(2H, m), 3.56-3.35(1H, m), 3.21-2.84(1H, m), 2.75-1.72(3H, m), 1.66-1.16(9H, m). |
| 151 | | NMR2(400 MHz); 7.75(1H, d, J = 2.4 Hz), 7.14(1H, dd, J = 8.3 Hz, 2.4 Hz), 6.71(1H, d, J = 8.3 Hz), 4.19-4.04(2H, m), 4.01-3.85(1H, m), 3.75-3.58(1H, m), 3.29-3.04(2H, m), 2.49-2.28(2H, m), 2.13-2.00(1H, m). |
| 152 | | NMR1(500 MHz); 7.64(1H, d, J = 2.4 Hz), 7.40-5.60(6H, m), 3.88-3.71(2H, m), 3.22(1H, d, J = 13.5 Hz), 2.90-2.71(1H, m), 2.49-2.27(1H, m), 2.26-2.10(1H, m). |
| 153 | | NMR2(400 MHz); 8.03-7.93(1H, m), 7.90-7.70(2H, m), 7.63-7.46(2H, m), 7.43-7.29(1H, m), 7.25-7.01(1H, m), 5.06-4.65(1H, m), 4.60-4.06(2H, m), 3.86-3.44(1H, m), 3.21-2.91(1H, m), 2.90-2.43(1H, m), 2.38-1.93(1H, m), 1.67-1.18(9H, m). |
| 154 | | NMR2(400 MHz); 8.03-7.93(1H, m), 7.90-7.70(2H, m), 7.63-7.46(2H, m), 7.43-7.29(1H, m), 7.25-7.01(1H, m), 5.06-4.65(1H, m), 4.60-4.06(2H, m), 3.86-3.44(1H, m), 3.21-2.91(1H, m), 2.90-2.43(1H, m), 2.38-1.93(1H, m), 1.67-1.18(9H, m). |
| 155 | | NMR2(500 MHz); 7.88-7.80(3H, m), 7.60-7.56(2H, m), 7.16(1H, dd, J = 8.3 Hz, 2.5 Hz), 6.72(1H, d, J = 8.3 Hz), 5.14(1H, d, J = 11.9 Hz), 4.66-4.58(1H, m), 3.93(1H, brs), 3.73(1H, d, J = 5.9 Hz), 3.34-3.24(1H, m), 3.16-3.07(1H, m), 2.60-2.28(2H, m). |
| 156 | | NMR2(500 MHz); 7.88-7.80(3H, m), 7.60-7.56(2H, m), 7.16(1H, dd, J = 8.3 Hz, 2.5 Hz), 6.72(1H, d, J = 8.3 Hz), 5.14(1H, d, J = 11.9 Hz), 4.66-4.58(1H, m), 3.93(1H, brs), 3.73(1H, d, J = 5.9 Hz), 3.34-3.24(1H, m), 3.16-3.07(1H, m), 2.60-2.28(2H, m). |
| 157 | | NMR2(500 MHz); 7.95-7.79(1H, m), 7.69-7.50(2H, m), 7.40-7.14(6H, m), 7.10-6.94(3H, m), 5.05-3.78(5H, m), 3.48(1H, s), 3.15-2.72(3H, m), 2.61-1.90(5H, m), 1.65-1.29(9H, m). |
| 158 | | NMR2(500 MHz); 7.95-7.81(1H, m), 7.66-7.51(2H, m), 7.37-6.93(9H, m), 5.10-4.84(1H, m), 4.75-3.70(4H, m), 3.61-3.48(1H, m), 3.15-2.81(3H, m), 2.55-1.90(5H, m), 1.65-1.20(9H, m). |
| 159 | | NMR2(500 MHz); 7.68(2H, d, J = 8.0 Hz), 7.59-7.53(1H, m), 7.33(2H, d, J = 8.0 Hz), 7.20(1H, dd, J = 8.5 Hz, 2.5 Hz), 6.80(1H, s), 3.92-3.62(2H, m), 3.44-3.02(1H, m), 2.81-2.52(1H, m), 2.46(3H, s), 2.42-2.26(1H, m). |
| 160 | | NMR2(500 MHz); 7.32(1H, d, J = 2.5 Hz), 7.15(1H, dd, J = 8.3 Hz, 2.5 Hz), 6.72(1H, d, J = 8.3 Hz), 3.70(1H, |

TABLE 2-continued

| REX | RProp | Data |
|---|---|---|
| | | brs), 3.60(1H, brs), 3.30-3.22(1H, m), 3.15-3.08(1H, m), 2.73-2.59(1H, m), 2.21-2.11(1H, m). |
| 161 | | NMR2(500 MHz); 7.95-7.79(1H, m), 7.69-7.50(2H, m), 7.40-7.14(6H, m), 7.10-6.94(3H, m), 5.05-3.78(5H, m), 3.48(1H, s), 3.15-2.72(3H, m), 2.61-1.90(5H, m), 1.65-1.29(9H, m). |
| 162 | | NMR2(500 MHz); 7.95-7.81(1H, m), 7.66-7.51(2H, m), 7.37-6.93(9H, m), 5.10-4.84(1H, m), 4.75-3.70(4H, m), 3.61-3.48(1H, m), 3.15-2.81(3H, m), 2.55-1.90(5H, m), 1.65-1.20(9H, m). |
| 163 | | NMR2(400 MHz); 9.60-9.40(1H, brs), 8.70-8.60(1H, m), 8.54(1H, t, J = 8.1 Hz), 7.90-7.72(2H, m), 7.72(1H, dd, J = 11.6 Hz, 1.8 Hz), 7.61(1H, dd, J = 9.0 Hz, 2.7 Hz), 7.58-7.45(2H, m), 7.37-7.20(2H, m), 3.90(3H, s). |
| 164 | | NMR2(400 MHz); 8.82(1H, d, J = 5.6 Hz), 8.40(1H, t, J = 7.9 Hz), 8.12-7.39(9H, m). |
| 165 | | NMR2(500 MHz); 7.74-7.68(1H, m), 7.61(2H, d, J = 8.3 Hz), 7.48-7.19(5H, m), 7.13(1H, dd, J = 8.3 Hz, 2.5 Hz), 6.99(2H, dd, J = 5.9 Hz, 2.2 Hz), 6.68(1H, d, J = 8.3 Hz), 4.98(1H, d, J = 9.2 Hz), 4.67(1H, d, J = 11.7 Hz), 4.29(1H, dd, J = 11.7 Hz, 1.7 Hz), 4.22-4.08(1H, m), 3.66(1H, d, J = 6.1 Hz), 3.41(1H, brs), 3.28-3.15(1H, m), 3.12-2.81(3H, m), 2.41(3H, s), 2.32-2.05(2H, m). |
| 166 | | NMR2(400 MHz); 7.65(2H, d, J = 8.0 Hz), 7.50(1H, d, J = 2.4 Hz), 7.31(2H, d, J = 8.0 Hz), 7.27(1H, dd, J = 8.4 Hz, 2.4 Hz), 7.13(1H, d, J = 8.4 Hz), 4.44-4.27(1H, m), 3.48-3.32(1H, m), 2.95-2.85(1H, m), 2.70-2.49(1H, m), 2.45(3H, s), 2.38-2.19(2H, m). |
| 167 | | NMR2(400 MHz); 7.49-7.43(2H, m), 7.41-7.36(1H, m), 7.35-7.29(1H, m), 7.23-7.15(3H, m), 5.38(1H, s), 4.87(1H, s), 4.04-3.82(2H, m), 2.41(3H, s), 2.28(2H, tt, J = 13.2 Hz, 5.6 Hz). |
| 168 | | NMR2(400 MHz); 8.00(1H, s), 7.80(2H, d, J = 8.0 Hz), 7.40(2H, d, J = 8.0 Hz), 7.19(1H, dd, J = 8.4 Hz, 2.4 Hz), 6.88-6.74(1H, m), 4.28-4.13(3H, m), 3.54(1H, brs), 3.31-3.13(1H, m), 2.93-2.70(1H, m), 2.49(3H, s), 2.40-2.24(1H, m), 2.20-2.08(1H, m). |
| 169 | | NMR2(400 MHz); 8.08-7.89(1H, m), 7.81(2H, d, J = 8.0 Hz), 7.49(2H, d, J = 8.0 Hz), 7.18(1H, dd, J = 8.4 Hz, 2.4 Hz), 7.00-6.74(1H, m), 4.37-3.98(1H, m), 3.33-3.02(1H, m), 3.02-2.73(1H, m), 2.73-2.56(1H, m), 2.49(3H, s), 2.34-2.12(1H, m), 1.80(3H, s). |
| 170 | | NMR2(400 MHz); 7.85(1H, brs), 7.38-6.99(2H, m), 4.81-4.63(1H, m), 4.63-4.45(1H, m), 4.40-3.86(1H, m), 3.19-2.33(4H, m), 2.33-1.81(1H, m), 1.57-1.26(9H, m). |
| 171 | | NMR2(400 MHz); 8.54-8.41(1H, m), 8.19(1H, d, J = 7.0 Hz), 8.07(1H, d, J = 7.8 Hz), 7.97-7.89(1H, m), 7.87(1H, d, J = 2.4 Hz), 7.68-7.45(3H, m), 7.44-7.24(1H, m), 7.24-6.70(6H, m), 5.40-5.00(1H, m), 4.75-3.34(5H, m), 3.28-1.78(5H, m), 1.67-1.17(9H, m). |
| 172 | | NMR2(400 MHz); 8.51-8.41(1H, m), 8.14(1H, dd, J = 7.4 Hz, 1.0 Hz), 8.04(1H, d, J = 8.2 Hz), 7.94-7.85(2H, m), 7.64-7.53(2H, m), 7.52-7.44(1H, m), 7.36-7.23(1H, m), 7.11-6.93(4H, m), 6.91-6.77(2H, m), 5.35-5.05(1H, m), 4.74-3.29(5H, m), 3.18-1.96(5H, m), 1.66-1.13(9H, m). |
| 173 | 165 | NMR2(400 MHz); 8.51-8.43(1H, m), 8.19(1H, dd, J = 7.4 Hz, 1.2 Hz), 8.05(1H, d, J = 8.3 Hz), 7.95-7.88(1H, m), 7.71(1H, d, J = 2.4 Hz), 7.64-7.55(2H, m), 7.54-7.47(1H, m), 7.12(1H, dd, J = 8.3 Hz, 2.5 Hz), 7.10-6.98(3H, m), 6.85-6.78(2H, m), 6.66(1H, d, J = 8.3 Hz), 5.20(1H, d, J = 9.0 Hz), 4.70(1H, d, J = 11.6 Hz), 4.25-4.06(2H, m), 3.74-3.56(1H, m), 3.50-3.34(1H, m), 3.28-3.15(1H, m), 3.08-2.95(1H, m), 2.91-2.75(2H, m), 2.26-2.06(2H, m). |
| 174 | | NMR2(400 MHz); 8.51-8.43(1H, m), 8.11(1H, dd, J = 7.3 Hz, 1.2 Hz), 8.03(1H, d, J = 8.2 Hz), 7.94-7.86(1H, m), 7.73(1H, d, J = 2.5 Hz), 7.64-7.55(2H, m), 7.51-7.43(1H, m), 7.12(1H, dd, J = 8.3 Hz, 2.5 Hz), 7.10-6.98(3H, m), 6.91-6.84(2H, m), 6.66(1H, d, J = 8.3 Hz), 5.37(1H, d, J = 9.0 Hz), 4.57(1H, d, J = 11.6 Hz), 4.32-4.23(1H, m), 4.17-4.05(1H, m), 3.83-3.24(2H, m), 3.24-3.11(1H, m), 3.09-2.94(1H, m), 2.93-2.78(2H, m), 2.27-2.08(2H, m). |

TABLE 2-continued

| REX | RProp | Data |
|---|---|---|
| 175 | | NMR2(400 MHz); 7.75(1H, d, J = 2.4 Hz), 7.14(1H, dd, J = 8.3 Hz, 2.4 Hz), 6.71(1H, d, J = 8.3 Hz), 4.19-3.44(4H, m), 3.29-3.02(2H, m), 2.51-1.82(3H, m). |
| 176 | | NMR1(500 MHz); 7.61(1H, d, J = 2.5 Hz), 7.11(1H, dd, J = 8.3 Hz, 2.5 Hz), 6.86(1H, d, J = 8.3 Hz), 5.75-5.20(1H, m), 4.06-3.27(4H, m), 3.19(1H, d, J = 14.3 Hz), 2.79-2.68(1H, m), 2.67-2.01(3H, m). |
| 177 | | NMR2(500 MHz); 7.81(1H, d, J = 2.0 Hz), 7.12(1H, dd, J = 6.8 Hz, 2.0 Hz), 6.67(1H, d, J = 6.8 Hz), 4.17(1H, brs), 3.73-3.54(2H, m), 3.54-3.43(1H, m), 3.32-3.17(1H, m), 3.08-2.98(1H, m), 2.67-2.57(1H, m), 2.56-2.36(1H, m), 2.32-2.18(2H, m), 2.15-2.06(1H, m). |
| 178 | | NMR2(500 MHz); 7.92(1H, d, J = 2.5 Hz), 7.10(1H, dd, J = 8.0 Hz, 2.5 Hz), 6.64(1H, d, J = 8.0 Hz), 5.37(1H, s), 3.73-3.64(1H, m), 3.59(1H, d, J = 6.5 Hz), 3.42-3.28(1H, m), 3.27-3.17(1H, m), 3.00(1H, t, J = 13.0 Hz), 2.58-2.34(2H, m), 2.32-2.12(2H, m), 0.91(9H, m), 0.032(3H, s), 0.027(3H, s). |
| 179 | | NMR2(500 MHz); 8.06-7.92(1H, m), 7.82(2H, d, J = 8.0 Hz), 7.41(2H, d, J = 8.0 Hz), 7.23(1H, dd, J = 8.5 Hz, 2.0 Hz), 6.88(1H, d, J = 8.5 Hz), 4.23(1H, d, J = 8.0 Hz), 4.00(2H, s), 3.31-3.24(1H, m), 3.20(1H, t, J = 14.0 Hz), 2.86-2.65(1H, m), 2.49(3H, s), 2.43-2.16(1H, m). |
| 180 | | NMR2(500 MHz); 8.03(1H, d, J = 2.5 Hz), 7.81(2H, d, J = 8.5 Hz), 7.42(2H, d, J = 8.0 Hz), 7.17(1H, dd, J = 8.5 Hz, 2.5 Hz), 6.70(1H, d, J = 8.5 Hz), 5.88(1H, s), 5.01(1H, dd, J = 6.5 Hz, 6.5 Hz), 4.20(1H, d, J = 15.0 Hz), 4.07(1H, dd, J = 10.0 Hz, 6.0 Hz), 3.97(1H, dd, J = 15.0 Hz, 7.0 Hz), 3.21(1H, t, J = 9.0 Hz), 3.00-2.71(1H, m), 2.50(3H, s), 2.40-2.24(1H, m), 1.14(9H, m). |
| 181 | | NMR2(500 MHz); 7.78(1H, d, J = 2.0 Hz), 7.12(1H, dd, J = 8.5 Hz, 2.0 Hz), 6.67(1H, d, J = 8.0 Hz), 4.63(1H, s), 4.51-4.08(1H, m), 4.02(1H, dd, J = 14.0 Hz, 6.5 Hz), 3.69(2H, dd, J = 14.0 Hz, 5.5 Hz), 3.29-3.16(1H, m), 3.05(1H, d, J = 12.2 Hz), 2.56-2.14(2H, m). 1.38(9H, s). |
| 182 | | NMR2(500 MHz); 9.00-7.30(5H, m), 7.28-6.43(5H, m), 5.30-4.52(3H, m), 4.32-1.97(8H, m), 1.52-1.33(9H, m). |
| 183 | | NMR2(500 MHz); 7.55-7.41(1H, m), 7.39-6.94(2H, m), 4.32-2.09(6H, m), 1.65-1.20(9H, m). |
| 184 | 183 | NMR2(500 MHz); 7.55-7.41(1H, m), 7.39-6.94(2H, m), 4.32-2.09(6H, m), 1.65-1.20(9H, m). |
| 185 | | NMR2(500 MHz); 8.05-6.95(3H, m), 4.50-4.16(1H, m), 3.17-2.37(3H, m), 2.30-2.11(1H, m), 1.85-1.20(12H, m). |
| 186 | 185 | NMR2(500 MHz); 8.05-6.95(3H, m), 4.50-4.16(1H, m), 3.17-2.37(3H, m), 2.30-2.11(1H, m), 1.85-1.20(12H, m). |
| 187 | | NMR2(500 MHz); 7.58(1H, d, J = 2.5 Hz), 7.13(1H, dd, J = 8.5 Hz, 2.5 Hz), 6.72(1H, d, J = 8.5 Hz), 4.55(1H, brs), 3.68(1H, brs), 3.21(1H, ddd, J = 13.5 Hz, 7.0 Hz, 4.0 Hz), 3.10(1H, ddd, J = 13.5 Hz, 9.0 Hz, 3.0 Hz), 2.57(1H, dddd, J = 30.5 Hz, 14.5 Hz, 9.0 Hz, 4.0 Hz), 2.27(1H, dddd, J = 27.5 Hz, 14.5 Hz, 7.5 Hz, 3.5 Hz), 1.69-1.63(3H, m). |
| 188 | 187 | NMR2(500 MHz); 7.58(1H, d, J = 2.5 Hz), 7.13(1H, dd, J = 8.5 Hz, 2.5 Hz), 6.72(1H, d, J = 8.5 Hz), 4.55(1H, brs), 3.68(1H, brs), 3.21(1H, ddd, J = 13.5 Hz, 7.0 Hz, 4.0 Hz), 3.10(1H, ddd, J = 13.5 Hz, 9.0 Hz, 3.0 Hz), 2.57(1H, dddd, J = 30.5 Hz, 14.5 Hz, 9.0 Hz, 4.0 Hz), 2.27(1H, dddd, J = 27.5 Hz, 14.5 Hz, 7.5 Hz, 3.5 Hz), 1.69-1.63(3H, m). |
| 189 | | NMR2(500 MHz); 8.80-8.60(1H, m), 8.21-7.90(2H, m), 7.80-7.52(5H, m), 7.50-7.35(1H, m), 7.20-7.13(1H, m), 6.73-6.60(1H, m), 5.18-5.02(1H, m), 3.70-3.60 (0.7H, m), 3.35-3.07(2H, m), 2.90-2.60(1H, m), 2.58-2.20(1.3H, m). |
| 190 | | NMR2(400 MHz): 7.68-7.66(2H, m), 7.56(1H, brs), 7.33(2H, d, J = 8.0 Hz), 7.20(1H, dd, J = 8.4 Hz, 2.4 Hz), 6.82(1H, brs), 4.74-4.68(1H, m), 3.78(1H, brs), 3.27(1H, brs), 2.62(1H, brs), 2.49(3H, s), 2.32(1H, brs). |

TABLE 2-continued

| REX | RProp | Data |
|---|---|---|
| 191 | | NMR2(400 MHz): 7.33(1H, d, J = 2.4 Hz), 7.15(1H, dd, J = 8.3 Hz, 2.4 Hz), 6.72(1H, d, J = 8.3 Hz), 4.70-4.63(1H, m), 3.70(1H, brs), 3.63-3.59(1H, m), 3.28-3.21(1H, m), 3.18-3.05(1H, m), 2.71-2.55(1H, m), 2.17-2.06(1H, m). |
| 192 | | NMR2(400 MHz); 8.48-8.22(3H, m), 8.04-7.94(1H, m), 7.84-7.72(1H, m), 7.65-7.56(3H, m), 7.27-7.28(1H, m), 7.16-7.13(1H, m), 6.64-6.61(1H, m), 5.45(1H, brs), 5.27-4.67(2H, m), 3.22-2.85(2H, m), 2.35-1.98(1H, m). |
| 193 | 192 | NMR2(400 MHz); 8.75-8.68(1H, m), 8.43(1H, brs), 8.24-3.10(1H, m), 7.92-7.85(1H, m), 7.64-7.30(3H, m), 7.20-7.10(2H, m), 6.67-6.60(1H, m), 5.30-4.75(2H, m), 4.12(1H, brs), 3.15-2.90(2H, m), 2.17(1H, brs). |
| 194 | 192 | NMR2(400 MHz); 8.51-8.28(2H, m), 7.83-7.25(4H, m), 7.20-6.53(4H, m), 5.23-4.75(2H, m), 3.30-2.73(3H, m), 2.55-2.08(1H, m). |
| 195 | | NMR2(500 MHz); 8.23-8.03(2H, m), 7.88-7.79(1H, m), 7.78-7.68(2H, m), 7.59-7.49(1H, m), 7.49-7.30(7H, m), 7.29-7.21(1H m), 7.10(1H, dd, J = 8.4 Hz, 2.1 Hz), 6.62-6.51(1H, m), 5.27-4.91(1H, m), 4.90-4.47(2H, m), 3.21-2.82(2H, m), 2.59-2.00 (1H, m). |
| 196 | | NMR2(500 MHz); 8.08 (1H, brs), 7.86-7.30 (7H, m), 7.22-7.02 (2H, m), 6.61 (1H, brs), 5.31-5.78 (2H, m), 3.48-2.42 (3H, m), 2.37-2.11 (1H, m). |
| 197 | 192 | NMR2(400 MHz): 8.47-8.28(2H, m), 7.58-7.52(1H, m), 7.52-7.29(3H, m), 7.10-6.55(2H, m), 5.28-4.82(2H, m), 3.20-2.94(3H, m), 2.55-2.17(1H, m). |
| 198 | 192 | NMR2(400 MHz): 7.88-7.13(7H, m), 7.08-7.03(1H, m), 6.58-6.50(1H, m), 5.80-4.71(2H, m), 3.25-2.82(3H, m), 2.61-2.10(1H, m). |
| 199 | | NMR1(500 MHz); 8.26-7.67(4H, m), 7.57-7.18(9H, m), 7.16-7.03(1H, m), 6.65-6.48(1H, m), 5.30-4.42(3H, m), 3.35-1.99(3H, m). |
| 200 | 192 | NMR2(400 MHz); 8.75-8.68(1H, m), 8.43(1H, br), 8.24-3.10(1H, m), 7.92-7.85(1H, m), 7.64-7.30(3H, m), 7.20-7.10(2H, m), 6.67-6.60(1H, m), 5.30-4.75(2H, m), 4.12(1H, brs), 3.15-2.90(2H, m), 2.17(1H, brs). |
| 201 | | NMR2(400 MHz); 7.90-7.15(10H, m), 7.14-6.78(5H, m), 6.61-6.42(1H, m), 5.36-4.63(2H, m), 3.99-3.27(1H, m), 3.18-2.74(1H, m), 2.62-1.95(2H, m). |
| 202 | 201 | NMR2(400 MHz); 7.91-7.15(9H, m), 7.13-6.90(5H, m), 6.66-6.43(1H, m), 5.32-4.66(2H, m), 3.55-2.75(3H, m), 2.62-1.99(1H, m). |

TABLE 3

| EX | STR |
|---|---|
| 1 | 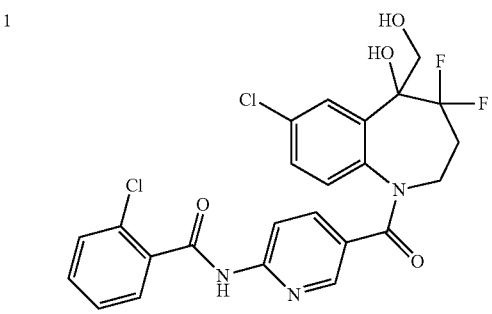 |
| 2 | 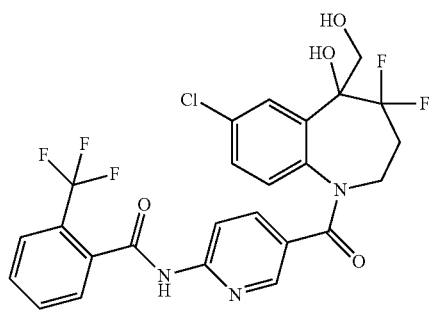 |

TABLE 3-continued

| EX | STR |
|---|---|
| 3 | (structure) |
| 4 | (structure) |
| 5 | (structure) |
| 6 | (structure) |
| 7 | (structure) |
| 8 | (structure) |
| 9 | (structure) |
| 10 | (structure) |
| 11 | (structure) |

TABLE 3-continued
| EX | STR |
|---|---|
| 12 | 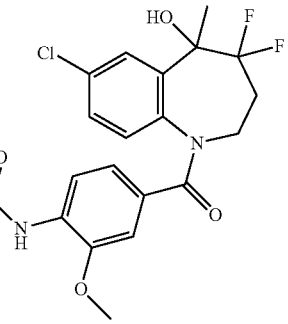 |
| 13 | 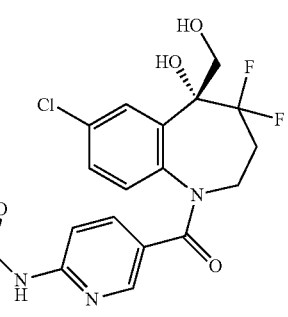 |
| 14 | 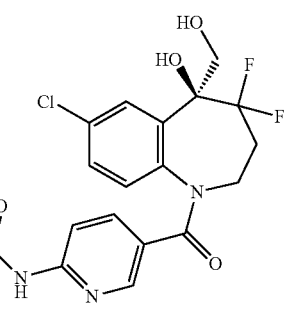 |
| 15 | 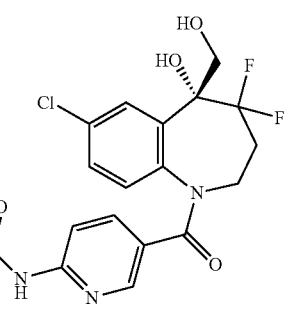 |
| 16 | 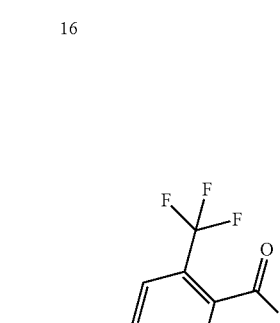 |
| 17 | 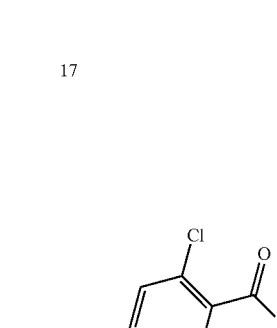 |
| 18 | 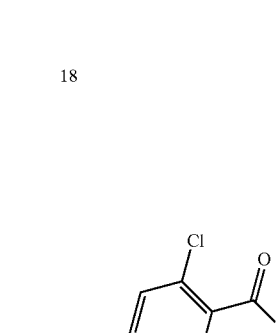 |
| 19 | 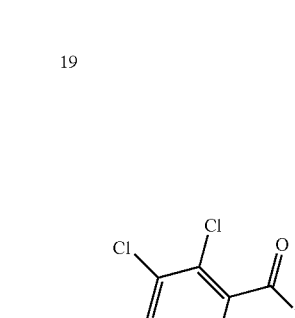 |

TABLE 3-continued
| EX | STR |
|---|---|
| 20 | 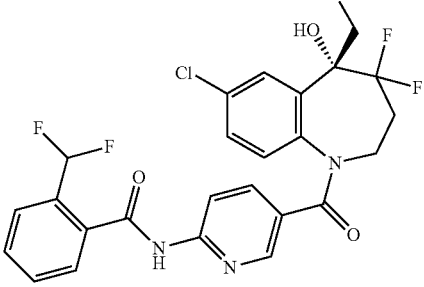 |
| 21 | 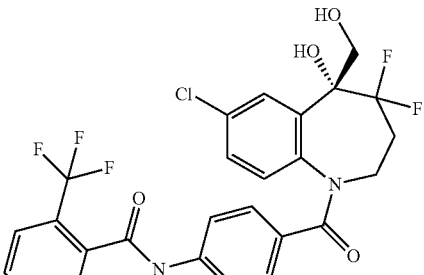 |
| 22 | 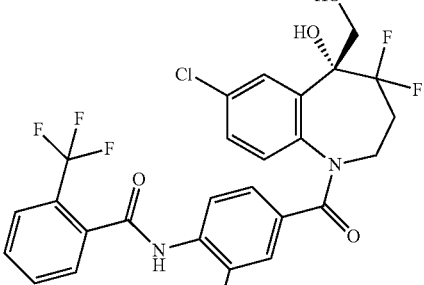 |
| 23 | 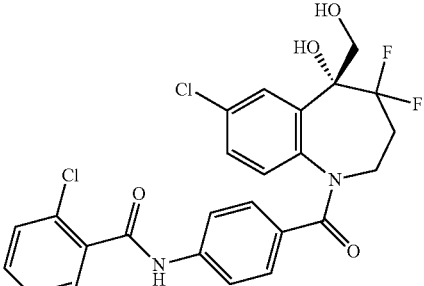 |
| 24 | 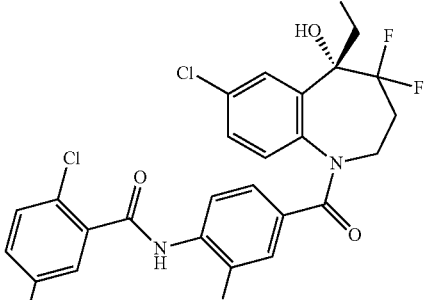 |
| 25 | 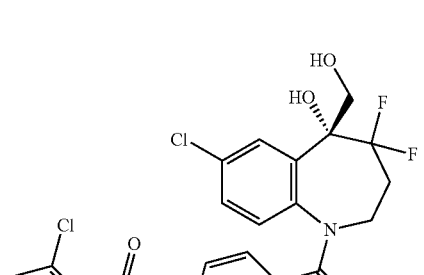 |
| 26 | 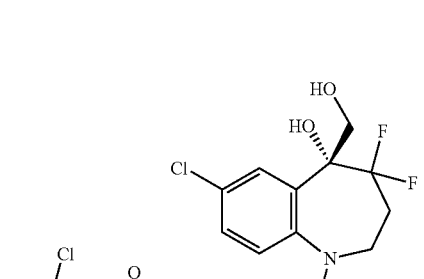 |
| 27 | 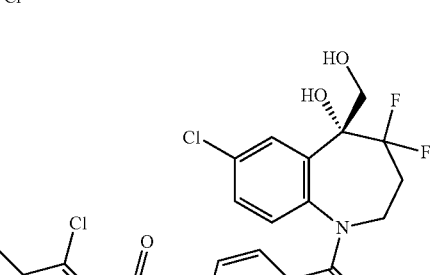 |

TABLE 3-continued

| EX | STR |
|---|---|
| 28 | |
| 29 | |
| 30 | |
| 31 | |
| 32 | |
| 33 | |
| 34 | |
| 35 | |

TABLE 3-continued

| EX | STR |
|---|---|
| 36 | (structure) |
| 37 | (structure) |
| 38 | (structure) |
| 39 | (structure) |
| 40 | (structure) |
| 41 | (structure) |
| 42 | (structure) |
| 43 | (structure) |

TABLE 3-continued

| EX | STR |
|---|---|
| 44 | |
| 45 | |
| 46 | |
| 47 | |
| 48 | |
| 49 | |
| 50 | |
| 51 | |

TABLE 3-continued
| EX | STR |
|---|---|
| 52 |  |
| 53 | |
| 54 | |
| 55 | |
TABLE 3-continued
| EX | STR |
|---|---|
| 56 |  |
| 57 | |
| 58 | |
| 59 | |

TABLE 3-continued

| EX | STR |
|---|---|
| 60 | (structure) |
| 61 | (structure) |
| 62 | (structure) |
| 63 | (structure) |
| 64 | (structure) |
| 65 | (structure) |
| 66 | (structure) |
| 67 | (structure) |

TABLE 3-continued

| EX | STR |
|---|---|
| 68 | |
| 69 | |
| 70 | |
| 71 | |
| 72 | |
| 73 | |
| 74 | |
| 75 | |

TABLE 3-continued

| EX | STR |
|---|---|
| 76 | (structure) |
| 77 | (structure) |
| 78 | (structure) |
| 79 | (structure) |
| 80 | (structure) |
| 81 | (structure) |
| 82 | (structure) |
| 83 | (structure) |

TABLE 3-continued
| EX | STR |
|---|---|
| 84 | 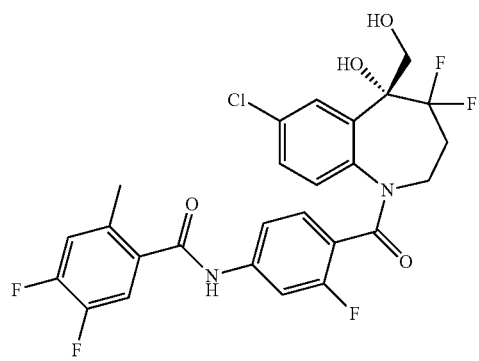 |
| 85 | 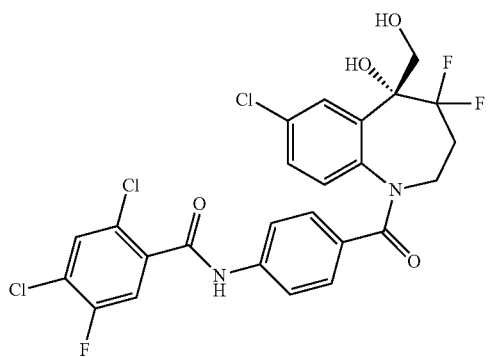 |
| 86 | 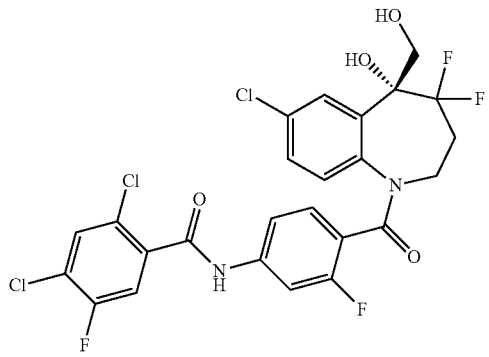 |
| 87 | 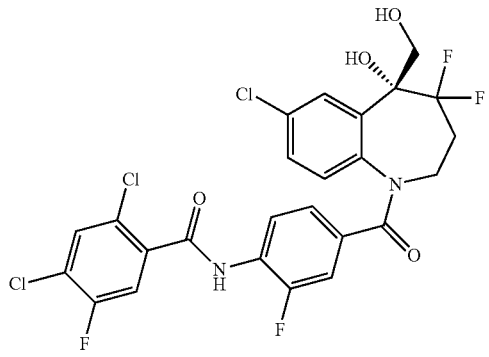 |
| 88 | 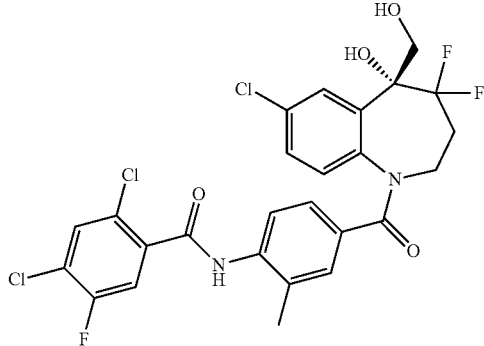 |
| 89 | 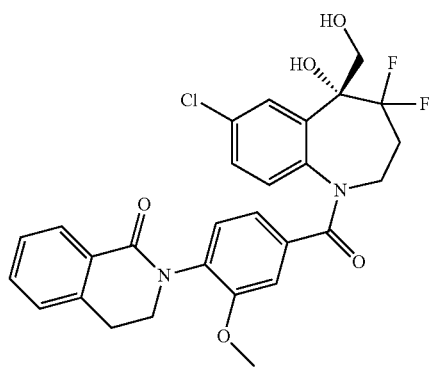 |
| 90 | 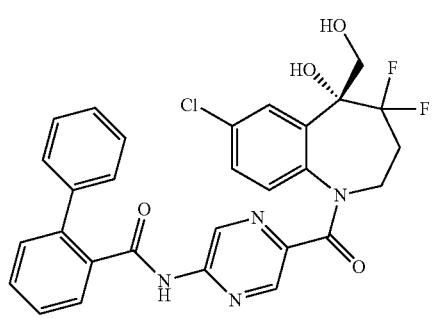 |
| 91 | 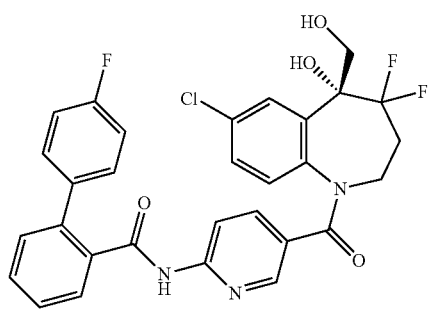 |

TABLE 3-continued

| EX | STR |
|---|---|
| 92 | |
| 93 | |
| 94 | |
| 95 | |
| 96 | |
| 97 | |
| 98 | |
| 99 | |

TABLE 3-continued

| EX | STR |
|---|---|
| 100 | |
| 101 | |
| 102 | |
| 103 | |
| 104 | |
| 105 | |
| 106 | |
| 107 | |
| 108 | |

TABLE 3-continued

| EX | STR |
|---|---|
| 109 | |
| 110 | |
| 111 | |
| 112 | |
| 113 | |
| 114 | |
| 115 | |
| 116 | |

TABLE 3-continued

| EX | STR |
|---|---|
| 117 | |
| 118 | |
| 119 | |
| 120 | |
| 121 | |
| 122 | |
| 123 | |
| 124 | |
| 125 | |
| 126 | |

TABLE 3-continued

| EX | STR |
|---|---|
| 127 | (structure) |
| 128 | (structure) |
| 129 | (structure) |
| 130 | (structure) |
| 131 | (structure) |
| 132 | (structure) |
| 133 | (structure) |
| 134 | (structure) |

TABLE 3-continued

| EX | STR |
|---|---|
| 135 | |
| 136 | |
| 137 | |
| 138 | |
| 139 | |
| 140 | |
| 141 | |
| 142 | |
| 143 | |
| 144 | |

TABLE 3-continued
| EX | STR |
|---|---|
| 145 | 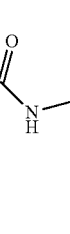 |
| 146 | 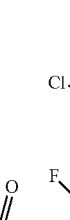 |
| 147 |  |
| 148 | 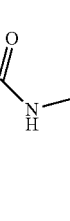 |
| 149 |  |
| 150 | 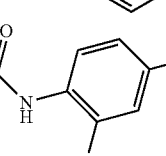 |
| 151 | 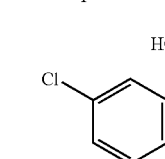 |
| 152 | 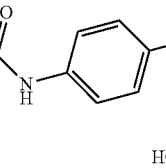 |
| 153 | 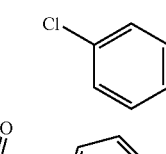 |
| 154 | 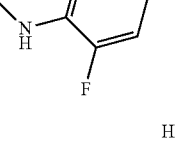 |

TABLE 3-continued
| EX | STR |
|---|---|
| 155 | 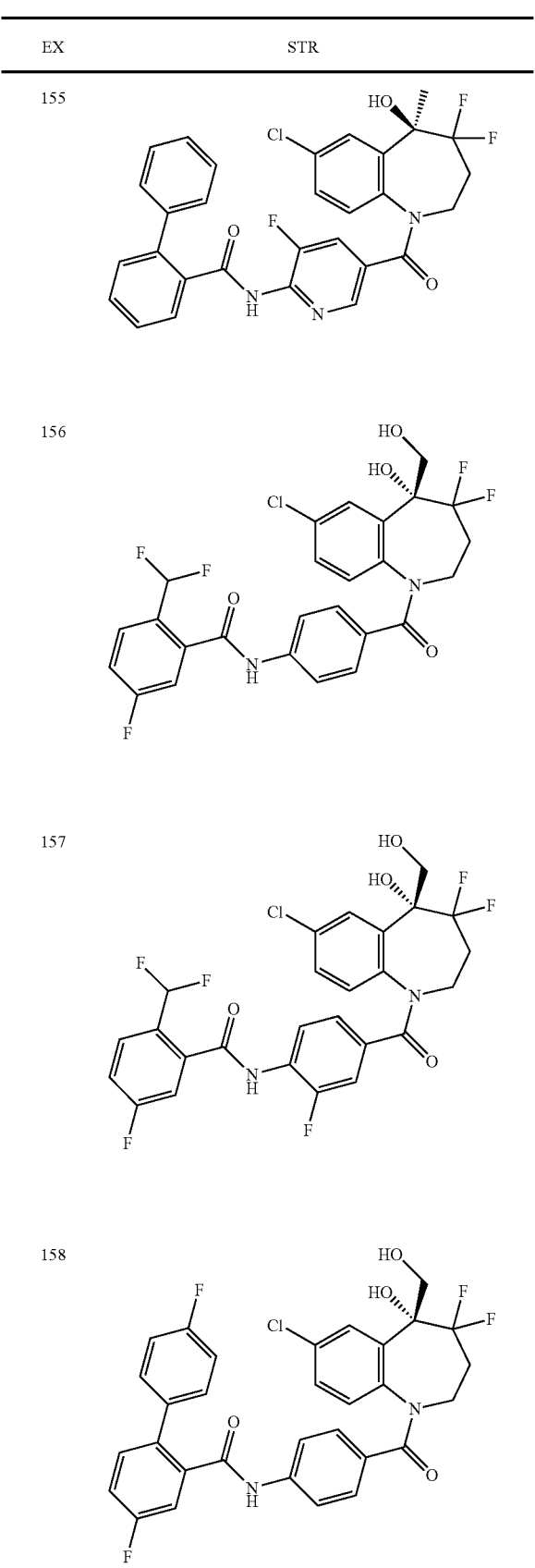 |
| 156 | |
| 157 | |
| 158 | |
TABLE 3-continued
| EX | STR |
|---|---|
| 159 | 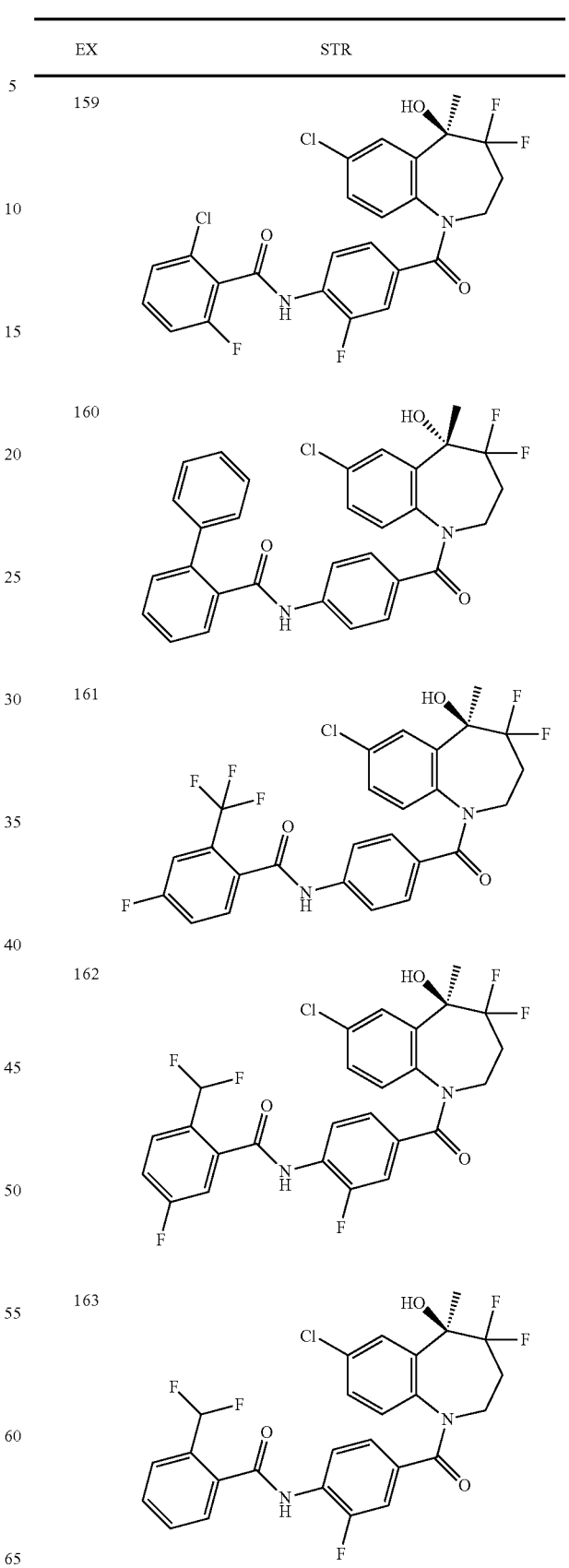 |
| 160 | |
| 161 | |
| 162 | |
| 163 | |

TABLE 3-continued
| EX | STR |
|---|---|
| 164 | 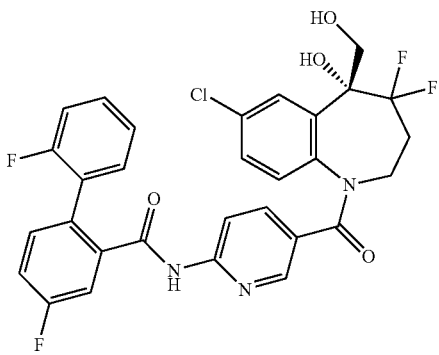 |
| 165 | 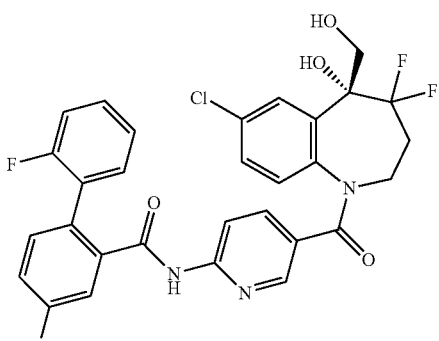 |
| 166 | 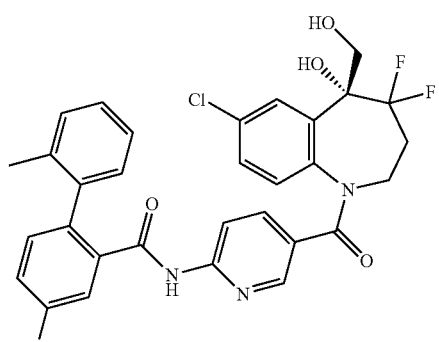 |
| 167 | 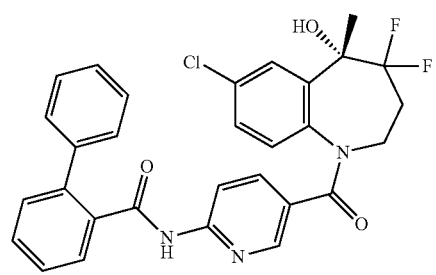 |
| 168 | 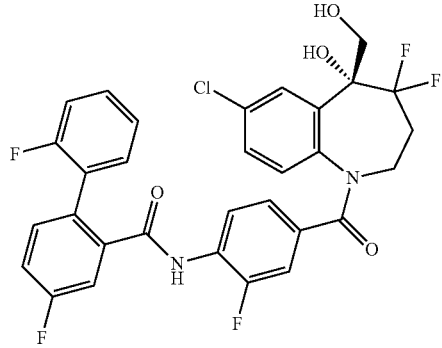 |
| 169 | 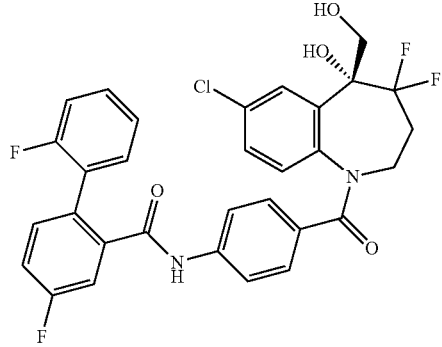 |
| 170 | 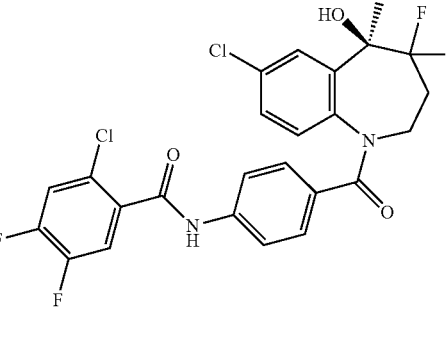 |
| 171 | 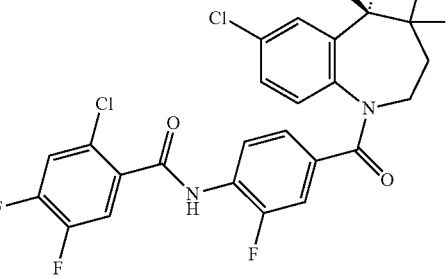 |

TABLE 3-continued

| EX | STR |
|---|---|
| 172 | |
| 173 | |
| 174 | |
| 175 | |
| 176 | |
| 177 | |
| 178 | |
| 179 | |
| 180 | |
| 181 | |

TABLE 3-continued
| EX | STR |
|---|---|
| 182 | 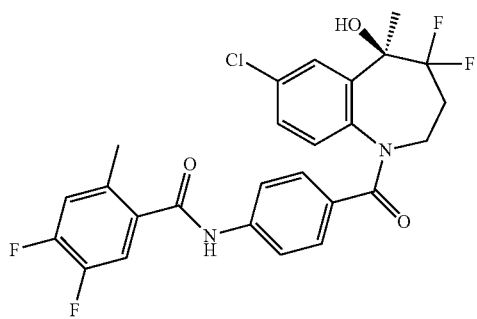 |
| 183 | 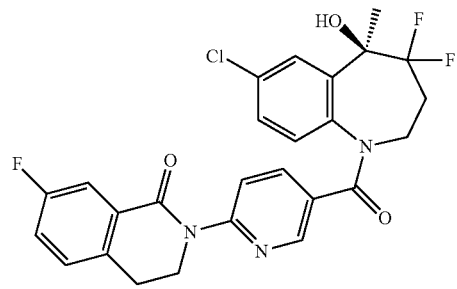 |
| 184 | 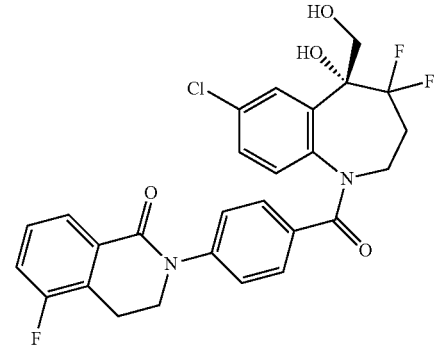 |
| 185 | 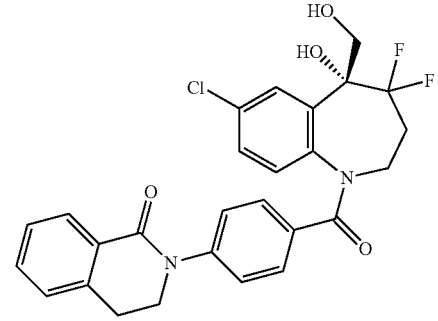 |
TABLE 3-continued
| EX | STR |
|---|---|
| 186 | 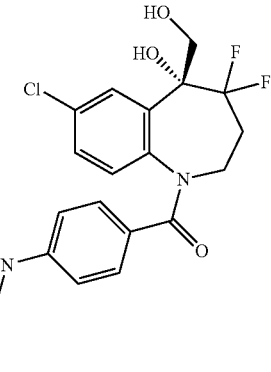 |
| 187 | 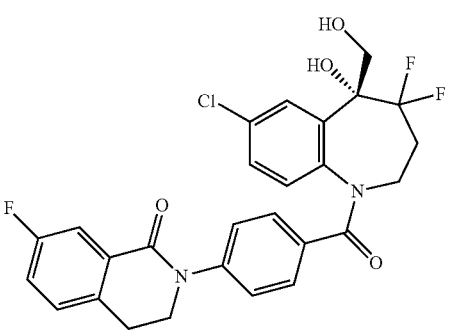 |
| 188 | 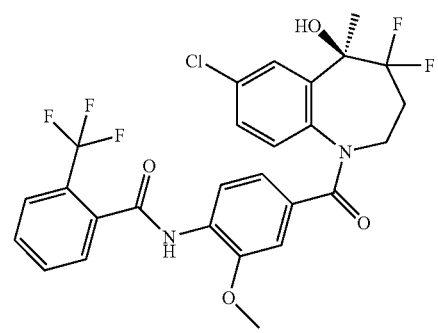 |
| 189 | 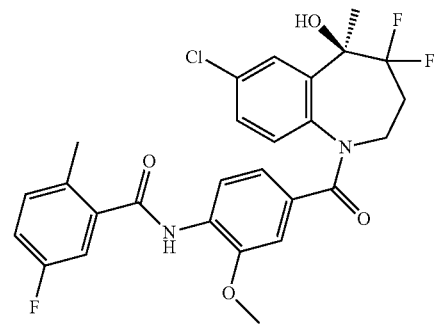 |

TABLE 3-continued
| EX | STR |
|---|---|
| 190 | 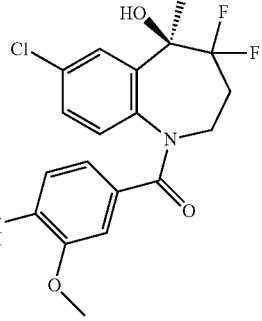 |
| 191 | 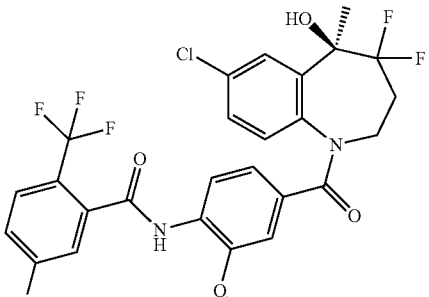 |
| 192 | 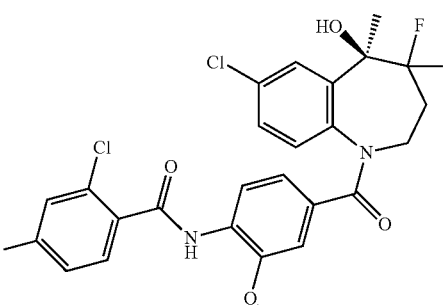 |
| 193 | 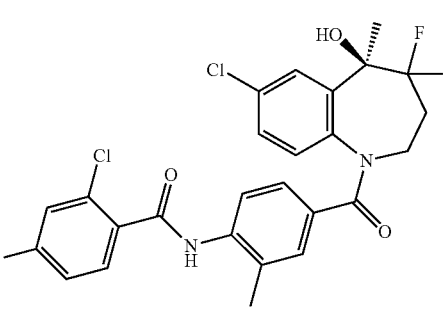 |
| 194 | 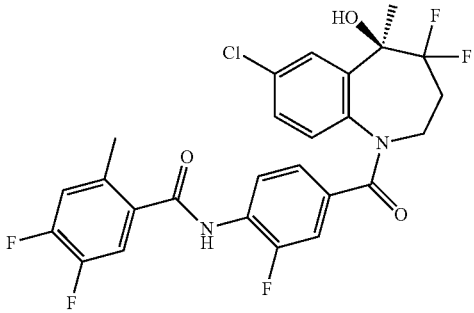 |
| 195 | 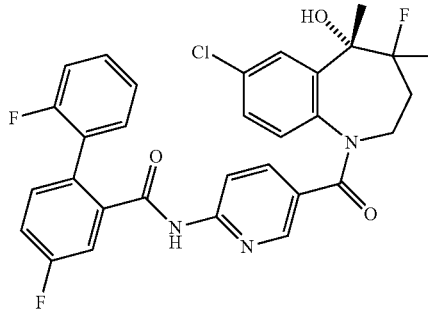 |
| 196 | 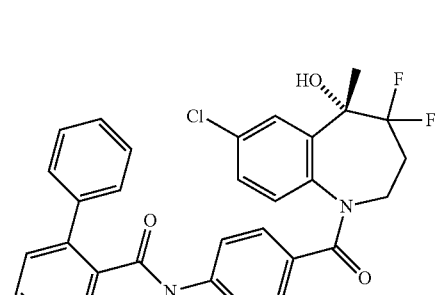 |
| 197 | 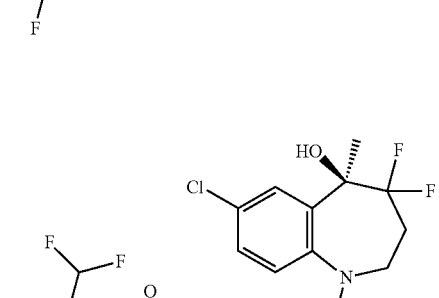 |
| 198 | 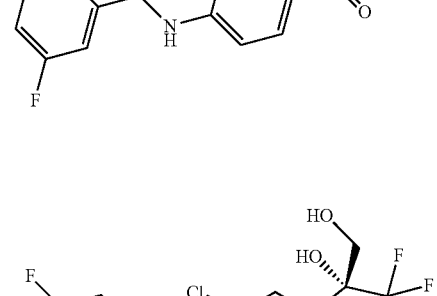 |

TABLE 3-continued

| EX | STR |
|---|---|
| 199 | |
| 200 | |
| 201 | |
| 202 | |
| 203 | |
| 204 | |
| 205 | |
| 206 | |

TABLE 3-continued

| EX | STR |
|---|---|
| 207 | |
| 208 | |
| 209 | |
| 210 | |
| 211 | |
| 212 | |
| 213 | |
| 214 | |

TABLE 3-continued
| EX | STR |
|---|---|
| 215 | 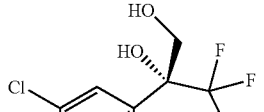 |
| 216 | 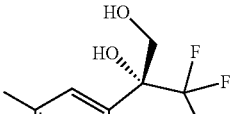 |
| 217 | 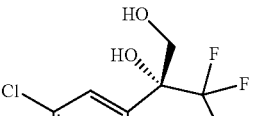 |
| 218 | 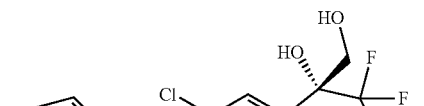 |
| 219 | 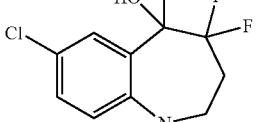 |
| 220 |  |
| 221 | 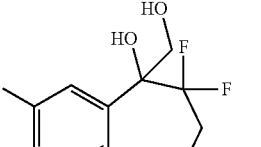 |
| 222 | 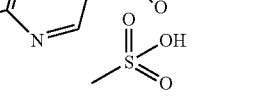 |

TABLE 3-continued

| EX | STR |
|---|---|
| 223 | (structure with HCl salt) |
| 224 | (structure with methanesulfonic acid) |
| 225 | (structure with methanesulfonic acid) |
| 226 | (structure with HCl salt) |
| 227 | (structure with methanesulfonic acid) |
| 228 | (structure with HCl salt) |
| 229 | (structure with methanesulfonic acid) |
| 230 | (structure with HCl salt) |

TABLE 3-continued
| EX | STR |
|---|---|
| 231 | 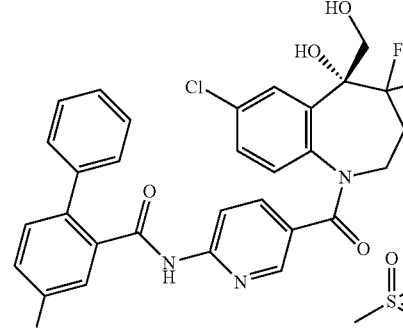 |
| 232 | |
| 233 | |
| 234 | |
TABLE 4
| EX | Prop | Data |
|---|---|---|
| 1 | | NMR1(400 MHz); 11.19-11.02(1H, m), 8.33-8.23(1H, m), 8.05-7.95(1H, m), 7.95-7.73(2H, m), 7.61-7.36(4H, m), 7.26-7.16(1H, m), 6.89-6.76(1H, m), 6.36-6.23(1H, m), 5.39-5.15(1H, m), 5.09-4.71(1H, m), 4.22-3.72(2H, m), 3.10-2.06(3H, m). |
| 2 | | NMR1(400 MHz); 11.25-11.16(1H, m), 8.30-8.26(1H, m), 8.01-7.64(7H, m), 7.25-7.18(1H, m), 6.89-6.79(1H, m), 6.33-6.24(1H, m), 5.39-5.19(1H, m), 5.04-4.72(1H, m), 4.21-4.07(1H, m), 4.04-3.72(1H, m), 3.07-2.82(1H, m), 2.70-2.05(2H, m). |
| 3 | | NMR1(400 MHz); 11.28-11.11(1H, m), 8.35-8.22(1H, m), 8.16-7.74(3H, m), 7.64-7.48(2H, m), 7.43-7.32(1H, m), 7.27-7.15(1H, m), 6.89-6.77(1H, m), 6.37-6.22(1H, m), 5.45-5.18(1H, m), 5.08-4.68(1H, m), 4.23-3.73(2H, m), 3.12-2.78(1H, m), 2.61-2.05(2H, m). |
| 4 | 1 | NMR1(400 MHz); 11.30-11.15(1H, m), 8.36-8.23(1H, m), 8.05-7.75(3H, m), 7.58-7.38(3H, m), 7.26-7.15(1H, m), 6.90-6.76(1H, m), 6.36-6.23(1H, m), 5.40-5.16(1H, m), 5.05-4.70(1H, m), 4.19-4.09(1H, m), 3.89-3.72(1H, m), 3.11-2.81(1H, m), 2.69-2.05(2H, m) |
| 5 | 1 | NMR1(400 MHz); 10.95-10.72(1H, m), 8.31-8.21(1H, m), 8.07-7.72(3H, m), 7.31-7.08(4H, m), 6.89-6.77(1H, m), 6.33-6.17(1H, m), 5.37-5.21(1H, m), 5.05-4.70(1H, m), 4.22-4.07(1H, m), 4.06-3.71(1H, m), 3.11-2.78(1H, m), 2.70-2.03(8H, m). |
| 6 | 1 | NMR1(400 MHz); 9.71-9.54(1H, m), 8.03-7.74(2H, m), 7.63-7.35(4H, m), 7.28-7.01(2H, m), 6.94-6.63(2H, m), 6.29-6.15(1H, m), 5.37-5.14(1H, m), 5.08-4.71(1H, m), 4.26-3.73(2H, m), 3.68-3.45(3H, m), 3.11-2.73(1H, m), 2.67-2.02(2H, m). |
| 7 | 1 | NMR1(400 MHz); 9.92-9.72(1H, m), 8.01-7.72(2H, m), 7.63-7.51(1H, m), 7.51-7.41(1H, m), 7.41-7.30(1H, m), 7.24-7.13(1H, m), 7.12-7.03(1H, m), 6.91-6.65(2H, m), 6.30-6.19(1H, m), 5.36-5.17(1H, m), 5.07-4.72(1H, m), 4.24-4.08(1H, m), 3.94-3.75(1H, m), 3.63-3.43(3H, m), 3.08-2.78(1H, m), 2.71-2.03(2H, m). |
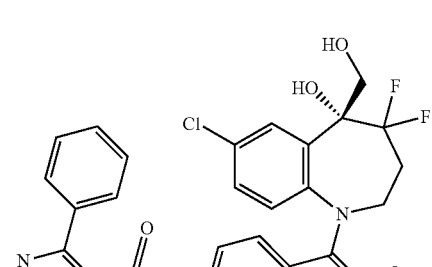

TABLE 4-continued

| EX | Prop | Data |
|---|---|---|
| 8 | | NMR1(400 MHz); 11.50-11.12(1H, m), 8.35-8.13(1H, m), 8.10-7.55(7H, m), 7.31-7.21(1H, m), 6.96-6.87(1H, m), 6.54-6.32(1H, m), 5.06-4.67(1H, m), 3.07-2.55(2H, m), 2.42-2.07(1H, m), 1.86-1.61(3H, m). |
| 9 | 8 | NMR1(400 MHz); 11.40-11.07(1H, m), 8.40-8.13(1H, m), 8.11-7.97(1H, m), 7.97-7.20(6H, m), 6.96-6.86(1H, m), 6.52-6.36(1H, m), 5.07-4.70(1H, m), 3.03-2.55(2H, m), 2.44-2.01(1H, m), 1.84-1.60(3H, m). |
| 10 | 8 | NMR1(400 MHz); 10.95-10.73(1H, m), 8.34-8.13(1H, m), 8.11-7.99(1H, m), 7.97-7.06(6H, m), 6.95-6.85(1H, m), 6.50-6.38(1H, m), 5.07-4.70(1H, m), 3.03-2.54(2H, m), 2.43-2.00(7H, m), 1.87-1.60(3H, m). |
| 11 | 8 | NMR1(400 MHz); 9.86-9.55(1H, m), 8.05-6.66(10H, m), 6.51-6.34(1H, m), 5.09-4.68(1H, m), 3.97-3.50(3H, m), 3.03-2.53(2H, m), 2.42-2.05(1H, m), 1.87-1.46(3H, m). |
| 12 | 8 | NMR1(400 MHz); 10.01-9.72(1H, m), 8.01-6.67(9H, m), 6.52-6.35(1H, m), 5.08-4.72(1H, m), 3.97-3.50(3H, m), 3.03-2.52(2H, m), 2.42-2.04(1H, m), 1.86-1.47(3H, m). |
| 13 | | NMR1(500 MHz); 11.46-11.10(1H, m), 8.37-8.19(1H, m), 8.07-7.54(7H, m), 7.29-7.14(1H, m), 6.93-6.74(1H, m), 6.40-6.16(1H, m), 5.43-5.11(1H, m), 5.10-4.68(1H, m), 4.27-3.70(2H, m), 3.11-2.05(3H, m). |
| 14 | | NMR1(500 MHz); 11.34-11.12(1H, m), 8.35-8.22(1H, m), 8.14-7.72(3H, m), 7.65-7.48(2H, m), 7.44-7.30(1H, m), 7.29-7.13(1H, m), 6.90-6.75(1H, m), 6.39-6.19(1H, m), 5.45-5.18(1H, m), 5.10-4.68(1H, m), 4.24-3.72(2H, m), 3.12-2.78(1H, m), 2.66-2.03(2H, m). |
| 15 | | NMR1(500 MHz); 11.34-11.12(1H, m), 8.35-8.22(1H, m), 8.14-7.72(3H, m), 7.65-7.48(2H, m), 7.44-7.30(1H, m), 7.29-7.13(1H, m), 6.90-6.75(1H, m), 6.39-6.19(1H, m), 5.45-5.18(1H, m), 5.10-4.68(1H, m), 4.24-3.72(2H, m), 3.12-2.78(1H, m), 2.66-2.03(2H, m). |
| 16 | | NMR1(500 MHz); 11.45-11.13(1H, m), 8.37-7.37(8H, m), 7.35-7.15(1H, m), 6.97-6.85(1H, m), 6.65-6.21(1H, m), 5.15-4.44(2H, m), 3.82-3.55(1H, m), 3.29-3.08(1H, m), 3.07-2.74(1H, m), 2.72-2.03(4H, m). |
| 17 | | NMR1(500 MHz); 11.21-11.04(1H, m), 8.34-8.21(1H, m), 8.05-7.95(1H, m), 7.95-7.73(2H, m), 7.62-7.36(4H, m), 7.26-7.16(1H, m), 6.90-6.76(1H, m), 6.43-6.15(1H, m), 5.44-5.14(1H, m), 5.05-4.71(1H, m), 4.22-3.72(2H, m), 3.11-2.06(3H, m). |
| 18 | 17 | NMR1(500 MHz); 9.92-9.72(1H, m), 8.01-7.72(2H, m), 7.63-7.51(1H, m), 7.51-7.41(1H, m), 7.41-7.30(1H, m), 7.24-7.13(1H, m), 7.13-7.02(1H, m), 6.91-6.65(2H, m), 6.38-6.10(1H, m), 5.42-5.13(1H, m), 5.07-4.72(1H, m), 4.24-3.74(2H, m), 3.63-3.40(3H, m), 3.08-2.78(1H, m), 2.67-2.02(2H, m). |
| 19 | | NMR4(500 MHz); 10.17-9.78(1H, m), 8.52-8.33(1H, m), 8.18-7.79(2H, m), 7.71-7.62 (1H, m), 7.60-7.53(1H, m), 7.49-7.42(1H, m), 7.35-7.26(1H, m), 7.11-7.03(1H, m), 6.73-6.51(1H, m), 5.63-5.34 (1H, m), 5.24-4.81(1H, m), 4.52-3.97(3H, m), 3.20-2.90(1H, m), 2.63-2.06(2H, m). |
| 20 | 19 | NMR2(400 MHz): 8.80-8.07(3H, m), 8.04-7.86(1H, m), 7.86-7.72(2H, m), 7.72-7.49(3H, m), 7.46-7.26(1H, m), 7.18-7.02(1H, m), 6.72-6.55(1H, m), 5.31-4.79(1H, m), 4.60-3.61(3H, m), 3.20-2.76(2H, m), 2.63-2.06(2H, m). |
| 21 | | NMR1(500 MHz); 10.87-10.57(1H, m), 7.92-7.82(2H, m), 7.82-7.75(1H, m), 7.75-7.65(2H, m), 7.52(2H, d, J = 8.7 Hz), 7.45-7.29(2H, m), 7.17(1H, dd, J = 8.4 Hz, 2.4 Hz), 6.74-6.62(1H, m), 6.29-6.02(1H, m), 5.49-5.10(1H, m), 5.10-4.65(1H, m), 4.35-3.68(2H, m), 3.13-2.70(1H, m), 2.64-2.39(1H, m), 2.39-2.05(1H, m). |
| 22 | 21 | NMR1(500 MHz); 10.76-10.34(1H, m), 8.11-7.55(6H, m), 7.55-7.09(3H, m), 7.05-6.57(1H, m), 6.57-6.01(1H, m), 5.50-5.16(1H, m), 5.14-4.63(1H, m), 4.31-3.65(2H, m), 3.11-2.74(1H, m), 2.73-2.44(1H, m), 2.43-2.05(1H, m). |
| 23 | | NMR1(500 MHz); 10.84-10.57(1H, m), 7.96-7.73(1H, m), 7.67-7.59(1H, m), 7.59-7.55(1H, m), 7.55-7.48(2H, m), 7.47-7.25(3H, m), 7.23-7.08(1H, m), 6.74-6.57(1H, m), 6.27-6.14(1H, m), 5.43-5.09(1H, m), 5.09-4.72(1H, m), 4.30-3.70(2H, m), 3.11-2.73(1H, m), 2.65-2.40(1H, m), 2.41-2.07(1H, m). |
| 24 | | NMR1(500 MHz); 10.61-10.42(1H, m), 7.94-7.86(1H, m), 7.86-7.75(1H, m), 7.68-7.56(1H, m), 7.56-7.50(1H, m), 7.48-7.13(4H, m), 6.95-6.64(1H, m), 6.43-6.14(1H, m), 5.45-5.13(1H, m), 5.08-4.67(1H, m), 4.27-3.71(2H, m), 3.10-2.77(1H, m), 2.71-2.05(2H, m). |

TABLE 4-continued

| EX | Prop | Data |
|---|---|---|
| 25 | | NMR2(500 MHz); 8.20-8.00(1H, m), 7.98(1H, d, J = 2.2 Hz), 7.86-7.61(1H, m), 7.59-7.28(6H, m), 7.06(1H, dd, J = 8.3 Hz, 2.3 Hz), 6.73-6.47(1H, m), 5.36-4.73(1H, m), 4.68-3.83(2H, m), 3.62-3.25(1H, m), 3.25-2.71(1H, m), 2.66-2.01(3H, m). |
| 26 | | NMR2(500 MHz); 8.50-8.11(2H, m), 7.99(1H, d, J = 2.4 Hz), 7.78(1H, s), 7.53-7.31(3H, m), 7.31-6.99(2H, m), 6.75-6.49(1H, m), 5.31-4.82(1H, m), 4.73-3.81(2H, m), 3.49-2.89(2H, m), 2.69-2.13(3H, m). |
| 27 | 21 | NMR1(500 MHz); 10.87-10.57(1H, m), 8.04-7.70(1H, m), 7.69-7.26(7H, m), 7.16(1H, dd, J = 8.4 Hz, 2.4 Hz), 6.74-6.60(1H, m), 6.28-6.11(1H, m), 5.46-5.10(1H, m), 5.10-4.69(1H, m), 4.28-3.71(2H, m), 3.11-2.73(1H, m), 2.63-2.22(2H, m). |
| 28 | 21 | NMR1(500 MHz); 10.78-10.41(1H, m), 8.13-7.71(2H, m), 7.71-7.38(3H, m), 7.38-7.00(3H, m), 6.92-6.63(1H, m), 6.41-6.14(1H, m), 5.42-5.18(1H, m), 5.04-4.68(1H, m), 4.28-3.66(2H, m), 3.10-2.77(1H, m), 2.60-2.24(2H, m). |
| 29 | 19 | NMR2(500 MHz); 10.29-9.93(1H, m), 8.58-8.31(1H, m), 8.28-7.72(2H, m), 7.71-7.55(1H, m), 7.45-7.30(1H, m), 7.29-7.16(1H, m), 7.15-6.96(2H, m), 6.72-6.50(1H, m), 5.52-5.27(1H, m), 5.23-4.80(1H, m), 4.49-3.91(3H, m), 3.21-2.46(2H, m), 2.45-1.95(1H, m). |
| 30 | 19 | NMR2(500 MHz); 8.68-8.21(2H, m), 8.21-8.08(1H, m), 8.02-7.85(1H, m), 7.85-7.70(2H, m), 7.43-7.24(2H, m), 7.23-7.06(2H, m), 6.73-6.56(1H, m), 5.23-4.84(1H, m), 4.62-3.90(2H, m), 3.71-2.95(2H, m), 2.79-2.07(2H, m), 1.66-1.54(1H, m). |
| 31 | 19 | NMR1(500 MHz); 11.49-11.32(1H, m), 8.35-8.23(1H, m), 8.07-7.95(1H, m), 7.94-7.71(2H, m), 7.59-7.40(3H, m), 7.27-7.16(1H, m), 6.94-6.78(1H, m), 6.34-6.17(1H, m), 5.40-5.15(1H, m), 5.07-4.69(1H, m), 4.21-3.72(2H, m), 3.10-2.54(2H, m), 2.39-2.06(1H, m). |
| 32 | 19 | NMR1(500 MHz); 11.32-11.10(1H, m), 8.35-8.23(1H, m), 8.10-7.99(1H, m), 7.96-7.72(2H, m), 7.39-7.30(2H, m), 7.30-7.17(2H, m), 6.93-6.76(1H, m), 6.36-6.20(1H, m), 5.40-5.17(1H, m), 5.07-4.69(1H, m), 4.21-3.72(2H, m), 3.11-2.45(2H, m), 2.44-2.04(4H, m). |
| 33 | | NMR4(500 MHz); 10.00-9.73(1H, m), 8.51-8.34(1H, m), 8.22-7.78(2H, m), 7.72-7.63(1H, m), 7.63-7.52(1H, m), 7.52-7.43(1H, m), 7.36-7.26(1H, m), 7.14-7.00(1H, m), 6.69-6.53(1H, m), 5.54-5.31(1H, m), 5.21-4.85(1H, m), 4.46-4.00(3H, m), 3.18-2.93(1H, m), 2.55-2.06(2H, m). |
| 34 | | NMR1(500 MHz); 10.00-9.75(1H, m), 8.25-6.74(9H, m), 6.60-6.12(1H, m), 5.15-4.40(2H, m), 4.00-3.50(4H, m), 3.29-2.56(3H, m), 2.46-2.01(3H, m). |
| 35 | 13 | NMR1(500 MHz); 10.96-10.75(1H, m), 8.34-8.21(1H, m), 8.07-7.98(1H, m), 7.94-7.72(2H, m), 7.49-7.42(1H, m), 7.42-7.32(1H, m), 7.32-7.16(3H, m), 6.90-6.76(1H, m), 6.42-6.16(1H, m), 5.43-5.13(1H, m), 5.10-4.69(1H, m), 4.24-3.72(2H, m), 3.11-2.07(6H, m). |
| 36 | 13 | NMR1(500 MHz); 11.07-10.87(1H, m), 8.33-8.23(1H, m), 8.04-7.98(1H, m), 7.92-7.72(2H, m), 7.38-7.15(4H, m), 6.90-6.77(1H, m), 6.44-6.17(1H, m), 5.46-5.16(1H, m), 5.05-4.69(1H, m), 4.22-3.72(2H, m), 3.12-2.07(6H, m). |
| 37 | | NMR1(500 MHz); 10.54-10.37(1H, m), 8.06-7.09(9H, m), 6.74-6.61(1H, m), 6.30-6.03(1H, m), 5.42-5.09(1H, m), 5.08-4.73(1H, m), 4.28-3.74(2H, m), 3.11-2.71(1H, m), 2.66-2.05(5H, m). |
| 38 | 37 | NMR1(500 MHz); 10.02-9.72(1H, m), 7.99-7.03(8H, m), 6.80-6.57(1H, m), 6.32-5.98(1H, m), 5.42-5.09(1H, m), 5.09-4.66(1H, m), 4.28-3.74(2H, m), 3.11-2.72(1H, m), 2.66-2.04(8H, m). |
| 39 | 37 | NMR1(500 MHz); 10.51-10.00(1H, m), 8.08-7.00(8H, m), 6.90-6.68(1H, m), 6.40-6.07(1H, m), 5.42-5.09(1H, m), 5.09-4.66(1H, m), 4.26-3.67(2H, m), 3.10-2.75(1H, m), 2.71-2.04(5H, m). |
| 40 | 37 | NMR1(500 MHz); 9.56-9.33(1H, m), 8.01-7.70(2H, m), 7.40-6.79(6H, m), 6.79-6.65(1H, m), 6.35-6.15(1H, m), 5.50-5.13(1H, m), 5.11-4.66(1H, m), 4.30-3.78(2H, m), 3.66-3.46(3H, m), 3.08-2.78(1H, m), 2.66-2.04(2H, m). |
| 41 | 21 | NMR1(500 MHz); 10.56-10.30(1H, m), 8.13-7.72(1H, m), 7.57(1H, d, J = 8.4 Hz), 7.53-7.23(6H, m), 7.16(1H, dd, J = 8.4 Hz.2.5 Hz), 6.75-6.60(1H, m), 6.29-5.99(1H, m), 5.45-5.09(1H, m), 5.09-4.74(1H, m), 4.31-3.70(2H, m), 3.13-2.73(1H, m), 2.63-2.43(1H, m), 2.43-2.21(4H, m). |
| 42 | 21 | NMR1(500 MHz); 9.96-9.51(1H, m), 8.19-7.70(1H, m), 7.70-7.01(8H, m), 6.91-6.47(1H, m), 6.40-5.92(1H, m), |

TABLE 4-continued

| EX | Prop | Data |
|---|---|---|
| | | 5.40-5.11(1H, m), 5.11-4.71(1H, m), 4.37-3.66(2H, m), 3.15-2.77(1H, m), 2.67-2.47(1H, m), 2.47-2.27(4H, m), 2.24-2.09(3H, m). |
| 43 | 21 | NMR1(500 MHz); 10.36-9.98(1H, m), 8.02-7.75(1H, m), 7.75-7.56(1H, m), 7.56-7.16(7H, m), 6.96-6.64(1H, m), 6.49-6.00(1H, m), 5.42-5.14(1H, m), 5.14-4.68(1H, m), 4.27-3.68(2H, m), 3.09-2.77(1H, m), 2.68-2.41(1H, m), 2.41-2.06(4H, m). |
| 44 | 21 | NMR1(500 MHz): 9.64-8.88(1H, m), 8.16-7.73(2H, m), 7.49-7.04(6H, m), 6.91-6.81(1H, m), 6.77-6.66(1H, m), 6.31-6.15(1H, m), 5.43-5.12(1H, m), 5.12-4.49(1H, m), 4.29-3.70(2H, m), 3.70-3.45(3H, m), 3.04-2.80(1H, m), 2.53-2.44(1H, m), 2.40-2.29(4H, m). |
| 45 | 37 | NMR1(500 MHz); 11.33-10.90(1H, m), 8.63-7.60(4H, m), 7.50-7.06(4H, m), 6.90-6.75(1H, m), 6.41-6.17(1H, m), 5.55-5.11(1H, m), 5.09-4.64(1H, m), 4.27-3.66(2H, m), 3.12-2.73(1H, m), 2.67-2.01(5H, m). |
| 46 | 37 | NMR1(500 MHz); 11.16-10.81(1H, m), 8.32-8.21(1H, m), 8.10-7.96(1H, m), 7.94-7.11(2H, m), 7.50-7.06(5H, m), 6.91-6.76(1H, m), 6.40-6.1 6(1H, m), 5.47-5.11(1H, m), 5.09-4.67(1H, m), 4.27-3.67(2H, m), 3.11-2.01(5H, m), 1.14(3H, t, J = 7.5 Hz). |
| 47 | 37 | NMR1(500 MHz); 10.60-10.31(1H, m), 7.98-7.08(10H, m), 6.75-6.61(1H, m), 6.29-6.11(1H, m), 5.41-5.08(1H, m), 5.09-4.74(1H, m), 4.29-3.74(2H, m), 3.11-2.01(5H, m), 1.22-1.08(3H, m). |
| 48 | 37 | NMR1(500 MHz); 9.98-9.70(1H, m), 8.6-7.75(1H, m), 7.66-6.60(9H, m), 6.35-6.02(1H, m), 5.38-5.11(1H, m), 5.07-4.69(1H, m), 4.29-3.74(2H, m), 3.09-2.01(8H, m), 1.23-1.13(3H, m). |
| 49 | 37 | NMR1(500 MHz): 10.38-10.02(1H, m), 8.00-7.09(9H, m), 6.90-6.71(1H, m), 6.39-6.04(1H, m), 5.51-5.17(1H, m), 5.08-4.70(1H, m), 4.26-3.74(2H, m), 3.11-2.01(5H, m), 1.21-1.12(3H, m). |
| 50 | 37 | NMR1(500 MHz); 9.34-9.18(1H, m), 7.94-7.72(2H, m), 7.56-6.62(8H, m), 6.35-6.15(1H, m), 5.46-5.15(1H, m), 5.01-4.72(1H, m), 4.30-3.49(5H, m), 3.09-1.97(5H, m), 1.21-1.07(3H, m). |
| 51 | | NMR2(500 MHz); 8.79-8.56(1H, m), 8.48-8.25(1H, m), 8.24-8.11(1H, m), 7.99(0.8H, d, J = 2.4 Hz), 7.95-7.71(1H, m), 7.71-7.62(1H, m), 7.55-7.42(1H, m), 7.42-7.33(1H, m), 7.33-7.28(0.2H, m), 7.19-7.06(1H, m), 6.77-6.51(1H, m), 5.33-4.82(1H, m), 4.66-3.91(2H, m), 3.48-2.93(2H, m), 2.70-2.08(3H, m). |
| 52 | | NMR2(500 MHz); 9.03-8.66(1H, m), 8.60-8.23(1H, m), 8.23-8.10(1H, m), 8.08-7.95(0.8H, m), 7.95-7.70(1H, m), 7.67-7.55(1H, m), 7.55-7.49(1H, m), 7.37-7.29(0.2H, m), 7.20-7.07(1H, m), 6.83-6.51(1H, m), 5.30-4.83(1H, m), 4.66-3.90(2H, m), 3.52-2.95(2H, m), 2.68-2.07(3H, m). |
| 53 | 21, 52 | NMR2(500 MHz); 9 32-9.12(1H, m), 9.01-8.73(1H, m), 8.41-8.22(1H, m), 8.16-7.83(1H, m), 7.83-7.75(1H, m), 7.75-7.57(3H, m), 7.19-7.04(1H, m), 6.76-6.41(1H, m), 5.23-4.82(1H, m), 4.64-3.70(2H, m), 3.49-2.96(3H, m), 2.80-2.09(2H, m). |
| 54 | 21, 52 | NMR2(500 MHz); 9.31-9.13(1H, m), 8.99-8.77(2H, m), 8.17-7.78(1H, m), 7.53(1H, dd, J = 8.3 Hz, 3.1 Hz), 7.50-7.41(1H, m), 7.24-7.17(1H, m), 7.17-6.99(1H, m), 6.68-6.44(1H, m), 5.21-4.88(1H, m), 4.66-3.74(2H, m), 3.55-2.99(3H, m), 2.76-2.09(2H, m). |
| 55 | 21, 52 | NMR2(500 MHz); 8.80-8.56(1H, m), 8.47-8.25(1H, m), 8.24-8.10(1H, m), 8.04-7.83(1H, m), 7.80-7.61(1.8H, m), 7.46-7.28(2.2H, m), 7.20-7.05(1H, m), 6.77-6.51(1H, m), 5.37-4.83(1H, m), 4.73-3.89(2H, m), 3.48-2.89(2H, m), 2.70-2.07(3H, m). |
| 56 | 21, 52 | NMR2(500 MHz); 8.63-8.38(1H, m), 8.15-7.90(2H, m), 7.84-7.72(1H, m), 7.72-7.55(3H, m), 7.55-7.39(1H, m), 7.11(1H, dd, J = 8.4 Hz, 2.5 Hz), 6.68-6.58(1H, m), 6.56(1H, d, J = 1.7 Hz), 5.33-5.10(1H, m), 5.10-4.87(1H, m), 4.87-4.64(1H, m), 4.52-4.23(1H, m), 4.02-3.83(1H, m), 3.61(1H, d, J = 2.4 Hz), 3.35-3.17(3H, m), 3.15-2.89(2H, m), 2.58-2.08(2H, m). |
| 57 | | NMR1(500 MHz); 8.85(1H, s), 7.89(1H, d, J = 2.5 Hz), 7.83-7.71(1H, m), 7.69-7.54(1H, m), 7.16(1H, dd, J = 8.3 Hz, 2.5 Hz), 7.12-7.03(1H, m), 6.97(1H, d, J = 1.6 Hz), 6.83(1H, d, J = 1.1 Hz), 6.78-6.60(1H, m), 6.43-6.16(1H, m), 5.46-5.17(1H, m), 5.12-4.72(1H, m), 4.24-4.07(1H, m), 4.07-3.74(1H, m), 3.63-3.49(3H, m), 3.10-2.75(1H, m), 2.66-2.22(5H, m). |

TABLE 4-continued

| EX | Prop | Data |
|---|---|---|
| 58 | | NMR2(500 MHz); 8.78-8.53(1H, m), 8.52-8.27(1H, m), 7.97(1H, d, J = 2.3 Hz), 7.90-7.70(1H, m), 7.23-7.15(1H, m), 7.15-7.01(3H, m), 6.78(1H, s), 6.73-6.55(1H, m), 5.40-4.79(1H, m), 4.70-4.16(1H, m), 4.08-3.85(1H, m), 3.80-3.49(3H, m), 3.38-3.15(1H, m), 3.15-2.86(1H, m), 2.67-2.07(3H, m). |
| 59 | 58 | NMR2(500 MHz); 8.51-8.26(1H, m), 8.23-8.03(1H, m), 7.97(1H, d, J = 2.4 Hz), 7.48-7.31(1H, m), 7.26-7.00(4H, m), 6.86-6.71(1H, m), 6.71-6.53(1H, m), 5.32-4.80(1H, m), 4.66-4.17(1H, m), 4.08-3.94(1H, m), 3.76-3.45(3H, m), 3.43-3.21(1H, m), 3.18-2.92(1H, m), 2.66-2.07(3H, m). |
| 60 | 37 | NMR1(500 MHz): 9.81-9.67(1H, m), 7.98-6.64(10H, m), 6.33-6.05(1H, m), 5.42-4.66(4H, m), 4.22-3.76(2H, m), 3.30-2.26(3H, m), 3.08-3.76(1H, m), 2.68-2.04(2H, m). |
| 61 | 37 | NMR1(500 MHz); 9.80-9.53(1H, m), 7.94-7.73(1H, m), 7.68-7.11(5H, m), 7.03-6.93(1H, m), 6.83-6.70(1H, m), 6.46-6.11(1H, m), 5.48-5.17(1H, m), 5.05-4.65(1H, m), 4.25-3.73(2H, m), 3.11-2.75(1H, m), 2.67-2.02(5H, m). |
| 62 | 37 | NMR1(500 MHz); 8.86-8.74(1H, m), 8.00-7.66(3H, m), 7.24-6.64(5H, m), 6.44-6.13(1H, m), 5.44-5.19(1H, m), 5.07-4.70(1H, m), 4.24-3.70(2H, m), 3.68-3.55(3H, m), 3.08-2.74(1H, m), 2.66-2.02(5H, m). |
| 63 | | NMR1(400 MHz); 10.91-10.69(1H, m), 8.22-8.13(1H, m), 7.92-7.65(3H, m), 7.63-7.13(10H, m), 6.85-6.71(1H, m), 6.38-6.16(1H, m), 5.46-5.13(1H, m), 5.07-4.64(1H, m), 4.24-3.65(2H, m), 3.10-2.01(3H, m). |
| 64 | 37, 63 | NMR1(500 MHz); 10.23-9.93(1H, m), 7.93-6.61(9H, m), 6.36-6.05(1H, m), 5.42-5.15(1H, m), 5.07-4.71(1H, m), 4.30-3.78(2H, m), 3.10-2.08(6H, m). |
| 65 | | NMR1(500 MHz); 10.01-9.69(1H, m), 8.47-6.04(10H, m), 5.10-3.47(4H, m), 3.29-2.03(5H, m), 1.90-1.32(2H, m). |
| 66 | | NMR1(500 MHz); 11.61-11.20(1H, m), 8.91-8.73(1H, m), 8.43-7.63(6H, m), 7.30-7.13(1H, m), 6.95-6.70(1H, m), 6.43-6.04(1H, m), 5.50-5.12(1H, m), 5.08-4.68(1H, m), 4.27-3.70(2H, m), 3.11-2.00(3H, m). |
| 67 | 37, 63 | NMR1(500 MHz); 8.46-8.30(1H, m), 8.07-7.72(4H, m), 7.62-7.50(1H, m), 7.47-7.32(2H, m), 7.29-7.15(1H, m), 6.95-6.78(1H, m), 6.43-6.18(1H, m), 5.45-5.16(1H, m), 5.08-4.71(1H, m), 4.40-3.74(4H, m), 3.18-2.02(5H, m). |
| 68 | 37, 63 | NMR1(500 MHz); 11.08-10.69(1H, m), 7.92-6.07(9H, m), 6.37-6.04(1H, m), 5.49-3.51(4H, m), 3.27-2.02(3H, m). |
| 69 | 37, 63 | NMR1(500 MHz); 10.80-10.51(1H, m), 7.96-6.58(10H, m), 6.32-6.02(1H, m), 5.45-5.12(1H, m), 5.09-4.73(1H, m), 4.293.75(2H, m), 3.18-2.02(3H, m). |
| 70 | 37, 63 | NMR1(500 MHz); 10.64-10.24(1H, m), 8.15-7.02(8H, m), 6.87-6.62(1H, m), 6.42-6.04(1H, m), 5.44-5.18(1H, m), 5.10-4.68(1H, m), 4.32-3.49(2H, m), 3.22-2.02(3H, m). |
| 71 | | NMR1(500 MHz); 10.16-9.86(1H, m), 7.95-7.07(8H, m), 6.80-6.60(1H, m), 6.37-6.08(1H, m), 5.45-5.11(1H, m), 5.10-4.65(1H, m), 4.31-3.72(2H, m), 3.09-2.01(6H, m). |
| 72 | 71 | NMR1(500 MHz); 11.04-10.65(1H, m), 8.00-6.68(9H, m), 6.34-5.99(1H, m), 5.50-3.93(4H, m), 3.12-2.00(3H, m). |
| 73 | 71 | NMR1(500 MHz); 10.60-10.27(1H, m), 8.04-7.03(9H, m), 6.77-6.55(1H, m), 6.31-6.14(1H, m), 5.44-5.09(1H, m), 5.09-4.72(1H, m), 4.29-3.67(2H, m), 3.10-2.71(1H, m), 2.68-2.02(5H, m). |
| 74 | 71 | NMR1(500 MHz); 10.81-10.43(1H, m), 7.96-6.67(9H, m), 6.37-6.05(1H, m), 5.47-3.54(4H, m), 3.27-2.02(6H, m). |
| 75 | 71 | NMR1(500 MHz); 10.37-10.03(1H, m), 8.08-7.03(8H, m), 6.88-6.68(1H, m), 6.40-6.17(1H, m), 5.43-5.15(1H, m), 5.10-4.66(1H, m), 4.25-3.70(2H, m), 3.10-2.76(1H, m), 2.69-2.03(5H, m). |
| 76 | 71 | NMR1(500 MHz); 10.00-9.63(1H, m), 8.01-6.94(8H, m), 6.82-6.57(1H, m), 6.37-6.02(1H, m), 5.41-5.14(1H, m), 5.11-4.70(1H, m), 4.28-3.70(2H, m), 3.09-2.72(1H, m), 2.68-2.22(5H, m), 2.22-2.03(3H, m). |
| 77 | 71 | NMR1(500 MHz); 11.47-11.19(1H, m), 8.85-8.69(1H, m), 8.42-8.23(1H, m), 8.23-8.07(1H, m), 8.07-7.95(1H, m), 7.93-7.74(2H, m), 7.74-7.60(1H, m), 7.33-6.94(2H, m), 6.90-6.76(1H, m), 6.37-6.20(1H, m), 5.48-5.10(1H, m), 5.10-4.63(1H, m), 4.26-3.64(2H, m), 3.10-1.99(3H, m). |
| 78 | 71 | NMR1(500 MHz); 10.72-10.58(1H, m), 8.10-7.07(8H, m), 6.75-6.56(1H, m), 6.32-6.02(1H, m), 5.43-5.09(1H, m), 5.07-4.68(1H, m), 4.33-3.71(2H, m), 3.01-2.75(1H, m), 2.67-2.04(2H, m). |
| 79 | 71 | NMR1(500 MHz); 11.10-10.73(1H, m), 8.04-6.71(8H, m), 6.31-6.01(1H, m), 5.42-3.53(4H, m), 3.27-2.00(3H, m). |

TABLE 4-continued

| EX | Prop | Data |
|---|---|---|
| 80 | 71 | NMR1(500 MHz); 10.63-10.36(1H, m), 8.24-7.00(7H, m), 6.86-6.66(1H, m), 6.39-6.12(1H, m), 5.47-5.14(1H, m), 5.14-4.66(1H, m), 4.33-3.62(2H, m), 3.12-2.02(3H, m). |
| 81 | 71 | NMR1(500 MHz); 10.25-9.90(1H, m), 8.02-7.04(7H, m), 6.79-6.61(1H, m), 6.27-6.05(1H, m), 5.42-5.11(1H, m), 5.09-4.68(1H, m), 4.32-3.54(2H, m), .320-2.74(1H, m), 2.67-2.00(5H, m). |
| 82 | 71 | NMR1(500 MHz); 9.87-9.75(1H, m), 8.01-7.69(4H, m), 7.22-6.62(4H, m), 6.35-6.18(1H, m), 5.45-5.16(1H, m), 5.08-4.71(1H, m), 4.22-3.45(5H, m), 3.07-2.81(1H, m), 2.67-2.03(2H, m). |
| 83 | 71 | NMR1(500 MHz); 10.56-10.33(1H, m), 7.96-7.72(1H, m), 7.72-7.28(6H, m), 7.22-7.08(1H, m), 6.74-6.60(1H, m), 6.28-6.05(1H, m), 5.39-5.10(1H, m), 5.08-4.70(1H, m), 4.28-3.73(2H, m), 3.09-2.73(1H, m), 2.68-2.00(5H, m). |
| 84 | 71 | NMR1(500 MHz): 10.88-10.44(1H, m), 7.93-6.68(8H, m), 6.30-6.02(1H, m), 5.44-3.49(4H, m), 3.27-2.01(6H, m). |
| 85 | 71 | NMR1(500 MHz); 10.76-10.60(1H, m), 8.04-7.74(3H, m), 7.55-7.29(4H, m), 7.19-7.10(1H, m), 6.74-6.61(1H, m), 6.27-6.14(1H, m), 5.46-5.10(1H, m), 5.08-4.69(1H, m), 4.30-3.72(2H, m), 3.10-2.75(1H, m), 2.66-2.01(2H, m). |
| 86 | 71 | NMR1(500 MHz); 11.12-10.74(1H, m), 8.10-6.70(8H, m), 6.30-6.05(1H, m), 5.44-3.52(4H, m), 3.27-2.01(3H, m). |
| 87 | 71 | NMR1(500 MHz); 10.62-10 40(1H, m), 8.18-7.09(7H, m), 6.85-6.67(1H, m), 6.38-6.18(1H, m), 5.42-5.17(1H, m), 5.08-4.67(1H, m), 4.25-3.69(2H, m), 3.10-2.03(3H, m). |
| 88 | 71 | NMR1(500 MHz); 10.24-9.95(1H, m), 8.06-7.08(7H, m), 6.77-6.61(1H, m), 6.30-6.02(1H, m), 5.41-5.13(1H, m), 5.09-4.69(1H, m), 4.27-3.70(1H, m), 3.12-2.74(1H, m), 2.66-2.02(6H, m). |
| 89 | 71 | NMR1(500 MHz); 7.97-6.72(10H, m), 6.34-6.05(1H, m), 5.39-5.16(1H, m), 5.11-4.69(1H, m), 4.22-3.44(7H, m), 3.20-2.00(5H, m). |
| 90 | 21, 52 | NMR1(500 MHz); 11.52-11.07(1H, m), 9.48-8.24(2H, m), 7.92-7.70(1H, m), 7.70-7.55(2H, m), 7.55-7.07(8H, m), 7.04-6.66(1H, m), 6.50-5.99(1H, m), 5.50-4.63(2H, m), 4.30-3.54(2H, m), 3.17-2.87(1H, m), 2.70-2.02(2H, m). |
| 91 |  | NMR1(500 MHz); 10.93-10.71(1H, m), 8.24-8.11(1H, m), 7.94-7.30(9H, m), 7.29-7.11(3H, m), 6.87-6.70(1H, m), 6.38-6.16(1H, m), 5.41-5.11(1H, m), 5.04-4.65(1H, m), 4.19-3.44(2H, m), 3.09-2.01(3H, m). |
| 92 | 71 | NMR1(500 MHz); 10.29-10.15(1H, m), 7.92-7.13(7H, m), 6.85-6.71(1H, m), 6.35-6.20(1H, m), 5.42-5.17(1H, m), 5.05-4.68(1H, m), 4.29-3.68(2H, m), 3.09-2.78(1H, m), 2.66-2.01(5H, m). |
| 93 | 71 | NMR1(500 MHz); 9.83-9.75(1H, m), 7.93-7.08(7H, m), 6.76-6.63(1H, m), 6.31-6.16(1H, m), 5.39-5.15(1H, m), 5.07-4.70(1H, m), 4.25-3.74(2H, m), 3.08-2.77(1H, m), 2.65-2.05(8H, m). |
| 94 | 71 | NMR1(500 MHz); 9.56-9.42(1H, m), 7.95-7.31(4H, m), 7.23-6.79(3H, m), 6.77-6.62(1H, m), 6.32-6.20(1H, m), 5.37-5.14(1H, m), 5.07-4.72(1H, m), 4.27-3.74(2H, m), 3.65-3.44(3H, m), 3.10-2.79(1H, m), 2.66-2.01(5H, m). |
| 95 | 96 | NMR1(500 MHz): 11.72-11.11(1H, m), 9.37-8.24(2H, m), 7.97-7.66(1H, m), 7.67-7.06(9H, m), 7.00-6.68(1H, m), 6.44-5.81(1H, m), 5.53-4.41(2H, m), 4.41-3.54(2H, m), 3.09-2.90(1H, m), 2.68-2.14(2H, m). |
| 96 |  | NMR1(500 MHz); 11.20-10.76(1H, m), 8.30-8.12(1H, m), 7.88(1H, d, J = 2.5 Hz), 7.85-7.63(2H, m), 7.59-7.04(9H, m), 6.90-6.72(1H, m), 6.37-6.00(1H, m), 5.44-5.11(1H, m), 5.08-4.63(1H, m), 4.21-3.68(2H, m), 3.11-2.76(1H, m), 2.71-2.03(2H, m). |
| 97 |  | NMR1(500 MHz); 11.36-10.85(1H, m), 8.74(1H, dd, J = 4.8 Hz, 1.5 Hz), 8.31-8.14(1H, m), 8.10-7.02(10H, m), 7.25-7.14(1H, m), 6.88-6.69(1H, m), 6.35-6.13(1H, m), 5.41-5.09(1H, m), 5.08-4.67(1H, m), 4.23-3.60(2H, m), 3.11-2.75(1H, m), 2.68-2.07(2H, m). |
| 98 | 58 | NMR1(500 MHz); 11.80-11.14(1H, m), 9.64-8.28(3H, m), 8.23-7.97(1H, m), 7.95-7.73(1H, m), 7.73-7.31(6H, m), 7.31-7.03(1H, m), 7.03-6.61(1H, m), 6.43-5.92(1H, m), 5.37-4.58(2H, m), 4.29-3.57(2H, m), 3.25-2.83(1H, m), 2.78-2.08(2H, m). |
| 99 |  | NMR1(500 MHz); 9.72-9.54(1H, m), 8.07-6.61(10H, m), 6.30-6.16(1H, m), 5.41-5.13(1H, m), 5.07-4.69(1H, m), 4.25-4.10(1H, m), 3.93-3.73(1H, m), 3.66-3.44(3H, m), 3.10-2.73(1H, m), 2.67-2.02(2H, m). |
| 100 |  | NMR1(500 MHz); 9.85-9.75(1H, m), 7.92-7.86(1H, m), 7.69-7.66(1H, m), 7.59-7.54(1H, m), 7.48-7.44(1H, m), |

TABLE 4-continued

| EX | Prop | Data |
|---|---|---|
| | | 7.39-7.32(1H, m), 7.25-6.97(1H, m), 6.91-6.75(1H, m), 4.91-4.60(1H, m), 3.65-3.54(3H, m), 2.98-2.90(1H, m), 2.86-2.70(1H, m), 2.21-2.12(1H, m). |
| 101 | | NMR1(500 MHz); 9.81-9.71(1H, m), 7.84-7.78(2H, m), 7.76-7.71(1H, m), 7.70-7.65(2H, m), 7.24-6.82(4H, m), 6.81-6.56(1H, m), 4.91-4.60(1H, m), 3.65-3.50(3H, m), 3.02-2.90(1H, m), 2.86-2.70(1H, m), 2.22-2.10(1H, m). |
| 102 | | NMR1(500 MHz); 10.45-10.11(1H, m), 8.05-7.53(2H, m), 7.53-6.78(7H, m), 6.58-6.24(1H, m), 5.07-4.68(1H, m), 3.03-2.05(6H, m), 1.90-1.43(3H, m). |
| 103 | 102 | NMR1(500 MHz); 10.39-10.06(1H, m), 8.05-6.78(9H, m), 6.56-6.24(1H, m), 5.17-4.65(1H, m), 3.04-2.03(6H, m), 1.86-1.41(3H, m). |
| 104 | 91 | NMR1(500 MHz): 10.37-10.25(1H, m), 7.87-7.75(1H, m), 7.60-7.22(13H, m), 7.1 6-7.11(1H, m), 6.67-6.60(1H, m), 6.19(1H, s), 5.35-4.75(2H, m), 4.16-3.76(2H, m), 3.03-2.76(1H, m), 2.57-2.07(2H, m). |
| 105 | 91 | NMR1(500 MHz); 10.23-9.99(1H, m), 7.90-7.76(1H, m), 7.64-7.28(1 0H, m), 7.23-7.10(3H, m), 6.79-6.68(1H, m), 6.31-6.19(1H, m), 5.36-4.71(2H, m), 4.17-3.75(2H, m), 3.05-2.80(1H, m), 2.61-2.08(2H, m). |
| 106 | 91 | NMR1(500 MHz); 10.60-10.34(1H, m), 7.97-7.71(2H, m), 7.61-7.37(4H, m), 7.33-7.13(3H, m), 6.84-6.69(1H, m), 6.35-6.07(1H, m), 5.39-4.72(2H, m), 4.22-3.73(2H, m), 3.07-2.81(1H, m), 2.65-2.07(2H, m). |
| 107 | 91 | NMR1(500 MHz); 10.85-10.72(1H, m), 7.91-7.72(2H, m), 7.57-7.51(1H, m), 7.48-7.17(5H, m), 6.84-6.74(1H, m), 6.33-6.07(1H, m), 5.38-4.73(2H, m), 4.19-3.77(2H, m), 3.07-2.82(1H, m), 2.65-2.08(2H, m). |
| 108 | 91 | NMR1(500 MHz); 10.65-10.55(1H, m), 7.90-7.76(1H, m), 7.63-7.31(8H, m), 7.19-7.13(1H, m), 6.72-6.63(1H, m), 6.24-6.18(1H, m), 5.36-4.77(2H, m), 4.20-3.79(2H, m), 3.05-2.78(1H, m), 2.59-2.08(2H, m). |
| 109 | 91 | NMR1(500 MHz); 10.93-10.84(1H, m), 7.89-7.77(1H, m), 7.59-7.33(7H, m), 7.19-7.14(1H, m), 6.73-6.65(1H, m), 6.23-6.19(1H, m), 5.36-4.76(2H, m), 4.19-3.78(2H, m), 3.05-2.80(1H, m), 2.59-2.08(2H, m). |
| 110 | 91 | NMR1(500 MHz); 8.42-8.36(1H, m), 7.99-7.76(4H, m), 7.53-7.44(2H, m), 7.25-7.17(1H, m), 6.90-6.81(1H, m), 6.35-6.25(1H, m), 5.46-4.76(2H, m), 4.19-3.77(4H, m), 3.10-3.05(2H, m), 2.94-2.85(1H, m), 2.64-2.09(2H, m). |
| 111 | 91 | NMR1(500 MHz); 10.97-10.71(1H, m), 7.88-7.80(1H, m), 7.75-7.67(1H, m), 7.65-6.76(8H, m), 6.26-6.07(1H, m), 5.37-3.58(4H, m), 3.24-2.07(3H, m) |
| 112 | 91 | NMR1(500 MHz); 10.71-10.41(1H, m), 7.86-7.14(13H, m), 7.01-6.70(2H, m), 6.22-6.05(1H, m), 5.36-3.58(4H, m), 3.24-2.07(3H, m). |
| 113 | 91 | NMR1(500 MHz); 7.90-7.78(1H, m), 7.65-7.16(8H, m), 6.78-6.71(1H, m), 6.27-6.20(1H, m), 5.36-4.76(2H, m), 4.18-3.80(4H, m), 3.18-2.99(2H, m), 2.91-2.82(1H, m), 2.64-2.10(2H, m). |
| 114 | 102 | NMR2(400 MHz): 8.40-8.25(1H, m), 8.10-7.30(7H, m), 7.25-6.90(2H, m), 6.68-6.58(1H, m), 5.23-4.35(1H, m), 3.20-2.48(3H, m), 2.45-2.08(1H, m), 2.00-1.70(3H, m). |
| 115 | 91 | NMR1(500 MHz); 11.05-10.79(1H, m), 7.90-7.81(1H, m), 7.75-7.69(1H, m), 7.62-6.76(7H, m), 6.25-6.06(1H, m), 5.36-3.58(4H, m), 3.24-2.06(6H, m). |
| 116 | 91 | NMR1(500 MHz); 10.73-10.63(1H, m), 7.90-7.77(1H, m), 7.58-7.51(2H, m), 7.43-7.31(3H, m), 7.19-7.11(3H, m), 6.72-6.65(1H, m), 6.21(1H, s), 5.36-4.77(2H, m), 4.20-3.79(2H, m), 3.05-2.77(1H, m), 2.64-2.08(5H, m). |
| 117 | 91 | NMR1(500 MHz); 7.93-7.78(2H, m), 7.52-7.36(4H, m), 7.31-7.09(3H, m), 6.86-6.69(1H, m), 6.27-6.19(1H, m), 5.46-4.75(2H, m), 4.18-3.80(4H, m), 3.13-2.82(3H, m), 2.64-2.08(2H, m). |
| 118 | 102 | NMR2(400 MHz); 8.04-7.29(6H, m), 7.05(1H, dd, J = 8.4 Hz, 2.5 Hz), 7.00-6.93(2H, m), 6.61(1H, d, J = 8.4 Hz), 5.22-4.93(1H, m), 3.14-2.79(2H, m), 2.78-2.51(1H, m), 2.47, 2.49(total 3H, each s), 2.42-2.06(1H, m), 1.90, 1.80(total 3H, each s). |
| 119 | 102 | NMR2(400 MHz): 8.38-8.18(1H, m), 8.17-7.30(6H, m), 7.26-7.01(3H, m), 6.59(1H, d, J = 8.4 Hz), 5.25-4.70(1H, m), 3.40-2.50(3H, m), 2.45-2.05(1H, m), 1.95-1.70(3H, m). |
| 120 | 102 | NMR2(400 MHz): 8.10-7.65(2H, m), 7.58-6.95(8H, m), 6.60(1H, d, J = 8.4 Hz), 5.25-4.80(1H, m), 3.30-2.50(3H, m), 2.48-2.08(4H, m), 1.92-1.70(3H, m). |

TABLE 4-continued

| EX | Prop | Data |
|---|---|---|
| 121 | 102 | NMR2(400 MHz); 8.44-8.30(2H, m), 8.09-6.92(7H, m), 6.67-6.59(1H, m), 5.20-4.88(1H, m), 3.14-2.81(2H, m), 2.74-2.57(1H, m), 2.45-2.07(1H, m), 1.91, 1.80(total 3H, each s). |
| 122 | 102 | NMR2(400 MHz): 8.75-7.26(7H, m), 7.26-6.65(5H, m), 5.10-4.65(1H, m), 4.00-2.05(5H, m), 1.90-1.60(5H, m). |
| 123 | 102 | NMR2(400 MHz): 8.09-7.76(3H, m), 7.52-7.44(3H, m), 7.36-7.00(4H, m), 6.60(1H, d, J = 8.4 Hz), 5.20-4.94(1H, m), 3.07-2.82(2H, m), 2.76-2.59(1H, m), 2.41-2.15(1H, m), 1.90, 1.80(total 3H, each s). |
| 124 | 102 | NMR2(400 MHz): 8.37-8.31(2H, m), 8.06-7.52(2H, m), 7.38-6.94(5H, m), 6.64-6.60(1H, m), 5.18-4.92(1H, m), 3.08-2.81(2H, m), 2.74-2.55(1H, m), 2.42-2.16(1H, m), 1.91, 1.80(total 3H, each s). |
| 125 |  | NMR2(500 MHz): 8.51-8.20(2H, m), 8.20-7.75(3H, m), 7.70-7.58(4H, m), 7.31-7.22(1H, m), 7.15-7.10(1H, m), 6.70-6.62(1H, m), 5.20-4.90(1H, m), 3.90-3.61(2H, m), 3.32-2.80(5H, m), 2.65-2.30(2H, m), 2.10-2.00(1H, m) |
| 126 | 102 | NMR2(400 MHz): 8.04-7.25(10H, m), 7.07(1H, dd, J = 8.4 Hz, 2.1 Hz), 6.61(1H, d, J = 8.3 Hz), 5.18-4.92(1H, m), 3.13-2.57(3H, m), 2.40-2.13(1H, m), 1.89, 1.79(total 3H, each s). |
| 127 |  | NMR1(500 MHz); 10.76-10.66(1H, m), 7.97-7.85(2H, m), 7.79-7.69(1H, m), 7.60-7.46(3H, m), 7.43-7.32(2H, m), 7.19-7.14(1H, m), 6.72-6.65(1H, m), 6.21(1H, s), 5.36-4.76(2H, m), 4.20-3.79(2H, m), 3.05-2.79(1H, m), 2.64-2.06(2H, m). |
| 128 | 91 | NMR1(500 MHz); 10.58-10.47(1H, m), 7.92-7.71(2H, m), 7.44-7.09(6H, m), 6.84-6.74(1H, m), 6.32-6.21(1H, m), 5.38-4.72(2H, m), 4.19-3.75(2H, m), 3.06-2.82(1H, m), 2.64-2.07(5H, m). |
| 129 | 91 | NMR1(500 MHz); 11.10-10.81(1H, m), 8.00-6.76(9H, m), 6.26-6.07(1H, m), 5.36-3.57(4H, m), 3.25-2.06(3H, m). |
| 130 | 102 | NMR2(400 MHz): 8.70-8.55(1H, m), 8.35-7.90(3H, m), 7.85-7.75(1H, m), 7.70-7.40(4H, m), 7.18-7.08(1H, m), 6.70-6.60(1H, m), 5.22-2.00(5H, m), 1.80-1.75(3H, m). |
| 131 | 91 | NMR1(500 MHz); 10.83(1H, brs), 8.24-8.20(1H, m), 7.91-7.70(2H, m), 7.36-7.21(4H, m), 7.00-6.88(1H, m), 6.44-6.28(1H, m), 5.39-4.70(2H, m), 4.18-3.74(2H, m), 3.09-2.89(1H, m), 2.67-2.09(5H, m). |
| 132 |  | NMR1(500 MHz); 10.62-10.48(1H, m), 8.16-7.44(5H, m), 7.33-7.17(3H, m), 6.84-6.73(1H, m), 6.33-6.23(1H, m), 5.47-4.68(2H, m), 4.20-3.74(2H, m), 3.12-2.75(1H, m), 2.68-2.09(2H, m). |
| 133 | 91 | NMR1(500 MHz); 11.06(1H, brs), 8.23-8.18(1H, m), 7.91-7.69(2H, m), 7.61-7.57(1H, m), 7.50-7.47(1H, m), 7.42-7.37(1H, m), 7.28-7.21(1H, m), 6.98-6.88(1H, m), 6.44-6.28(1H, m), 5.39-4.70(2H, m), 4.17-3.74(2H, m), 3.09-2.88(1H, m), 2.66-2.11(2H, m). |
| 134 | 91 | NMR1(500 MHz); 10.83(1H, brs), 8.10(1H, brs), 7.90-7.79(1H, m), 7.64-7.57(1H, m), 7.50-7.19(9H, m), 6.95-6.83(1H, m), 6.42-6.26(1H, m), 5.39-4.68(2H, m), 4.15-3.72(2H, m), 3.08-2.86(1H, m), 2.64-2.07(2H, m). |
| 135 | 91 | NMR1(500 MHz); 10.73-10.63(1H, m), 7.90-7.77(3H, m), 7.71-7.64(1H, m), 7.53-7.31(4H, m), 7.19-7.14(1H, m), 6.72-6.64(1H, m), 6.23-6.18(1H, m), 5.36-4.77(2H, m), 4.20-3.78(2H, m), 3.06-2.79(1H, m), 2.64-2.08(2H, m). |
| 136 | 91 | NMR1(500 MHz); 10.56-10.46(1H, m), 7.90-7.62(5H, m), 7.32-7.14(3H, m), 6.86-6.73(1H, m), 6.34-6.23(1H, m), 5.45-4.58(2H, m), 4.18-3.77(2H, m), 3.06-2.82(1H, m), 2.64-2.07(2H, m). |
| 137 | 102 | NMR2(400 MHz); 9.12-9.04(1H, m), 8.62-8.57(1H, m), 8.04-7.30(11H, m), 7.09-6.95(1H, m), 6.60-6.43(1H, m), 6.33(1H, s), 5.15-4.86(1H, m), 3.26-2.96(2H, m), 2.73-2.07(1H, m), 1.84-1.73(3H, m). |
| 138 | 102 | NMR2(400 MHz); 8.01-7.79(2H, m), 7.63-7.35(8H, m), 7.25-6.89(4H, m), 6.79-6.42(2H, m), 5.06-4.77(1H, m), 3.15-2.58(3H, m), 2.40-2.05(1H, m), 1.88, 1.70(total 3H, etach s). |
| 139 | 102 | NMR2(400 MHz): 9.10-7.25(13H, m), 7.12-7.00(1H, m), 6.68-6.50(1H, m), 5.20-4.75(1H, m), 4.10-2.00(4H, m), 1.73-1.50(3H, m). |
| 140 | 102 | NMR2(400 MHz); 8.05-7.99(14H, m), 7.10-7.06(1H, m), 6.56-6.59(1H, m), 5.14-4.89(1H, m), 3.14-2.55(3H, m), 2.40-2.08(1H, m), 1.88, 1.73(total 3H, etach s). |
| 141 | 1 | NMR2(500 MHz); 8.30-7.02(14H, m), 6.65-6.51(1H, m), 5.28-3.90(3H, m), 3.29-2.90(2H, m), 2.61-2.02(3H, m). |

TABLE 4-continued

| EX | Prop | Data |
|---|---|---|
| 142 | 102 | NMR2(400 MHz): 8.80-8.60(1H, m), 8.35-8.25(1H, m), 8.07-7.46(2H, m), 7.45-7.35(1H, m), 7.20-6.73(4H, m), 6.70-6.55(1H, m), 5.25-4.90(1H, m), 3.76-3.62(3H, m), 3.15-2.10(4H, m), 1.92-1.77(3H, m). |
| 143 | 102 | NMR2(400 MHz); 8.82(1H, dd, J = 9.6 Hz, 3.8 Hz), 8.73, 8.60(total 1H, each s), 8.19-7.86(4H, m), 7.63-7.53(2H, m), 7.25-7.00(1H, m), 6.65(1H, dd, J = 8.4 Hz, 2.4 Hz), 5.17-4.87(1H, m), 3.51-2.58(3H, m), 2.42-2.08(1H, m), 1.82, 1.77(total 3H, etach s). |
| 144 | 91 | NMR1(500 MHz); 10.80-10.50(1H, m), 7.87-7.71(1H, m), 7.68-7.15(11H, m), 7.03-6.69(2H, m), 6.22-6.06(1H, m), 5.35-3.55(4H, m), 3.22-2.05(3H, m). |
| 145 | 102 | NMR1(400 MHz): 10.25-9.95(1H, m), 8.00-6.25(11H, m), 5.10-4.70(1H, m), 3.00-1.40(1 0H, m). |
| 146 | 91 | NMR1(400 MHz); 10.77-10.66(1H, m), 8.15-8.10(1H, brs), 7.90-7.79(1H, m), 7.66-7.19(11H, m), 6.95-6.84(1H, m), 6.42-6.27(1H, m), 5.38-4.69(2H, m), 4.15-3.73(2H, m), 3.07-2.86(1H, m), 2.64-2.08(2H, m). |
| 147 | 102 | NMR2(400 MHz); 8.04-7.44(5H, m), 7.35-7.20(1H, m), 7.07(1H, dd, J = 8.3 Hz, 2.4 Hz), 6.60(1H, d, J = 8.4 Hz), 5.18-4.89(1H, m), 3.27-2.57(3H, m), 2.40-2.12(1H, m), 1.89, 1.79(total 3H, etach s). |
| 148 | 102 | NMR2(400 MHz); 8.30-7.52(4H, m), 7.36-6.94(5H, m), 6.64-6.61(1H, m), 5.17-4.90(1H, m), 3.08-2.58(3H, m), 2.41-2.12(1H, m), 1.90, 1.79(total 3H, etach s). |
| 149 | 102 | NMR2(400 MHz); 7.34-7.17(7H, m), 7.28-7.21(3H, m), 7.07-7.04(1H, m), 6.61(1H, d, J = 8.4 Hz), 5.20-4.95(1H, m), 3.06-2.58(3H, m), 2.48, 2.46(total 3H, each s), 2.40-2.15(1H, m), 1.89, 1.80(total 3H, etach s). |
| 150 | 102 | NMR2(400 MHz); 8.37(1H, t, J = 8.1 Hz), 8.06-6.96(9H, m), 6.64-6.61(1H, m), 5.19-4.91(1H, m), 3.09-2.51(3H, m), 2.50, 2.49(total 3H, each s), 2.43-2.13(1H, m), 1.91, 1.79(total 3H, etach s). |
| 151 | 102 | NMR2(400 MHz); 8.04-7.70(3H, m), 7.55-7.29(7H, m), 7.09-7.02(1H, m), 6.60(1H, d, J = 8.3 Hz), 5.22-4.93(1H, m), 3.09-2.77(2H, m), 2.74-2.56(1H, m), 2.43-2.12(1H, m), 1.88, 1.80(total 3H, etach s). |
| 152 | 102 | NMR2(400 MHz); 8.42-8.26(2H, m), 8.08-7.27(6H, m), 7.32-6.92(2H, m), 6.66-6.59(1H, m), 5.20-4.90(1H, m), 3.09-2.75(2H, m), 2.75-2.53(1H, m), 2.45-2.10(1H, m), 1.91, 1.80(total 3H, etach s). |
| 153 | | NMR1(500 MHz); 10.64-10.33(1H, m), 7.95-7.75(1H, m), 7.74-7.22(12H, m), 7.21-7.07(1H, m), 6.69-6.56(1H, m), 6.20(1H, s), 5.47-4.69(2H, m), 4.22-3.73(2H, m), 3.08-2.72(1H, m), 2.59-2.04(2H, m). |
| 154 | 91 | NMR1(500 MHz); 10.21-10.12(1H, m), 7.89-7.77(1H, m), 7.59-7.29(9H, m), 7.24-7.12(3H, m), 6.78-6.68(1H, m), 6.31-6.22(1H, m), 5.37-4.70(2H, m), 4.16-3.75(2H, m), 3.04-2.82(1H, m), 2.60-2.05(2H, m). |
| 155 | 102 | NMR1(400 MHz): 10.95-10.60(1H, m), 8.26-7.20(13H, m), 7.05-6.93(1H, m), 6.61-6.40(1H, m), 5.00-4.64(1H, m), 3.04-2.06(3H, m), 1.93-1.60(3H, m). |
| 156 | 91 | NMR1(500 MHz); 10.72-10.64(1H, m), 7.90-7.08(10H, m), 6.86-6.68(1H, m), 6.25-6.18(1H, m), 5.47-4.58(2H, m), 4.21-3.74(2H, m), 3.06-2.70(1H, m), 2.60-2.06(2H, m). |
| 157 | | NMR1(500 MHz); 10.52(1H, s), 8.03-7.39(5H, m), 7.39-7.08(4H, m), 6.86-6.70(1H, m), 6.37-6.20(1H, m), 5.44-4.70(2H, m), 4.22-3.74(2H, m), 3.10-2.77(1H, m), 2.67-2.05(2H, m). |
| 158 | 91 | NMR1(500 MHz); 10.46-10.38(1H, m), 7.88-7.76(1H, m), 7.52-7.16(12H, m), 6.67-6.60(1H, m), 6.19(1H, s), 5.35-4.75(2H, m), 4.16-3.77(2H, m), 3.04-2.78(1H, m), 2.56-2.10(2H, m). |
| 159 | 102 | NMR2(400 MHz): 8.42-8.25(1H, m), 8.10-6.90(8H, m), 6.69-6.58(1H, m), 5.22-4.85(1H, m), 3.15-2.06(4H, m), 1.95-1.70(3H, m). |
| 160 | | NMR2(400 MHz); 8.06-7.78(2H, m), 7.62-7.30(9H, m), 7.16-6.81(5H, m), 6.60-6.44(1H, m), 5.21-4.85(1H, m), 3.12-2.45(3H, m), 2.43-2.01(1H, m), 1.92-1.72(3H, m). |
| 161 | 102 | NMR2(400 MHz): 8.20-6.98(10H, m), 6.65-6.54(1H, m), 5.20-4.78(1H, m), 3.85-2.03(4H, m), 1.95-1.74(3H, m). |
| 162 | 102 | NMR2(400 MHz): 8.35-6.90(10H, m), 6.67-6.55(1H, m), 5.23-4.85(1H, m), 3.15-2.07(4H, m), 1.95-1.73(3H, m). |
| 163 | 102 | NMR2(400 MHz): 8.40-8.20(1H, m), 8.11-6.90(10H, m), 6.70-6.55(1H, m), 5.23-4.85(1H, m), 3.15-2.08(4H, m), 1.95-1.73(3H, m). |

TABLE 4-continued

| EX | Prop | Data |
|---|---|---|
| 164 | 91 | NMR1(500 MHz); 10.82-10.53(1H, m), 7.87-7.15(11H, m), 7.05-6.72(2H, m), 6.23-6.07(1H, m), 5.35-3.55(4H, m), 3.23-2.04(3H, m). |
| 165 | | NMR1(500 MHz); 11.25-10.84(1H, m), 8.27-8.16(1H, m), 7.92-7.65(3H, m), 7.63-7.29(5H, m), 7.27-7.11(3H, m), 6.87-6.73(1H, m), 6.33-6.19(1H, m), 5.39-4.70(2H, m), 4.19-3.70(2H, m), 3.10-2.77(1H, m), 2.66-2.06(2H, m). |
| 166 | 91 | NMR1(500 MHz); 10.84-10.67(1H, m), 8.21-8.15(1H, m), 7.89-7.79(1H, m), 7.72-7.62(2H, m), 7.50-7.45(1H, m), 7.39-7.25(2H, m), 7.21-7.08(5H, m), 6.82-6.73(1H, m), 6.29-6.22(1H, m), 5.35-4.71(2H, m), 4.13-3.73(2H, m), 3.05-2.81(1H, m), 2.59-2.04(5H, m). |
| 167 | 160 | NMR2(400 MHz); 8.24-7.95, 7.85-7.22(total 14H, each m), 7.15-7.02(1H, m), 6.63-6.51(1H, m), 5.22-4.81(1H, m), 3.14-2.50(3H, m), 2.42-2.03(1H, m), 1.85, 1.73(total 3H, etach s). |
| 168 | | NMR1(500 MHz); 10.38-10.09(1H, m), 7.90-7.73(1H, m), 7.63-7.30(6H, m), 7.28-7.08(5H, m), 6.81-6.65(1H, m), 6.34-6.19(1H, m), 5.39-4.66(2H, m), 4.19-3.71(2H, m), 3.07-2.74(1H, m), 2.67-2.06(2H, m). |
| 169 | | NMR1(500 MHz); 10.66-10.32(1H, m), 7.89-7.74(1H, m), 7.73-7.43(3H, m), 7.40-7.07(9H, m), 6.69-6.58(1H, m), 6.19(1H, s), 5.48-4.73(2H, m), 4.21-3.72(2H, m), 3.23-2.74(1H, m), 2.58-2.04(2H, m) |
| 170 | 102 | NMR2(400 MHz): 8.55-8.25(1H, m), 8.08-7.15(7H, m), 7.11-6.98(1H, m), 6.59(1H, d, J = 8.4 Hz), 5.23-4.80(1H, m), 3.55-2.05(4H, m), 1.94-1.73(3H, m). |
| 171 | 102 | NMR2(400 MHz): 8.60-6.90(9H, m), 6.61(1H, d, J = 8.4 Hz), 5.22-4.83(1H, m), 3.18-2.06(4H, m), 1.95-1.73(3H, m). |
| 172 | 102 | NMR2(400 MHz): 8.50-7.93(4H, m), 7.63-7.53(1H, m), 7.52-7.36(2H, m), 7.35-7.28(1H, m), 7.28-7.20(1H, m), 7.17-7.06(1H, m), 6.64(1H, d, J = 8.4 Hz), 5.23-4.87(1H, m), 3.28-2.92(2H, m), 2.84(2H, q, J = 7.5 Hz), 2.77-2.03(3H, m), 1.80-1.60(3H, m), 1.30-1.20(3H, m). |
| 173 | 102 | NMR2(400 MHz); 8.17-6.60(1 0H, m), 5.21-4.55(1H, m), 4.27-3.86(4H, m), 3.32-2.18(6H, m). |
| 174 | 91 | NMR1(500 MHz); 10.70-10.50(1H, m), 8.23-8.16(1H, m), 7.91-7.60(3H, m), 7.47-7.13(6H, m), 7.01-6.85(2H, m), 6.82-6.71(1H, m), 6.33-6.22(1H, m), 5.46-4.58(2H, m), 4.16-3.73(2H, m), 3.61-3.41(3H, m), 3.07-2.82(1H, m), 2.61-2.07(2H, m). |
| 175 | 91 | NMR1(500 MHz); 11.17-11.03(1H, m), 8.31-8.25(1H, m), 8.00-7.76(3H, m), 7.71-7.61(2H, m), 7.52-7.44(2H, m), 7.23-7.17(1H, m), 6.87-6.78(1H, m), 6.33-6.24(1H, m), 5.37-4.74(2H, m), 4.17-3.77(2H, m), 3.08-2.85(1H, m), 2.64-2.08(2H, m). |
| 176 | 37 | NMR2(400 MHz); 7.98-6.46(15H, m), 5.19-4.51(1H, m), 4.22(1H, d, J = 10.4 Hz), 4.04(1H, d, J = 10.4 Hz), 3.60, 3.58(total 3H, each s), 3.31-3.23(1H, m), 3.08-2.92(1H, m), 2.59-2.04(3H, m). |
| 177 | 37 | NMR2(400 MHz); 8.29-6.50(14H, m), 5.22-4.56(1H, m), 4.23-3.88(2H, m), 3.63, 3.61(total 3H, each s), 3.25-3.16(1H, m), 3.13-2.94(1H, m), 2.59-2.05(3H, m). |
| 178 | 102 | NMR2(400 MHz): 8.08-6.88(1 0H, m), 6.61(1H, d, J = 8.3 Hz), 5.25-4.87(1H, m), 3.15-2.10(10H, m), 1.93-1.75(3H, m). |
| 179 | 102 | NMR2(400 MHz): 8.10-7.23(6H, m), 7.10-6.86(3H, m), 6.61(1H, d, J = 8.3 Hz), 5.24-4.86(1H, m), 3.13-2.07(10H, m), 1.93-1.73(3H, m). |
| 180 | 102 | NMR2(400 MHz): 8.08-6.90(11H, m), 6.62(1H, d, J = 8.3 Hz), 5.23-4.83(1H, m), 3.15-2.50(3H, m), 2.45-2.25(1H, m), 2.17(3H, s), 1.89(1H, brs), 1.84-1.57(4H, m). |
| 181 | 102 | NMR1(400 MHz); 10.00-9.98(1H, m), 8.03-6.90(9H, m), 6.78(1H, t, J = 8.8 Hz), 6.45-6.25(1H, m), 5.06-4.70(1H, m), 3.00-2.73(4H, m), 2.40-2.24(1H, m), 2.23-2.05(3H, m), 1.96(1H, s), 1.83-1.60(3H, m). |
| 182 | 102 | NMR2(400 MHz); 8.06-7.18(7H, m), 7.12-6.97(2H, m), 6.59(1H, d, J = 8.4 Hz), 5.21-4.90(1H, m), 3.08-2.79(2H, m), 2.75-2.56(1H, m), 2.45-2.08(4H, m), 1.90, 1.80(total 3H, each s). |
| 183 | 102 | NMR2(400 MHz); 8.51-8.22(1H, m), 8.09-7.50(4H, m), 7.21-7.08(2H, m), 7.18-7.08(1H, m), 7.03-6.63(1H, m), 5.21-4.90(1H, m), 4.32-4.20(2H, m), 3.13-2.58(5H, m), 2.44-2.12(1H, m), 1.89, 1.79(total 3H, etach s). |
| 184 | 37 | NMR1(500 MHz); 7.88(1H, d, J = 2.2 Hz), 7.80-7.75(1H, m), 7.48-7.38(4H, m), 7.30-7.15(3H, m), 6.78-6.71(1H, m), 6.27-6.21(1H, m), 5.36-4.76(2H, m), 4.18-3.80(4H, m), 3.11-2.82(3H, m), 2.64-2.08(2H, m). |

TABLE 4-continued

| EX | Prop | Data |
|----|------|------|
| 185 | 99 | NMR1(500 MHz); 7.93-7.78(2H, m), 7.55-7.25(7H, m), 7.19-7.14(1H, m), 6.78-6.71(1H, m), 6.26-6.21(1H, m), 5.36-4.77(2H, m), 4.18-3.81(4H, m), 3.13-2.81(3H, m), 2.64-2.08(2H, m). |
| 186 | 99 | NMR1(500 MHz); 7.95-7.79(2H, m), 7.69-7.60(2H, m), 7.51-7.38(3H, m), 7.19-7.14(1H, m), 6.78-6.70(1H, m), 6.26-6.20(1H, m), 5.36-4.77(2H, m), 4.18-3.81(4H, m), 3.06-2.81(1H, m), 2.64-1.92(8H, m). |
| 187 |  | NMR1(500 MHz); 7.91-7.55(2H, m), 7.53-7.36(4H, m), 7.35-7.24(2H, m), 7.22-7.11(1H, m), 6.81-6.66(1H, m), 6.30-6.05(1H, m), 5.39-4.74(2H, m), 4.22-3.76(4H, m), 3.20-2.77(3H, m), 2.66-2.06(2H, m). |
| 188 | 102 | NMR2(400 MHz); 8.09-7.40(7H, m), 7.22-6.55(4H, m), 5.25-4.90(1H, m), 3.80-3.50(3H, m), 3.20-2.50(3H, m), 2.50-2.07(1H, m), 1.92-1.72(3H, m). |
| 189 | 102 | NMR2(400 MHz); 8.32(1H, brd, J = 8.3 Hz), 8.20-7.48(2H, m), 7.25-6.54(7H, m), 5.28-4.33(1H, m), 3.80-3.60(3H, m), 3.18-2.07(7H, m), 1.93-1.73(3H, m). |
| 190 | 102 | NMR2(400 MHz); 8.40-7.40(4H, m), 7.43-6.56(6H, m), 5.30-4.90(1H, m), 3.83-3.58(3H, m), 3.20-2.55(3H, m), 2.54-2.46(3H, m), 2.45-2.08(1H, m), 1.93-1.74(3H, m). |
| 191 | 102 | NMR2(400 MHz); 8.34-7.45(4H, m), 7.40-6.55(6H, m), 5.27-4.86(1H, m), 3.80-3.50(3H, m), 3.20-2.08(4H, m), 1.93-1.70(3H, m). |
| 192 | 102 | NMR2(400 MHz); 8.78-8.50(1H, m), 8.43-8.24(1H, m), 8.10-7.46(2H, m), 7.24-6.55(6H, m), 5.26-4.90(1H, m), 3.83-3.55(3H, m), 3.15-2.53(3H, m), 2.47-2.10(1H, m), 1.95-1.70(3H, m). |
| 193 | 102 | NMR2(400 MHz); 8.13-7.30(5H, m), 7.25-6.85(4H, m), 6.60(1H, brd, J = 8.4 Hz), 5.25-4.86(1H, m), 3.20-2.50(3H, m), 2.48-2.28(1H, m), 2.27-2.17(3H, m), 1.93-1.72(3H, m). |
| 194 | 102 | NMR2(400 MHz); 8.35-8.10(1H, m), 8.10-7.45(2H, m), 7.42-6.90(5H, m), 6.61(1H, d, J = 8.4 Hz), 5.22-4.82(1H, m), 3.20-2.53(3H, m), 2.50-2.41(3H, m), 2.40-2.07(1H, m), 1.96-1.70(3H, m). |
| 195 | 160 | NMR2(400 MHz); 8.29-7.76(4H, m), 7.54-7.44(2H, m), 7.44-7.29(4H, m), 7.32-7.13(1H, m), 7.13-6.97(2H, m), 6.63-6.55(1H, m), 5.17-4.88(1H, m), 3.10-2.54(3H, m), 2.44-2.08(1H, m), 1.84, 1.74(total 3H, etach s). |
| 196 | 160 | NMR2(400 MHz); 8.22-7.75(3H, m), 7.69(1H, s), 7.55-7.30(8H, m), 7.31-7.20(1H, m), 7.12-7.03(1H, m), 7.02-6.53(1H, m), 5.16-4.87(1H, m), 3.08-2.53(3H, m), 2.39-2.04(1H, m), 1.82, 1.73(total 3H, etach s). |
| 197 | 102 | NMR2(400 MHz); 8.15-6.93(11H, m), 6.59(1H, d, J = 8.4 Hz), 5.22-4.78(1H, m), 3.30-2.50(3H, m), 2.45-2.05(1H, m), 1.94-1.70(3H, m). |
| 198 | 91 | NMR1(400 MHz); 10.28-10.18(1H, m), 7.89-7.76(1H, m), 7.61-7.36(5H, m), 7.27-7.10(6H, m), 6.80-6.68(1H, m), 6.33-6.23(1H, m), 5.38-4.69(2H, m), 4.17-3.74(2H, m), 3.06-2.86(1H, m), 2.62-2.05(2H, m). |
| 199 | 91 | NMR1(400 MHz); 10.50-10.40(1H, m), 7.88-7.76(1H, m), 7.57-7.24(8H, m), 7.21-7.09(4H, m), 6.67-6.60(1H, m), 6.21(1H, s), 5.46-4.58(2H, m), 4.17-3.76(2H, m), 3.05-2.77(1H, m), 2.58-2.05(2H, m). |
| 200 | 91 | NMR1(400 MHz); 11.05-10.88(1H, m), 8.24-8.16(1H, m), 7.91-7.67(3H, m), 7.54-7.32(4H, m), 7.22-7.10(4H, m), 6.83-6.74(1H, m), 6.30-6.21(1H, m), 5.37-4.71(2H, m), 4.16-3.73(2H, m), 3.08-2.80(1H, m), 2.68-2.05(2H, m). |
| 201 | 99 | NMR1(400 MHz); 7.88(1H, d, J = 2.5 Hz), 7.85(1H, d, J = 2.1 Hz), 7.60(1H, dd, J = 8.1 Hz, 2.2 Hz), 7.48-7.38(3H, m), 7.31-7.25(2H, m), 7.20-7.14(1H, m), 6.77-6.70(1H, m), 6.25(1H, brs), 5.38-4.76(2H, m), 4.19-3.80(4H, m), 3.11-2.81(3H, m), 2.68-2.08(2H, m). |
| 202 | 99 | NMR1(400 MHz); 7.91(1H, d, J = 7.7 Hz), 7.88(1H, d, J = 2.5 Hz), 7.69(1H, d, J = 7.2 Hz), 7.48-7.37(3H, m), 7.32-7.25(2H, m), 7.19-7.14(1H, m), 6.78-6.70(1H, m), 6.27-6.22(1H, m), 5.37-4.76(2H, m), 4.19-3.80(4H, m), 3.13-3.11(2H, m), 3.08-2.81(1H, m), 2.68-2.07(2H, m). |
| 203 | 91 | NMR1(400 MHz): 11.04-10.75(1H, m), 7.89-7.43(6H, m), 7.39-6.75(4H, m), 6.28-6.08(1H, m), 5.37-3.57(4H, m), 3.27-2.05(3H, m). |
| 204 | 99 | NMR1(400 MHz); 10.99-10.84(1H, m), 8.26-8.20(1H, m), 7.91(1H, d, J = 8.7 Hz), 7.90(1H, d, J = 2.5 Hz), 7.86-7.74(1H, m), 7.40-7.32(2H, m), 7.25-7.17(2H, m), 6.99(1H, d, J = 7.7 Hz), 6.88-6.78(1H, m), 6.34-6.23(1H, m), 5.38-4.74(2H, m), 4.18-3.76(2H, m), 3.08-2.83(1H, m), 2.68-2.09(3H, m), 0.94-0.81(2H, m), 0.72-0.61(2H, m). |

TABLE 4-continued

| EX | Prop | Data |
|---|---|---|
| 205 | 91 | NMR1(400 MHz); 10.25-10.14(1H, m), 7.89(1H, d, J = 2.4 Hz), 7.82-7.65(1H, m), 7.47-7.16(6H, m), 6.99(1H, d, J = 7.7 Hz), 6.84-6.73(1H, m), 6.34-6.23(1H, m), 5.38-4.73(2H, m), 4.21-3.77(2H, m), 3.07-2.80(1H, m), 2.64-2.08(3H, m), 0.97-0.84(2H, m), 0.75-0.60(2H, m). |
| 206 | 91 | NMR1(400 MHz)(; 10.50-10.41(1H, m), 7.88(1H, d, J = 2.5 Hz), 7.58(2H, d, J = 8.5 Hz), 7.41-7.30(4H, m), 7.26-7.13(2H, m), 6.99(1H, d, J = 8.0 Hz), 6.71-6.64(1H, m), 6.21(1H, brs), 5.37-4.77(2H, m), 4.20-3.79(2H, m), 3.06-2.78(1H, m), 2.68-2.07(3H, m), 0.95-0.82(2H, m), 0.74-0.60(2H, m). |
| 207 | 99 | NMR1(400 MHz); 7.88(1H, brs), 7.78(1H, d, J = 7.4 Hz), 7.49-7.36(3H, m), 7.33-7.22(3H, m), 7.20-7.14(1H, m), 6.79-6.70(1H, m), 6.27-6.18(1H, m), 5.36-4.76(2H, m), 4.20-3.79(4H, m), 3.10-2.81(3H, m), 2.68-2.07(5H, m). |
| 208 | 99 | NMR1(400 MHz); 7.88(1H, d, J = 2.5 Hz), 7.81-7.71(1H, m), 7.47-7.22(6H, m), 7.19-7.14(1H, m), 6.78-6.71(1H, m), 6.26-6.21(1H, m), 5.36-4.76(2H, m), 4.19-3.81(4H, m), 3.07-2.81(3H, m), 2.63-2.09(5H, m). |
| 209 | 91 | NMR1(400 MHz); 8.43-8.35(1H, m), 7.93-7.76(4H, m), 7.62(1H, dd, J = 8.1 Hz, 2.2 Hz), 7.44(1H, d, J = 8.1 Hz), 7.25-7.18(1H, m), 6.91-6.81(1H, m), 6.37-6.30(1H, m), 5.39-4.74(2H, m), 4.20-3.77(4H, m), 3.10-2.84(3H, m), 2.68-2.07(2H, m). |
| 210 | 91 | NMR1(400 MHz); 7.95(1H, dd, J = 8.6 Hz, 6.0 Hz), 7.90-7.79(1H, m), 7.38-7.17(6H, m), 6.89-6.78(1H, m), 6.36-6.24(1H, m), 5.37-4.71(2H, m), 4.19-3.78(4H, m), 3.15-2.83(3H, m), 2.68-2.07(2H, m). |
| 211 | 91 | NMR1(400 MHz); 8.08-7.86(1H, m), 7.80-7.26(6H, m), 7.20-7.12(1H, m), 6.83-6.70(1H, m), 6.29-6.23(1H, m), 5.37-4.72(2H, m), 4.22-3.61(4H, m), 3.12-2.84(3H, m), 2.67-2.07(2H, m). |
| 212 | 91 | NMR1(400 MHz): 8.05-7.74(2H, m), 7.70-6.79(7H, m), 6.30-6.09(1H, m), 5.37-3.58(6H, m), 3.28-2.89(3H, m), 2.70-2.05(2H, m). |
| 213 | 91 | NMR1(400 MHz); 8.42-8.34(1H, m), 8.06-7.74(4H, m), 7.30-7.18(3H, m), 6.90-6.80(1H, m), 6.36-6.26(1H, m), 5.40-4.74(2H, m), 4.22-3.75(4H, m), 3.12-2.83(3H, m), 2.69-2.07(2H, m). |
| 214 | 91 | NMR1(400 MHz); 7.98-7.82(2H, m), 7.70-6.79(7H, m), 6.30-6.09(1H, m), 5.37-3.58(6H, m), 3.30-2.91(3H, m), 2.70-2.05(2H, m). |
| 215 | 91 | NMR1(400 MHz); 7.91-7.78(2H, m), 7.53-7.43(2H, m), 7.38-7.17(4H, m), 6.89-6.77(1H, m), 6.37-6.25(1H, m), 5.38-4.71(2H, m), 4.17-3.77(4H, m), 3.15-2.82(3H, m), 2.68-2.07(2H, m). |
| 216 | 91 | NMR1(400 MHz); 7.93-7.80(2H, m), 7.54(1H, td, J = 7.5 Hz, 1.2 Hz), 7.43-7.18(6H, m), 6.89-6.79(1H, m), 6.36-6.24(1H, m), 5.37-4.73(2H, m), 4.19-3.78(4H, m), 3.15-2.84(3H, m), 2.69-2.08(2H, m). |
| 217 | 91 | NMR1(400 MHz); 7.91-7.79(1H, m), 7.60(1H, dd, J = 9.2 Hz, 2.5 Hz), 7.49-7.18(6H, m), 6.89-6.78(1H, m), 6.36-6.24(1H, m), 5.38-4.72(2H, m), 4.19-3.77(4H, m), 3.14-2.84(3H, m), 2.65-2.07(2H, m). |
| 218 | 99 | NMR1(400 MHz); 10.22-10.13(1H, m), 8.47(1H, d, J = 4.0 Hz), 7.90-7.62(5H, m), 7.49-7.40(2H, m), 7.32-7.14(4H, m), 6.79-6.69(1H, m), 6.33-6.24(1H, m), 5.37-4.72(2H, m), 4.18-3.75(2H, m), 3.07-2.81(1H, m), 2.67-2.07(2H, m). |
| 219 |  | NMR1(400 MHz); 10.55(1H, s), 7.94-7.90(2H, m), 7.81-7.77(2H, m), 7.53(1H, d, J = 8.6 Hz), 7.20(1H, d, J = 11.4 Hz), 7.07-7.00(2H, m), 4.80-3.60 (2H, br), 2.78-2.65 (2H, br). |
| 220 |  | NMR1(500 MHz); 11.25-11.16(1H, m), 8.31-8.28(1H, m), 7.99-7.78(3H, m), 7.59-7.52(2H, m), 7.39-7.35(1H, m), 7.24-7.19(1H, m), 6.87-6.80(1H, m), 5.00-4.75(1H, m), 4.16-3.78(2H, m), 3.07-2.86(1H, m), 2.64-2.13(5H, m). |
| 221 | 220 | NMR1(500 MHz): 11.23-11.13(1H, m), 8.31-8.28(1H, m), 7.99-7.73(4H, m), 7.61-7.59(1H, m), 7.53-7.51(1H, m), 7.23-7.19(1H, m), 6.87-6.80(1H, m), 5.00-4.75(1H, m), 4.15-3.98(1H, m), 3.79(1H, br d, J = 10.9 Hz), 3.07-2.86(1H, m), 2.64-2.10(5H, m). |
| 222 | 220 | NMR1(500 MHz); 11.25-11.16(1H, m), 8.31-8.28(1H, m), 7.99-7.77(3H, m), 7.59-7.52(2H, m), 7.39-7.35(1H, m), 7.24-7.19(1H, m), 6.87-6.80(1H, m), 5.00-4.75(1H, m), 4.16-3.78(2H, m), 3.07-2.86(1H, m), 2.64-2.13(5H, m). |

TABLE 4-continued

| EX | Prop | Data |
|---|---|---|
| 223 |  | NMR1(500 MHz); 11.28-11.18(1H, m), 8.31-8.28(1H, m), 7.98-7.77(5H, m), 7.23-7.19(1H, m), 6.87-6.80(1H, m), 4.99-4.75(1H, m), 4.15-3.78(2H, m), 3.07-2.86(1H, m), 2.64-2.12(2H, m). |
| 224 | 220 | NMR1(500 MHz); 11.28-11.18(1H, m), 8.32-8.28(1H, m), 7.98-7.77(5H, m), 7.23-7.19(1H, m), 6.87-6.80(1H, m), 4.99-4.75(1H, m), 4.15-3.78(2H, m), 3.07-2.86(1H, m), 2.64-2.12(5H, m). |
| 225 | 220 | NMR1(500 MHz); 10.85-10.74(1H, m), 8.19-8.16(1H, m), 7.88-7.67(3H, m), 7.57-7.54(2H, m), 7.47-7.27(7H, m), 7.22-7.17(1H, m), 6.82-6.76(1H, m), 4.98-4.74(1H, m), 4.12-3.76(2H, m), 3.05-2.84(1H, m), 2.64-2.11(5H, m). |
| 226 | 223 | NMR1(500 MHz); 11.41-11.31(1H, m), 8.84-8.83(1H, m), 8.32-8.19(2H, m), 7.98-7.79(4H, m), 7.24-7.20(1H, m), 6.88-6.81(1H, m), 5.00-4.75(1H, m), 4.15-3.78(2H, m), 3.07-2.13(3H, m). |
| 227 | 220 | NMR1(500 MHz); 11.41-11.31(1H, m), 8.84-8.83(1H, m), 8.32-8.19(2H, m), 7.98-7.79(4H, m), 7.24-7.20(1H, m), 6.88-6.81(1H, m), 5.00-4.75(1H, m), 4.16-3.78(2H, m), 3.07-2.13(6H, m). |
| 228 | 223 | NMR1(500 MHz); 11.26-11.17(1H, m), 8.30-8.26(1H, m), 7.98-7.66(7H, m), 7.24-7.20(1H, m), 6.88-6.81(1H, m), 5.00-4.75(1H, m), 4.15-3.78(2H, m), 3.07-2.86(1H, m), 2.62-2.13(2H, m). |
| 229 | 220 | NMR1(500 MHz); 11.27-11.17(1H, m), 8.30-8.27(1H, m), 7.98-7.66(7H, m), 7.24-7.19(1H, m), 6.88-6.81(1H, m), 5.00-4.76(1H, m), 4.16-3.78(2H, m), 3.07-2.86(1H, m), 2.62-2.10(5H, m). |
| 230 | 223 | NMR1(500 MHz); 11.25-11.16(1H, m), 8.31-8.28(1H, m), 7.99-7.77(3H, m), 7.63-7.52(2H, m), 7.39-7.35(1H, m), 7.24-7.13(1H, m), 6.93-6.80(1H, m), 5.00-4.75(1H, m), 4.18-3.77(2H, m), 3.22-2.12(3H, m). |
| 231 | 220 | NMR1(500 MHz); 11.25-11.16(1H, m), 8.31-8.28(1H, m), 7.99-7.77(3H, m), 7.64-7.52(2H, m), 7.39-7.35(1H, m), 7.24-7.15(1H, m), 6.93-6.80(1H, m), 5.00-4.75(1H, m), 4.16-3.78(2H, m), 3.23-2.10(6H, m). |
| 232 | 220 | NMR1(500 MHz); 11.01-10.89(1H, m), 8.24-8.20(1H, m), 7.88-7.68(3H, m), 7.55-7.33(5H, m), 7.23-7.15(3H, m), 6.84-6.77(1H, m), 4.99-4.74(1H, m), 4.13-3.76(2H, m), 3.05-2.85(1H, m), 2.60-2.11(5H, m). |
| 233 | 220 | NMR1(500 MHz); 10.97-10.87(1H, m), 8.21-8.17 (1H, m), 7.88-7.68(3H, m), 7.48-7.17(9H, m), 6.82-6.75(1H, m), 4.98-4.73(1H, m), 4.12-3.76(2H, m), 3.05-2.84(1H, m), 2.59-2.11(5H, m). |
| 234 | 220 | NMR1(500 MHz); 11.14-11.03(1H, m), 8.77-8.76(1H, m), 8.22-7.17(12H, m), 6.83-6.76(1H, m), 4.98-4.74(1H, m), 4.13-3.76(2H, m), 3.06-2.85(1H, m), 2.60-2.12(5H, m). |

Test Example

Test Example 1: Binding Affinities for Vasopressin $V_{1a}$ and $V_2$ Receptors

Various compounds were studied in binding affinities for vasopressin receptors with an indicator of binding inhibition of rat vasopressin $V_{1a}$ receptor and vasopressin $V_2$ receptor of $^3$H-arginine vasopressin (AVP) (NET800, available from PerkinElmer Inc., Life Sciences). (1) Binding inhibition test for rat Via receptor ($rV_{1a}R$)

50 μg of $V_{1a}$ receptor fractions derived from rat hepatic membrane were diluted with a reaction solution (100 mM Tris-HCl (pH 8.0), 0.1% BSA, 5 mM MgCl$_2$, 1 mM EDTA) and added to each well of a 96-well plate. A compound was added to each well in various concentrations (0.3 nM to 100 nM), and $^3$H-AVP was added thereto in the range of 1 nM to 3 nM. Reactions were carried out at 4° C. for 2 hours on the plate. $V_{1a}$ receptor fractions were collected with a 96-well glass filter (Unifilter GF/B) after the reactions and washed with a washing solution (10 mM Tris-HCl (pH 8.0), 5 mM MgCl2, 1 mM EDTA) three times, and then the radioactivity of $^3$H-AVP was measured with a scintillation counter.

(2) Binding inhibition test for rat V2 receptor ($rV_2R$)

Rat $V_2$ receptor-expressed CHO cells (rV2R-CHO) were incubated on 10% FBS-containing DMEM/F12 in a 24-well plate, and each cell was washed with D-PBS twice. A reaction solution (D-PBS containing 0.1% BSA and 0.05% sodium azide) comprising a compound in various concentrations (0.3 nM to 100 nM) was added to each well, and a certain amount of $^3$H-AVP was added thereto (100-fold dilution). Reactions were carried out at 4° C. for 2 hours on the plate. Then, each well was washed with D-PBS twice and 0.1N NaOH was added to each well. The cells were collected, and the radioactivity of $^3$H-AVP was measured with a scintillation counter.

(3) Calculation of $IC_{50}$ $^3$H-AVP binding rate in the presence of a compound was calculated by the following equation. Binding rate (%)=(B-NSB)/(TB-NSB)×100

(B: Binding amount of $^3$H-AVP in the presence of each compound, NSB: Binding amount of $^3$H-AVP in the presence of 1 μM of unlabeled AVP, TB: Binding amount of $^3$H-AVP in the absence of 1 μM of unlabeled AVP)

The concentration ($IC_{50}$) where each compound inhibits 50% of $^3$H-AVP binding amounts was calculated using $^3$H-AVP binding rates and compound concentrations.

Results are shown below. equation.

TABLE 5

Table 1. Binding affinities for vasopressin $V_{1a}$ and $V_2$ receptors ($IC_{50}$: nM)

| Compound (EX) | $rV_{1a}$ | $rV_2$ |
|---|---|---|
| 2 | 3.4 | 2.1 |
| 3 | 9.5 | 2.1 |
| 15 | 2.9 | 1.0 |
| 23 | 2.6 | 1.0 |
| 24 | 2.7 | 1.5 |
| 51 | 16.1 | 1.7 |
| 52 | 8.8 | 3.0 |
| 58 | 9.3 | 1.3 |
| 63 | 1.4 | 1.1 |
| 66 | 21.1 | 3.5 |
| 96 | 2.0 | 5.0 |
| 97 | 5.4 | 1.4 |
| 127 | 7.2 | 1.8 |
| 132 | 5.2 | 2.3 |
| 153 | 3.6 | 4.5 |
| 157 | 12.0 | 3.2 |
| 165 | 1.7 | 3.4 |
| 168 | 2.2 | 4.7 |
| 169 | 1.6 | 3.3 |
| 187 | 2.6 | 0.4 |

Test Example 2: Metabolic Stability Test

Reaction System and Incubation

According to methods of Obach and Jones, et al. (methods described in R. S. Obach, Drug Metab. Dispos. 1999 (27): 1350-1359 and H. Jones and J. B. Houston, Drug Metab. Dispos. 2004 (32): 973-982), the reaction system shown below was prepared and metabolic stabilities of test compounds (the present compounds and, tolvaptan) were evaluated using the reaction system shown below. Human liver microsomes purchased from Corning Inc. were used. Test compounds were dissolved in DMSO at the concentration of 10 mmol/L and then diluted with acetonitrile to prepare a 100 µmol/L solution for use in the test. The 100 µmol/L solutions were used in the experiment.

<Reaction system>
Test compound 1 µmol/L
Human liver microsome 1 mg/mL
Co-factor (NADPH and NADH) 1 mmol/L each
Magnesium chloride 5 mmol/L
100 mmol/L Potassium phosphate buffer (pH 7.4)
Number of samples: n=4

<Reaction condition>
The reaction mixture without co-factors was pre-incubated at 37° C. for 5 minutes, and then the reaction was initiated by the addition of the co-factors. The mixture was incubated for 0, 5, 10, 20, 30, and 60 minutes after the addition of the co-factors. An aliquot of the reaction mixture was removed and added to a methanol solution containing an internal standard (IS) and mixed to terminate the reaction at each predetermined time.

Analytic Method

After the reaction was terminated, the mixture was separated by centrifugation and the supernatant was injected into a liquid chromatograph-tandem mass spectrometer (LC-MS/MS) to measure unchanged substances remained in the reaction system. The mass spectrometer was operated in a positive ion mode of the electrospray ionization (ESI) method. Unchanged substances and the IS were detected by multiple reaction monitoring (MRM) transitions using selected precursor and product ions set.

Data Analysis

The remaining ratios of test compounds were calculated by the following equation. Remaining ratio=(Peak area ratio of a test compound to IS at t minutes after incubation)÷(Peak area ratio of a test compound to IS at 0 minute)

The slope of X-axis (the incubation time) and Y-axis (logarithm of the remaining ratio) was calculated by a nonlinear least square method. Hepatic intrinsic clearance ($CL_{int}$) was calculated by the following equation.

$$CL_{int}(\mu L/min/mg) = -(\text{Slope}(min^{-1})) \div 1(mg/mL) \times 1000$$

Results are shown below.

TABLE 6

Table 2. Hepatic intrinsic clearance of test compounds measured in human liver microsomal metabolic stability test

| Test compounds | $CL_{int}$ (µL/min/mg) mean ± SD |
|---|---|
| EX2 | <4 |
| EX3 | <4 |
| EX15 | <4 |
| EX23 | 1.11 ± 2.21 |
| EX24 | <4 |
| EX51 | <4 |
| EX52 | <4 |
| EX58 | 1.81 ± 2.10 |
| EX63 | 3.10 ± 3.58 |
| EX66 | <4 |
| EX96 | 0.953 ± 1.905 |
| EX97 | 6.98 ± 4.77 |
| EX127 | <4 |
| EX132 | <4 |
| EX153 | 1.91 ± 2.22 |
| EX157 | <4 |
| EX165 | 3.61 ± 2.43 |
| EX168 | 7.48 ± 1.50 |
| EX169 | 5.09 ± 0.32 |
| EX187 | <4 |
| Tolvaptan | 105 ± 11 | n = 4
SD: Standard deviation

Test Example 3: Pharmacokinetics Study in Mice

Test Method

A pharmacokinetics (PK) study was performed using male ICR mice to compare the oral absorption properties of the present compounds with tolvaptan. A test compound was suspended in a 1% hydroxypropyl methylcellulose (HPMC) solution to be adjusted to the cocentration of 4.5 mg/mL. The present compounds were used as the forms obtained in the above examples (including the amorphous form) for a test compound, or used after spray drying, if needed.

Male ICR mice (7-week old) were freely fed food and water and weighed on an electronic scale. Then, a test compound was orally administered at the dose of 30 mg/kg (15 mL/kg). After the oral administration, blood was collected from the abdominal vena cava under isoflurane anesthesia using a 1 mL heparinized syringe with a 26 G injection needle. Blood was separated by centrifugation at 4° C., 3000 rpm for 10 minutes to give plasma in a supernatant. The plasma concentration of a test compound was measured by LC-MS/MS.

Test Results

The following PK parameters were calculated using the mean plasma concentrations of unchanged substances obtained from two animals at each time point.

$C_{max}$: Maximum plasma concentration (g/mL)
$t_{max}$: Time-to-maximum plasma concentration (h)
$AUC_{inf}$: Area under the plasma concentration-time curve from administration to infinite time (g h/mL)

The results showed that the $C_{max}$ and $AUC_{inf}$ values of the present compounds were higher than those of tolvaptan. Results are shown below.

TABLE 7

Table 3. Pharmacokinetics parameters in single-dose oral administration of 30 mg/kg of test compounds in male ICR mice

| Test compounds | Cmax (µg/mL) | $t_{max}$ (h) | $AUC_{inf}$ (µg h/mL) |
| --- | --- | --- | --- |
| EX2 | 9.232 | 1 | 95.68 |
| EX3 | 4.819 | 1 | 38.91 |
| EX15 | 6.182 | 1 | 63.07 |
| EX23 | 5.420 | 4 | 71.32 |
| EX24 | 4.081 | 4 | 44.05 |
| EX51 | 5.068 | 1 | 53.78 |
| EX52 | 5.571 | 1 | 62.68 |
| EX58 | 5.888 | 1 | 44.86 |
| EX63 | 4.436 | 1 | 14.41 |
| EX66 | 4.553 | 1 | 38.31 |
| EX96 | 5.551 | 4 | 42.96 |
| EX97 | 3.131 | 1 | 8.313 |
| EX127 | 7.952 | 1 | 93.76 |
| EX132 | 3.589 | 4 | 56.52 |
| EX153 | 5.482 | 1 | 33.96 |
| EX157 | 6.212 | 1 | 80.54 |
| EX165 | 7.716 | 1 | 41.49 |
| EX168 | 7.111 | 1 | 40.91 |
| EX169 | 5.651 | 1 | 32.25 |
| EX187 | 2.043 | 1 | 5.438 |
| Tolvaptan | 0.6815 | 1 | 1.783 |

Test Example 4

The pharmacological effects of several compounds among the present compounds on polycystic kidney disease were evaluated according to the tests disclosed in WO 2015/056805 using PKD model animals, pcy mice and PCK rats, and positive results of the present compounds that support the test results of Test Examples 1 to 3 were obtained.

INDUSTRIAL APPLICABILITY

The present compound with vasopressin antagonisms may be useful for diagnosis, prevention, and/or treatment of various diseases associated with vasopressin receptors.

The invention claimed is:

1. A benzazepine compound of Formula (1):

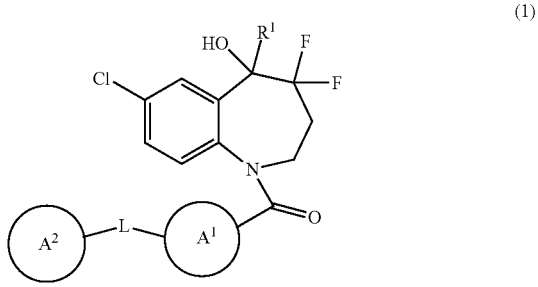

(1)

wherein $R^1$ is $C_{1-6}$ alkyl substituted with OH;
L is a direct bond or —C(=O)—NH—;
Ring $A^1$ is a hydrocarbon ring or heterocycle;
Ring $A^2$ is a hydrocarbon ring or heterocycle; and
each of Rings $A^1$ and $A^2$ may have at least one substituent, or a salt thereof.

2. The compound according to claim 1, wherein Ring $A^1$ is a saturated or unsaturated 3- to 8-membered monocyclic hydrocarbon ring, or a saturated or unsaturated 3- to 15-membered monocyclic, bicyclic, or tricyclic heterocycle comprising as the ring member 1 to 5 heteroatoms independently selected from the group consisting of nitrogen, oxygen, and sulfur,
Ring $A^2$ is a saturated or unsaturated 3- to 8-membered monocyclic hydrocarbon ring, or a saturated or unsaturated 3- to 15-membered monocyclic, bicyclic, or tricyclic heterocycle comprising as the ring member 1 to 5 heteroatoms independently selected from the group consisting of nitrogen, oxygen, and sulfur, and
each of Rings $A^1$ and $A^2$ may have at least one substituent, or a salt thereof.

3. The compound according to claim 1, or a salt thereof, wherein Ring $A^1$ is a saturated or unsaturated 3- to 8-membered monocyclic hydrocarbon ring, a saturated or unsaturated 5- or 6-membered heteromonocycle comprising as the ring heteroatom 1 to 4 nitrogen atoms, a saturated or unsaturated 7- to 15-membered heterobicycle comprising as the ring heteroatom 1 to 5 nitrogen atoms, a saturated or unsaturated 5- or 6-membered heteromonocycle comprising as the ring heteroatom 1 or 2 oxygen atoms and at least one nitrogen atom, or a saturated or unsaturated 5- or 6-membered heteromonocycle comprising as the ring heteroatom 1 or 2 sulfur atoms and at least one nitrogen atom,
Ring $A^2$ is a saturated or unsaturated 3- to 8-membered monocyclic hydrocarbon ring, a saturated or unsaturated 5- or 6-membered heteromonocycle comprising as the ring heteroatom 1 to 4 nitrogen atoms, a saturated or unsaturated 5- or 6-membered heteromonocycle comprising as the ring heteroatom 1 or 2 oxygen atoms, a saturated or unsaturated 7- to 12-membered heterobicycle comprising as the ring heteroatom 1 to 3 oxygen atoms, a saturated or unsaturated 5- or 6-membered heteromonocycle comprising as the ring heteroatom 1 or 2 sulfur atoms, a saturated or unsaturated 7- to 15-membered heterobicycle comprising as the ring heteroatom 1 to 5 nitrogen atoms, a saturated or unsaturated 5- or 6-membered heteromonocycle comprising as the ring heteroatom 1 or 2 oxygen atoms and at least one nitrogen atom, or a saturated or unsaturated 5- or 6-membered heteromonocycle comprising as the ring heteroatom 1 or 2 sulfur atoms and at least one nitrogen atom, and
each of Rings $A^1$ and $A^2$ may have at least one substituent, or a salt thereof.

4. The compound according to claim 1, wherein Ring $A^1$ is benzene, pyridine, pyrazine, or tetrahydroisoquinoline and Ring $A^1$ may have 1 to 4 substituents independently selected from the group consisting of optionally substituted $C_{1-6}$ alkyl, optionally substituted $C_{1-6}$ alkyl-O—, halogen, and oxo;
Ring $A^2$ is benzene, pyridine, furan, thiophene, or tetrahydroisoquinoline and Ring $A^2$ may have 1 to 4 substituents independently selected from the group consisting of optionally substituted $C_{1-6}$ alkyl, optionally substituted $C_{1-6}$ alkyl-O—, optionally substituted $C_{3-6}$ cycloalkyl, halogen, oxo, optionally substituted phenyl, and optionally substituted pyridyl,
provided that when Ring $A^2$ has multiple substituents on its ring carbon atoms, then the substituents may combine together with the carbon atoms to form $C_{3-6}$ cycloalkyl; or a salt thereof.

5. The compound according to claim 4, wherein, in Ring $A^1$, a substituent of the optionally substituted $C_{1-6}$ alkyl or optionally substituted $C_{1-6}$ alkyl-O— is each independently the same or different 1 to 3 groups selected from the group consisting of halogen and $C_{1-6}$ alkyl-O—, in Ring $A^2$, a substituent of the optionally substituted $C_{1-6}$ alkyl or optionally substituted $C_{1-6}$ alkyl-O— is each independently the same or different 1 to 3 halogen, a substituent of the optionally substituted $C_{3-6}$ cycloalkyl is the same or different 1 to 3 halogen, a substituent of the optionally substituted phenyl is 1 to 3 groups independently selected from the group consisting of halogen, $C_{1-6}$ alkyl, and $C_{1-6}$ alkyl-O—, and a substituent of the optionally substituted pyridyl is the same or different 1 to 3 halogen, or a salt thereof.

6. The compound according to claim 1, wherein Ring $A^1$ is benzene optionally substituted with halogen, $C_{1-6}$ alkyl, halo-$C_{1-6}$ alkyl, $C_{1-6}$ alkyl-O—, halo-$C_{1-6}$ alkyl-O—, $C_{1-6}$ alkyl-O—$C_{1-6}$ alkyl-O—, halo-$C_{1-6}$ alkyl-O—$C_{1-6}$ alkyl-O—, $C_{1-6}$ alkyl-O-halo-$C_{1-6}$ alkyl-O—, or halo-$C_{1-6}$ alkyl-O-halo-$C_{1-6}$ alkyl-O—; pyridine optionally substituted with halogen; pyrazine; or tetrahydroisoquinoline optionally substituted with oxo; and Ring $A^2$ is benzene optionally substituted with 1 to 3 groups independently selected from the group consisting of halogen, $C_{1-6}$ alkyl, halo-$C_{1-6}$ alkyl, $C_{1-6}$ alkyl-O—, halo-$C_{1-6}$ alkyl-O—, $C_{3-6}$ cycloalkyl, optionally substituted phenyl, and pyridyl, the optionally substituted phenyl being phenyl optionally substituted with halogen, $C_{1-6}$ alkyl, halo-$C_{1-6}$ alkyl, $C_{1-6}$ alkyl-O—, or halo-$C_{1-6}$ alkyl-O—; pyridine optionally substituted with $C_{1-6}$ alkyl, halo-$C_{1-6}$ alkyl, or phenyl; furan optionally substituted with $C_{1-6}$ alkyl; thiophene optionally substituted with $C_{1-6}$ alkyl; or tetrahydroisoquinoline optionally substituted with 1 to 3 groups independently selected from the group consisting of halogen, $C_{1-6}$ alkyl, and oxo, provided that when tetrahydroisoquinoline has multiple $C_{1-6}$ alkyl groups on its ring carbon atoms, then the $C_{1-6}$ alkyl groups may combine together with the carbon atoms to form $C_{3-6}$ cycloalkyl, or a salt thereof.

7. The compound according to claim 1, wherein Ring $A^1$ is benzene optionally substituted with halogen, $C_{1-6}$ alkyl, $C_{1-6}$ alkyl-O—, or $C_{1-6}$ alkyl-O—$C_{1-6}$ alkyl-O—; or pyridine optionally substituted with halogen, and Ring $A^2$ is benzene optionally substituted with 1 to 3 groups independently selected from the group consisting of halogen, $C_{1-6}$ alkyl, halo-$C_{1-6}$ alkyl, $C_{1-6}$ alkyl-O—, halo-$C_{1-6}$ alkyl-O—, $C_{3-6}$ cycloalkyl, optionally substituted phenyl, and pyridyl, the optionally substituted phenyl being phenyl optionally substituted with halogen, $C_{1-6}$ alkyl, halo-$C_{1-6}$ alkyl, $C_{1-6}$ alkyl-O—, or halo-$C_{1-6}$ alkyl-O—, or a salt thereof.

8. The compound according to claim 1, wherein Ring $A^1$ is benzene optionally substituted with halogen, $C_{1-6}$ alkyl-O—, or halo-$C_{1-6}$ alkyl-O—; or pyridine, and Ring $A^2$ is benzene optionally substituted with 1 to 3 groups independently selected from the group consisting of halogen, $C_{1-6}$ alkyl, halo-$C_{1-6}$ alkyl, and phenyl optionally substituted with halogen; pyridine optionally substituted with phenyl or halo-$C_{1-6}$ alkyl; or tetrahydroisoquinoline optionally substituted with 1 to 3 groups independently selected from the group consisting of halogen and oxo, or a salt thereof.

9. The compound according to claim 1, wherein L is —C(=O)—NH—, or a salt thereof.

10. A compound, or a salt thereof, selected from the following compound group:

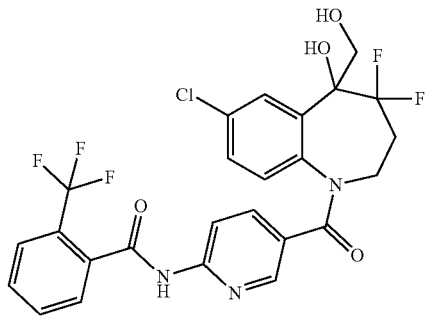

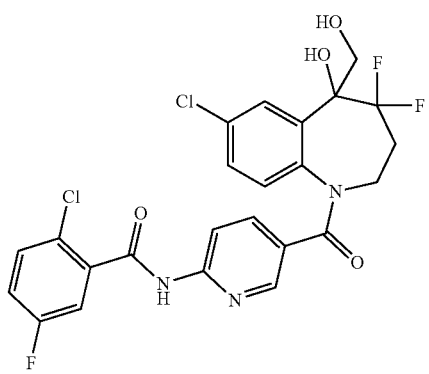

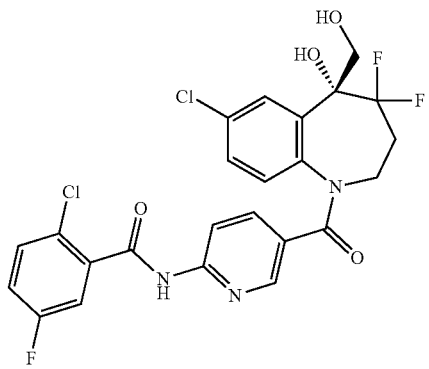

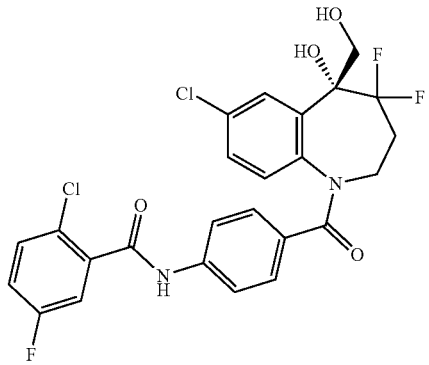

215
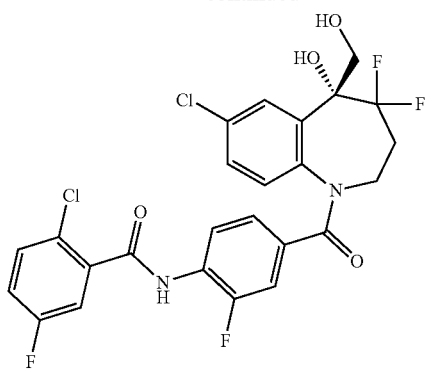
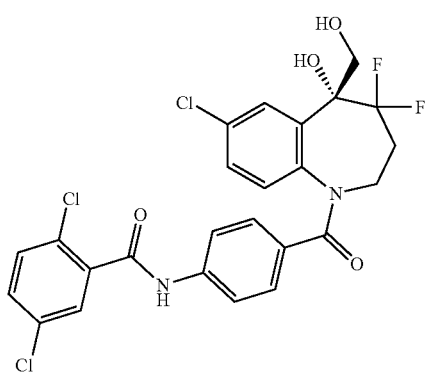
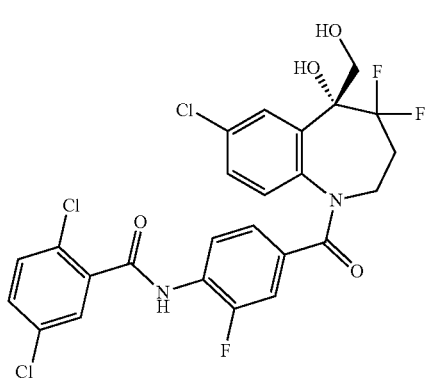
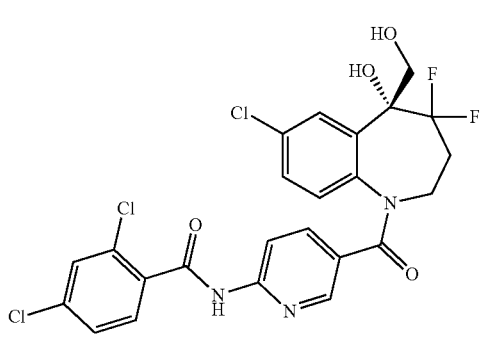
216
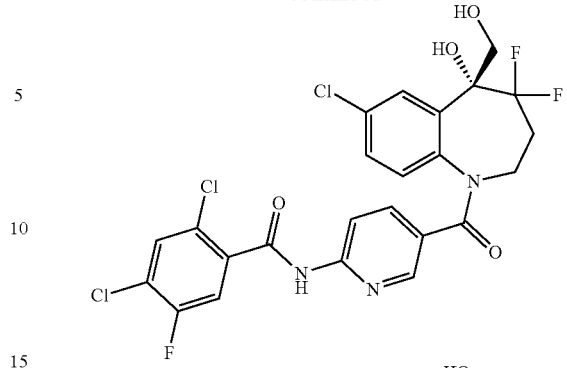
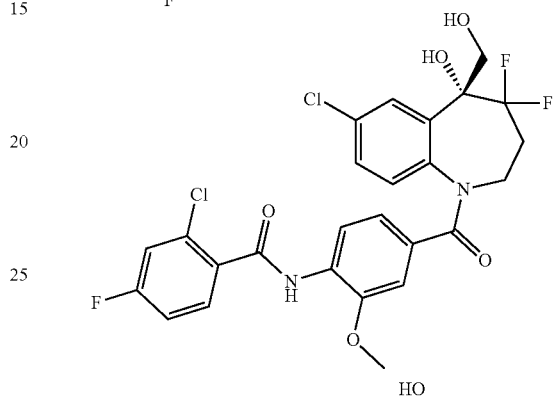
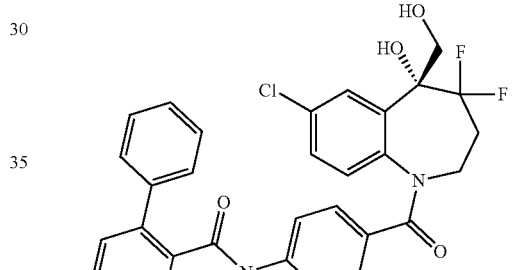
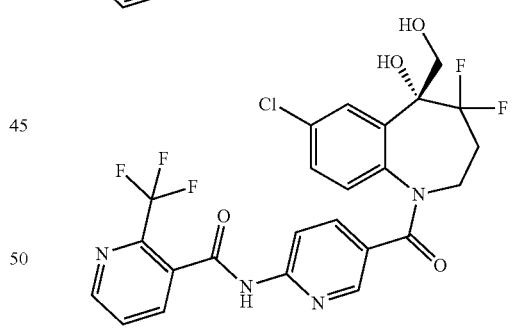
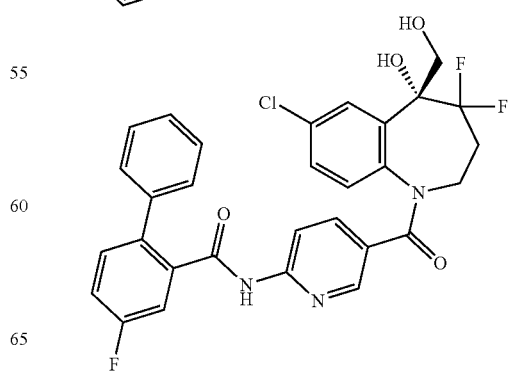

217
-continued
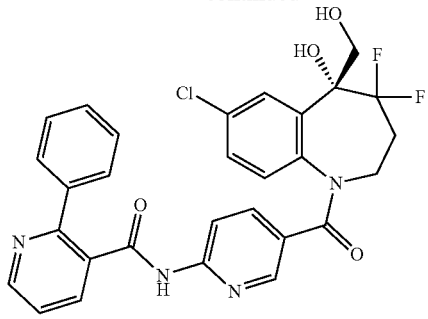
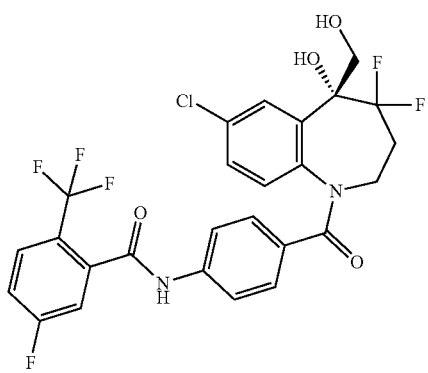
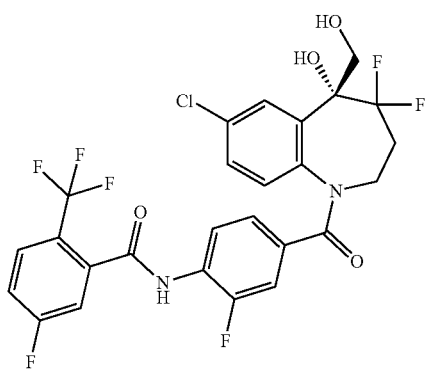
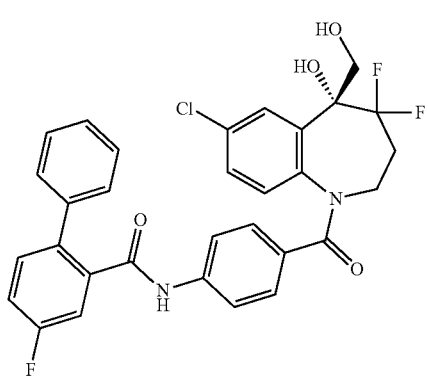
218
-continued
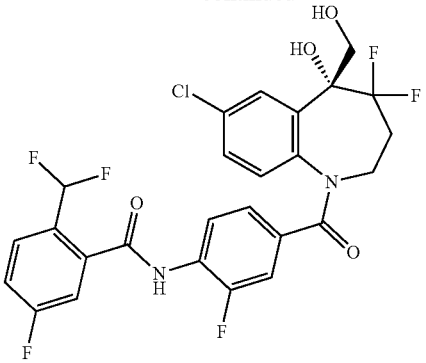
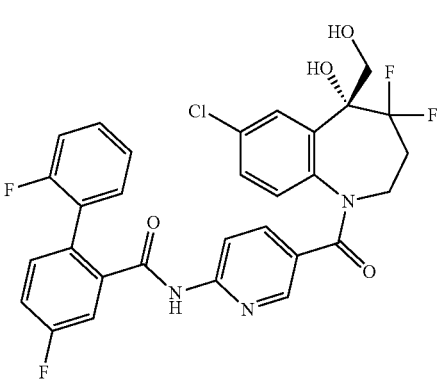
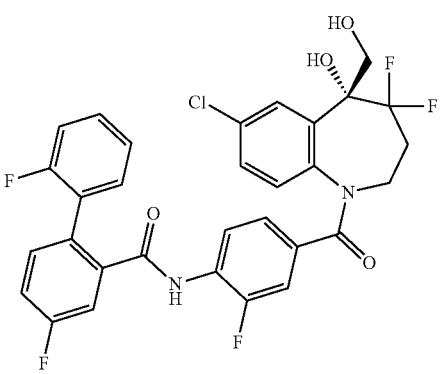
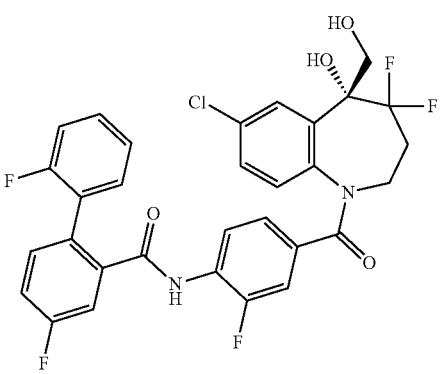

-continued

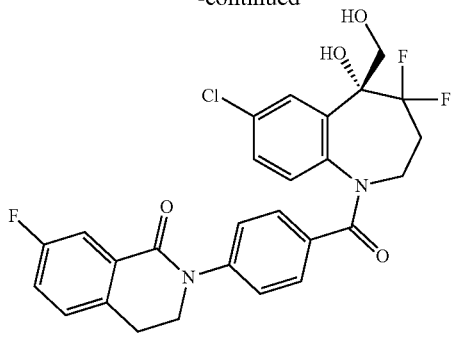

11. The compound according to claim 10, wherein the compound is:

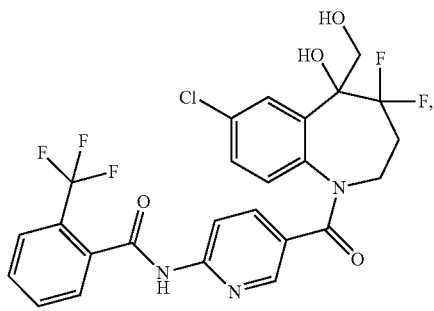 [SMILES: O=C(Nc1ccc(C(=O)N2CCC(F)(F)C(O)(CO)c3cc(Cl)ccc32)cn1)c1ccccc1C(F)(F)F]

or a salt thereof.

12. The compound according to claim 10, wherein the compound is:

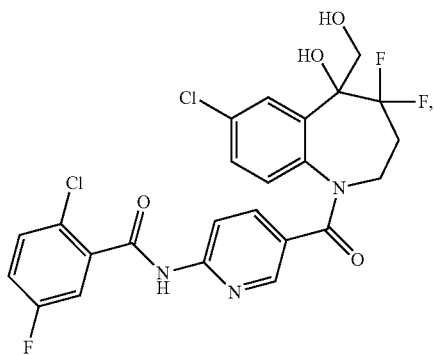 [SMILES: O=C(Nc1ccc(C(=O)N2CCC(F)(F)C(O)(CO)c3cc(Cl)ccc32)cn1)c1cc(F)ccc1Cl]

or a salt thereof.

13. The compound according to claim 10, wherein the compound is:

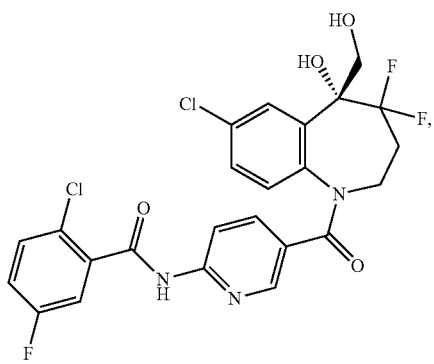 [SMILES: O=C(Nc1ccc(C(=O)N2CCC(F)(F)[C@](O)(CO)c3cc(Cl)ccc32)cn1)c1cc(F)ccc1Cl]

or a salt thereof.

14. The compound according to claim 10, wherein the compound is:

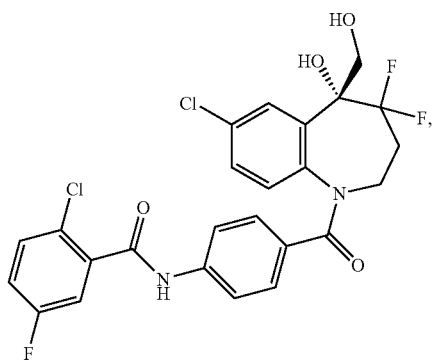 [SMILES: O=C(Nc1ccc(C(=O)N2CCC(F)(F)[C@](O)(CO)c3cc(Cl)ccc32)cc1)c1cc(F)ccc1Cl]

or a salt thereof.

15. The compound according to claim 10, wherein the compound is:

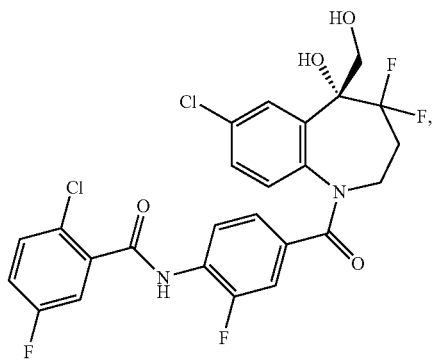 [SMILES: O=C(Nc1ccc(C(=O)N2CCC(F)(F)[C@](O)(CO)c3cc(Cl)ccc32)cc1F)c1cc(F)ccc1Cl]

or a salt thereof.

16. The compound according to claim 10, wherein the compound is:

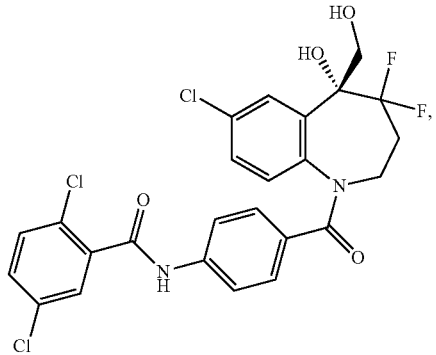 [SMILES: O=C(Nc1ccc(C(=O)N2CCC(F)(F)[C@](O)(CO)c3cc(Cl)ccc32)cc1)c1cc(Cl)ccc1Cl]

or a salt thereof.

17. The compound according to claim 10, wherein the compound is:

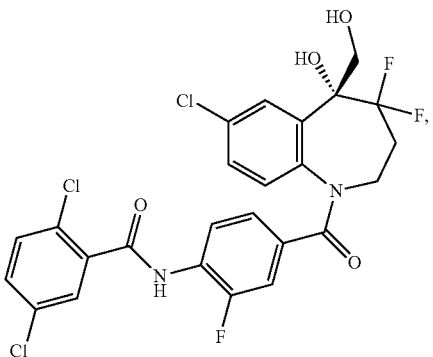

or a salt thereof.

18. The compound according to claim 10, wherein the compound is:

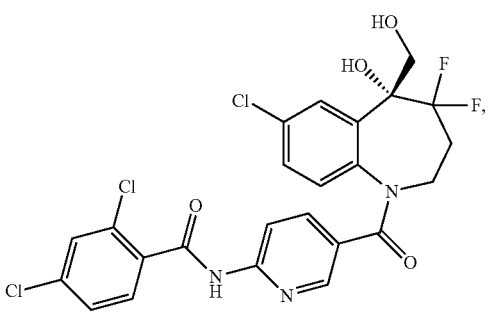 [SMILES: O=C(Nc1ccc(C(=O)N2CCC(F)(F)[C@](O)(CO)c3cc(Cl)ccc32)cn1)c1ccc(Cl)cc1Cl]

or a salt thereof.

19. The compound according to claim 10, wherein the compound is:

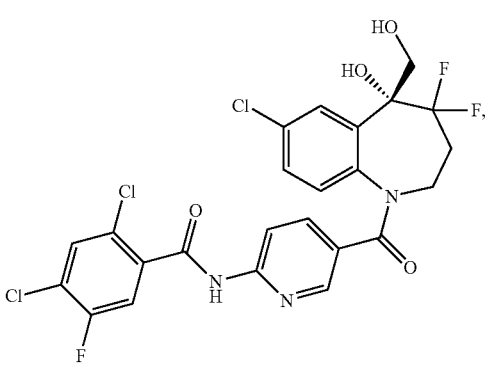 [SMILES: O=C(Nc1ccc(C(=O)N2CCC(F)(F)[C@](O)(CO)c3cc(Cl)ccc32)cn1)c1cc(F)c(Cl)cc1Cl]

or a salt thereof.

20. The compound according to claim 10, wherein the compound is:

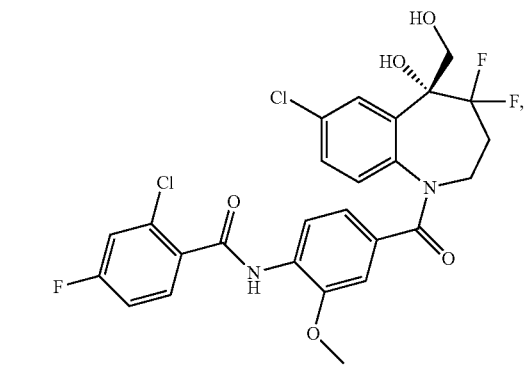 [SMILES: COc1cc(C(=O)N2CCC(F)(F)[C@](O)(CO)c3cc(Cl)ccc32)ccc1NC(=O)c1ccc(F)cc1Cl]

or a salt thereof.

21. The compound according to claim 10, wherein the compound is:

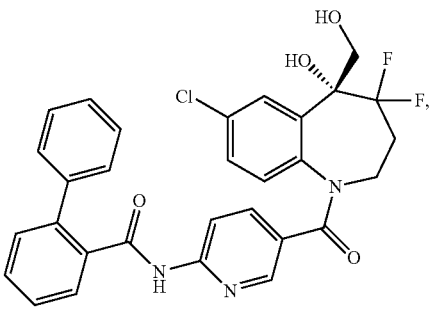 [SMILES: O=C(Nc1ccc(C(=O)N2CCC(F)(F)[C@](O)(CO)c3cc(Cl)ccc32)cn1)c1ccccc1-c1ccccc1]

or a salt thereof.

22. The compound according to claim 10, wherein the compound is:

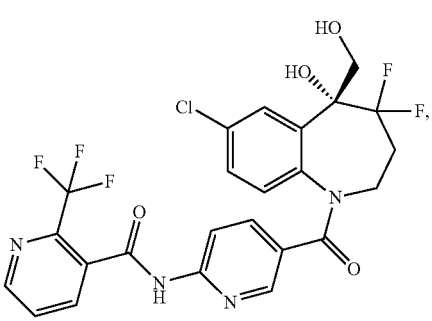 [SMILES: O=C(Nc1ccc(C(=O)N2CCC(F)(F)[C@](O)(CO)c3cc(Cl)ccc32)cn1)c1cccnc1C(F)(F)F]

or a salt thereof.

23. The compound according to claim 10, wherein the compound is:

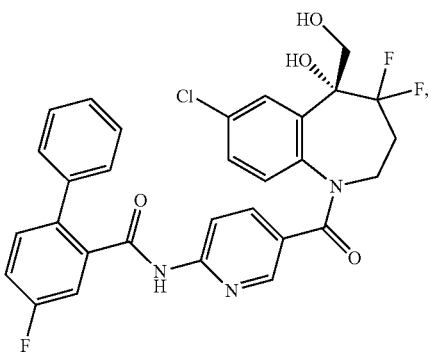 [SMILES: O=C(Nc1ccc(C(=O)N2CCC(F)(F)[C@](O)(CO)c3cc(Cl)ccc32)cn1)c1cc(F)ccc1-c1ccccc1]

or a salt thereof.

24. The compound according to claim 10, wherein the compound is:

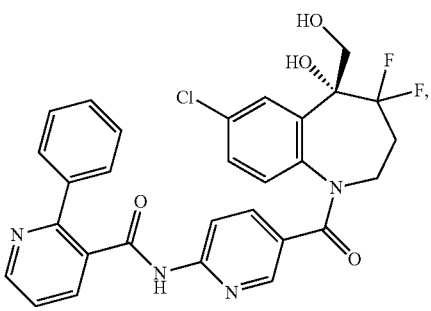 [SMILES: O=C(Nc1ccc(C(=O)N2CCC(F)(F)[C@](O)(CO)c3cc(Cl)ccc32)cn1)c1cccnc1-c1ccccc1]

or a salt thereof.

25. The compound according to claim 10, wherein the compound is:

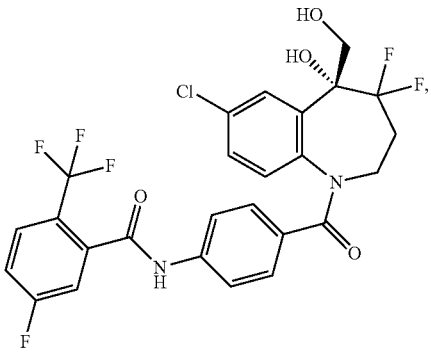 [SMILES: O=C(Nc1ccc(C(=O)N2CCC(F)(F)[C@](O)(CO)c3cc(Cl)ccc32)cc1)c1cc(F)ccc1C(F)(F)F]

or a salt thereof.

26. The compound according to claim 10, wherein the compound is:

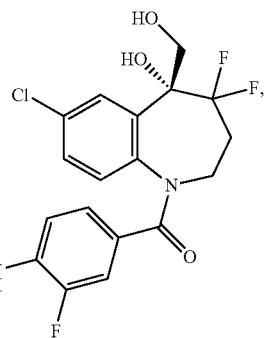

or a salt thereof.

27. The compound according to claim 10, wherein the compound is:

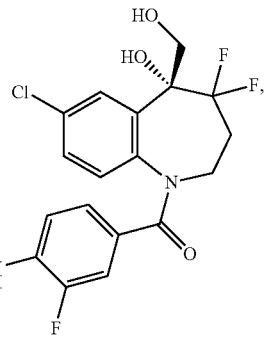

or a salt thereof.

28. The compound according to claim 10, wherein the compound is:

or a salt thereof.

29. The compound according to claim 10, wherein the compound is:

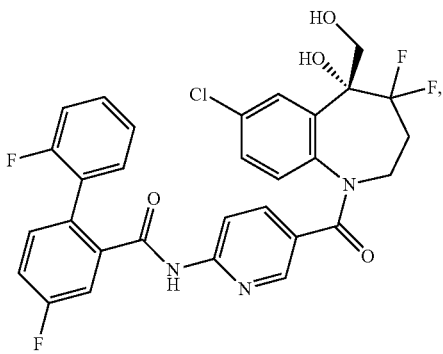 [SMILES: O=C(Nc1ccc(C(=O)N2CCC(F)(F)[C@](O)(CO)c3cc(Cl)ccc32)cn1)c1cc(F)ccc1-c1ccccc1F]

or a salt thereof.

30. The compound according to claim 10, wherein the compound is:

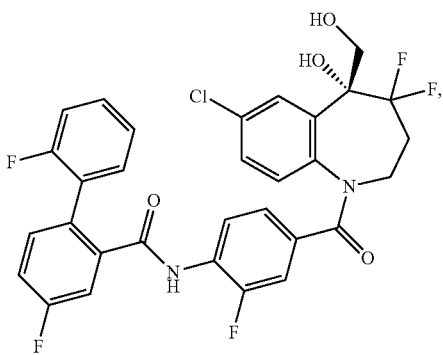 [SMILES: O=C(Nc1ccc(C(=O)N2CCC(F)(F)[C@](O)(CO)c3cc(Cl)ccc32)cc1F)c1cc(F)ccc1-c1ccccc1F]

or a salt thereof.

31. The compound according to claim 10, wherein the compound is:

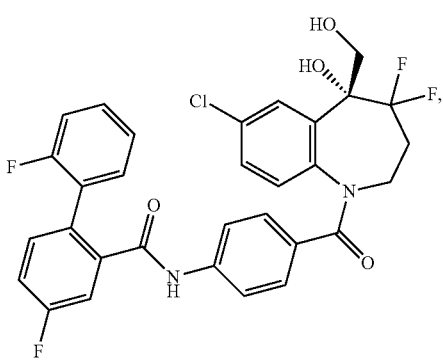 [SMILES: O=C(Nc1ccc(C(=O)N2CCC(F)(F)[C@](O)(CO)c3cc(Cl)ccc32)cc1)c1cc(F)ccc1-c1ccccc1F]

or a salt thereof.

32. The compound according to claim 10, wherein the compound is:

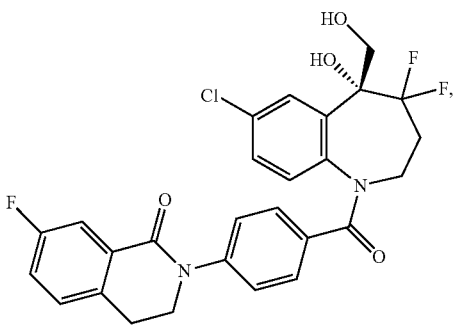 [SMILES: O=C1c2cc(F)ccc2CCN1c1ccc(C(=O)N2CCC(F)(F)[C@](O)(CO)c3cc(Cl)ccc32)cc1]

or a salt thereof.

33. The compound according to claim 10, wherein the compound is:

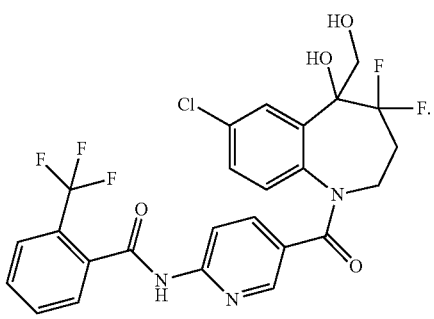 [SMILES: O=C(Nc1ccc(C(=O)N2CCC(F)(F)C(O)(CO)c3cc(Cl)ccc32)cn1)c1ccccc1C(F)(F)F]

34. The compound according to claim 10, wherein the compound is:

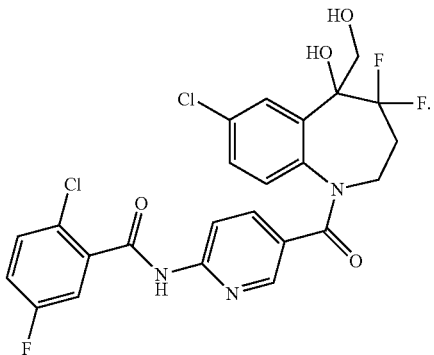 [SMILES: O=C(Nc1ccc(C(=O)N2CCC(F)(F)C(O)(CO)c3cc(Cl)ccc32)cn1)c1cc(F)ccc1Cl]

35. The compound according to claim 10, wherein the compound is:

36. The compound according to claim 10, wherein the compound is:
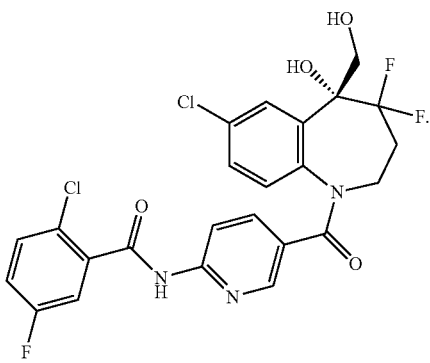 [SMILES: O=C(Nc1ccc(C(=O)N2CCC(F)(F)[C@](O)(CO)c3cc(Cl)ccc32)cn1)c1cc(F)ccc1Cl]
37. The compound according to claim 10, wherein the compound is:
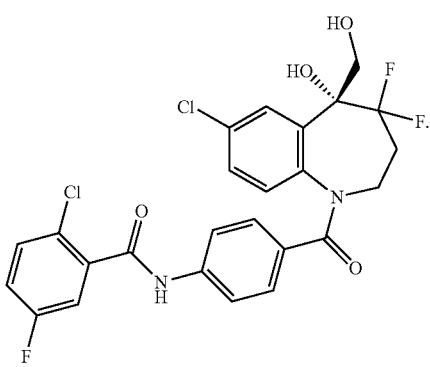 [SMILES: O=C(Nc1ccc(C(=O)N2CCC(F)(F)[C@](O)(CO)c3cc(Cl)ccc32)cc1)c1cc(F)ccc1Cl]
38. The compound according to claim 10, wherein the compound is:
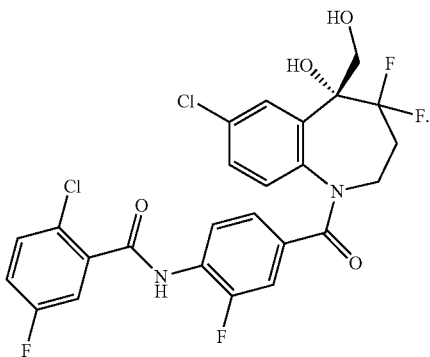 [SMILES: O=C(Nc1ccc(C(=O)N2CCC(F)(F)[C@](O)(CO)c3cc(Cl)ccc32)cc1F)c1cc(F)ccc1Cl]
39. The compound according to claim 10, wherein the compound is:
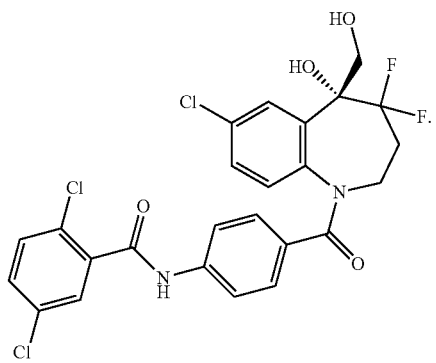 [SMILES: O=C(Nc1ccc(C(=O)N2CCC(F)(F)[C@](O)(CO)c3cc(Cl)ccc32)cc1)c1cc(Cl)ccc1Cl]
40. The compound according to claim 10, wherein the compound is:
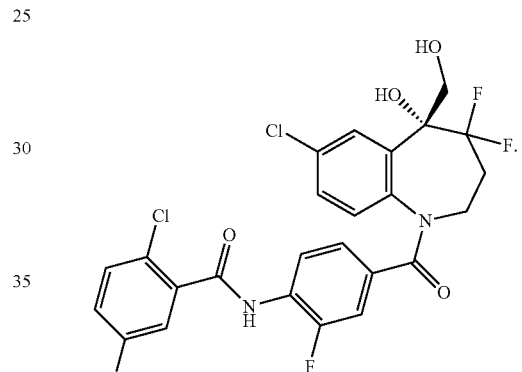
41. The compound according to claim 10, wherein the compound is:
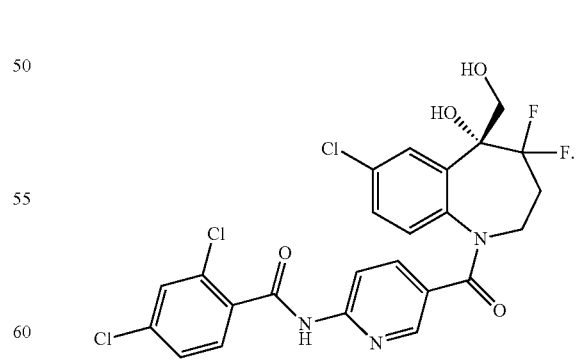

42. The compound according to claim 10, wherein the compound is:
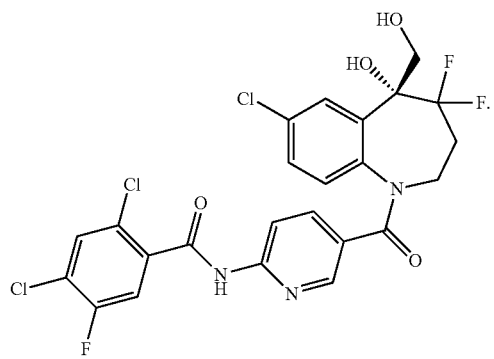 [SMILES: O=C(Nc1ccc(C(=O)N2CCC(F)(F)[C@](O)(CO)c3cc(Cl)ccc32)cn1)c1cc(F)c(Cl)cc1Cl]
43. The compound according to claim 10, wherein the compound is:
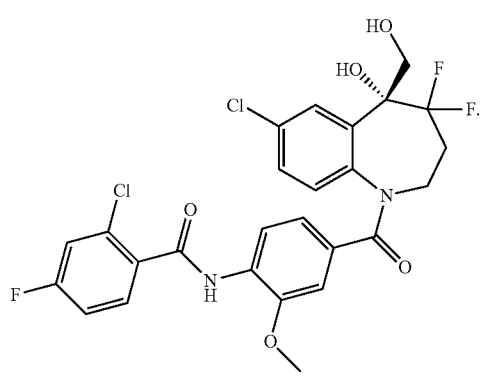 [SMILES: COc1cc(C(=O)N2CCC(F)(F)[C@](O)(CO)c3cc(Cl)ccc32)ccc1NC(=O)c1ccc(F)cc1Cl]
44. The compound according to claim 10, wherein the compound is:
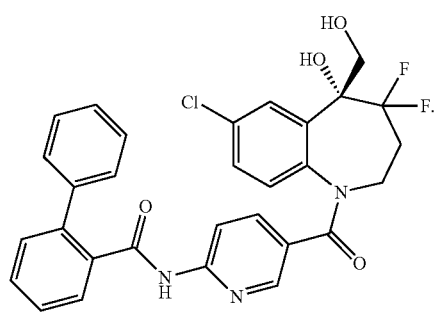 [SMILES: O=C(Nc1ccc(C(=O)N2CCC(F)(F)[C@](O)(CO)c3cc(Cl)ccc32)cn1)c1ccccc1-c1ccccc1]
45. The compound according to claim 10, wherein the compound is:
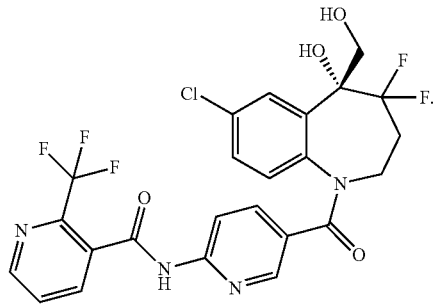 [SMILES: O=C(Nc1ccc(C(=O)N2CCC(F)(F)[C@](O)(CO)c3cc(Cl)ccc32)cn1)c1cccnc1C(F)(F)F]
46. The compound according to claim 10, wherein the compound is:
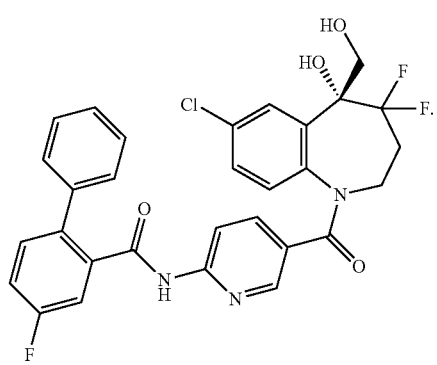 [SMILES: O=C(Nc1ccc(C(=O)N2CCC(F)(F)[C@](O)(CO)c3cc(Cl)ccc32)cn1)c1cc(F)ccc1-c1ccccc1]
47. The compound according to claim 10, wherein the compound is:
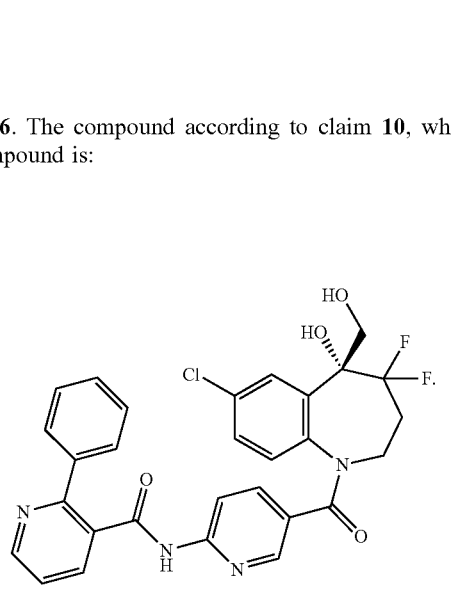

48. The compound according to claim 10, wherein the compound is:
49. The compound according to claim 10, wherein the compound is:
50. The compound according to claim 10, wherein compound is:
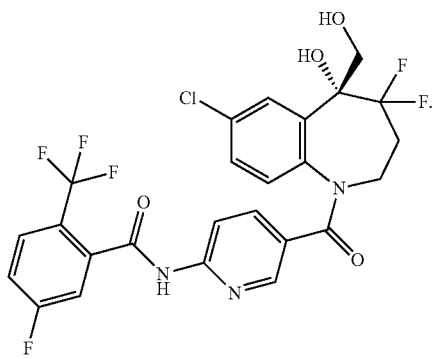 [SMILES: O=C(Nc1ccc(C(=O)N2CCC(F)(F)[C@](O)(CO)c3cc(Cl)ccc32)cn1)c1cc(F)ccc1C(F)(F)F]
51. The compound according to claim 10, wherein the compound is:
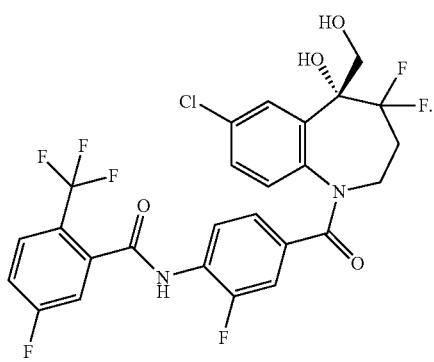 [SMILES: O=C(Nc1ccc(C(=O)N2CCC(F)(F)[C@](O)(CO)c3cc(Cl)ccc32)cc1F)c1cc(F)ccc1C(F)(F)F]
52. The compound according to claim 10, wherein the compound is:
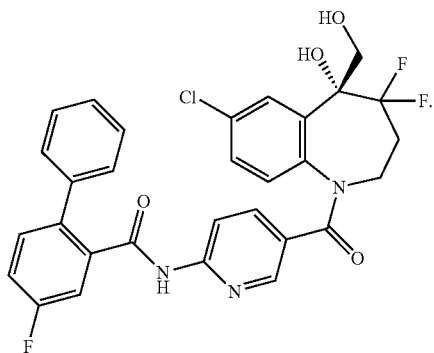 [SMILES: O=C(Nc1ccc(C(=O)N2CCC(F)(F)[C@](O)(CO)c3cc(Cl)ccc32)cn1)c1cc(F)ccc1-c1ccccc1]
53. The compound according to claim 10, wherein the compound is:

54. The compound according to claim 10, wherein the compound is:
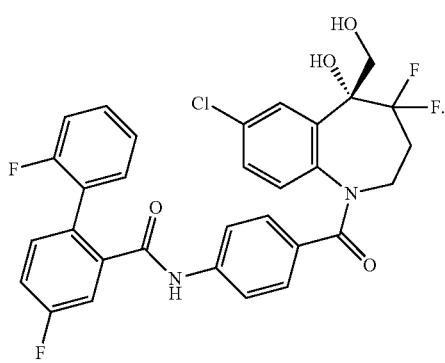 [SMILES: O=C(Nc1ccc(C(=O)N2CCC(F)(F)[C@](O)(CO)c3cc(Cl)ccc32)cc1)c1cc(F)ccc1-c1ccccc1F]
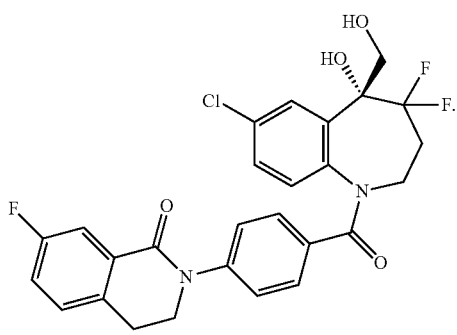 [SMILES: O=C1c2cc(F)ccc2CCN1c1ccc(C(=O)N2CCC(F)(F)[C@](O)(CO)c3cc(Cl)ccc32)cc1]
55. A compound selected from the following compound group:
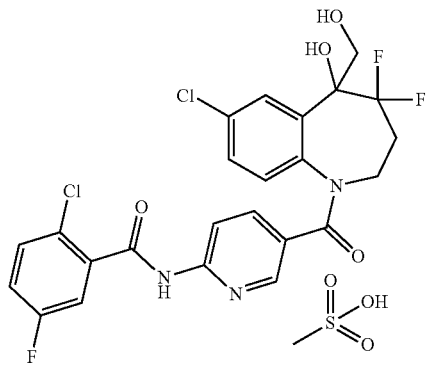
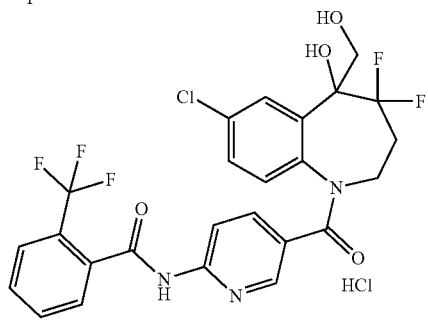
56. The compound according to claim 55, wherein the compound is:
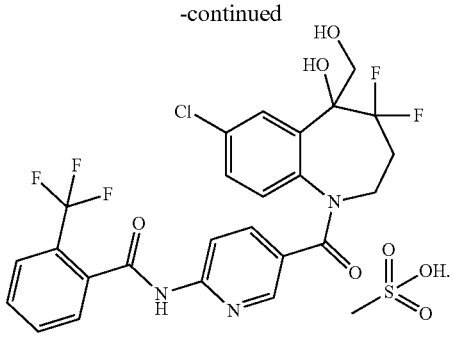
57. The compound according to claim 55, wherein the compound is:
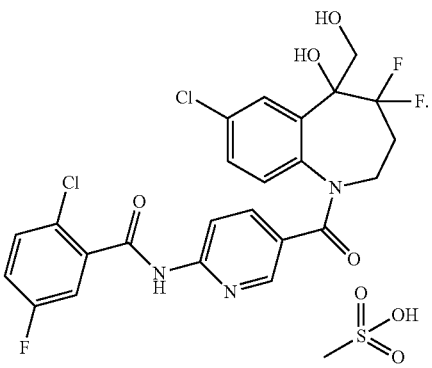
58. The compound according to claim 55, wherein the compound is:
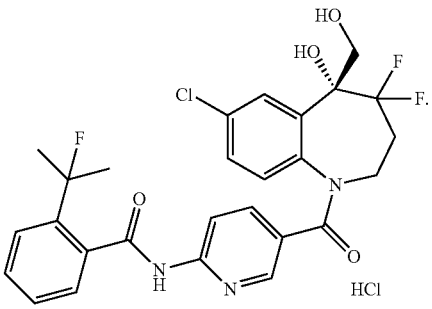 [SMILES: CC(C)(F)c1ccccc1C(=O)Nc1ccc(C(=O)N2CCC(F)(F)[C@](O)(CO)c3cc(Cl)ccc32)cn1 ; Cl]
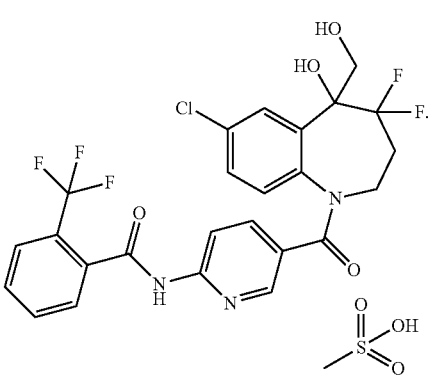
* * * * *